(12) United States Patent
Arslan et al.

(10) Patent No.: US 11,781,185 B2
(45) Date of Patent: Oct. 10, 2023

(54) METHODS AND REAGENTS FOR NUCLEIC ACID ANALYSIS

(71) Applicant: Element Biosciences, Inc., San Diego, CA (US)

(72) Inventors: Sinan Arslan, San Diego, CA (US); Molly He, San Diego, CA (US); Michael Previte, San Diego, CA (US); Ramreddy Tippana, San Diego, CA (US); Hua Yu, San Diego, CA (US); William Light, San Diego, CA (US); Junhua Zhao, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 17/947,984

(22) Filed: Sep. 19, 2022

(65) Prior Publication Data
US 2023/0065693 A1 Mar. 2, 2023

Related U.S. Application Data

(63) Continuation of application No. PCT/US2021/057441, filed on Oct. 29, 2021.

(60) Provisional application No. 63/108,207, filed on Oct. 30, 2020.

(51) Int. Cl.
*C12Q 1/68* (2018.01)
*C12Q 1/6874* (2018.01)
*C12Q 1/6806* (2018.01)

(52) U.S. Cl.
CPC .......... *C12Q 1/6874* (2013.01); *C12Q 1/6806* (2013.01)

(58) Field of Classification Search
CPC .................................................... C12Q 1/6869
See application file for complete search history.

(56) References Cited

U.S. PATENT DOCUMENTS

| | | | |
|---|---|---|---|
| 5,558,991 A | 9/1996 | Trainor | |
| 8,632,975 B2 | 1/2014 | Vander Horn et al. | |
| 9,951,385 B1* | 4/2018 | Vijayan | C12Q 1/6869 |
| 9,994,541 B2 | 6/2018 | Batthyany et al. | |
| 10,400,272 B1* | 9/2019 | Middleton | C12Q 1/6832 |
| 10,704,094 B1 | 7/2020 | Arslan et al. | |
| 10,768,173 B1 | 9/2020 | Arslan et al. | |
| 10,876,148 B2 | 12/2020 | Zhou et al. | |
| 10,982,280 B2 | 4/2021 | Arslan et al. | |
| 11,053,540 B1 | 7/2021 | Chen et al. | |
| 11,060,138 B1 | 7/2021 | Chen et al. | |
| 11,118,214 B2 | 9/2021 | Matthiesen et al. | |
| 11,162,129 B2* | 11/2021 | Andruzzi | C07D 311/66 |
| 11,198,121 B1 | 12/2021 | Guo et al. | |
| 11,200,446 B1 | 12/2021 | Zhou et al. | |
| 11,261,489 B2 | 3/2022 | Chen et al. | |
| 11,287,422 B2 | 3/2022 | Previte et al. | |
| 11,365,444 B2 | 6/2022 | Chen et al. | |
| 11,408,032 B2 | 8/2022 | Chen et al. | |
| 11,426,732 B2 | 8/2022 | Guo et al. | |
| 11,459,608 B2 | 10/2022 | Chen et al. | |
| 11,558,125 B2 | 1/2023 | Connor et al. | |
| 2009/0186343 A1 | 7/2009 | Wang et al. | |
| 2009/0247414 A1 | 10/2009 | Obradovic et al. | |
| 2010/0093992 A1 | 4/2010 | Cherkasov et al. | |
| 2013/0165350 A1 | 6/2013 | Kuimelis et al. | |
| 2013/0171631 A1 | 7/2013 | Becker et al. | |
| 2014/0206550 A1 | 7/2014 | Bjornson et al. | |
| 2015/0050659 A1 | 2/2015 | Sebo et al. | |
| 2015/0086981 A1 | 3/2015 | Cherkasov et al. | |
| 2018/0187245 A1* | 7/2018 | Dambacher | C12Q 1/6816 |
| 2018/0305749 A1* | 10/2018 | Stromberg | C12Q 1/6874 |
| 2019/0119740 A1 | 4/2019 | Ahn et al. | |
| 2020/0149095 A1 | 5/2020 | Arslan et al. | |
| 2020/0179921 A1 | 6/2020 | Arslan et al. | |
| 2020/0182866 A1 | 6/2020 | Arslan et al. | |
| 2020/0216899 A1 | 7/2020 | Arslan et al. | |

(Continued)

FOREIGN PATENT DOCUMENTS

WO WO-2004018493 A1 3/2004
WO WO-2004018497 A2 3/2004
(Continued)

OTHER PUBLICATIONS

Eschenmoser et al., Chemical etiology of nucleic acid structure. Science. 284(5423):2118-2124 (1999).
Fasman: Practical Handbook of Biochemistry and Molecular Biology. Section 2: UV Spectral Characteristics and Acidic Dissociation Constants of 280 Alkyl Bases, Nucleosides, And Nucleotides, Singer. CRC Press, Boca Raton, Fla., pp. 385-394 (1989).
Ferraro et al., Biocatalytic selective modifications of conventional nucleosides, carbocyclic nucleosides, and C-nucleosides. Chem Rev. 100(12):4319-4348 (2000).
Forster et al.: Intermolecular Energy Migration and Fluorescence. Ann. Phys. 437(1-2):55-75 (1948)—Abstract: English Machine Translation.

(Continued)

*Primary Examiner* — Kenneth R Horlick
(74) *Attorney, Agent, or Firm* — Wilson Sonsini Goodrich & Rosati

(57) ABSTRACT

Provided herein are fluorescently-labeled nucleotide conjugates for nucleic acid analysis. Also provided are reagents used for forming binding complexes between a fluorescently-labeled nucleotide conjugate and a target nucleic acid sequence in the presence of one or more reagents disclosed herein. Binding complexes can be detected in the presence of the one or more reagents. For example, the one or more reagents may contain a photobleaching reducing agent configured to reduce photobleaching resulting from use of the fluorescently-labeled nucleotide conjugate to form the binding complex in a nucleic acid analysis. Such nucleic acid analysis may be used to identify sites of nucleobase binding or incorporation between the target nucleic acid sequence and one or more nucleotide moieties of the fluorescently-labeled nucleotide conjugate in a nucleic acid sequence reaction.

29 Claims, 50 Drawing Sheets

Specification includes a Sequence Listing.

(56) References Cited

U.S. PATENT DOCUMENTS

| | | |
|---|---|---|
| 2020/0248258 A1 | 8/2020 | Arslan et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332430 A1 | 10/2021 | Arslan et al. |
| 2021/0373000 A1 | 12/2021 | Arslan et al. |
| 2021/0387184 A1 | 12/2021 | Guo et al. |
| 2022/0290216 A1 | 9/2022 | Middleton et al. |

FOREIGN PATENT DOCUMENTS

| | | |
|---|---|---|
| WO | WO-2005111240 A2 | 11/2005 |
| WO | WO-2009073201 A2 | 6/2009 |
| WO | WO-2009105077 A2 | 8/2009 |
| WO | WO-2012027625 A2 | 3/2012 |
| WO | WO-2019241305 A1 | 12/2019 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022094332 A1 | 5/2022 |

OTHER PUBLICATIONS

Jeong et al., Structure-activity relationships of beta-D-(2S,5R)- and alpha-D-(2S,5S)-1,3-oxathiolanyl nucleosides as potential anti-HIV agents. J Med Chem. 36(18):2627-2638 (1993).

Kim et al., 1,3-dioxolanylpurine nucleosides (2R,4R) and (2R,4S) with selective anti-HIV-1 activity in human lymphocytes. J Med Chem. 36(1):30-37 (1993).

Laitala et al.: Homogeneous assay based on anti-Stokes' shift time-resolved fluorescence resonance energy-transfer measurement. Anal Chem. 77(5):1483-1487 doi:10.1021/ac048414o (2005).

Lakowicz: Principles of Fluorescence Spectroscopy: Chapter 13: Energy Transfer. Springer New York, NY, pp. 443-475 doi:10.1007/978-0-387-46312-4 (2006).

Martinez et al., Acyclic nucleoside triphosphate analogs as terminators in biocatalytic DNA replication. Bioorganic & Medicinal Chemistry Letters 7(23): 3013-3016 (1997).

Martinez et al., An allylic/acyclic adenosine nucleoside triphosphate for termination of DNA synthesis by DNA template-dependent polymerases. Nucleic Acids Res 27(5):1271-1274 (1999).

PCT/US2021/057441 International Search Report and Written Opinion dated Mar. 17, 2022.

PCT/US2021/057441 Invitation to Pay Additional Fees dated Jan. 18, 2022.

Anderson et al., Fluorescent Structural DNA Nanoballs Functionalized with Phosphate-Linked Nucleotide Triphosphates. Nano Letters 10(3): 788-792 (2010).

* cited by examiner

Wild type DNA polymerase from Candidatus altiarchaeales archaeon (SEQ ID NO:1)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFDMEVYNPRGEPKAERDPIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSLYPSI
IISHNIDPSTIDCECCPEDSYRSPTGHYFCKKKRGLIPETLNELVQRRIEVKKGLKNEKN
PERRRFLDVKQQALKLLANSMYGYFGFPRARWYCRECAESITALGRKYILHTIDIVPKFG
FDVIYGDTDSVYLIKPNITDRERVMKNAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 3

Mutant DNA polymerase from Candidatus altiarchaeales archaeon (SEQ ID NO:2)

MMKKTLLDADYITREEKAVVRLFYKTEEGREIQEVADFRPYMYVLPEEHDLKKLQREIKELKNI
TNVEIKRMIEGDREVEVLKVMVNQPRDVPNLRGLIKELEGCKEVREAHIPFAERYLIDSGLIPM
QDCENFDLRIAAFAMAVYNPRGEPKAERDPIIISYADNRGLRRVWTYKTVENLNLDYMEVLKD
EREIIRRFIDTIREREIDIIVTYNGDNFDFPYLKERAEKHRIPVSLGVDGSPLRLERRGMNLGA
RVTGRPHIDMYPVCRQIFNLSRYTLEDVYLEITGREKKDIRVGEMAGIWDNPEKEKFKELIEYA
MSDAESTLEIAITLLPLHYEISRITRELIYQSSRAGSGQRVESLLIKKAFEKSILVPNRPSDRV
VNERQRKTYIGAYVVEPKRGIHDNILLFDFRSSAGSIIISHNIDPSTIDCECCPEDSYRSPTGH
YFCKKKRGLIPETLNELVQRRIEVKKGLKNEKNPERRRFLDVKQQSLKLLANSMYGYFGFPRAR
WYCLECAESITALGRKYHLHTIDIVPKFGFDVIYGDTDSVYLIKPNITDRERVMKNAEHFLDKI
NSELPEAMELEFEGFYPRGIFITKKRYALIDERGKLIVKGLETKRRDWANIAKDTQEKVLDALL
KDKNPEKAASIVKDVIRNIKTGKIPLKDLAINTQITRGMAEYKTEGPHIVAAKKAMKRGLEFKQ
GNIVTYVVTKKGKSISDKARVIDFVEEGDYDPDYYINNQVLPSVLRILEALGYSEDELKGLGKQ
MKLGGF

FIG. 4

Mutant DNA polymerase from Candidatus altiarchaeales archaeon (SEQ ID NO:3)

MMKKTLLDADYITREEKAVVRLFYKTEEGREIQEVADFRPYMYVLPEEHDLKKLQREIKELKNI
TNVEIKRMIEGDREVEVLKVMVNQPRDVPNLRGLIKELEGCKEVREAHIPFAERYLIDSGLIPM
QDCENFDLRIAAFAMAVYNPRGEPKAERDPIIISYADNRGLRRVWTYKTVENLNLDYMEVLKD
EREIIRRFIDTIREREIDIIVTYNGDNFDFPYLKERAEKHRIPVSLGVDGSPLRLERRGMNLGA
RVTGRPHIDMYPVCRQIFNLSRYTLEDVYLEITGREKKDIRVGEMAGIWDNPEKEKFKELIEYA
MSDAESTLEIAITLLPLHYEISRITRELIYQSSRAGSGQRVESLLIKKAFEKSILVPNRPSDRV
VNERQRKTYIGAYVVEPKRGIHDNILLFDFRSSAGSIIISHNIDPSTIDCECCPEDSYRSPTGH
YFCKKKRGLIPETLNELVQRRIEVKKGLKNEKNPERRRFLDVKQQSLKLLANSMYGYFGFPRAR
WYCLECAESITALGRKYHLHTIDIVPKFGFDVIYGDTDSVYLIKPNITDRERVMKDAEHFLDKI
NSELPEAMELEFEGFYPRGIFITKKRYALIDERGKLIVKGLETKRRDWANIAKDTQEKVLDALL
KDKNPEKAASIVKDVIRNIKTGKIPLKDLAINTQITRGMAEYKTEGPHIVAAKKAMKRGLEFKQ
GNIVTYVVTKKGKSISDKARVIDFVEEGDYDPDYYINNQVLPSVLRILEALGYSEDELKGLGKQ
MKLGGF

FIG. 5

Mutant DNA polymerase from Candidatus altiarchaeales archaeon (SEQ ID NO:4)

MMKKTLLDADYITREEKAVVRLFYKTEEGREIQEVADFRPYMYVLPEEHDLKKLQREIKELKNI
TNVEIKRMIEGDREVEVLKVMVNQPRDVPNLRGLIKELEGCKEVREAHIPFAERYLIDSGLIPM
QDCENFDLRIAAFAMAVYNPRGEPKAERDPIIISYADNRGLRRVWTYKTVENLNLDYMEVLKD
EREIIRRFIDTIREREIDIIVTYNGDNFDFPYLKERAEKHRIPVSLGVDGSPLRLERRGMNLGA
RVTGRPHIDMYPVCRQIFNLSRYTLEDVYLEITGREKKDIRVGEMAGIWDNPEKEKFKELIEYA
MSDAESTLEIAITLLPLHYEISRITRELIYQSSRAGSGQRVESLLIKKAFEKSILVPNRPSDRV
VNERQRKTYIGAYVVEPKRGIHDNILLFDFRSFAGSIIISHNIDPSTIDCECCPEDSYRSPTGH
YFCKKKRGLIPETLNELVQRRIEVKKGLKNEKNPERRRFLDVKQQSLKLLANSMYGYFGFPRAR
WYCLECAESITALGRKYHLHTIDIVPKFGFDVIYGDTDSVYLIKPNITDRERVMKDAEHFLDKI
NSELPEAMELEFEGFYPRGIFITKKRYALIDERGKLIVKGLETKRRDWANIAKDTQEKVLDALL
KDKNPEKAASIVKDVIRNIKTGKIPLKDLAINTQITRGMAEYKTEGPHIVAAKKAMKRGLEFKQ
GNIVTYVVTKKGKSISDKARVIDFVEEGDYDPDYYINNQVLPSVLRILEALGYSEDELKGLGKQ
MKLGGF

FIG. 6

Mutant DNA polymerase from Candidatus altiarchaeales archaeon (SEQ ID NO:5)

```
MMKKTLLDADYITREEKAVVRLFYKTEEGREIQEVADFRPYMYVLPEEHDLKKLQREIKELKNI
TNVEIKRMIEGDREVEVLKVMVNQPRDVPNLRGLIKELEGCKEVREAHIPFAERYLIDSGLIPM
QDCENFDLRIAAFAMAVYNPRGEPKAERDPIIISYADNRGLRRVWTYKTVENLNLDYMEVLKD
EREIIRRFIDTIREREIDIIVTYNGDNFDFPYLKERAEKHRIPVSLGVDGSPLRLERRGMNLGA
RVTGRPHIDMYPVCRQIFNLSRYTLEDVYLEITGREKKDIRVGEMAGIWDNPEKEKFKELIEYA
MSDAESTLEIAITLLPLHYEISRITRELIYQSSRAGSGQRVESLLIKKAFEKSILVPNRPSDRV
VNERQRKTYIGAYVVEPKRGIHDNILLFDFRSYAGSIIISHNIDPSTIDCECCPEDSYRSPTGH
YFCKKKRGLIPETLNELVQRRIEVKKGLKNEKNPERRRFLDVKQQSLKLLANSMYGYFGFPRAR
WYCLECAESITALGRKYHLHTIDIVPKFGDVIYGDTDSVYLIKPNITDRERVMKDAEHFLDKI
NSELPEAMELEFEGFYPRGIFITKKRYALIDERGKLIVKGLETKRRDWANIAKDTQEKVLDALL
KDKNPEKAASIVKDVIRNIKTGKIPLKDLAINTQITRGMAEYKTEGPHIVAAKKAMKRGLEFKQ
GNIVTYVVTKKGKSISDKARVIDFVEEGDYDPDYYINNQVLPSVLRILEALGYSEDELKGLGKQ
MKLGGF
```

FIG. 7

9°N polymerase (SEQ ID NO:6)

MILDTDYITENGKPVIRVFKKENGEFKIEYDRTFEPYFYALLKDDSAIEDVKKVTAKRHG
TVVKVKRAEKVQKKFLGRPIEVWKLYFNHPDVPAIRDRIRAHPAVVDIYEYDIPFAKRY
LIDKGLIPAEGDEELTMLAFDIETLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRAIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK

FIG. 8

9°N polymerase UniProtKB - Q56366 (DPOL_THES9) (SEQ ID NO:7)

MILDTDYITENGKPVIRVFKKENGEFKIEYDRTFEPYFYALLKDDSAIEDVKKVTAKRHG
TVVKVKRAEKVQKKFLGRPIEVWKLYFNHPDVPAIRDRIRAHPAVVDIYEYDIPFAKRY
LIDKGLIPMEGDEELTMLAFDIETLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRAIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK

FIG. 9

Therminator polymerase (SEQ ID NO:8)

```
MILDTDYITENGKPVIRVFKKENGEFKIEYDRTFEPYFYALLKDDSAIEDVKKVTAKRHG
TVVKVKRAEKVQKKFLGRPIEVWKLYFNHPQDVPAIRDRIRAHPAVVDIYEYDIPFAKRY
LIDKGLIPAEGDEELTMLAFAIATLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRLIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK
```

FIG. 10

Vent polymerase UniProtKB - P30317 (DPOL_THELI) (SEQ ID NO:9)

MILDTDYITKDGKPIIRIFKKENGEFKIELDPHFQPYIYALLKDDSAIEEIKAIKGERHG
KTVRVLDAVKVRKKFLGREVEVWKLIFEHPQDVPAMRGKIREHPAVVDIYEYDIPFAKRY
LIDKGLIPMEGDEELKLLAFDIETFYHEGDEFGKGEIIMISYADEEEARVITWKNIDLPY
VDVVSNEREMIKRFVQVVKEKDPDVIITYNGDNFDLPYLIKRAEKLGVRLVLGRDKEHPE
PKIQRMGDSFAVEIKGRIHFDLFPVVRRTINLPTYTLEAVYEAVLGKTKSKLGAEEIAAI
WETEESMKKLAQYSMEDARATYELGKEFFPMEAELAKLIGQSVWDVSRSSTGNLVEWYLL
RVAYARNELAPNKPDEEEYKRRLRTTYLGGYVKEPEKGLWENIIYLDFRSLYPSIIVTHN
VSPDTLEKEGCKNYDVAPIVGYRFCKDFPGFIPSILGDLIAMRQDIKKKMKSTIDPIEKK
MLDYRQRAIKLLANSILPNEWLPIIENGEIKFVKIGEFINSYMEKQKENVKTVENTEVLE
VNNLFAFSFNKKIKESEVKKVKALIRHKYKGKAYEIQLSSGRKINITAGHSLFTVRNGEI
KEVSGDGIKEGDLIVAPKKIKLNEKGVSINIPELISDLSEEETADIVMTISAKGRKNFFK
GMLRTLRWMFGEENRRIRTFNRYLFHLEKLGLIKLLPRGYEVTDWERLKKYQLYEKLAG
SVKYNGNKREYLVMFNEIKDFISYFPQKELEEWKIGTLNGFRTNCILKVDEDFGKLLGYY
VSEGYAGAQKNKTGGISYSVKLYNEDPNVLESMKNVAEKFFGKVRVDRNCVSISKKMAYL
VMKCLCGALAENKRIPSVILTSPEPVRWSFLEAYFTGDGDIHPSKRFRLSTKSELLANQL
VFLLNSLGISSVKIGFDSGVYRVYINEDLQFPQTSREKNTYYSNLIPKEILRDVFGKEFQ
KNMTFKKFKELVDSGKLNREKAKLLEFFINGDIVLDRVKSVKEKDYEGYVYDLSVEDNEN
FLVGFGLLYAHNSYYGYMGYPKARWYSKECAESVTAWGRHYIEMTIREIEEKFGFKVLYA
DSVSGESEIIIRQNGKIRFVKIKDLFSKVDYSIGEKEYCILEGVEALTLDDDGKLVWKPV
PYVMRHRANKRMFRIWLTNSWYIDVTEDHSLIGYLNTSKTKTAKKIGERLKEVKPFELGK
AVKSLICPNAPLKDENTKTSEIAVKFWELVGLIVGDGNWGGDSRWAEYYLGLSTGKDAEE
IKQKLLEPLKTYGVISNYYPKNEKGDFNILAKSLVKFMKRHFKDEKGRRKIPEFMYELPV
TYIEAFLRGLFSADGTVTIRKGVPEIRLTNIDADFLREVRKLLWIVGISNSIFAETTPNR
YNGVSTGTYSKHLRIKNKWRFAERIGFLIERKQKRLLEHLKSARVKRNTIDFGFDLVHVK
KVEEIPYEGYVYDIEVEETHRFFANNILVHNTDGFYATIPGEKPELIKKKAKEFLNYINS
KLPGLLELEYEGFYLRGFFVTKKRYAVIDEEGRITTRGLEVVRRDWSEIAKETQAKVLEA
ILKEGSVEKAVEVVRDVVEKIAKYRVPLEKLVIHEQITRDLKDYKAIGPHVAIAKRLAAR
GIKVKPGTIISYIVLKGSGKISDRVILLTEYDPRKHKYDPDYYIENQVLPAVLRILEAFG
YRKEDLRYQSSKQTGLDAWLKR

FIG. 11

Deep Vent polymerase UniProtKB - Q51334 (DPOL_PYRSD) (SEQ ID NO:10)

MILDADYITEDGKPIIRIFKKENGEFKVEYDRNFRPYIYALLKDDSQIDEVRKITAERHG
KIVRIIDAEKVRKKFLGRPIEVWRLYFEHPQDVPAIRDKIREHSAVIDIFEYDIPFAKRY
LIDKGLIPMEGDEELKLLAFDIETLYHEGEEFAKGPIIMISYADEEEAKVITWKKIDLPY
VEVVSSEREMIKRFLKVIREKDPDVIITYNGDSFDLPYLVKRAEKLGIKLPLGRDGSEPK
MQRLGDMTAVEIKGRIHFDLYHVIRRTINLPTYTLEAVYEAIFGKPKEKVYAHEIAEAWE
TGKGLERVAKYSMEDAKVTYELGREFFPMEAQLSRLVGQPLWDVSRSSTGNLVEWYLLRK
AYERNELAPNKPDEREYERRLRESYAGGYVKEPEKGLWEGLVSLDFRSLYPSIIITHNVS
PDTLNREGCREYDVAPEVGHKFCKDFPGFIPSLLKRLLDERQEIKRKMKASKDPIEKKML
DYRQRAIKILANSILPEEWVPLIKNGKVKIFRIGDFVDGLMKANQGKVKKTGDTEVLEVA
GIHAFSFDRKSKKARVMAVKAVIRHRYSGNVYRIVLNSGRKITITEGHSLFVYRNGDLVE
ATGEDVKIGDLLAVPRSVNLPEKRERLNIVELLLNLSPEETEDIILTIPVKGRKNFFKGM
LRTLRWIFGEEKRVRTASRYLRHLENLGYIRLRKIGYDIIDKEGLEKYRTLYEKLVDVVR
YNGNKREYLVEFNAVRDVISLMPEEELKEWRIGTRNGFRMGTFVDIDEDFAKLLGYYVSE
GSARKWKNQTGGWSYTVRLYNENDEVLDDMEHLAKKFFGKVKRGKNYVEIPKKMAYIIFE
SLCGTLAENKRVPEVIFTSSKGVRWAFLEGYFIGDGDVHPSKRVRLSTKSELLVNGLVLL
LNSLGVSAIKLGYDSGVYRVYVNEELKFTEYRKKKNVYHSHIVPKDILKETFGKVFQKNI
SYKKFRELVENGKLDREKAKRIEWLLNGDIVLDRVVEIKREYYDGYVYDLSVDEDENFLA
GFGFLYAHNSYYGYYGYAKARWYCKECAESVTAWGREYIEFVRKELEEKFGFKVLYIDTD
GLYATIPGAKPEEIKKKALEFVDYINAKLPGLLELEYEGFYVRGFFVTKKKYALIDEEGK
IITRGLEIVRRDWSEIAKETQAKVLEAILKHGNVEEAVKIVKEVTEKLSKYEIPPEKLVI
YEQITRPLHEYKAIGPHVAVAKRLAARGVKVRPGMVIGYIVLRGDGPISKRAILAEEFDL
RKHKYDAEYYIENQVLPAVLRILEAFGYRKEDLRWQKTKQTGLTAWLNIKKK

FIG. 12

Pfu polymerase UniProtKB - P61875 (DPOL_PYRFU) (SEQ ID NO:11)

MILDVDYITEEGKPVIRLFKKENGKFKIEHDRTFRPYIYALLRDDSKIEEVKKITGERHG
KIVRIVDVEKVEKKFLGKPITVWKLYLEHPQDVPTIREKVREHPAVVDIFEYDIPFAKRY
LIDKGLIPMEGEEELKILAFDIETLYHEGEEFGKGPIIMISYADENEAKVITWKNIDLPY
VEVVSSEREMIKRFLRIIREKDPDIIVTYNGDSFDFPYLAKRAEKLGIKLTIGRDGSEPK
MQRIGDMTAVEVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTGNLVEWFLLRK
AYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILL
DYRQKAIKLLANSFYGYYGYAKARWYCKECAESVTAWGRKYIELVWKELEEKFGFKVLYI
DTDGLYATIPGGESEEIKKKALEFVKYINSKLPGLLELEYEGFYKRGFFVTKKRYAVIDE
EGKVITRGLEIVRRDWSEIAKETQARVLETILKHGDVEEAVRIVKEVIQKLANYEIPPEK
LAIYEQITRPLHEYKAIGPHVAVAKKLAAKGVKIKPGMVIGYIVLRGDGPISNRAILAEE
YDPKKHKYDAEYYIENQVLPAVLRILEGFGYRKEDLRYQKTRQVGLTSWLNIKKS

FIG. 13

Pyrococcus abyssi polymerase UniProtKB - P0CL77 (DPOL_PYRAB) (SEQ ID NO:12)

MIIDADYITEDGKPIIRIFKKEKGEFKVEYDRTFRPYIYALLKDDSAIDEVKKITAERHG
KIVRITEVEKVQKKFLGRPIEVWKLYLEHPQDVPAIREKIREHPAVVDIFEYDIPFAKRY
LIDKGLTPMEGNEELTFLAVDIETLYHEGEEFGKGPIIMISYADEEGAKVITWKSIDLPY
VEVVSSEREMIKRLVKVIREKDPDVIITYNGDNFDFPYLLKRAEKLGIKLPLGRDNSEPK
MQRMGDSLAVEIKGRIHFDLFPVIRRTINLPTYTLEAVYEAIFGKSKEKVYAHEIAEAWE
TGKGLERVAKYSMEDAKVTFELGKEFFPMEAQLARLVGQPVWDVSRSSTGNLVEWFLLRK
AYERNELAPNKPDEREYERRLRESYEGGYVKEPEKGLWEGIVSLDFRSLYPSIIITHNVS
PDTLNRENCKEYDVAPQVGHRFCKDFPGFIPSLLGNLLEERQKIKKRMKESKDPVEKKLL
DYRQRAIKILANSYYGYYGYAKARWYCKECAESVTAWGRQYIDLVRRELESRGFKVLYID
TDGLYATIPGAKHEEIKEKALKFVEYINSKLPGLLELEYEGFYARGFFVTKKKYALIDEE
GKIVTRGLEIVRRDWSEIAKETQAKVLEAILKHGNVDEAVKIVKEVTEKLSKYEIPPEKL
VIYEQITRPLSEYKAIGPHVAVAKRLAAKGVKVKPGMVIGYIVLRGDGPISKRAIAIEEF
DPKKHKYDAEYYIENQVLPAVERILRAFGYRKEDLKYQKTKQVGLGAWLKF

FIG. 14

RB69 polymerase UniProtKB - Q38087 (DPOL_BPR69) (SEQ ID NO:13

MKEFYLTVEQIGDSIFERYIDSNGRERTREVEYKPSLFAHCPESQATKYFDIYGKPCTRK
LFANMRDASQWIKRMEDIGLEALGMDDFKLAYLSDTYNYEIKYDHTKIRVANFDIEVTSP
DGFPEPSQAKHPIDAITHYDSIDDRFYVFDLLNSPYGNVEEWSIEIAAKLQEQGGDEVPS
EIIDKIIYMPFDNEKELLMEYLNFWQQKTPVILTGWNVESFDIPYVYNRIKNIFGESTAK
RLSPHRKTRVKVIENMYGSREIITLFGISVLDYIDLYKKFSFTNQPSYSLDYISEFELNV
GKLKYDGPISKLRESNHQRYISYNIIDVYRVLQIDAKRQFINLSLDMGYYAKIQIQSVFS
PIKTWDAIIFNSLKEQNKVIPQGRSHPVQPYPGAFVKEPIPNRYKYVMSFDLTSLYPSII
RQVNISPETIAGTFKVAPLHDYINAVAERPSDVYSCSPNGMMYYKDRDGVVPTEITKVFN
QRKEHKGYMLAAQRNGEIIKEALHNPNLSVDEPLDVDYRFDFSDEIKEKIKKLSAKSLNE
MLFRAQRTEVAGMTAQINRKLLINSLYGALGNVWFRYYDLRNATAITTFGQMALQWIERK
VNEYLNEVCGTEGEAFVLYGDTDSIYVSADKIIDKVGESKFRDTNHWVDFLDKFARERME
PAIDRGFREMCEYMNNKQHLMFMDREAIAGPPLGSKGIGGFWTGKKRYALNVWDMEGTRY
AEPKLKIMGLETQKSSTPKAVQKALKECIRRMLQEGEESLQEYFKEFEKEFRQLNYISIA
SVSSANNIAKYDVGGFPGPKCPFHIRGILTYNRAIKGNIDAPQVVEGEKVYVLPLREGNP
FGDKCIAWPSGTEITDLIKDDVLHWMDYTVLLEKTFIKPLEGFTSAAKLDYEKKASLFDM
FDF

FIG. 15

Spacer:
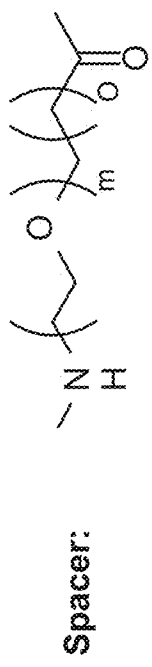
Linkers:
11 atom Linker:
16 atom Linker:
23 atom Linker:
N3 Linker:
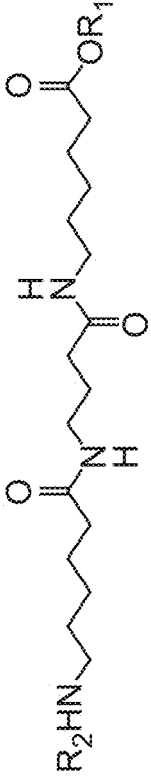
FIG. 25

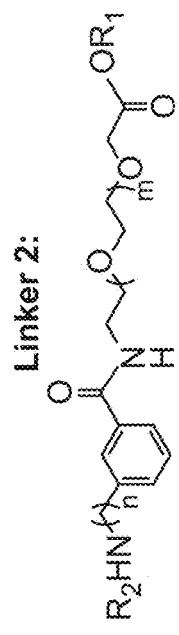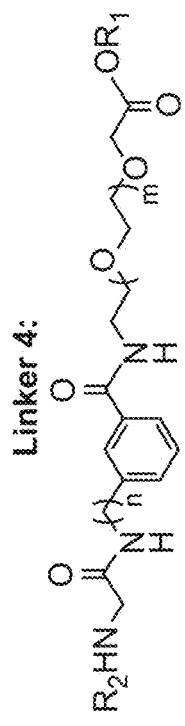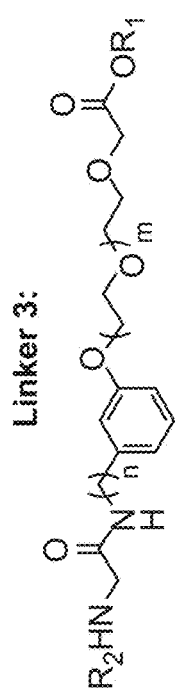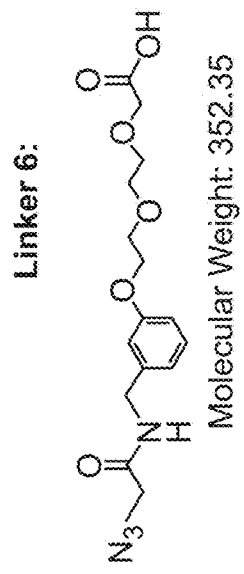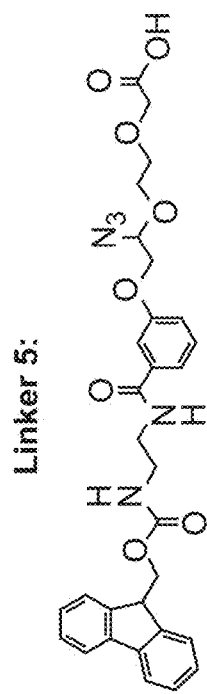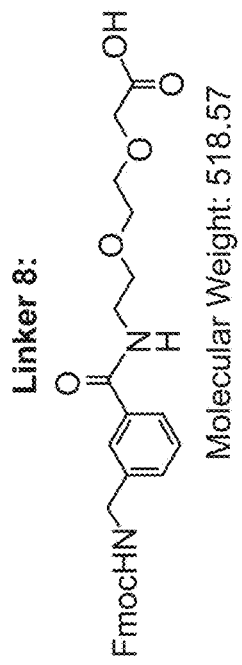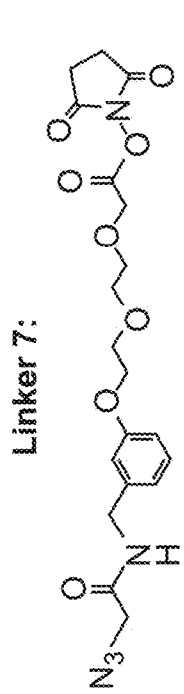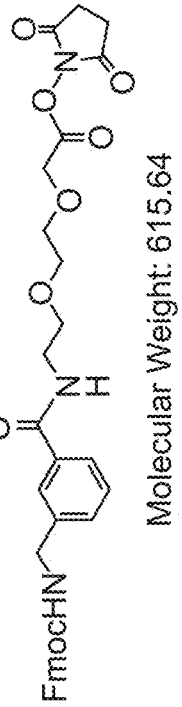
FIG. 26 dNTP-PA-NH₂:
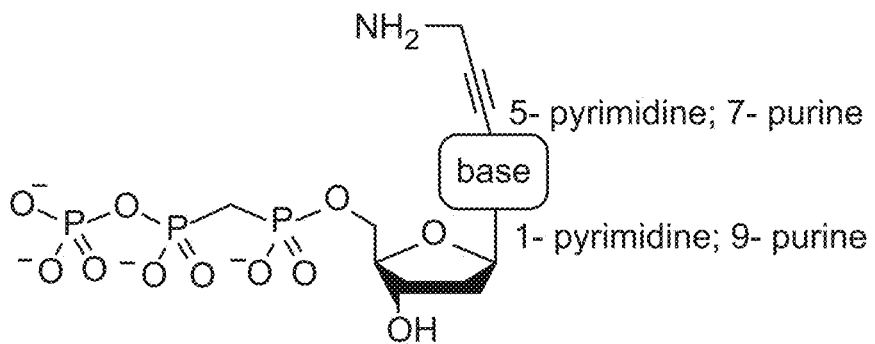
dNTP-PA-11 Atom Linker-NH₂:
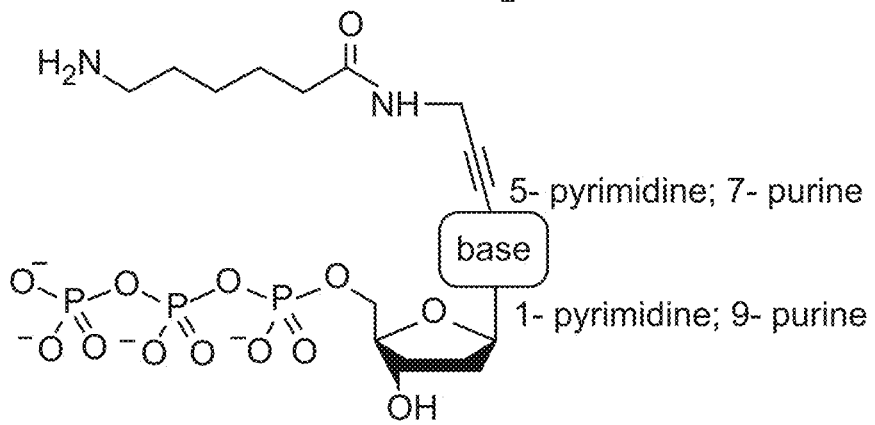
dNTP-PA-16 Atom Linker-NH₂:
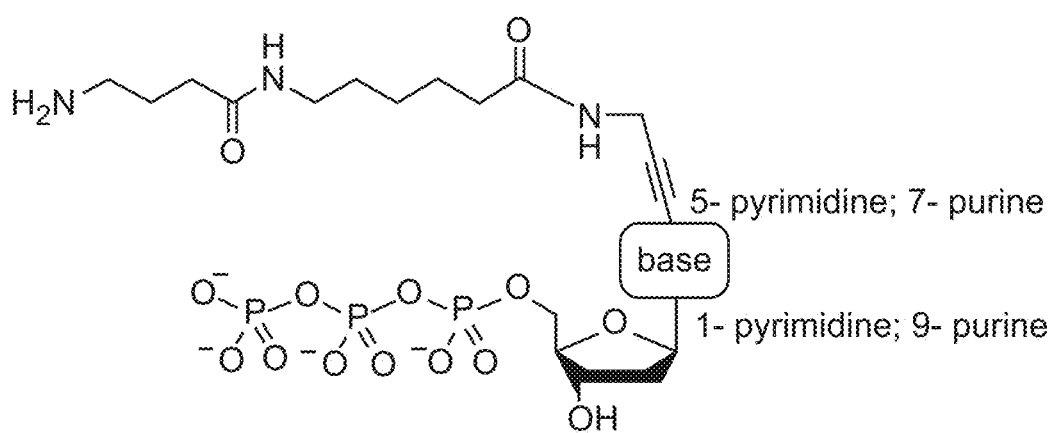
FIG. 27

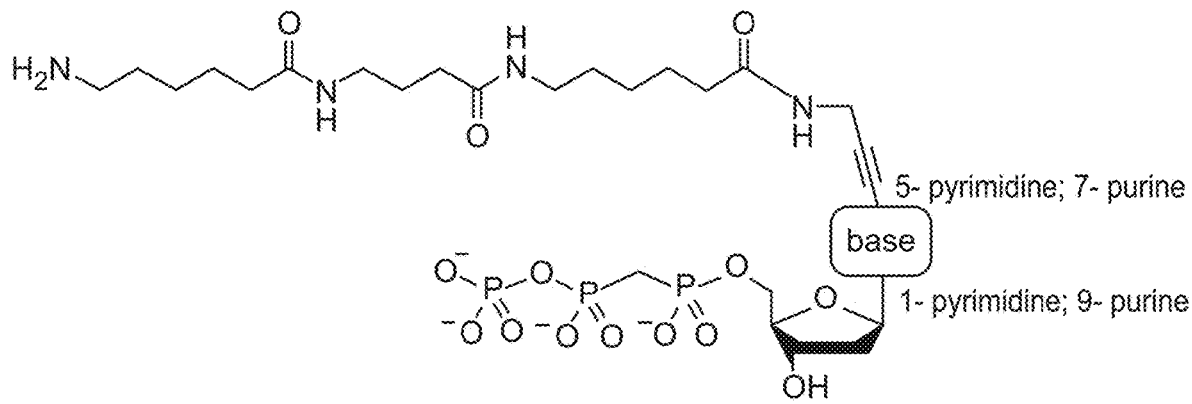
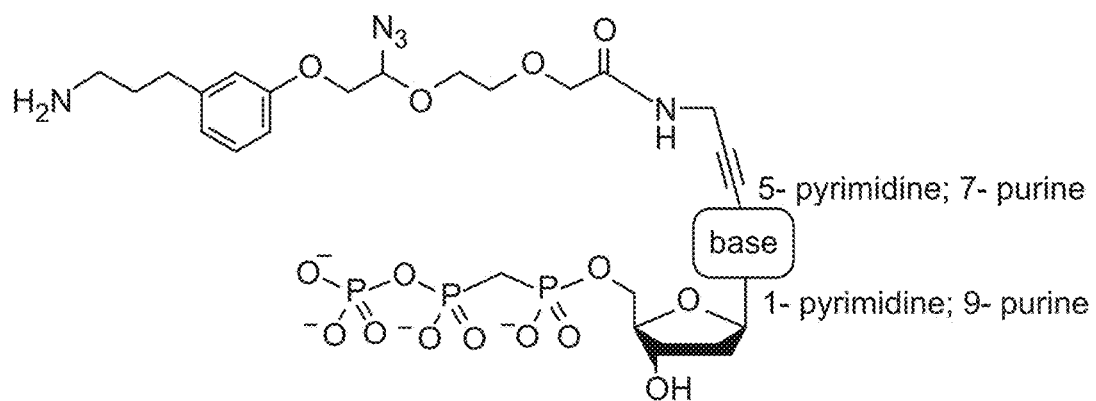
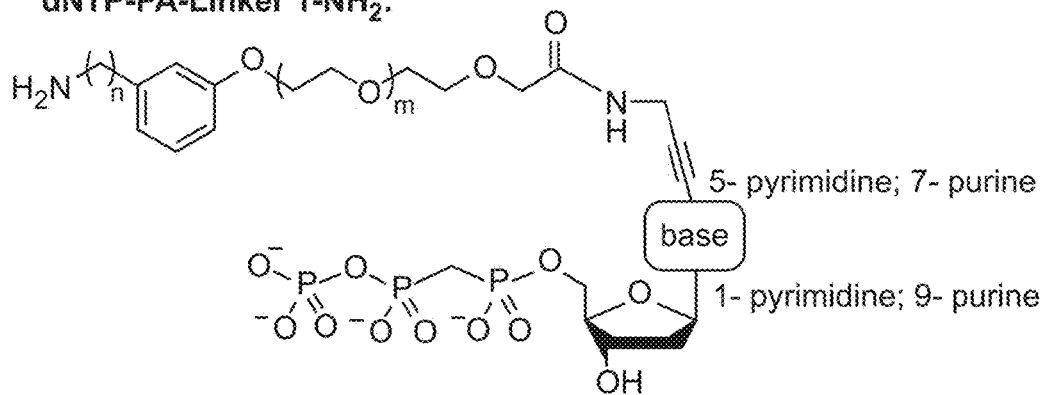
FIG. 28

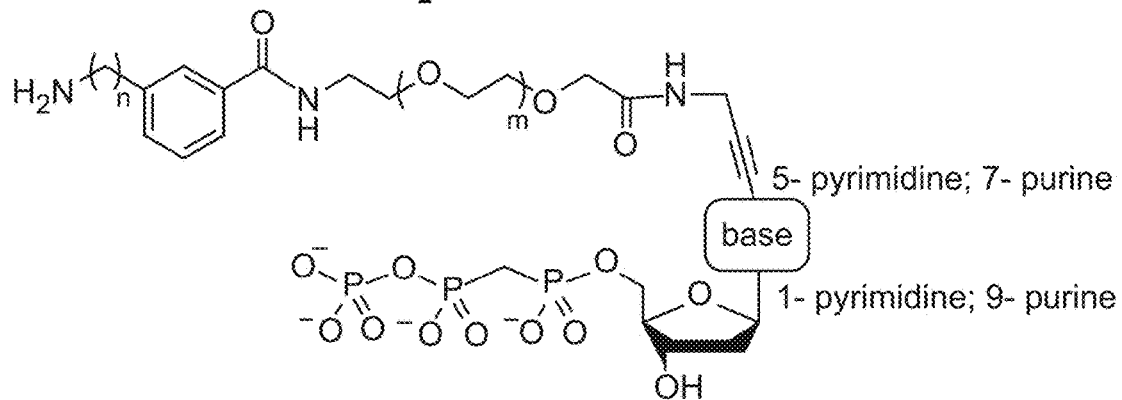
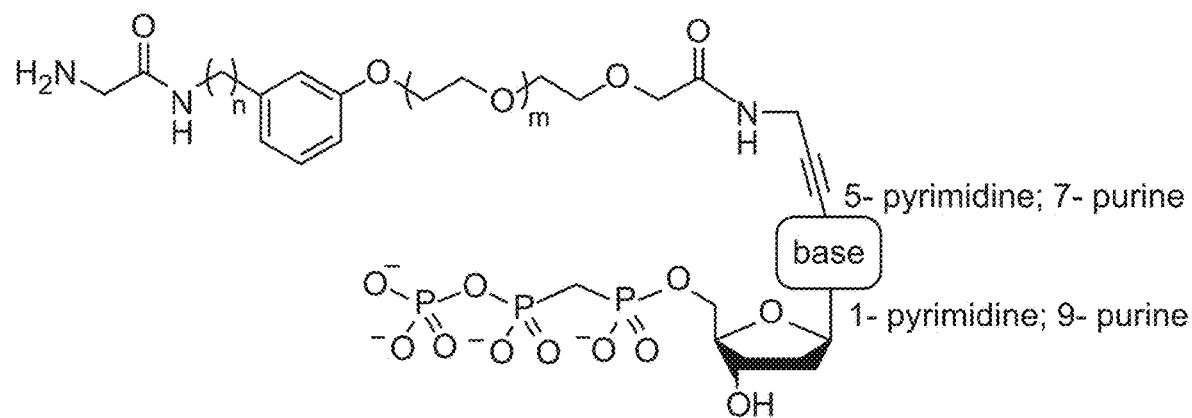
FIG. 29 dNTP-PA-Linker 4-NH₂:
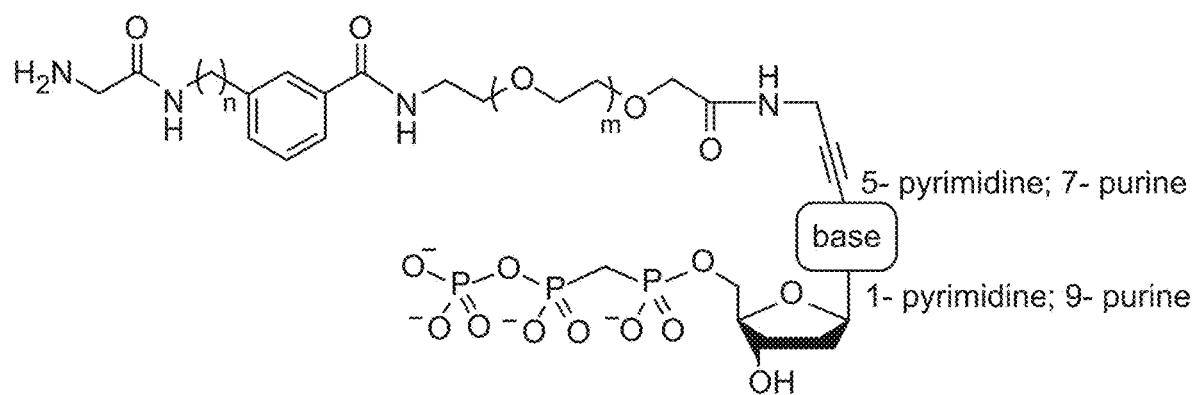
dNTP-PA-N3 Linker-NH₂:
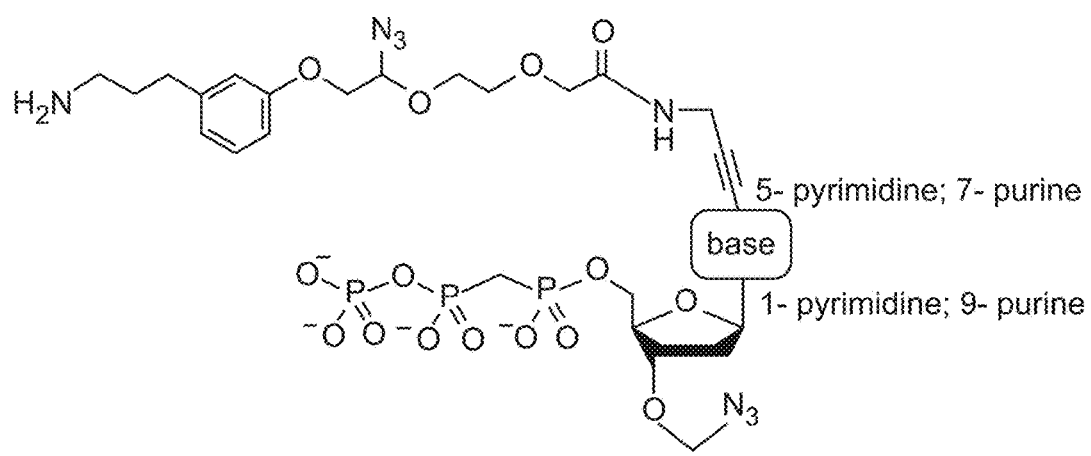
FIG. 30

Wild type DNA polymerase from Candidatus altiarchaeales archaeon (SEQ ID NO:221)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFDMEVYNPRGEPKAERDPIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSLYPSI
IISHNIDPSTIDCECCPEDSYRSPTGHYFCKKKRGLIPETLNELVQRRIEVKKGLKNEKN
PERRRFLDVKQQALKLLANSMYGYFGFPRARWYCRECAESITALGRKYILHTIDIVPKFG
FDVIYGDTDSVYLIKPNITDRERVMKNAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 44

Mutant DNA polymerase from Candidatus altiarchaeales archaeon (SEQ ID NO:222)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFAMAVYNPRGEPKAERDPIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSSAGSI
IISHNIDPSTIDCECCPEDSYRSPTGHYFCKKKRGLIPETLNELVQRRIEVKKGLKNEKN
PERRRFLDVKQQSLKLLANSMYGYFGFPRARWYCLECAESITALGRKYHLHTIDIVPKFG
FDVIYGDTDSVYLIKPNITDRERVMKNAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 45

Mutant DNA polymerase from Candidatus altiarchaeales archaeon (SEQ ID NO:223)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFAMAVYNPRGEPKAERDPIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSSAGSI
IISHNIDPSTIDCECCPEDSYRSPTGHYFCKKKRGLIPETLNELVQRRIEVKKGLKNEKN
PERRRFLDVKQQSLKLLANSMYGYFGFPRARWYCLECAESITALGRKYHLHTIDIVPKFG
FDVIYGDTDSVYLIKPNITDRERVMKDAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 46

Mutant DNA polymerase from Candidatus altiarchaeales archaeon (SEQ ID NO:224)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFAMAVYNPRGEPKAERDPIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSFAGSI
IISHNIDPSTIDCECCPEDSYRSPTGHYFCKKKRGLIPETLNELVQRRIEVKKGLKNEKN
PERRRFLDVKQQSLKLLANSMYGYFGFPRARWYCLECAESITALGRKYHLHTIDIVPKFG
FDVIYGDTDSVYLIKPNITDRERVMKDAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 47

Mutant DNA polymerase from Candidatus altiarchaeales archaeon (SEQ ID NO:225)

MKKTLLDADYITREEKAVVRLFYKTEEGREIQEVADFRPYMYVLPEEHDLKKLQREIKEL
KNITNVEIKRMIEGDREVEVLKVMVNQPRDVPNLRGLIKELEGCKEVREAHIPFAERYLI
DSGLIPMQDCENFDLRIAAFAMAVYNPRGEPKAERDPIIIISYADNRGLRRVWTYKTVEN
LNLDYMEVLKDEREIIRRFIDTIREREIDIIVTYNGDNFDFPYLKERAEKHRIPVSLGVD
GSPLRLERRGMNLGARVTGRPHIDMYPVCRQIFNLSRYTLEDVYLEITGREKKDIRVGEM
AGIWDNPEKEKFKELIEYAMSDAESTLEIAITLLPLHYEISRITRELIYQSSRAGSGQRV
ESLLIKKAFEKSILVPNRPSDRVVNERQRKTYIGAYVVEPKRGIHDNILLFDFRSYAGSI
IISHNIDPSTIDCECCPEDSYRSPTGHYFCKKKRGLIPETLNELVQRRIEVKKGLKNEKN
PERRRFLDVKQQSLKLLANSMYGYFGFPRARWYCLECAESITALGRKYHLHTIDIVPKFG
FDVIYGDTDSVYLIKPNITDRERVMKDAEHFLDKINSELPEAMELEFEGFYPRGIFITKK
RYALIDERGKLIVKGLETKRRDWANIAKDTQEKVLDALLKDKNPEKAASIVKDVIRNIKT
GKIPLKDLAINTQITRGMAEYKTEGPHIVAAKKAMKRGLEFKQGNIVTYVVTKKGKSISD
KARVIDFVEEGDYDPDYYINNQVLPSVLRILEALGYSEDELKGLGKQMKLGGF

FIG. 48

9°N polymerase (SEQ ID NO:226)

MILDTDYITENGKPVIRVFKKENGEFKIEYDRTFEPYFYALLKDDSAIEDVKKVTAKRHG
TVVKVKRAEKVQKKFLGRPIEVWKLYFNHPQDVPAIRDRIRAHPAVVDIYEYDIPFAKRY
LIDKGLIPAEGDEELTMLAFDIETLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRAIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK

FIG. 49

9°N polymerase UniProtKB - Q56366 (DPOL_THES9) (SEQ ID NO:227)

MILDTDYITENGKPVIRVFKKENGEFKIEYDRTFEPYFYALLKDDSAIEDVKKVTAKRHG
TVVKVKRAEKVQKKFLGRPIEVWKLYFNHPQDVPAIRDRIRAHPAVVDIYEYDIPFAKRY
LIDKGLIPMEGDEELTMLAFDIETLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRAIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK

FIG. 50

Therminator polymerase (SEQ ID NO:228)

MILDTDYITENGKPVIRVFKKENGEFKIEYDRTFEPYFYALLKDDSAIEDVKKVTAKRHG
TVVKVKRAEKVQKKFLGRPIEVWKLYFNHPQDVPAIRDRIRAHPAVVDIYEYDIPFAKRY
LIDKGLIPAEGDEELTMLAFAIATLYHEGEEFGTGPILMISYADGSEARVITWKKIDLPY
VDVVSTEKEMIKRFLRVVREKDPDVLITYNGDNFDFAYLKKRCEELGIKFTLGRDGSEPK
IQRMGDRFAVEVKGRIHFDLYPVIRRTINLPTYTLEAVYEAVFGKPKEKVYAEEIAQAWE
SGEGLERVARYSMEDAKVTYELGREFFPMEAQLSRLIGQSLWDVSRSSTGNLVEWFLLRK
AYKRNELAPNKPDERELARRRGGYAGGYVKEPERGLWDNIVYLDFRSLYPSIIITHNVSP
DTLNREGCKEYDVAPEVGHKFCKDFPGFIPSLLGDLLEERQKIKRKMKATVDPLEKKLLD
YRQRLIKILANSFYGYYGYAKARWYCKECAESVTAWGREYIEMVIRELEEKFGFKVLYAD
TDGLHATIPGADAETVKKKAKEFLKYINPKLPGLLELEYEGFYVRGFFVTKKKYAVIDEE
GKITTRGLEIVRRDWSEIAKETQARVLEAILKHGDVEEAVRIVKEVTEKLSKYEVPPEKL
VIHEQITRDLRDYKATGPHVAVAKRLAARGVKIRPGTVISYIVLKGSGRIGDRAIPADEF
DPTKHRYDAEYYIENQVLPAVERILKAFGYRKEDLRYQKTKQVGLGAWLKVKGKK

FIG. 51

Vent polymerase UniProtKB - P30317 (DPOL_THELI) (SEQ ID NO:229)

MILDTDYITKDGKPIIRIFKKENGEFKIELDPHFQPYIYALLKDDSAIEEIKAIKGERHG
KTVRVLDAVKVRKKFLGREVEVWKLIFEHPQDVPAMRGKIREHPAVVDIYEYDIPFAKRY
LIDKGLIPMEGDEELKLLAFDIETFYHEGDEFGKGEIIMISYADEEEARVITWKNIDLPY
VDVVSNEREMIKRFVQVVKEKDPDVIITYNGDNFDLPYLIKRAEKLGVRLVLGRDKEHPE
PKIQRMGDSFAVEIKGRIHFDLFPVVRRTINLPTYTLEAVYEAVLGKTKSKLGAEEIAAI
WETEESMKKLAQYSMEDARATYELGKEFFPMEAELAKLIGQSVWDVSRSSTGNLVEWYLL
RVAYARNELAPNKPDEEEYKRRLRTTYLGGYVKEPEKGLWENIIYLDFRSLYPSIIVTHN
VSPDTLEKEGCKNYDVAPIVGYRFCKDFPGFIPSILGDLIAMRQDIKKKMKSTIDPIEKK
MLDYRQRAIKLLANSILPNEWLPIIENGEIKFVKIGEFINSYMEKQKENVKTVENTEVLE
VNNLFAFSFNKKIKESEVKKVKALIRHKYKGKAYEIQLSSGRKINITAGHSLFTVRNGEI
KEVSGDGIKEGDLIVAPKKIKLNEKGVSINIPELISDLSEEETADIVMTISAKGRKNFFK
GMLRTLRWMFGEENRRIRTFNRYLFHLEKLGLIKLLPRGYEVTDWERLKKYKQLYEKLAG
SVKYNGNKREYLVMFNEIKDFISYFPQKELEEWKIGTLNGFRTNCILKVDEDFGKLLGYY
VSEGYAGAQKNKTGGISYSVKLYNEDPNVLESMKNVAEKFFGKVRVDRNCVSISKKMAYL
VMKCLCGALAENKRIPSVILTSPEPVRWSFLEAYFTGDGDIHPSKRFRLSTKSELLANQL
VFLLNSLGISSVKIGFDSGVYRVYINEDLQFPQTSREKNTYYSNLIPKEILRDVFGKEFQ
KNMTFKKFKELVDSGKLNREKAKLLEFFINGDIVLDRVKSVKEKDYEGYVYDLSVEDNEN
FLVGFGLLYAHNSYYGYMGYPKARWYSKECAESVTAWGRHYIEMTIREIEEKFGFKVLYA
DSVSGESEIIIRQNGKIRFVKIKDLFSKVDYSIGEKEYCILEGVEALTLDDDGKLVWKPV
PYVMRHRANKRMFRIWLTNSWYIDVTEDHSLIGYLNTSKTKTAKKIGERLKEVKPFELGK
AVKSLICPNAPLKDENTKTSEIAVKFWELVGLIVGDGNWGGDSRWAEYYLGLSTGKDAEE
IKQKLLEPLKTYGVISNYYPKNEKGDFNILAKSLVKFMKRHFKDEKGRRKIPEFMYELPV
TYIEAFLRGLFSADGTVTIRKGVPEIRLTNIDADFLREVRKLLWIVGISNSIFAETTPNR
YNGVSTGTYSKHLRIKNKWRFAERIGFLIERKQKRLLEHLKSARVKRNTIDFGFDLVHVK
KVEEIPYEGYVYDIEVEETHRFFANNILVHNTDGFYATIPGEKPELIKKKAKEFLNYINS
KLPGLLELEYEGFYLRGFFVTKKRYAVIDEEGRITTRGLEVVRRDWSEIAKETQAKVLEA
ILKEGSVEKAVEVVRDVVEKIAKYRVPLEKLVIHEQITRDLKDYKAIGPHVAIAKRLAAR
GIKVKPGTIISYIVLKGSGKISDRVILLTEYDPRKHKYDPDYYIENQVLPAVLRILEAFG
YRKEDLRYQSSKQTGLDAWLKR

FIG. 52

Deep Vent polymerase UniProtKB - Q51334 (DPOL_PYRSD) (SEQ ID NO:230)

MILDADYITEDGKPIIRIFKKENGEFKVEYDRNFRPYIYALLKDDSQIDEVRKITAERHG
KIVRIIDAEKVRKKFLGRPIEVWRLYFEHPQDVPAIRDKIREHSAVIDIFEYDIPFAKRY
LIDKGLIPMEGDEELKLLAFDIETLYHEGEEFAKGPIIMISYADEEEAKVITWKKIDLPY
VEVVSSEREMIKRFLKVIREKDPDVIITYNGDSFDLPYLVKRAEKLGIKLPLGRDGSEPK
MQRLGDMTAVEIKGRIHFDLYHVIRRTINLPTYTLEAVYEAIFGKPKEKVYAHEIAEAWE
TGKGLERVAKYSMEDAKVTYELGREFFPMEAQLSRLVGQPLWDVSRSSTGNLVEWYLLRK
AYERNELAPNKPDEREYERRLRESYAGGYVKEPEKGLWEGLVSLDFRSLYPSIIITHNVS
PDTLNREGCREYDVAPEVGHKFCKDFPGFIPSLLKRLLDERQEIKRKMKASKDPIEKKML
DYRQRAIKILANSILPEEWVPLIKNGKVKIFRIGDFVDGLMKANQGKVKKTGDTEVLEVA
GIHAFSFDRKSKKARVMAVKAVIRHRYSGNVYRIVLNSGRKITITEGHSLFVYRNGDLVE
ATGEDVKIGDLLAVPRSVNLPEKRERLNIVELLLNLSPEETEDIILTIPVKGRKNFFKGM
LRTLRWIFGEEKRVRTASRYLRHLENLGYIRLRKIGYDIIDKEGLEKYRTLYEKLVDVVR
YNGNKREYLVEFNAVRDVISLMPEEELKEWRIGTRNGFRMGTFVDIDEDFAKLLGYYVSE
GSARKWKNQTGGWSYTVRLYNENDEVLDDMEHLAKKFFGKVKRGKNYVEIPKKMAYIIFE
SLCGTLAENKRVPEVIFTSSKGVRWAFLEGYFIGDGDVHPSKRVRLSTKSELLVNGLVLL
LNSLGVSAIKLGYDSGVYRVYVNEELKFTEYRKKKNVYHSHIVPKDILKETFGKVFQKNI
SYKKFRELVENGKLDREKAKRIEWLLNGDIVLDRVVEIKREYYDGYVYDLSVDEDENFLA
GFGFLYAHNSYYGYYGYAKARWYCKECAESVTAWGREYIEFVRKELEEKFGFKVLYIDTD
GLYATIPGAKPEEIKKKALEFVDYINAKLPGLLELEYEGFYVRGFFVTKKKYALIDEEGK
IITRGLEIVRRDWSEIAKETQAKVLEAILKHGNVEEAVKIVKEVTEKLSKYEIPPEKLVI
YEQITRPLHEYKAIGPHVAVAKRLAARGVKVRPGMVIGYIVLRGDGPISKRAILAEEFDL
RKHKYDAEYYIENQVLPAVLRILEAFGYRKEDLRWQKTKQTGLTAWLNIKKK

FIG. 53

Pfu polymerase UniProtKB - P61875 (DPOL_PYRFU) (SEQ ID NO:231)

MILDVDYITEEGKPVIRLFKKENGKFKIEHDRTFRPYIYALLRDDSKIEEVKKITGERHG
KIVRIVDVEKVEKKFLGKPITVWKLYLEHPQDVPTIREKVREHPAVVDIFEYDIPFAKRY
LIDKGLIPMEGEEELKILAFDIETLYHEGEEFGKGPIIMISYADENEAKVITWKNIDLPY
VEVVSSEREMIKRFLRIIREKDPDIIVTYNGDSFDFPYLAKRAEKLGIKLTIGRDGSEPK
MQRIGDMTAVEVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTGNLVEWFLLRK
AYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILL
DYRQKAIKLLANSFYGYYGYAKARWYCKECAESVTAWGRKYIELVWKELEEKFGFKVLYI
DTDGLYATIPGGESEEIKKKALEFVKYINSKLPGLLELEYEGFYKRGFFVTKKRYAVIDE
EGKVITRGLEIVRRDWSEIAKETQARVLETILKHGDVEEAVRIVKEVIQKLANYEIPPEK
LAIYEQITRPLHEYKAIGPHVAVAKKLAAKGVKIKPGMVIGYIVLRGDGPISNRAILAEE
YDPKKHKYDAEYYIENQVLPAVLRILEGFGYRKEDLRYQKTRQVGLTSWLNIKKS

FIG. 54

Pyrococcus abyssi polymerase UniProtKB - P0CL77 (DPOL_PYRAB) (SEQ ID NO:232)

MIIDADYITEDGKPIIRIFKKEKGEFKVEYDRTFRPYIYALLKDDSAIDEVKKITAERHG
KIVRITEVEKVQKKFLGRPIEVWKLYLEHPQDVPAIREKIREHPAVVDIFEYDIPFAKRY
LIDKGLTPMEGNEELTFLAVDIETLYHEGEEFGKGPIIMISYADEEGAKVITWKSIDLPY
VEVVSSEREMIKRLVKVIREKDPDVIITYNGDNFDFPYLLKRAEKLGIKLPLGRDNSEPK
MQRMGDSLAVEIKGRIHFDLFPVIRRTINLPTYTLEAVYEAIFGKSKEKVYAHEIAEAWE
TGKGLERVAKYSMEDAKVTFELGKEFFPMEAQLARLVGQPVWDVSRSSTGNLVEWFLLRK
AYERNELAPNKPDEREYERRLRESYEGGYVKEPEKGLWEGIVSLDFRSLYPSIIITHNVS
PDTLNRENCKEYDVAPQVGHRFCKDFPGFIPSLLGNLLEERQKIKKRMKESKDPVEKKLL
DYRQRAIKILANSYYGYYGYAKARWYCKECAESVTAWGRQYIDLVRRELESRGFKVLYID
TDGLYATIPGAKHEEIKEKALKFVEYINSKLPGLLELEYEGFYARGFFVTKKKYALIDEE
GKIVTRGLEIVRRDWSEIAKETQAKVLEAILKHGNVDEAVKIVKEVTEKLSKYEIPPEKL
VIYEQITRPLSEYKAIGPHVAVAKRLAAKGVKVKPGMVIGYIVLRGDGPISKRAIAIEEF
DPKKHKYDAEYYIENQVLPAVERILRAFGYRKEDLKYQKTKQVGLGAWLKF

FIG. 55

RB69 polymerase UniProtKB - Q38087 (DPOL_BPR69) (SEQ ID NO:233)

MKEFYLTVEQIGDSIFERYIDSNGRERTREVEYKPSLFAHCPESQATKYFDIYGKPCTRK
LFANMRDASQWIKRMEDIGLEALGMDDFKLAYLSDTYNYEIKYDHTKIRVANFDIEVTSP
DGFPEPSQAKHPIDAITHYDSIDDRFYVFDLLNSPYGNVEEWSIEIAAKLQEQGGDEVPS
EIIDKIIYMPFDNEKELLMEYLNFWQQKTPVILTGWNVESFDIPYVYNRIKNIFGESTAK
RLSPHRKTRVKVIENMYGSREIITLFGISVLDYIDLYKKFSFTNQPSYSLDYISEFELNV
GKLKYDGPISKLRESNHQRYISYNIIDVYRVLQIDAKRQFINLSLDMGYYAKIQIQSVFS
PIKTWDAIIFNSLKEQNKVIPQGRSHPVQPYPGAFVKEPIPNRYKYVMSFDLTSLYPSII
RQVNISPETIAGTFKVAPLHDYINAVAERPSDVYSCSPNGMMYYKDRDGVVPTEITKVFN
QRKEHKGYMLAAQRNGEIIKEALHNPNLSVDEPLDVDYRFDFSDEIKEKIKKLSAKSLNE
MLFRAQRTEVAGMTAQINRKLLINSLYGALGNVWFRYYDLRNATAITTFGQMALQWIERK
VNEYLNEVCGTEGEAFVLYGDTDSIYVSADKIIDKVGESKFRDTNHWVDFLDKFARERME
PAIDRGFREMCEYMNNKQHLMFMDREAIAGPPLGSKGIGGFWTGKKRYALNVWDMEGTRY
AEPKLKIMGLETQKSSTPKAVQKALKECIRRMLQEGEESLQEYFKEFEKEFRQLNYISIA
SVSSANNIAKYDVGGFPGPKCPFHIRGILTYNRAIKGNIDAPQVVEGEKVYVLPLREGNP
FGDKCIAWPSGTEITDLIKDDVLHWMDYTVLLEKTFIKPLEGFTSAAKLDYEKKASLFDM
FDF

FIG. 56

METHODS AND REAGENTS FOR NUCLEIC ACID ANALYSIS

CROSS REFERENCE

This application is a continuation of International Application No. PCT/US21/57441, filed Oct. 29, 2021, which claims the benefit of U.S. Provisional Application No. 63/108,207, filed Oct. 30, 2020, which is hereby incorporated by reference in its entirety.

SEQUENCE LISTING

The instant application contains a Sequence Listing which has been submitted electronically in XML format and is hereby incorporated by reference in its entirety. Said XML copy, created on Sep. 19, 2022, is named 52933-740_301SL.xml and is 99,644 bytes in size.

BACKGROUND

Sequences of nucleic acid molecules may be determined using massively parallel sequencing. Massively parallel sequencing may be performed using sequencing by synthesis in which, in a primer extension reaction, a polymerizing enzyme adds nucleotides sequentially to a growing strand to yield a strand that is complementary to a template strand, and the nucleotides being incorporated are detected. Such sequences may be used in various applications, such as, for example, disease (e.g., cancer) diagnostics.

SUMMARY

Aspects disclosed herein provide methods of analyzing a nucleic acid, the method comprising: (a) bringing a primed nucleic acid sequence into contact with a fluorescently-labeled nucleotide conjugate under conditions sufficient to form a binding complex comprising a first nucleotide of the primed nucleic acid molecule bound to a second nucleotide of the fluorescently-labeled nucleotide conjugate; (b) contacting the binding complex with an imaging reagent; and (c) obtaining an image of the binding complex in a presence of the imaging reagent, thereby reducing a risk of photo-bleaching of the fluorescently-labeled nucleotide conjugate as compared to a risk of photo-bleaching under like conditions in absence of the imaging reagent.

In some embodiments, the method further comprises identifying the first nucleotide by analyzing the image obtained in (c). In some embodiments, the imaging reagent comprises ascorbic acid. In some embodiments, the ascorbic acid comprises sodium ascorbate. In some embodiments, the concentration of the ascorbic acid is at least 20 mM. In some embodiments, the concentration of the ascorbic acid is between about 10 mM and about 100 mM. In some embodiments, the concentration of the ascorbic acid is about 50 mM. In some embodiments, the fluorescently-labeled nucleotide conjugate comprises: (i) a core, (ii) a plurality of the second nucleotide coupled thereto, and (ii) one or more fluorophores directly coupled to the core. In some embodiments, the fluorescently-labeled nucleotide conjugate further comprises a core attachment moiety linking the plurality of the second nucleotide to the core. In some embodiments, the second nucleotide comprises between about 3 and about 10 phosphate groups. In some embodiments, the second nucleotide is a nucleotide triphosphate comprising a removable chain terminating moiety.

In some embodiments, the method further comprises bringing the primed nucleic acid sequence into contact with a polymerase under conditions sufficient to form the binding complex, wherein the binding complex further comprises the polymerase. In some embodiments, the polymerase lacks a detectable label. In some embodiments, the polymerase comprises a detectable label. In some embodiments, the binding complex is immobilized to a support. In some embodiments, the support comprises a surface, and wherein the surface comprises a hydrophilic coating layer coupled thereto. In some embodiments, the hydrophilic coating layer comprises a water contact angle of less than 50 degrees.

In some embodiments, the method further comprises bringing the primed nucleic acid sequence into contact with a second fluorescently-labeled nucleotide conjugate under conditions sufficient to form a second binding complex comprising the next nucleotide of the primed nucleic acid molecule bound to a third nucleotide of the fluorescently-labeled nucleotide conjugate, wherein the third nucleotide is different than the second nucleotide. In some embodiments, the primed nucleic acid sequence is comprised in a concatemer nucleic acid molecules comprising tandem repeats of the primed nucleic acid sequence. In some embodiments, the imaging reagent comprises a non-catalytic divalent cation that inhibits incorporation of the second nucleotide, wherein the non-catalytic divalent cation comprises strontium, barium, scandium, titanium, calcium, vanadium, chromium, iron, cobalt, nickel, copper, zinc, gallium, germanium, arsenic, selenium, rhodium, europium, tin or terbium ions.

In some aspects, the present disclosure describes a formulation for reducing photo-bleaching of a biological entity during imaging, the formulation comprising: at least one solvent, a pH buffering agent, a chelating agent, at least one monovalent cation, a non-catalytic divalent cation, a detergent and ascorbic acid. In some embodiments, the pH buffering agent comprises Tris-HCl. In some embodiments, the pH of the Tris-HCL is about 8.8. In some embodiments, the chelating agent comprises EDTA. In some embodiments, the monovalent cation comprises NaCl, KCl, (NH4)2SO4 or potassium glutamate. In some embodiments, the non-catalytic divalent cation comprises strontium, barium, scandium, titanium, calcium, vanadium, chromium, iron, cobalt, nickel, copper, zinc, gallium, germanium, arsenic, selenium, rhodium, europium, tin or terbium ions, or a combination thereof. In some embodiments, the formulation lacks a catalytic divalent cation which comprises magnesium or manganese, or a combination thereof. In some embodiments, the detergent comprises Triton™ X-100 (2-[4-(2,4,4-trimethylpentan-2-yl)phenoxy]ethanol). In some embodiments, the formulation further comprises a sugar. In some embodiments, the formulation further comprises a viscosity agent comprising glycerol. In some embodiments, the formulation further comprises 1,3,5,7 cyclo-octatetraene (COT). In some embodiments, the COT has a concentration of about 2 micromolar (mM). In some embodiments, the ascorbic acid comprises sodium ascorbate. In some embodiments, the concentration of the ascorbic acid is at least 10 mM. In some embodiments, the concentration of the ascorbic acid is at least 20 mM. In some embodiments, the concentration of the ascorbic acid is between about 10 mM and about 100 mM. In some embodiments, the concentration of the ascorbic acid is about 50 mM. In some embodiments, the formulation further comprises Trolox. In some embodiments, the concentration of the Trolox is about 2 mM. In some embodiments, the formulation further comprises 3-nitrobenzoic acid (NBA). In some embodiments, the formulation further comprises cystamine.

Aspects disclosed herein provide formulations comprising (i) at least one solvent, (ii) a pH buffering agent, (iii) a chelating agent, (iv) at least one monovalent cation, (v) a non-catalytic divalent cation, (vi) a detergent, (vii) a plurality of multivalent molecules and (viii) a sequencing polymerase enzyme, wherein each of the plurality of multivalent molecules comprises (1) a core, and (2) a plurality of nucleotides and a plurality of detectable moieties coupled to the core, and wherein the sequencing polymerase enzyme comprises an amino acid sequence that is at least 80% identical to any of SEQ ID NOS: 2-5. In some embodiments, each of the plurality of multivalent molecules further comprises a linker that couples the plurality of nucleotides to the core, and wherein the linker comprises an aliphatic chain having 2-6 subunits or an oligo ethylene glycol chain having 2-6 subunits. In some embodiments, the core is spheroidal. In some embodiments, the plurality of nucleotides are of the same type of nucleotide selected from a group consisting of dATP, dGTP, dCTP, dTTP and dUTP. In some embodiments, the plurality of the multivalent molecules comprises two or more different types of multivalent molecules, wherein each of the two or more different types of the multivalent molecules comprise a different plurality of nucleotides. In some embodiments, the sequencing polymerase comprises a mutation in the amino acid sequence comprising a substitution at one or more positions relative to SEQ ID NO: 1 comprising Leu416, Tyr417, Pro418, Ala493, Arg515, Ile529 and Asn567. In some embodiments, the sequencing polymerase comprises the amino acid sequence of any one of SEQ ID NOS: 2-5.

Aspects disclosed herein provide kits comprising one or more containers containing a formulation described herein. In some embodiments, the kit further comprises instructions for reducing photo-damage to the biological entity while imaging the biological entity during a biochemical reaction in the presence of the formulation. In some embodiments, the biochemical reaction comprises a sequencing reaction. In some embodiments, the instructions comprise submerging the biological entity in the formulation during the biochemical reaction prior to imaging the biological entity.

Aspects disclosed herein provide kits comprising: a trap reagent comprising at least one solvent, a pH buffering agent, a chelating agent, at least one monovalent cation, a non-catalytic divalent cation, a detergent, a plurality of fluorescently-labeled nucleotide conjugates and a first sequencing polymerase enzyme; a post-trap reagent comprising at least one solvent, a pH buffering agent, a chelating agent, at least one monovalent cation, a non-catalytic divalent cation, a detergent and a first sequencing polymerase enzyme; an imaging reagent comprising at least one solvent, a pH buffering agent, a chelating agent, at least one monovalent cation, a non-catalytic divalent cation, a detergent and ascorbic acid; and a stepping reagent comprising at least one solvent, at least one pH buffering agent, at least one monovalent cation, a catalytic divalent cation, a detergent, a second sequencing polymerase enzyme and a plurality of nucleotides, wherein each nucleotide of the plurality of nucleotides comprises a cleavable terminator moiety attached to a 3' sugar position.

In some embodiments, the kit further comprises instructions for using the trap reagent, wherein the instructions comprise contacting a plurality of immobilized template nucleic acid molecules with (i) the trap reagent and (ii) a plurality of sequencing primers under conditions sufficient to form a plurality of immobilized fluorescently-labeled ternary complexes without incorporating the plurality of fluorescently-labeled nucleotide conjugates into the sequencing primer.

In some embodiments, the kit further comprises instructions for using the post-trap reagent, wherein the instructions comprise contacting the plurality of immobilized fluorescently-labeled ternary complexes with a post-trap reagent under conditions sufficient for preserving the plurality of immobilized fluorescently-labeled ternary complexes without incorporation of the plurality of immobilized fluorescently-labeled ternary complexes into the sequencing primer.

In some embodiments, the kit further comprises instructions for using the stepping reagent, wherein the instructions comprise contacting the plurality of immobilized template nucleic acid molecules with the stepping reagent under conditions sufficient to extend the immobilized template nucleic acid molecule.

In some embodiments, the kit further comprises a first amplification reagent comprising at least one solvent, a pH buffering agent, at least one monovalent cation, ammonium ions, a plurality of nucleotides and an amplification polymerase enzyme; and a second amplification reagent comprising at least one solvent, a pH buffering agent, at least one monovalent cation, ammonium ions and a plurality of nucleotides.

In some embodiments, the kit further comprises instructions for using the first amplification reagent and the second amplification reagent, wherein the instructions comprise: contacting the immobilized template nucleic acid molecules with a first amplification reagent under conditions that inhibit activity of the amplification polymerase enzyme; and contacting the immobilized template nucleic acid molecules with a second amplification reagent under a condition suitable for reviving the activity of the amplification polymerase enzyme to perform a plurality of nucleic acid amplification reactions.

In some embodiments, the kit further comprises a wash-removal reagent comprising at least one solvent, a pH buffering agent, a chelating agent, a detergent and a chaotropic agent.

In some embodiments, the kit further comprises a nucleic acid hybridization reagent, comprising: at least one solvent, a pH buffering agent, and at least one monovalent cation; and a detergent, a reducing agent, a chaotropic agent, a chelating agent, an alcohol, a zwitterion, a sugar alcohol or a crowding agent, or a combination thereof.

INCORPORATION BY REFERENCE

Throughout this application various publications, patents, and/or patent applications are referenced. The disclosures of the publications, patents and/or patent applications are hereby incorporated by reference in their entireties into this application to the same extent as if each individual publication, patent, or patent application was specifically and individually indicated to be incorporated by reference in its entirety. In the event of a conflict between a term herein and a term in an incorporated reference, the term herein controls.

DESCRIPTION OF THE DRAWINGS

Some novel features of the inventive concepts are set forth with particularity in the appended claims. A better understanding of the features and advantages of the present inventive concepts will be obtained by reference to the following detailed description that sets forth illustrative embodiments, in which the principles of the inventive concepts are utilized, and the accompanying drawings of which:

FIG. 3 is an amino acid sequence (SEQ ID NO: 1) of a wild type DNA polymerase from Candidatus altiarchaeales archaeon.

FIG. 4 is an amino acid sequence (SEQ ID NO: 2) of a mutant DNA polymerase from Candidatus altiarchaeales archaeon comprising amino acid substitution mutations.

FIG. 5 is an amino acid sequence (SEQ ID NO: 3) of a mutant DNA polymerase from Candidatus altiarchaeales archaeon comprising amino acid substitution mutations.

FIG. 6 is an amino acid sequence (SEQ ID NO: 4) of a mutant DNA polymerase from Candidatus altiarchaeales archaeon comprising amino acid substitution mutations.

FIG. 7 is an amino acid sequence (SEQ ID NO: 5) of a mutant DNA polymerase from Candidatus altiarchaeales archaeon comprising amino acid substitution mutations.

FIG. 8 is an amino acid sequence SEQ ID NO: 6) of a wild type (9° N DNA polymerase.

FIG. 9 is an amino acid sequence (SEQ ID NO: 7) of a mutant 9° N DNA polymerase.

FIG. 10 is an amino acid sequence (SEQ ID NO: 8) of a variant 9° N DNA polymerase.

FIG. 11 is an amino acid sequence (SEQ ID NO: 9) of a Vent DNA polymerase.

FIG. 12 is an amino acid sequence (SEQ ID NO: 10) of a Deep Vent DNA polymerase.

FIG. 13 is an amino acid sequence (SEQ ID NO: 11) of a Pfu DNA polymerase.

FIG. 14 is an amino acid sequence (SEQ ID NO: 12) of a *Pyrococcus abyssi* DNA polymerase.

FIG. 15 is an amino acid sequence (SEQ ID NO: 13) of an RB69 DNA polymerase.

FIG. 25 shows the chemical structure of an exemplary spacer (top), and the chemical structures of various exemplary linkers, including an 11-atom Linker, 16-atom Linker, 23-atom Linker and an N3 Linker (bottom).

FIG. 26 shows the chemical structures of various exemplary linkers, including Linkers 1-9.

FIG. 27 shows the chemical structures of various exemplary linkers joined/attached to nucleotide units.

FIG. 28 shows the chemical structures of various exemplary linkers joined/attached to nucleotide units.

FIG. 29 shows the chemical structures of various exemplary linkers joined/attached to nucleotide units.

FIG. 30 shows the chemical structures of various exemplary linkers joined/attached to nucleotide units.

FIG. 44 is an amino acid sequence of wild type DNA polymerase from Candidatus altiarchaeales archaeon (SEQ ID NO:221).

FIG. 45 is an amino acid sequence of mutant DNA polymerase from Candidatus altiarchaeales archaeon (SEQ ID NO:222).

FIG. 46 is an amino acid sequence of mutant DNA polymerase from Candidatus altiarchaeales archaeon (SEQ ID NO:223).

FIG. 47 is an amino acid sequence of mutant DNA polymerase from Candidatus altiarchaeales archaeon (SEQ ID NO:224).

FIG. 48 is an amino acid sequence of mutant DNA polymerase from Candidatus altiarchaeales archaeon (SEQ ID NO:225).

FIG. 49 is an amino acid sequence of 9° N polymerase (SEQ ID NO:226).

FIG. 50 is an amino acid sequence of 9° N polymerase UniProtKB—Q56366 (DPOL_THES9) (SEQ ID NO:227).

FIG. 51 is an amino acid sequence of therminator polymerase (SEQ ID NO:228).

FIG. 52 is an amino acid sequence of vent polymerase UniProtKB—P30317 (DPOL_THELI) (SEQ ID NO:229).

FIG. 53 is an amino acid sequence deep vent polymerase UniProtKB—Q51334 (DPOL_PYRSD) (SEQ ID NO:230).

FIG. 54 is an amino acid sequence of Pfu polymerase UniProtKB—P61875 (DPOL_PYRFU) (SEQ ID NO:231).

FIG. 55 is an amino acid sequence of *Pyrococcus abyssi* polymerase UniProtKB—P0CL77 (DPOL_PYRAB) (SEQ ID NO:232).

FIG. 56 is an amino acid sequence of RB69 polymerase UniProtKB—Q38087 (DPOL_BPR69) (SEQ ID NO:233).

DETAILED DESCRIPTION

Figure 1:
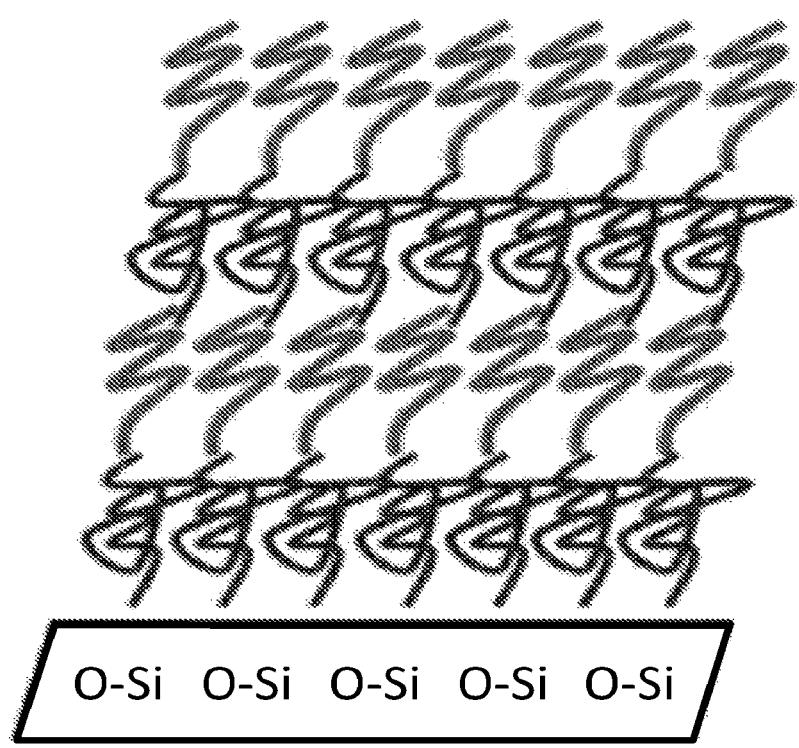
FIG. 1 is an exemplary schematic illustration of one embodiment of alternating layers of hydrophilic coatings which are covalently or non-covalently adhered to a support structure (e.g., glass, plastic or other polymer material), where the coatings comprise chemically-reactive functional groups that serve as attachment sites for oligonucleotide primers (e.g., surface capture primers).

The headings provided herein are not limitations of the various aspects of the disclosure, which aspects can be understood by reference to the specification as a whole.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative term (e.g., "or") is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects: "A, B, and C"; "A, B, or C"; "A or C"; "A or B"; "B or C"; "A and B"; "B and C"; "A and C"; "A" (A alone); "B" (B alone); and "C" (C alone).

As used herein and in the appended claims, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the terms "about" and "approximately" refer to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The term "cellular biological sample" refers to a single cell, a plurality of cells, a tissue, an organ, an organism, or section of any of these cellular biological samples. The cellular biological sample can be extracted (e.g., biopsied) from an organism, or obtained from a cell culture grown in liquid or in a culture dish. The cellular biological sample comprises a sample that is fresh, frozen, fresh frozen, or archived (e.g., formalin-fixed paraffin-embedded; FFPE). The cellular biological sample can be embedded in a wax, resin, epoxy or agar. The cellular biological sample can be fixed, for example in any one or any combination of two or more of acetone, ethanol, methanol, formaldehyde, paraformaldehyde-Triton™ X-100 (2-[4-(2,4,4-trimethylpentan-2-yl)phenoxy]ethanol) or glutaraldehyde. The cellular biological sample can be sectioned or non-sectioned. The cellular biological sample can be stained, de-stained or non-stained.

The nucleic acids of interest can be extracted from cells or cellular biological samples using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, Md.), or the Maxwell® and ReliaPrep™ series of kits from Promega (Madison, Wis.).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids (PNA) and non-naturally occurring nucleotide analogs), and chimeric forms containing DNA and RNA. Nucleic acids can be single-stranded or double-stranded. Nucleic acids comprise polymers of nucleotides, where the nucleotides include natural or non-natural bases and/or sugars. Nucleic acids comprise naturally-occurring internucleosidic linkages, for example phosphodiester linkages. Nucleic acids can lack a phosphate group. Nucleic acids comprise non-natural internucleoside linkages, including phosphorothioate, phosphorothiolate, or peptide nucleic acid (PNA) linkages. In some embodiments, nucleic acids comprise a one type of polynucleotides or a mixture of two or more different types of polynucleotides.

The term "template nucleic acid", "template polynucleotide", "target nucleic acid" "target polynucleotide", "template strand" and other variations refer to a nucleic acid strand that serves as the basis nucleic acid molecule for any of the analysis methods describe herein (e.g., hybridization, amplifying and/or sequencing). The template nucleic acid can be single-stranded or double-stranded, or the template nucleic acid can have single-stranded or double-stranded portions. The template nucleic acid can be clonally amplified. The template nucleic acid can be a concatemer having tandem repeats of the nucleic acid sequence of interest operably joined to at least one adaptor sequence. The template nucleic acid can be obtained from a naturally-occurring source, recombinant form, or chemically synthesized to include any type of nucleic acid analog. The template nucleic acid can be linear, circular, or other forms. The template nucleic acids can include an insert portion having an insert sequence. The template nucleic acids can also include at least one adaptor sequence. The insert portion can be isolated in any form, including chromosomal, genomic, organellar (e.g., mitochondrial, chloroplast or ribosomal), recombinant molecules, cloned, amplified, cDNA, RNA such as precursor mRNA or mRNA, oligonucleotides, whole genomic DNA, obtained from fresh frozen paraffin embedded tissue, needle biopsies, circulating tumor cells, cell free circulating DNA, or any type of nucleic acid library. The insert portion can be isolated from any source including from organisms such as prokaryotes, eukaryotes (e.g., humans, plants and animals), fungus, viruses cells, tissues, normal or diseased cells or tissues, body fluids including blood, urine, serum, lymph, tumor, saliva, anal and vaginal secretions, amniotic samples, perspiration, semen, environmental samples, culture samples, or synthesized nucleic acid molecules prepared using recombinant molecular biology or chemical synthesis methods. The insert portion can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs. The template nucleic acid can be subjected to nucleic acid analysis, including sequencing and composition analysis. The template nucleic acid can be linear, concatemeric, circular, or other forms.

The term "primer" and related terms used herein refers to an oligonucleotide that is capable of hybridizing with a DNA and/or RNA polynucleotide template to form a duplex molecule. Primers comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer). Primers can be single-stranded along their entire length or have single-stranded and double-stranded portions The term "universal sequence" and related terms refers to a sequence in a nucleic acid molecule that is common among two or more polynucleotide molecules. For example, an adaptor having a universal sequence can be operably joined to a plurality of polynucleotides so that the population of co-joined molecules carry the same universal adaptor sequence. Examples of universal adaptor sequences include an amplification primer sequence, a sequencing primer sequence or a capture primer sequence (e.g., soluble or immobilized capture primers).

The term "adaptor" and related terms refers to oligonucleotides that can be operably linked (appended) to a target polynucleotide, where the adaptor confers a function to the co-joined adaptor-target molecule. Adaptors comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear, stem-looped, hairpin, or Y-shaped forms. Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed. An adaptor can include a universal sequence. At least a portion of the adaptors comprise a known and pre-determined sequence. An adaptor can include a sequence that is complementary to at least a portion of a primer, such as an amplification primer, a sequencing primer, or a capture primer (e.g., soluble or immobilized capture primers). Adaptors can include a random sequence or degenerate sequence. Adaptors can include at least one inosine residue. Adaptors can include at least one phosphorothioate, phosphorothiolate and/or phosphoramidate linkage. Adaptors can include a barcode sequence which can be used to distinguish polynucleotides (e.g., insert sequences) from different sample sources in a multiplex assay. Adaptors can include a unique identification sequence (e.g., unique molecular index, UMI; or a unique molecular tag) that can be used to uniquely identify a nucleic acid molecule to which the adaptor is appended. In some embodiments, a unique identification sequence can be used to increase error correction and accuracy, reduce the rate of false-positive variant calls and/or increase sensitivity of variant detection. Adaptors can include at least one restriction enzyme recognition sequence, including any one or any combination of two or more selected from a group consisting of type I, type II, type III, type IV, type IIs or type IIB.

The term "operably linked" and "operably joined" or related terms as used herein refers to juxtaposition of components. The juxtaposed components can be linked together covalently. For example, two nucleic acid components can be enzymatically ligated together where the linkage that joins together the two components comprises phosphodiester linkage. A first and second nucleic acid component can be linked together, where the first nucleic acid component can confer a function on a second nucleic acid component. For example, linkage between a primer binding sequence and a sequence of interest forms a nucleic acid library molecule having a portion that can bind to a primer. In another example, a transgene (e.g., a nucleic acid encoding a polypeptide or a nucleic acid sequence of interest) can be ligated to a vector where the linkage permits expression or functioning of the transgene sequence contained in the vector. In some embodiments, a transgene is operably linked to a host cell regulatory sequence (e.g., a promoter sequence) that affects expression of the transgene. In some embodiments, the vector comprises at least one host cell regulatory sequence, including a promoter sequence, enhancer, transcription and/or translation initiation sequence, transcription and/or translation termination sequence, polypeptide secretion signal sequences, and the like. In some embodiments, the host cell regulatory sequence controls expression of the level, timing and/or location of the transgene.

The terms "linked", "joined", "attached", "appended" and variants thereof comprise any type of fusion, bond, adherence or association between any combination of compounds or molecules that is of sufficient stability to withstand use in the particular procedure. The procedure can include but are not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. In some embodiments, such linkage occurs intramolecularly, for example linking together the ends of a single-stranded or double-stranded linear nucleic acid molecule to form a circular molecule. In some embodiments, such linkage can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

When used in reference to concentrations, the symbol "%" may refer to % by volume. When used in reference to concentrations, the symbol "%" may refer to % by mass. When used in reference to concentrations, the symbol "%" may refer to % by mol.

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides.

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand, resulting in extension of the nucleic acid strand. Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

In some embodiments, any of the amplification primer sequences, sequencing primer sequences, capture primer sequences (capture oligonucleotides), target capture sequences, circularization anchor sequences, sample barcode sequences, spatial barcode sequences, or anchor region sequences can be about 3-50 nucleotides in length, or about 5-40 nucleotides in length, or about 5-25 nucleotides in length.

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. A polymerase can be any enzyme that can catalyze polymerization of nucleotides (including analogs thereof) into a nucleic acid strand. Typically but not necessarily such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze nucleotide polymerization (e.g., catalytically active fragment). The polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

The term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include phi29 DNA polymerase, large fragment of Bst DNA polymerase, large fragment of Bsu DNA polymerase (exo-), Bca DNA polymerase (exo-), Klenow fragment of $E.\ coli$ DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

The term "nucleotides" and related terms refers to a molecule comprising an aromatic base, a five carbon sugar (e.g., ribose or deoxyribose), and at least one phosphate group. Canonical or non-canonical nucleotides are consistent with use of the term. The phosphate in some embodiments comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety. The nucleotides can have 1-10 phosphate groups.

Nucleotides (and nucleosides) typically comprise a hetero cyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), etheno-adenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methylcytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises: ribosyl; 2'-deoxyribosyl; 3'-deoxyribosyl; 2',3'-dideoxyribosyl; 2',3'-didehydrodideoxyribosyl; 2'-alkoxyribosyl; 2'-azidoribosyl; 2'-aminoribosyl; 2'-fluororibosyl; 2'-mercaptoriboxyl; 2'-alkylthioribosyl; 3'-alkoxyribosyl; 3'-azidoribosyl; 3'-aminoribosyl; 3'-fluororibosyl; 3'-mercaptoriboxyl; 3'-alkylthioribosyl carbocyclic; acyclic or other modified sugars.

In some embodiments, nucleotides comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

A reporter moiety (or label) comprises a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiazolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenine, benzo-indolium, pyridium, thiazolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenine, and the benzo-derivatized Cy3.5, Cy5.5 and Cy7.5 are exceptions to this rule.

In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell or multiple cells. Examples of biological samples include but are not limited to saliva, phlegm, mucus, blood, plasma, serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support can be substantially planar, concave, convex, or any combination thereof. In some embodiments, the support can be cylindrical, for example comprising a capillary or interior surface of a capillary.

In some embodiments, the surface of the support can be substantially smooth. In some embodiments, the support can be regularly or irregularly textured, including bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The support can have a plurality (e.g., two or more) of nucleic acid templates immobilized thereon. The plurality of immobilized nucleic acid templates have the same sequence or have different sequences. In some embodiments, individual nucleic acid template molecules in the plurality of nucleic acid templates are immobilized to a different site on the support. In some embodiments, two or more individual nucleic acid template molecules in the plurality of nucleic acid templates are immobilized to a site on the support.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^5$ sites or more) are immobilized with nucleic acid templates to form a nucleic acid template array. In some embodiments, the nucleic acid templates that are immobilized at a plurality of pre-determined sites by hybridization to immobilized surface capture primers, or the nucleic acid templates are covalently attached to the surface capture primer. In some embodiments, the nucleic acid templates that are immobilized at a plurality of pre-determined sites, for example immobilized at $10^2$-$10^{15}$ sites or more. In some embodiments, the immobilized nucleic acid templates are clonally-amplified to generate immobilized nucleic acid clusters at the plurality of pre-determined sites. In some embodiments, individual immobilized nucleic acid clusters comprise linear clusters, or comprise single-stranded or double-stranded concatemers.

In some embodiments, a support comprising a plurality of sites located at random locations on the support is referred to herein as a support having randomly located sites thereon. The location of the randomly located sites on the support are not pre-determined. The plurality of randomly-located sites is arranged on the support in a disordered and/or unpredictable fashion. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more) are immobilized with nucleic acid templates to form a support immobilized with nucleic acid templates. In some embodiments, the nucleic acid templates that are immobilized at a plurality of randomly located sites by hybridization to immobilized surface capture primers, or the nucleic acid templates are covalently attached to the surface capture primer. In some embodiments, the nucleic acid templates that are immobilized at a plurality of randomly located sites, for example immobilized at $10^2$-$10^{15}$ sites or more. In some embodiments, the immobilized nucleic acid templates are clonally-amplified to generate immobilized nucleic acid clusters at the plurality of randomly located sites. In some embodiments, individual immobilized nucleic acid clusters comprise linear clusters, or comprise single-stranded or double-stranded concatemers.

When used in reference to support, the term "feature" refers to a region on a support. In some embodiments, the feature is a region on a coating which is layered on the support. In some embodiments, the feature is a region on a low non-specific binding coating which is layered on a support. A support or coating can have a plurality of regions (e.g., features) located at different pre-determined locations on the support or coating (FIG. 3, right). The different features on the support can be placed at non-overlapping positions or at overlapping positions on the support. The features can be configured to have any shape, for example circular, ovular, square, rectangular, or polygonal. The features can be arranged in a grid pattern having rows and columns, or can be arranged in a row or a column. In some embodiments, any given feature contains a plurality of capture oligonucleotides and/or a plurality of circularization oligonucleotides immobilized to the support or to the coating. The plurality of features includes at least a first and second feature.

In some embodiment, the plurality of immobilized surface capture primers on the support are in fluid communication with each other to permit flowing a solution of reagents (e.g., nucleic acid template molecules, soluble primers, enzymes, nucleotides, divalent cations, buffers, and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA, MDA, PCR and bridge amplification) essentially simultaneously on the plurality of immobilized surface capture primers.

In some embodiment, the plurality of immobilized nucleic acid clusters on the support are in fluid communication with each other to permit flowing a solution of reagents (e.g., enzymes, nucleotides, divalent cations, and the like) onto the support so that the plurality of immobilized nucleic acid clusters on the support can be essentially simultaneously reacted with the reagents in a massively parallel manner. In some embodiments, the fluid communication of the plurality of immobilized nucleic acid clusters can be used to conduct nucleotide binding assays and/or conduct nucleotide polymerization reactions (e.g., primer extension or sequencing) essentially simultaneously on the plurality of immobilized nucleic acid clusters, and optionally to conduct detection and imaging for massively parallel sequencing.

When used in reference to immobilized enzymes, the term "immobilized" and related terms refer to enzymes (e.g., polymerases) that are attached to a support through covalent bond or non-covalent interaction, or attached to a coating on the support, or buried within a matrix formed by a coating on the support.

When used in reference to immobilized nucleic acids, the term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers includes nucleic acid single copy molecules having one copy of insert sequences and at least one adaptor sequence, and includes concatemers having repeat tandem copies of insert and adaptor sequences. The nucleic acid molecules can be immobilized at pre-determined or random locations on the support. The nucleic acid molecules can be immobilized at pre-determined or random locations on or within a coating passivated on the support. In some embodiments, the term "immobilized" and related terms refer to enzymes (e.g., polymerases) that are attached to a support through covalent bond or non-covalent interaction, or attached to a coating on the support, or buried within a matrix formed by a coating on the support. The enzymes can be immobilized at pre-determined or random locations on the support. The enzymes can be immobilized at pre-determined or random locations on or within a coating passivated on the support.

In some embodiments, one or more nucleic acid templates are immobilized on the support, for example immobilized at the sites on the support. In some embodiments, the one or more nucleic acid templates are clonally-amplified. In some embodiments, the one or more nucleic acid templates are clonally-amplified off the support (e.g., in-solution) and then deposited onto the support and immobilized on the support. In some embodiments, the clonal amplification reaction of the one or more nucleic acid templates is conducted on the support resulting in immobilization on the support. In some embodiments, the one or more nucleic acid templates are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface capture primer", "capture primer", "capture oligonucleotide" and related terms refers to single-stranded oligonucleotides that are immobilized to a support and comprise a sequence that can hybridize to at least a portion of a nucleic acid template molecule. Surface capture primers can be used to immobilize template molecules to a support via hybridization. Surface capture primers can be immobilized to a support in a manner that resists primer removal during flowing, washing, aspirating, and changes in temperature, pH, salts, chemical and/or enzymatic conditions. Typically, but not necessarily, the 5' end of a surface capture primer can be immobilized to a support. Alternatively, an interior portion or the 3' end of a surface capture primer can be immobilized to a support.

The sequence of surface capture primers can be wholly or partially complementary along their length to at least a portion of the nucleic acid template molecule. A support can include a plurality of immobilized surface capture primers having the same sequence, or having two or more different sequences. Surface capture primers can be any length, for example 4-50 nucleotides, or 50-100 nucleotides, or 100-150 nucleotides, or longer lengths.

A surface capture primer can have a terminal 3' nucleotide having a 3' sugar moiety which is extendible for nucleotide polymerization (e.g., polymerase catalyzed polymerization). A surface capture primer can have a terminal 3' nucleotide having the 3' sugar position linked to a chain-terminating moiety that inhibits nucleotide polymerization. The 3' chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine)palladium(0) (Pd(PPh$_3$)$_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothreitol (DTT), for chain-terminating groups amine, amide, keto, isocyanate, phosphate, thio and disulfide. Examples of de-blocking agents include potassium carbonate (K$_2$CO$_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

The term "branched polymer" and related terms refers to a polymer having a plurality of functional groups that help conjugate a biologically active molecule such as a nucleotide, and the functional group can be either on the side chain of the polymer or directly attaches to a central core or central backbone of the polymer. The branched polymer can have linear backbone with one or more functional groups coming off the backbone for conjugation. The branched polymer can also be a polymer having one or more sidechains, wherein the side chain has a site suitable for conjugation. Examples of the functional group include but are limited to hydroxyl, ester, amine, carbonate, acetal, aldehyde, aldehyde hydrate, alkenyl, acrylate, methacrylate, acrylamide, active sulfone, hydrazide, thiol, alkanoic acid, acid halide, isocyanate, isothiocyanate, maleimide, vinylsulfone, dithiopyridine, vinylpyridine, iodoacetamide, epoxide, glyoxal, dione, mesylate, tosylate, and tresylate.

The term "sequencing" and related terms refers to a method for obtaining nucleotide sequence information from a nucleic acid molecule, typically by determining the identity of at least some nucleotides (including their nucleobase components) within the nucleic acid molecule. In some embodiments, the sequence information of a given region of a nucleic acid molecule includes identifying each and every nucleotide within a region that is sequenced. In some embodiments, sequencing information determines only some of the nucleotides a region, while the identity of some nucleotides remains undetermined or incorrectly determined. Any suitable method of sequencing may be used. In an exemplary embodiment, sequencing can include label-free or ion based sequencing methods. In some embodiments, sequencing can include labeled or dye-containing nucleotide or fluorescent based nucleotide sequencing methods. In some embodiments, sequencing can include cluster-based sequencing or bridge sequencing methods. In some embodiments, the sequencing employs polymerases and multivalent molecules for generating at least one avidity complex, wherein individual multivalent molecules comprise a plurality of nucleotide units tethered to a core. In some embodiments, the sequencing employs polymerases and free nucleotides for performing sequencing-by-synthesis. In some embodiments, the sequencing employs a ligase enzyme and a plurality of sequence-specific oligonucleotides for performing sequence-by-ligation.

The term "persistence time" and related terms refers to the length of time that a binding complex, which is formed between the target nucleic acid, a polymerase, a conjugated or unconjugated nucleotide, remains stable without any binding component dissociates from the binding complex. The persistence time is indicative of the stability of the binding complex and strength of the binding interactions.

Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label.

When used in reference to nucleic acids, the terms "amplify", "amplifying", "amplification", and other related terms include producing multiple copies of an original polynucleotide template molecule, where the copies comprise a sequence that is complementary to the template sequence, or the copies comprise a sequence that is the same as the template sequence. In some embodiments, the copies comprise a sequence that is substantially identical to a template sequence, or is substantially identical to a sequence that is complementary to the template sequence.

The term "rolling circle" amplification generally refers to an amplification method that employs a circularized nucleic acid template molecule containing a target sequence of interest, an amplification primer binding sequence, and optionally one or more adaptor sequences such as a sequencing primer binding sequence and/or a barcode. The rolling circle amplification reaction can be conducted under isothermal amplification conditions, and includes the circularized nucleic acid template molecule, an amplification primer, a strand-displacing polymerase and a plurality of nucleotides, to generate a concatemer containing tandem repeat sequences of the circular template molecule and any adaptor sequences present in the original circularized nucleic acid template molecule. The concatemer can self-collapse to form a nucleic acid nanoball. The shape and size of the nanoball can be further compacted by including a pair of inverted repeat sequences in the circular template molecule, or by conducting the rolling circle amplification reaction with one or more compaction oligonucleotides. One of the advantages of using rolling circle amplification to generate clonal amplicons for a sequencing workflow, is that the repeat copies of the target sequence in the nanoball can be simultaneously sequenced to increase signal intensity. In some embodiments, the rolling circle amplification reaction can be conducted in the presence of a plurality of compaction oligonucleotides having at least four consecutive guanines. The rolling circle amplification reaction generates concatemers comprising repeat copies of the universal binding sequence for the compaction oligonucleotide. At least one compaction oligonucleotide can form a guanine tetrad and hybridize to the universal binding sequences for the compaction oligonucleotide, and the resulting concatemer can fold to form an intramolecular G-quadruplex structure. The concatemers can self-collapse to form compact nanoballs. Formation of the guanine tetrads and G-quadruplexes in the nanoballs may increase the stability of the nanoballs to retain their compact size and shape which can withstand repeated flows of reagents for conducting any of the sequencing workflows described herein.

When used in reference to nucleic acids, the terms "amplify", "amplifying", "amplification", and other related terms include producing multiple copies of an original polynucleotide template molecule, where the copies comprise a sequence that is complementary to the template sequence, and/or the copies comprise a sequence that is the same as the template sequence. In some embodiments, the copies comprise a sequence that is substantially identical to a template sequence, and/or is substantially identical to a sequence that is complementary to the template sequence.

The terms "resonance energy transfer" and "RET" and related terms used herein, refer to a radiationless transmission of excitation energy from a first moiety which is a donor moiety, to a second moiety which is an acceptor moiety. One type of RET includes Forster Resonance Energy Transfer (FRET), in which a donor fluorophore in an excited state transfers its energy to a proximal acceptor molecule by non-radiative dipole-dipole interaction. A description of FRET can be found in T. Forster, 1948, "Intermolecular Energy Migration and Fluorescence", Ann. Phys., 2:55-75; and J. R. Lakowicz, 1999, "Principles of Fluorescence Spectroscopy", 2nd ed. Plenum, New York. 367-394. RET also includes luminescence resonance energy transfer, bioluminescence resonance energy transfer, chemiluminescence resonance energy transfer, and similar types of energy transfer that do not strictly follow the Forster's theory, such as nonoverlapping energy transfer occurring when nonoverlapping acceptors are utilized. See for example, Anal. Chem. 2005, 77: 1483-1487.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to post-translation modification such as proteolytic cleavage, cleavage due to ribosomal skipping, hydroxylation, methylation, lipidation, acetylation, SUMOylation, ubiquitination, glycosylation, phosphorylation and/or disulfide bond formation. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins.

The present disclosure provides various reagents, and methods that employ the reagents for conducing massively parallel nucleic acid polony formation and sequencing. The various reagents can include at least one pH buffering agent. The full name of the pH buffering agents is listed herein.

The term "Tris" refers to a pH buffering agent Tris (hydroxymethyl)-aminomethane.

The term "Tris-HCl" refers to a pH buffering agent Tris(hydroxymethyl)-aminomethane hydrochloride. The term "Tris-acetate" refers to a pH buffering agent comprising an acetate salt of Tris (hydroxymethyl)-aminomethane.

The term "Tricine" refers to a pH buffering agent N-[tris (hydroxymethyl) methyl]glycine.

The term "Bicine" refers to a pH buffering agent N,N-bis(2-hydroxyethyl)glycine.

The term "Bis-Tris propane" refers to a pH buffering agent 1,3 Bis[tris(hydroxymethyl)methylamino]propane The term "HEPES" refers to a pH buffering agent 4-(2-hydroxyethyl)-1-piperazineethanesulfonic acid.

The term "MES" refers to a pH buffering agent 2-(N-morpholino)ethanesulfonic acid).

The term "MOPS" refers to a pH buffering agent 3-(N-morpholino)propanesulfonic acid.

The term "MOPSO" refers to a pH buffering agent 3-(N-morpholino)-2-hydroxypropanesulfonic acid.

The term "BES" refers to a pH buffering agent N,N-bis (2-hydroxyethyl)-2-aminoethanesulfonic acid.

The term "TES" refers to a pH buffering agent 2-[(2-Hydroxy-1,1bis(hydroxymethyl) ethyl)amino]ethanesulfonic acid).

The term "CAPS" refers to a pH buffering agent 3-(cyclohexylamino)-1-propanesuhinic acid.

The term "TAPS" refers to a pH buffering agent N-[Tris (hydroxymethyl)methyl]-3-amino propane sulfonic acid.

The term "TAPSO" refers to a pH buffering agent N-[Tris (hydroxymethyl)methyl]-3-amino-2-hydroxypropanesulfonic acid.

The term "ACES" refers to a pH buffering agent N-(2-Acetamido)-2-aminoethanesulfonic acid.

The term "PIPES" refers to a pH buffering agent piperazine-1,4-bis(2-ethanesulfonic acid.

The term "Tris-acetate" refers to a pH buffering agent comprising an acetate salt of Tris (hydroxymethyl)-aminomethane.

Figure 2A:
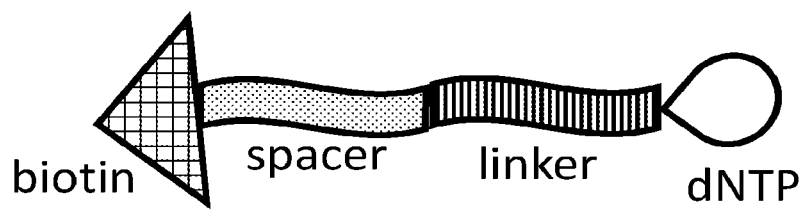
FIG. 2A is an exemplary schematic showing a nucleotide arm of a multivalent molecule.
Figure 2B:
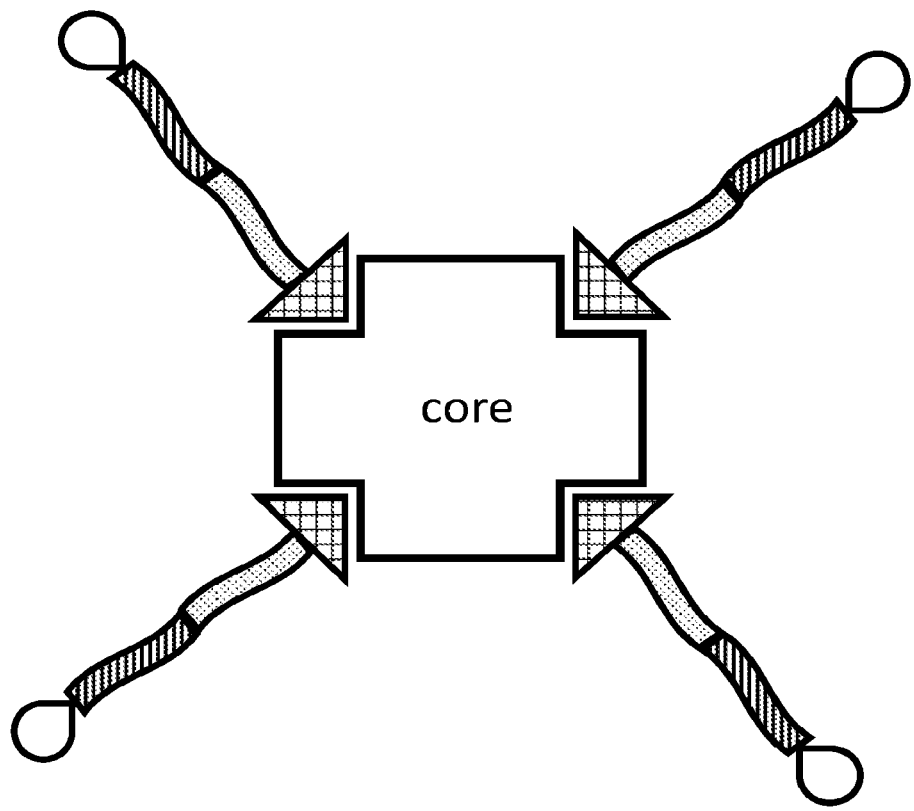
FIG. 2B is an exemplary schematic of a multivalent molecule comprising a core attached to a plurality of nucleotide arms where each nucleotide arm comprises (i) a core attachment moiety, (ii) a spacer, (iii) a linker, and (iv) a nucleotide unit.
Figure 2C:
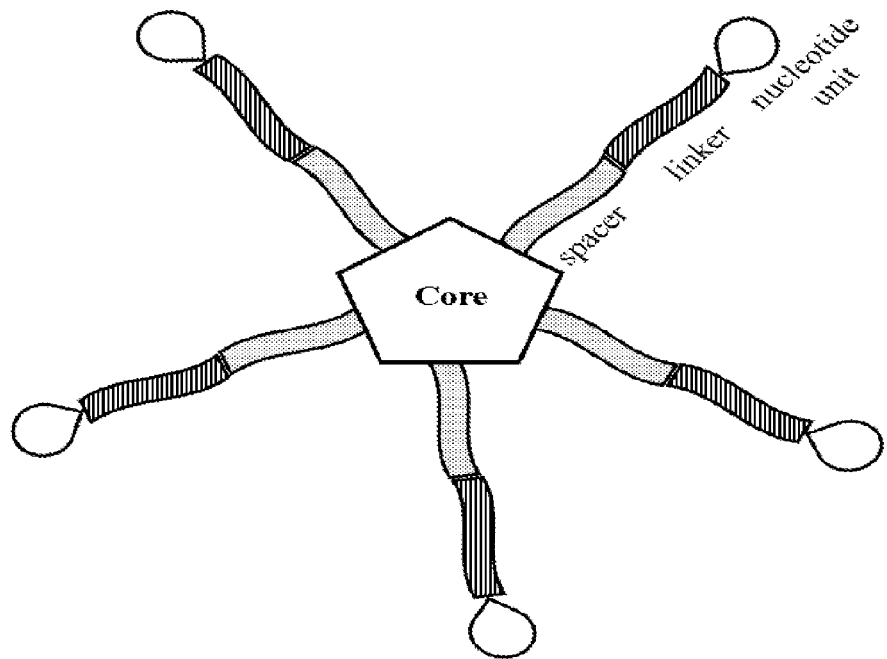
FIG. 2C is a schematic of an exemplary multivalent molecule comprising a generic core attached to a plurality of nucleotide-arms.
Figure 2D:
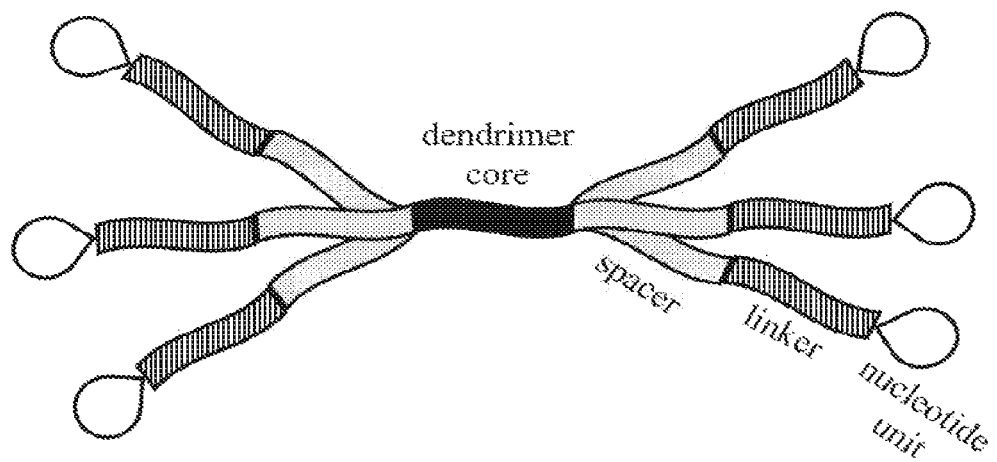
FIG. 2D is a schematic of an exemplary multivalent molecule comprising a dendrimer core attached to a plurality of nucleotide-arms.

The term "multivalent molecule" refers to a molecule comprising a plurality of binding motifs. In some embodiments, the plurality of binding motifs are each configured to bind to a nucleic acid base (e.g., A, C, T, G, or U). In some cases, the multivalent molecule comprises: (a) a core; and (b) a plurality of nucleotide arms which each comprise (i) a core attachment moiety, (ii) a spacer comprising a PEG moiety, (iii) a linker, and (iv) a nucleotide unit. FIG. 2B illustrates an example of a multivalent molecule, in accordance with some embodiments.

The term, "ternary complex" or "ternary binding complex" refers to a complex comprising three components. In some embodiments, the ternary complex comprises: (a) a multivalent molecule disclosed herein, (b) a primed nucleic acid sequence, and (c) a polymerizing enzyme.

INTRODUCTION

The present disclosure provides compositions and methods that employ the compositions for conducting massively parallel nucleic acid sequencing workflows, where the workflows include, but are not limited to nucleic acid library preparation, library circularization, library molecule amplification, library immobilization to a support, polony formation of nucleic acid template molecules and sequencing the nucleic acid template molecules.

The present disclosure provides compositions comprising reagents used to conduct nucleic acid sequencing workflows, where the compositions include: a universal wash reagent; a nucleic acid hybridization reagent; a first and second amplification reagent; a wash-removal reagent; a trap reagent; a post-trap reagent; an imaging reagent; stepping reagent; and a cleaving reagent.

The present disclosure provides a nucleic acid sequencing workflow which employs the various reagents described above, where the sequencing workflow generally comprises polony formation and sequence-determining reactions.

In some embodiments, the polony-forming workflow generally comprises: hybridizing nucleic acid template molecules to amplification primers to form nucleic acid duplexes; amplifying the nucleic acid duplexes to form a plurality of concatemers where an individual concatemer in the plurality of concatemers is a polony.

In some embodiments, the sequence-determining reaction workflow generally comprises: forming ternary complexes by binding together the concatemer template molecules with sequencing primers, sequencing polymerases and multivalent molecules under conditions suitable for inhibiting polymerase-catalyzed incorporation of nucleotide units from the multivalent molecules; imaging signals from the bound multivalent molecules in the ternary complexes; dissociating the ternary complexes; forming ternary complexes by binding together the concatemer template molecules with sequencing primers, sequencing polymerases and nucleotides (e.g., chain terminator nucleotides) under conditions suitable for promoting polymerase-catalyzed incorporation of nucleotides thereby extending the sequencing primers with the nucleotides to form a nascent sequencing primer chain; and forming 3' terminal extendible ends of the nascent sequencing primer chains.

Nucleic Acid Fragmentation

The present disclosure provides reagents, kits and methods for preparing a population of fragmented nucleic acids. In some embodiments, individual fragmented nucleic acids will be covalently joined to at least one universal adaptor sequence for library preparation.

The insert region of a nucleic acid library molecule comprises a sequence of interest extracted from any source including a biological sample (e.g., fresh or live sample) such as a single cell, a plurality of cells or tissue. The insert region can be isolated from healthy or diseases cells or tissues. The insert region can be obtained from an archived sample such as a fresh frozen paraffin embedded (FFPE) sample, or from needle biopsies, circulating tumor cells, cell free circulating DNA (e.g., from tumor cells or a fetus). Cells or tissues are typically treated with a lysis buffer to release their DNA and RNA, and the desired nucleic acid is separated from non-desired macromolecules such as proteins.

The insert region of a nucleic acid library molecule can be isolated in any form, including chromosomal, genomic (e.g., whole genomic), organellar (e.g., mitochondrial, chloroplast or ribosomal), recombinant molecules, cloned or amplified. The insert region of a nucleic acid library molecule can be methylated or non-methylated.

The insert region can be isolated from any organism including viruses, fungi, prokaryotes or eukaryotes. The insert region can be isolated from any organism including human, simian, ape, canine, feline, bovine, equine, murine, porcine, caprine, lupine, ranine, piscine, plant, insect or bacteria. The insert region can be isolated from organisms borne in air, water, soil or food.

The insert region can be isolated from any biological fluid, including blood, urine, serum, lymph, tumor, saliva, anal secretions, vaginal secretions, amniotic samples, perspiration, semen, environmental samples or culture samples. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

The insert region can be prepared using recombinant nucleic acid technology including but not limited to any combination of vector cloning, transgenic host cell preparation, host cell culturing and/or PCR amplification.

The insert region can be in fragmented or un-fragmented form. Fragmented insert regions can be obtained by mechanical force, enzymatic or chemical fragmentation methods. The fragmented insert regions can be generated using procedures that yield a population of fragments having overlapping sequences or non-overlapping sequences.

Mechanical fragmentation typically generates randomly fragmented nucleic acid molecules. Mechanical fragmentation methods include mechanical shearing such as fluid shear, constant shear and pulsatile shear. Mechanical fragmentation methods also include mechanical stress including sonication, nebulization and acoustic cavitation. In some embodiments focused acoustic energy can be used to randomly fragment nucleic acid molecules. A commercially-available apparatus (e.g., Covaris) can be used to fragment nucleic acid molecules using focused acoustic energy.

Enzymatic fragmentation procedures can be conducted under conditions suitable to generate randomly or non-randomly fragmented nucleic acid molecules. For example, restriction endonuclease enzyme digestion can be conducted to completion to generate non-randomly fragmented nucleic acid molecule. Alternatively, partial or incomplete restriction enzyme digestion can be conducted to generate randomly-fragmented nucleic acid molecules. Enzymatic fragmentation using restriction endonuclease enzymes includes any one or any combination of two or more restriction enzymes selected from a group consisting of type I, type II, type IIs, type IIB, type III, or type IV restriction enzymes. Enzymatic fragmentation includes digestion of the nucleic acid with a rare-cutting restriction enzyme, comprising Not I, Asc I, Bae I, AspC I, Pac I, Fse I, Sap I, Sfi I or Psr I. Enzymatic fragmentation include use of any combination of a nicking restriction endonuclease, endonuclease and/or exonuclease. Enzymatic fragmentation can be achieved by conducting a nick translation reaction.

In some embodiments, enzymatic fragmentation can be achieved by reacting nucleic acids with an enzyme mixture, for example an enzyme that generates single-stranded nicks and another enzyme that catalyzes double-stranded cleavage. An exemplary enzyme mixture is FRAGMENTASE (e.g., from New England Biolabs).

Fragments of the insert region can be generated with PCR using sequence-specific primers that hybridize to target regions in genomic DNA samples to generate insert regions having known fragment lengths and sequences.

Targeted genome fragmentation methods using CRISPR/Cas9 can be used to generate fragmented insert regions.

Fragments of the insert portion can also be generated using a transposase-based tagmentation method using NEXTERA (from Epicentre).

The insert region can be single-stranded or double-stranded. The ends of the double-stranded insert region can be blunt-ended, or have a 5' overhang or a 3' overhang end, or any combination thereof. One or both ends of the insert region can be subjected to an enzymatic tailing reaction to generate a non-template poly-A tail by employing a terminal transferase reaction. The ends of the insert region can be compatible for joining to at least one universal adaptor sequence.

The insert region can be any length, for example the insert region can be about 50-250, or about 250-500, or about 500-750, or about 750-1000 bases or base pairs in length.

The fragments containing the insert region can be subjected to a size selection process, or the fragments are not size selected. For example, the fragments can be size selected by gel electrophoresis and gel slice extraction. The fragments can be size selected using a solid phase adherence/immobilization method which typically employs micro paramagnetic beads coated with a chemical functional group that interacts with nucleic acids under certain ionic strength conditions with or without polyethylene glycol or polyalkylene glycol. Commercially-available solid phase adherence beads include SPRI (Solid Phase Reversible Immobilization) beads from Beckman Coulter (AMPUR XP paramagnetic beads, catalog No. B23318), MAGNA PURE magnetic glass particles (Roche Diagnostics, catalog No. 03003990001), MAGNASIL paramagnetic beads from Promega (catalog No. MD1360), MAGTRATION paramagnetic beads and system from Precision System Science (catalog Nos. A1120 and A1060), MAG-BIND from Omega Bio-Tek (catalog No. M1378-01), MAGPREP silica from Millapore (catalog No. 101193), SNARE DNA purification systems from Bangs Laboratories (catalog Nos. BP691, BP692 and BP693), and CHEMAGEN M-PVA beads from Perkin Elmer (catalog No. CMG-200).

In some embodiments, the fragmented nucleic acids can be subjected to enzymatic reactions for end-repair and/or A-tailing. The fragmented nucleic acids can be contacted with a plurality of enzymes under a condition suitable to generate nucleic acid fragments having blunt-ended 5' phosphorylated ends. In some embodiments, the plurality of enzymes generates blunt-ended fragment having a non-template A-tail at their 3' ends. The plurality of enzymes comprise two or more enzymes that can catalyze nucleic acid end-repair, phosphorylation and/or A-tailing. The end-repair enzymes include a DNA polymerase (e.g., T4 DNA polymerase) and Klenow fragment. The 5' end phosphorylation enzyme comprises T4 polynucleotide kinase. The A-tailing enzyme includes a Taq polymerase (e.g., non-proof-reading polymerase) and dATP. In some embodiments, the fragmenting, end-repair, phosphorylation and A-tailing can be conducted in a one-pot reaction using a mixture of enzymes.

Appending Adaptors to Fragmented Nucleic Acids

The present disclosure provides reagents, kits and methods used to append one or more adaptor sequences to fragmented nucleic acids. In some embodiments, individual fragmented nucleic acids will be covalently joined to at least one universal adaptor sequence for library preparation. In general, a nucleic acid fragment is covalently joined at both ends to one or more universal adaptors to generate a linear library molecule having the arrangement left adaptor-insert-right adaptor. In some embodiments, at least one fragment in the population of fragmented nucleic acids comprises a sequence-of-interest. Individual library molecules in the population of library molecules can have an insert region that is the same or different as other library molecules in the population. In some embodiments, about 1-10 ng, or about 10-50 ng, or about 50-100 ng of input fragmented nucleic acids can be appended to one or more universal adaptors to generate a linear library.

Individual nucleic acid fragments can be appended on one or both ends to at least one universal adaptor sequence to form a recombinant nucleic acid linear library molecule having the general arrangement left adaptor-insert-right adaptor.

In some embodiments, the nucleic acid fragments can be appended with any one or any combination of two or more adaptor sequences comprising a left universal adaptor sequence having a binding sequence for a first surface primer, a right universal adaptor sequence having a binding sequence for a second surface primer, a left universal adaptor sequence having a binding sequence for a first sequencing primer, a right universal adaptor sequence having a binding sequence for a second sequencing primer, a left sample index sequence, a right sample index sequence, a left unique identification sequence, a right unique identification sequence and/or a universal adaptor sequence for binding a compaction oligonucleotide.

The universal adaptors can be prepared using chemical synthesis procedures using native nucleotides with or without nucleotide analogs or modified nucleotide linkages that confer certain properties, including resistance to enzymatic digestion, or increased thermal stability. Examples of nucleotide analogs and modified nucleotide linkages that inhibit nuclease digestion include phosphorothioate, 2'-O-methyl RNA, inverted dT, and 2' 3' dideoxy-dT. Insert regions that include locked nucleic acids (LNA) have increased thermal stability.

The insert region can be joined at one or both ends to at least one universal adaptor sequence using a ligase enzyme and/or primer extension reaction to generate a linear library molecule. Covalent linkage between an insert region and the universal adaptor(s) can be achieved with a DNA or RNA ligase. Exemplary DNA ligases that can ligate double-stranded DNA molecules include T4 DNA ligase and T7 DNA ligase. A universal adaptor sequence can be appended to an insert sequence by PCR using a tailed primer having 5' region carrying a universal adaptor sequence and a 3' region that is complementary to a portion of the insert sequence. A universal adaptor sequence can be appended to an insert sequence which is flanked one side or both sides with first and second universal adaptor sequences by PCR using a tailed primer having 5' region carrying a third universal adaptor sequence and a 3' region that is complementary to a portion of the first or second adaptor sequence.

Nucleic Acid Hybridization Reagents and Methods of Use

The present disclosure provides one or more nucleic acid hybridization reagents, and methods that employ the nucleic acid hybridization reagents where the methods comprise hybridizing nucleic acid template molecules to amplification primers to form a plurality of nucleic acid duplexes (e.g., step (a) of the methods described herein). The hybridization reagents can promote specific hybridization between template molecules of interest with amplification primers. The nucleic acid hybridization reagents can reduce background signals when determining the sequences of the amplified template molecules in a downstream step.

In some embodiments, the nucleic acid hybridization reagents can be used to hybridize library molecules to amplification primers that are immobilized to a support. The support can be a planar support or at least one bead. The nucleic acid hybridization reagents can be used for the massively parallel sequencing workflow step (a) as described below.

In some embodiments, the nucleic acid hybridization reagents comprise at least one solvent, a pH buffering agent, and at least one monovalent cation. The hybridization reagents further comprise any one or any combination of two or more of a detergent, a reducing agent, a chaotropic agent, a chelating agent, an alcohol, a zwitterion, a sugar alcohol and/or a crowding agent.

In some embodiments, the nucleic acid hybridization reagents further comprise at least one nucleic acid template molecule which comprises DNA or RNA, or a mixture of RNA and DNA. In some embodiments, the nucleic acid template molecules comprise linear or circularized molecules, or a mixture of linear and circular molecules. In some embodiments, the nucleic acid template molecules comprise single-stranded molecules, double-stranded molecules or nucleic acid molecules having single- and double-stranded portions. In some embodiments, individual nucleic acid template molecules are operably linked to at least one adaptor, where the adaptor includes a capture primer binding sequence, an amplification primer binding sequence and/or a sequencing primer binding sequence. In some embodiments, individual nucleic acid template molecules are operably linked to at least one adaptor having a sample barcode sequence or a unique molecular tag sequence. In some embodiments, individual nucleic acid template molecules are operably linked to at least one adaptor having a sequence that binds at least a portion of a condenser oligonucleotide.

In some embodiments, the nucleic acid hybridization reagents further comprise at least one nucleic acid amplification duplex which comprises a nucleic acid template molecule hybridized to an amplification oligonucleotide primer. The amplification primer can hybridize to at least a portion of the nucleic acid template molecule. The amplification primer comprises a 3' extendible end or a 3' non-extendible end.

In some embodiments, the amplification primer comprises soluble oligonucleotide primers (e.g., in-solution), or the amplification primer is immobilized to a support or immobilized to a coating (e.g., polymer coating) on the support.

In some embodiments, the nucleic acid hybridization reagents further comprise at least one nucleic acid duplex immobilized to a support, where the nucleic acid duplex comprise a nucleic acid template molecule hybridized to an amplification primer, and where the template molecule and/or the amplification primer is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, a plurality of amplification primers are immobilized to one or more layers of the coatings on the support where the density of the immobilized amplification primers is about 100-100,000 amplification primers per $mm^2$.

In some embodiments, the plurality of immobilized nucleic acid amplification duplexes on the support are in fluid communication with each other to permit flowing a solution of the nucleic acid hybridization reagent onto the support so that the plurality of immobilized amplification duplexes on the support can be essentially simultaneously reacted with the nucleic acid hybridization reagents in a massively parallel manner. In some embodiments, the fluid communication of the plurality of immobilized amplification duplexes can be used to conduct nucleic acid hybridization reactions in a massively parallel manner on the support.

In some embodiments, a nucleic acid hybridization reagent may comprise MES (50 mM, pH 8.8), EDTA (0.5 mM), NaCl (50 mM), and Triton™ X-100 (2-[4-(2,4,4-trimethylpentan-2-yl)phenoxy]ethanol) (0.1%). In some cases, this formulation may be referred to as Formulation HR-A.

In some embodiments, a nucleic acid hybridization reagent may comprise MES (100 mM, pH 8.8), EDTA (0.25 mM), $MgCl_2$ (75 mM), ethylene glycol (5%) and Tween-20 (0.3%). In some cases, this formulation may be referred to as Formulation HR-B.

In some embodiments, a nucleic acid hybridization reagent may comprise MES (200 mM, pH 8.3), EDTA (0.5 mM), NaCl (100 mM), SDS (0.5 M), glycerol (5%), and Tween-20 (0.3%). In some cases, this formulation may be referred to as Formulation HR-C.

In some embodiments, a nucleic acid hybridization reagent may comprise MES (50 mM, pH 7.7), EDTA (5 mM), NaCl (200 mM), SDS (0.25 M), and Triton™ X-100 (2-[4-(2,4,4-trimethylpentan-2-yl)phenoxy]ethanol) (0.03%). In some cases, this formulation may be referred to as Formulation HR-D.

In some embodiments, a nucleic acid hybridization reagent may comprise MES (50 mM, pH 8.2), EDTA (50 mM), $MgCl_2$ (1 M), and Tween-20 (0.1%). In some cases, this formulation may be referred to as Formulation HR-E.

In some embodiments, a nucleic acid hybridization reagent may comprise MES (50 mM, pH 7.6), EDTA (0.5 mM), NaCl (100 mM), guanidium chloride (1 M), and Tween-20 (0.3%). In some cases, this formulation may be referred to as Formulation HR-F.

In some embodiments, a nucleic acid hybridization reagent may comprise MES (50 mM, pH 8), EDTA (0.5 mM), NaCl (100 mM), guanidium chloride (1 M), and Tween-20 (0.3%). In some cases, this formulation may be referred to as Formulation HR-G.

In some embodiments, a nucleic acid hybridization reagent may comprise MES (50 mM, pH 8), EDTA (5 mM), NaCl (100 mM), methanol (1 M), and Triton™ X-100 (2-[4-(2,4,4-trimethylpentan-2-yl)phenoxy]ethanol) (0.3%). In some cases, this formulation may be referred to as Formulation HR-H.

In some embodiments, a nucleic acid hybridization reagent may comprise MES (50 mM, pH 7.9), EDTA (2 mM), NaCl (200 mM), phenol (2 M), and Triton™ X-100 (2-[4-(2,4,4-trimethylpentan-2-yl)phenoxy]ethanol) (0.1%). In some cases, this formulation may be referred to as Formulation HR-I.

In some embodiments, a nucleic acid hybridization reagent may comprise MES (50 mM, pH 8), EDTA (0.5 mM), NaCl (10 mM), guanidium chloride (1 M), and Tween-20 (1%). In some cases, this formulation may be referred to as Formulation HR-J.

Nucleic Acid Amplification Reagents and Methods of Use

The present disclosure provides one or more nucleic acid amplification reagents, and methods that employ the nucleic acid amplification reagents where the methods comprise forming a plurality of complexed amplification polymerases each comprising an amplification polymerase and a nucleotide bound to a nucleic acid amplification duplex (e.g., a nucleic acid template molecule hybridized to an amplification primer). In some embodiments, the nucleic acid amplification reactions can be conducted as a two-stage amplification reaction that employs first and second amplification reagents, respectively. The first amplification reagents can seed a plurality of nucleic acid duplexes with amplification polymerases under a condition that inhibits amplification. The second amplification reagents can promote amplification of the plurality of nucleic acid duplexes so that amplification coincides on the plurality of duplexes at the same time. In some embodiments, the two-stage amplification reaction can be used to generate clonally amplified template molecules which are copied from library molecules, where the clonally amplified template molecules are immobilized to a support.

In some embodiments, the nucleic acid amplification reagents comprises a first amplification reagent, and methods that employ the first amplification reagent where the methods comprise contacting a plurality of nucleic acid duplexes with the first amplification reagent under a condition suitable for forming a plurality of complexed amplification polymerases each comprising an amplification polymerase and a nucleotide bound to a nucleic acid duplex but amplification is inhibited. The first amplification reagent can be used for the massively parallel sequencing workflow of step (c) as described below. In some embodiments, the first amplification reagent comprises at least one solvent, a pH buffering agent, at least one monovalent cation, ammonium ions, a plurality of nucleotides and an amplification polymerase enzyme. In some embodiments, the first amplification reagent further comprises any one or any combination of two or more of a detergent, a reducing agent, a viscosity agent. In some embodiments, the pH of the first amplification reagent is suitable for binding the amplification polymerase to a nucleic acid duplex which comprises a nucleic acid template molecule hybridized to an amplification oligonucleotide primer. In some embodiments, the pH of the first amplification reagent can reduce/inhibit activity of the amplification polymerase (e.g., polymerase-catalyzed nucleotide incorporation activity). For example, the pH of the first amplification reagent can be about pH 8 or lower (e.g., pH 7-8).

In some embodiments, the amplification polymerase has strand displacement activity. The amplification polymerase comprises a wild type or mutant amino acid sequence.

In some embodiments, the plurality of nucleotides comprise a mixture of two or more nucleotides selected from a group consisting of dATP, dGTP, dCTP and dTTP. In some embodiments, the plurality of nucleotides comprise a mixture of four types of nucleotides including dATP, dGTP, dCTP and dTTP.

In some embodiments, the first amplification reagents further comprise at least one nucleic acid template molecule which comprises DNA or RNA, or a mixture of RNA and DNA. In some embodiments, the nucleic acid template molecules comprise linear or circularized molecules, or a mixture of linear and circular molecules. In some embodiments, the nucleic acid template molecules comprise single-stranded molecules, double-stranded molecules or nucleic acid molecules having single- and double-stranded portions. In some embodiments, individual nucleic acid template molecules are operably linked to at least one adaptor, where the adaptor includes a capture primer binding sequence, an amplification primer binding sequence and/or a sequencing primer binding sequence. In some embodiments, individual nucleic acid template molecules are operably linked to at least one adaptor having a sample barcode sequence or a unique molecular tag sequence. In some embodiments, the amount of circular or linear library molecules that can be reacted with the first amplification reagent is about 1-10 fmol, or about 10-25 fmol, or about 25-50 fmol, or about 50-100 fmol, or about 100-200 fmol. In some embodiments, the amount of circular or linear library molecules that can be reacted with the first amplification reagent is about 1-10 pmol, or about 10-25 pmol, or about 25-50 pmol, or about 50-100 pmol, or about 100-200 pmol.

In some embodiments, the first amplification reagents further comprise at least one nucleic acid amplification duplex which comprises a nucleic acid template molecule hybridized to an amplification oligonucleotide primer. The amplification primer can hybridize to at least a portion of the nucleic acid template molecule. The amplification primer comprises a 3' extendible end or a 3' non-extendible end.

In some embodiments, the amplification primer comprises soluble oligonucleotide primers (e.g., in-solution), or the amplification primer is immobilized to a support or immobilized to a coating (e.g., polymer coating) on the support.

In some embodiments, the first amplification reagents further comprise at least one nucleic acid duplex immobilized to a support, where the nucleic acid duplex comprise a nucleic acid template molecule hybridized to an amplification primer, and where the template molecule and/or the amplification primer is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, a plurality of amplification primers are immobilized to one or more layers of the coatings on the support where the density of the immobilized amplification primers is about 100-100,000 amplification primers per $mm^2$.

In some embodiments, the plurality of immobilized nucleic acid amplification duplexes on the support are in fluid communication with each other to permit flowing a solution of the first amplification reagent onto the support so that the plurality of immobilized amplification duplexes on the support can be essentially simultaneously reacted with the first amplification reagent in a massively parallel manner. In some embodiments, the fluid communication of the plurality of immobilized amplification duplexes can be used to conduct nucleic acid amplification reactions in a massively parallel manner on the support.

In some embodiments, the nucleic acid amplification reagents comprises a second amplification reagent, and methods that employ the nucleic acid amplification reagents where the methods comprise contacting a plurality of the complexed amplification polymerases with a second amplification reagent under a condition that is suitable for retaining the complexed amplification polymerases and promoting amplification to generate amplicons having sequences that are complementary to their respective library molecule. The second amplification reagents can be used for the massively parallel sequencing workflow of step (d) described below).

In some embodiments, the amplification reaction can generate concatemer template molecules containing tandem repeat sequences of the circular library molecule including any insert and adaptor sequences present in the original circularized nucleic acid library molecule. In some embodiments, the amplification reaction can generate linear template molecules having one copy of the linear library molecule including any insert and adaptor sequences present in the original linear nucleic acid library molecule. In some embodiments, the second amplification reagent comprises at least one solvent, a pH buffering agent, at least one monovalent cation, ammonium ions and a plurality of nucleotides. In some embodiments, the second amplification reagent lacks an amplification polymerase enzyme. In some embodiments, the second amplification reagent further comprise any one or any combination of two or more of a detergent, a reducing agent, a viscosity agenT. In some embodiments, the first and second amplification reagents have a different pH. In some embodiments, the pH of the second amplification reagent is suitable for retaining a complex having the amplification polymerase (e.g., from the first amplification reagent) bound to a nucleic acid duplex which comprises a nucleic acid template molecule hybridized to an amplification oligonucleotide primer. In some embodiments, the pH of the second amplification reagent can be suitable for promoting activity of the amplification polymerase (e.g., polymerase-catalyzed nucleotide incorporation activity). For example, the pH of the second amplification reagent can be about pH 8.5 or higher (e.g., pH 8.5-8.8).

In some embodiments, the plurality of nucleotides comprise a mixture of two or more nucleotides selected from a group consisting of dATP, dGTP, dCTP and dTTP. In some embodiments, the plurality of nucleotides comprise a mixture of four types of nucleotides including dATP, dGTP, dCTP and dTTP. In some embodiments, the plurality of nucleotides comprise a mixture of five types of nucleotides including dATP, dGTP, dCTP, dTTP and dUTP.

In some embodiments, the second amplification reagents further comprise at least one nucleic acid amplification duplex which comprises a nucleic acid template molecule (e.g., linear or circular template molecules) hybridized to an amplification oligonucleotide primer. The amplification primer can hybridize to at least a portion of the nucleic acid template molecule. The amplification primer comprises a 3' extendible end or a 3' non-extendible end.

In some embodiments, the amplification primer comprises soluble oligonucleotide primers (e.g., in-solution), or the amplification primer is immobilized to a support or immobilized to a coating (e.g., polymer coating) on the support.

In some embodiments, the second amplification reagents further comprise at least one nucleic acid duplex immobilized to a support, where the nucleic acid duplex comprise a nucleic acid template molecule (e.g., linear or circular template molecule) hybridized to an amplification primer, and where the template molecule and/or the amplification primer is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, a plurality of amplification primers are immobilized to one or more layers of the coatings on the support where the density of the immobilized amplification primers is about 100-100,000 amplification primers per $mm^2$.

In some embodiments, the plurality of immobilized nucleic acid amplification duplexes on the support are in fluid communication with each other to permit flowing a solution of the second amplification reagent onto the support so that the plurality of immobilized amplification duplexes on the support can be essentially simultaneously reacted with the second amplification reagent in a massively parallel manner. In some embodiments, the fluid communication of the plurality of immobilized amplification duplexes can be used to conduct nucleic acid amplification reactions in a massively parallel manner on the support.

In some embodiments, the second amplification reagents further comprise at least one concatemer immobilized to a support, and where the concatemer is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, a plurality of concatemers are immobilized to one or more layers of the coatings on the support where the density of the immobilized concatemers is about 100-100,000 amplification primers per $mm^2$.

In some embodiments, the plurality of immobilized concatemers on the support are in fluid communication with each other to permit flowing a solution of the second amplification reagent onto the support so that the plurality of immobilized concatemers on the support can be essentially simultaneously reacted with the second amplification reagent in a massively parallel manner. In some embodiments, the fluid communication of the plurality of immobilized concatemers can be used to conduct nucleic acid amplification reactions in a massively parallel manner on the support.

In some embodiments, a first amplification reagent may comprise Tris (50 mM, pH 8), $MgSO_4$ (20 mM), KCl (50 mM), $(NH_4)SO_4$ (30 mM), Tween-80 (0.5%), DTT (1 mM), Betaine (0.8 M), sucrose (0.3 M), dATP (2 mM), dGTP (2 mM), dCTP (2 mM), dTTP (2 mM), dUTP (0.01 mM), and an amplification polymerase (120 nM). In some cases, this formulation may be referred to as Formulation AR1-A.

In some embodiments, a first amplification reagent may comprise Tris (10 mM, pH 8), $MgSO_4$ (30 mM), KCl (20 mM), Triton™ X-100 (2-[4-(2,4,4-trimethylpentan-2-yl) phenoxy]ethanol) (0.2%), DTT (2 mM), Betaine (0.8 M), sucrose (0.1 M), dATP (1 mM), dGTP (1 mM), dCTP (1 mM), dTTP (0.99 mM), dUTP (0.02 mM), and an amplification polymerase (240 nM). In some cases, this formulation may be referred to as Formulation AR1-B.

In some embodiments, a first amplification reagent may comprise Tris (50 mM, pH 8), MgSO$_4$ (5 mM), KCl (50 mM), NaCl (40 mM), (NH$_4$)SO$_4$ (5 mM), Tween-80 (0.5%), DTT (2 mM), Betaine (0.1 M), sucrose (0.1 M), dATP (2 mM), dGTP (2 mM), dCTP (2 mM), dTTP (0.99 mM), dUTP (0.02 mM), and an amplification polymerase (120 nM). In some cases, this formulation may be referred to as Formulation AR1-C.

In some embodiments, a first amplification reagent may comprise Tris (50 mM, pH 7), MgSO$_4$ (10 mM), KCl (90 mM), (NH$_4$)SO$_4$ (10 mM), Tween-80 (0.1%), DTT (5 mM), Betaine (0.4 M), sucrose (0.4 M), dATP (1 mM), dGTP (1 mM), dCTP (1 mM), dTTP (0.99 mM), dUTP (0.01 mM), and an amplification polymerase (240 nM). In some cases, this formulation may be referred to as Formulation AR1-D.

In some embodiments, a first amplification reagent may comprise Tris (50 mM, pH 7), MgSO$_4$ (70 mM), KCl (30 mM), NaCl (40 mM), (NH$_4$)SO$_4$ (20 mM), Tween-80 (0.5%), DTT (5 mM), Betaine (0.4 M), sucrose (1 M), dATP (1 mM), dGTP (1 mM), dCTP (1 mM), dTTP (0.99 mM), dUTP (0.01 mM), and an amplification polymerase (500 nM). In some cases, this formulation may be referred to as Formulation AR1-E.

In some embodiments, a first amplification reagent may comprise Tris (25 mM, pH 7), MgSO$_4$ (10 mM), KCl (90 mM), (NH$_4$)SO$_4$ (20 mM), Triton™ X-100 (2-[4-(2,4,4-trimethylpentan-2-yl)phenoxy]ethanol) (0.1%), DTT (5 mM), Betaine (0.4 M), sucrose (0.4 M), dATP (1 mM), dGTP (1 mM), dCTP (1 mM), dTTP (0.99 mM), dUTP (0.01 mM), and an amplification polymerase (500 nM). In some cases, this formulation may be referred to as Formulation AR1-F.

In some embodiments, a first amplification reagent may comprise Tris (50 mM, pH 7.5), MgSO$_4$ (10 mM), KCl (10 mM), (NH$_4$)SO$_4$ (30 mM), Tween-80 (0.1%), DTT (5 mM), Betaine (0.4 M), sucrose (0.4 M), dATP (1 mM), dGTP (1 mM), dCTP (1 mM), dTTP (0.99 mM), dUTP (0.01 mM), and an amplification polymerase (120 nM). In some cases, this formulation may be referred to as Formulation AR1-G.

In some embodiments, a first amplification reagent may comprise Tris (50 mM, pH 7.5), KCl (90 mM), (NH$_4$)SO$_4$ (100 mM), Triton™ X-100 (2-[4-(2,4,4-trimethylpentan-2-yl)phenoxy]ethanol) (0.1%), DTT (10 mM), Betaine (0.4 M), sucrose (0.4 M), dATP (1 mM), dGTP (1 mM), dCTP (1 mM), dTTP (0.99 mM), dUTP (0.01 mM), and an amplification polymerase (240 nM). In some cases, this formulation may be referred to as Formulation AR1-H.

In some embodiments, a second amplification reagent may comprise Tris (75 mM, pH 8.5), MgSO$_4$ (10 mM), KCl (200 mM), (NH$_4$)SO$_4$ (30 mM), Tween-80 (0.3%), DTT (10 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-A.

In some embodiments, a second amplification reagent may comprise Tris (50 mM, pH 8.5), MgSO$_4$ (10 mM), KCl (90 mM), (NH$_4$)SO$_4$ (10 mM), Tween-80 (0.1%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-B.

In some embodiments, a second amplification reagent may comprise Tris (50 mM, pH 8.5), MgSO$_4$ (20 mM), KCl (150 mM), (NH$_4$)SO$_4$ (10 mM), Tween-80 (0.1%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-C.

In some embodiments, a second amplification reagent may comprise Tris (50 mM, pH 8.5), MgSO$_4$ (10 mM), KCl (90 mM), (NH$_4$)SO$_4$ (10 mM), Triton™ X-100 (2-[4-(2,4,4-trimethylpentan-2-yl)phenoxy]ethanol) (0.5%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-D.

In some embodiments, a second amplification reagent may comprise Tris (50 mM, pH 8.5), MgSO$_4$ (50 mM), NaCl (150 mM), (NH$_4$)SO$_4$ (10 mM), Triton™ X-100 (2-[4-(2,4,4-trimethylpentan-2-yl)phenoxy]ethanol) (0.1%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-E.

In some embodiments, a second amplification reagent may comprise Tris (50 mM, pH 8.5), MgSO$_4$ (10 mM), NaCl (200 mM), (NH$_4$)SO$_4$ (30 mM), Tween-80 (0.3%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-F.

In some embodiments, a second amplification reagent may comprise Tris (50 mM, pH 8.5), MgSO$_4$ (5 mM), NaCl (90 mM), (NH$_4$)SO$_4$ (10 mM), SDS (0.5%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-G.

In some embodiments, a second amplification reagent may comprise Tris (50 mM, pH 8.5), MgSO$_4$ (20 mM), KCl (15 mM), (NH$_4$)SO$_4$ (10 mM), SDS (0.3%), DTT (5 mM), Betaine (0.4 M), sucrose (0.4 M), dATP (1 mM), dGTP (1 mM), dCTP (1 mM), dTTP (0.99 mM), and dUTP (0.01 mM). In some cases, this formulation may be referred to as Formulation AR2-H.

In some embodiments, a second amplification reagent may comprise Tris (50 mM, pH 8.5), NaCl (45 mM), (NH$_4$)SO$_4$ (50 mM), Tween-80 (0.1%), DTT (5 mM), Betaine (0.4 M), sucrose (0.8 M), dATP (1 mM), dGTP (1 mM), dCTP (1 mM), dTTP (0.99 mM), and dUTP (0.05 mM). In some cases, this formulation may be referred to as Formulation AR2-I.

Universal Wash Reagents and Methods of Use

The present disclosure provides one or more universal wash reagents, and methods that employ the universal wash reagents. The universal wash reagents can be used to wash away unreacted components after any of the steps described herein. In some embodiments, the universal wash reagent comprises at least one solvent, a pH buffering agent, a chelating agent, at least one monovalent cation and a detergent.

The universal wash reagents can be used for the massively parallel sequencing workflow prior to step (a), at step (b), at step (f), at step (l), at step (o) and/or at step (q), as described below.

In some embodiments, methods using the universal wash reagents include: conducting a step pre-(a) which is conducted prior to conducting the nucleic acid hybridization of step (a). the step pre(a) comprises: washing the immobilized amplification primers with the wash reagent.

In some embodiments, methods using the universal wash reagents include: conducting a washing step (b) which comprises washing the plurality of immobilized nucleic acid duplexes with a universal wash reagent.

In some embodiments, methods using the universal wash reagents include: conducting a washing step (f) which comprises washing the plurality of concatemers with the universal wash reagent.

In some embodiments, methods using the universal wash reagents include: conducting a washing step (l) which comprises washing the plurality of immobilized nucleic acid duplexes with the universal wash reagent.

In some embodiments, methods using the universal wash reagents include: conducting a washing step (o) which comprises washing the plurality of immobilized nucleic acid duplexes having extended sequencing primers with the universal wash reagent.

In some embodiments, methods using the universal wash reagents include: conducting a washing step (q) which comprises washing the plurality of immobilized nucleic acid duplexes having extended sequencing primers with the universal wash reagent.

In some embodiments, a universal wash reagent may comprise Tris (10 mM, pH 8), EDTA (0.5 mM), NaCl (100 mM), Tween-20 (0.3%). In some cases, this formulation may be referred to as Formulation UWR-A.

In some embodiments, a universal wash reagent may comprise Tris (20 mM, pH 8), EDTA (0.5 mM), NaCl (100 mM), Tween-20 (0.3%). In some cases, this formulation may be referred to as Formulation UWR-B.

In some embodiments, a universal wash reagent may comprise Tris (30 mM, pH 8), EDTA (0.5 mM), NaCl (100 mM), Tween-20 (0.3%). In some cases, this formulation may be referred to as Formulation UWR-C.

In some embodiments, a universal wash reagent may comprise Tris (40 mM, pH 8), EDTA (0.5 mM), NaCl (100 mM), Tween-20 (0.3%). In some cases, this formulation may be referred to as Formulation UWR-D.

In some embodiments, a universal wash reagent may comprise Tris (10 mM, pH 8.2), EDTA (0.5 mM), NaCl (100 mM), Tween-20 (0.3%). In some cases, this formulation may be referred to as Formulation UWR-E.

In some embodiments, a universal wash reagent may comprise Tris (10 mM, pH 8.4), EDTA (0.5 mM), NaCl (100 mM), Tween-20 (0.3%). In some cases, this formulation may be referred to as Formulation UWR-F.

In some embodiments, a universal wash reagent may comprise Tris (10 mM, pH 8.6), EDTA (0.5 mM), NaCl (100 mM), Tween-20 (0.3%). In some cases, this formulation may be referred to as Formulation UWR-G.

In some embodiments, a universal wash reagent may comprise Tris (10 mM, pH 8.8), EDTA (0.5 mM), NaCl (100 mM), Tween-20 (0.3%). In some cases, this formulation may be referred to as Formulation UWR-H.

In some embodiments, a universal wash reagent may comprise Tris (10 mM, pH 8), EDTA (1 mM), NaCl (100 mM), Tween-20 (0.3%). In some cases, this formulation may be referred to as Formulation UWR-I.

In some embodiments, a universal wash reagent may comprise Tris (10 mM, pH 8), EDTA (1.5 mM), NaCl (100 mM), Tween-20 (0.3%). In some cases, this formulation may be referred to as Formulation UWR-J.

In some embodiments, a universal wash reagent may comprise Tris (10 mM, pH 8), EDTA (2 mM), NaCl (100 mM), Tween-20 (0.3%). In some cases, this formulation may be referred to as Formulation UWR-K.

In some embodiments, a universal wash reagent may comprise Tris (10 mM, pH 8), EDTA (2.5 mM), NaCl (100 mM), Tween-20 (0.3%). In some cases, this formulation may be referred to as Formulation UWR-L.

In some embodiments, a universal wash reagent may comprise Tris (10 mM, pH 8), EDTA (0.5 mM), NaCl (100 mM), Tween-20 (0.5%). In some cases, this formulation may be referred to as Formulation UWR-M.

In some embodiments, a universal wash reagent may comprise Tris (10 mM, pH 8), EDTA (0.5 mM), NaCl (100 mM), Tween-20 (1%). In some cases, this formulation may be referred to as Formulation UWR-N.

In some embodiments, a universal wash reagent may comprise Tris (10 mM, pH 8), EDTA (0.5 mM), NaCl (100 mM), Tween-20 (2%). In some cases, this formulation may be referred to as Formulation UWR-O.

In some embodiments, a universal wash reagent may comprise Tris (10 mM, pH 8), EDTA (0.5 mM), NaCl (100 mM), Tween-20 (3%). In some cases, this formulation may be referred to as Formulation UWR-P.

In some embodiments, a universal wash reagent may comprise Tris (10 mM, pH 8.2), EDTA (0.1 mM), NaCl (100 mM), Triton™ X-100 (2-[4-(2,4,4-trimethylpentan-2-yl)phenoxy]ethanol) (0.1%). In some cases, this formulation may be referred to as Formulation UWR-Q.

In some embodiments, a universal wash reagent may comprise Tris (10 mM, pH 8.6), EDTA (0.2 mM), NaCl (100 mM), Triton™ X-100 (2-[4-(2,4,4-trimethylpentan-2-yl)phenoxy]ethanol) (0.1%). In some cases, this formulation may be referred to as Formulation UWR-R.

In some embodiments, a universal wash reagent may comprise Tris (10 mM, pH 8.4), EDTA (0.3 mM), NaCl (100 mM), Triton™ X-100 (2-[4-(2,4,4-trimethylpentan-2-yl)phenoxy]ethanol) (0.1%). In some cases, this formulation may be referred to as Formulation UWR-S.

In some embodiments, a universal wash reagent may comprise Tris (10 mM, pH 8.0), EDTA (0.4 mM), NaCl (100 mM), Triton™ X-100 (2-[4-(2,4,4-trimethylpentan-2-yl)phenoxy]ethanol) (0.1%). In some cases, this formulation may be referred to as Formulation UWR-T.

In some embodiments, a universal wash reagent may comprise Tris (10 mM, pH 8.8), EDTA (0.5 mM), NaCl (10 mM), Triton™ X-100 (2-[4-(2,4,4-trimethylpentan-2-yl)phenoxy]ethanol) (0.3%). In some cases, this formulation may be referred to as Formulation UWR-U.

In some embodiments, a universal wash reagent may comprise Tris (10 mM, pH 8.8), EDTA (0.5 mM), NaCl (25 mM), Triton™ X-100 (2-[4-(2,4,4-trimethylpentan-2-yl)phenoxy]ethanol) (1%). In some cases, this formulation may be referred to as Formulation UWR-V.

In some embodiments, a universal wash reagent may comprise Tris (10 mM, pH 8.8), EDTA (0.5 mM), NaCl (50 mM), Triton™ X-100 (2-[4-(2,4,4-trimethylpentan-2-yl)phenoxy]ethanol) (0.2%). In some cases, this formulation may be referred to as Formulation UWR-W.

In some embodiments, a universal wash reagent may comprise Tris (10 mM, pH 8.8), EDTA (0.5 mM), NaCl (75 mM), Triton™ X-100 (2-[4-(2,4,4-trimethylpentan-2-yl)phenoxy]ethanol) (2%). In some cases, this formulation may be referred to as Formulation UWR-X.

In some embodiments, a universal wash reagent may comprise Tris (40 mM, pH 8.8), EDTA (0.4 mM), NaCl (100 mM), Triton™ X-100 (2-[4-(2,4,4-trimethylpentan-2-yl)phenoxy]ethanol) (0.1%). In some cases, this formulation may be referred to as Formulation UWR-Y.

In some embodiments, a universal wash reagent may comprise Tris (30 mM, pH 8.8), EDTA (0.1 mM), NaCl (100 mM), Triton™ X-100 (2-[4-(2,4,4-trimethylpentan-2-yl)phenoxy]ethanol) (0.1%). In some cases, this formulation may be referred to as Formulation UWR-Z.

In some embodiments, a universal wash reagent may comprise Tris (20 mM, pH 8.8), EDTA (0.3 mM), NaCl (100 mM), Triton™ X-100 (2-[4-(2,4,4-trimethylpentan-2-yl)phenoxy]ethanol) (0.1%). In some cases, this formulation may be referred to as Formulation UWR-AA.

In some embodiments, a universal wash reagent may comprise Tris (10 mM, pH 8.0), EDTA (0.1 mM), NaCl (100 mM), Triton™ X-100 (2-[4-(2,4,4-trimethylpentan-2-yl)phenoxy]ethanol) (0.1%). In some cases, this formulation may be referred to as Formulation UWR-AB.

In some embodiments, a universal wash reagent may comprise Tris (10 mM, pH 8.2), EDTA (0.2 mM), NaCl (100 mM), Triton™ X-100 (2-[4-(2,4,4-trimethylpentan-2-yl)phenoxy]ethanol) (0.1%). In some cases, this formulation may be referred to as Formulation UWR-AC.

In some embodiments, a universal wash reagent may comprise Tris (10 mM, pH 8.4), EDTA (0.5 mM), NaCl (100 mM), Triton™ X-100 (2-[4-(2,4,4-trimethylpentan-2-yl)phenoxy]ethanol) (0.2%). In some cases, this formulation may be referred to as Formulation UWR-AD.

In some embodiments, a universal wash reagent may comprise Tris (10 mM, pH 8.6), EDTA (1 mM), NaCl (100 mM), Triton™ X-100 (2-[4-(2,4,4-trimethylpentan-2-yl)phenoxy]ethanol) (0.4%). In some cases, this formulation may be referred to as Formulation UWR-AE.

In some embodiments, a universal wash reagent may comprise Tris (10 mM, pH 8.4), EDTA (0.3 mM), NaCl (100 mM), Triton™ X-100 (2-[4-(2,4,4-trimethylpentan-2-yl)phenoxy]ethanol) (0.2%). In some cases, this formulation may be referred to as Formulation UWR-AF.

In some embodiments, a universal wash reagent may comprise Tris (10 mM, pH 8.8), EDTA (0.5 mM), NaCl (100 mM), Triton™ X-100 (2-[4-(2,4,4-trimethylpentan-2-yl)phenoxy]ethanol) (0.1%). In some cases, this formulation may be referred to as Formulation UWR-AG.

In some embodiments, a universal wash reagent may comprise Tris-HCl (5 mM, pH 8.8), EDTA (0.1 mM), NaCl (50 mM), Triton™ X-100 (2-[4-(2,4,4-trimethylpentan-2-yl)phenoxy]ethanol) (0.1%). In some cases, this formulation may be referred to as Formulation UWR-AH.

In some embodiments, a universal wash reagent may comprise Tris-HCl (25 mM, pH 8.5), EDTA (0.5 mM), NaCl (60 mM), Triton™ X-100 (2-[4-(2,4,4-trimethylpentan-2-yl)phenoxy]ethanol) (0.1%). In some cases, this formulation may be referred to as Formulation UWR-AI.

In some embodiments, a universal wash reagent may comprise Tris-HCl (10 mM, pH 8.2), EDTA (0.2 mM), NaCl (70 mM), Triton™ X-100 (2-[4-(2,4,4-trimethylpentan-2-yl)phenoxy]ethanol) (0.1%). In some cases, this formulation may be referred to as Formulation UWR-AJ.

In some embodiments, a universal wash reagent may comprise Tris-HCl (25 mM, pH 8.7), EDTA (0.7 mM), NaCl (80 mM), Triton™ X-100 (2-[4-(2,4,4-trimethylpentan-2-yl)phenoxy]ethanol) (0.1%). In some cases, this formulation may be referred to as Formulation UWR-AK.

In some embodiments, a universal wash reagent may comprise Tris-HCl (50 mM, pH 8.4), EDTA (0.4 mM), NaCl (90 mM), Triton™ X-100 (2-[4-(2,4,4-trimethylpentan-2-yl)phenoxy]ethanol) (0.1%). In some cases, this formulation may be referred to as Formulation UWR-AL.

In some embodiments, a universal wash reagent may comprise Tris-HCl (25 mM, pH 8.8), EDTA (0.1 mM), NaCl (100 mM), Triton™ X-100 (2-[4-(2,4,4-trimethylpentan-2-yl)phenoxy]ethanol) (0.1%). In some cases, this formulation may be referred to as Formulation UWR-AM.

In some embodiments, a universal wash reagent may comprise Tris-HCl (5 mM, pH 8.5), EDTA (0.4 mM), NaCl (75 mM), Triton™ X-100 (2-[4-(2,4,4-trimethylpentan-2-yl)phenoxy]ethanol) (0.4%). In some cases, this formulation may be referred to as Formulation UWR-AN.

In some embodiments, a universal wash reagent may comprise Tris-HCl (20 mM, pH 8.2), EDTA (0.2 mM), NaCl (75 mM), Triton™ X-100 (2-[4-(2,4,4-trimethylpentan-2-yl)phenoxy]ethanol) (0.7%). In some cases, this formulation may be referred to as Formulation UWR-AO.

In some embodiments, a universal wash reagent may comprise Tris-HCl (40 mM, pH 8.4), EDTA (0.7 mM), NaCl (200 mM), Triton™ X-100 (2-[4-(2,4,4-trimethylpentan-2-yl)phenoxy]ethanol) (0.3%). In some cases, this formulation may be referred to as Formulation UWR-AP.

In some embodiments, a universal wash reagent may comprise Tris-HCl (100 mM, pH 8.6), EDTA (0.3 mM), NaCl (50 mM), Triton™ X-100 (2-[4-(2,4,4-trimethylpentan-2-yl)phenoxy]ethanol) (2%). In some cases, this formulation may be referred to as Formulation UWR-AQ.

In some embodiments, a universal wash reagent may comprise Tris-HCl (30 mM, pH 8.1), EDTA (0.2 mM), NaCl (20 mM), Triton™ X-100 (2-[4-(2,4,4-trimethylpentan-2-yl)phenoxy]ethanol) (0.1%). In some cases, this formulation may be referred to as Formulation UWR-AR.

In some embodiments, a universal wash reagent may comprise Tris-HCl (50 mM, pH 8), EDTA (0.1 mM, pH 7.5), NaCl (750 mM), Tween-20 (0.01%). In some cases, this formulation may be referred to as Formulation UWR-AS.

In some embodiments, a universal wash reagent may comprise Tris-HCl (60 mM, pH 8), EDTA (0.1 mM, pH 7.8), NaCl (50 mM), Tween-20 (0.05%). In some cases, this formulation may be referred to as Formulation UWR-AT.

In some embodiments, a universal wash reagent may comprise Tris-HCl (70 mM, pH 8), EDTA (0.2 mM, pH 7.8), NaCl (250 mM), Tween-20 (0.07%). In some cases, this formulation may be referred to as Formulation UWR-AU.

In some embodiments, a universal wash reagent may comprise Tris-HCl (70 mM, pH 8), EDTA (0.2 mM, pH 7.7), NaCl (100 mM), Tween-20 (0.04%). In some cases, this formulation may be referred to as Formulation UWR-AV.

In some embodiments, a universal wash reagent may comprise Tris-HCl (50 mM, pH 8), EDTA (0.3 mM, pH 7.6), NaCl (300 mM), Tween-20 (0.02%). In some cases, this formulation may be referred to as Formulation UWR-AW.

In some embodiments, a universal wash reagent may comprise Tris-HCl (60 mM, pH 8), EDTA (0.3 mM, pH 7.5), NaCl (20 mM), Tween-20 (0.01%). In some cases, this formulation may be referred to as Formulation UWR-AX.

In some embodiments, a universal wash reagent may comprise Tris-HCl (70 mM, pH 8), EDTA (0.4 mM, pH 7.7), NaCl (10 mM), Tween-20 (0.05%). In some cases, this formulation may be referred to as Formulation UWR-AY.

In some embodiments, a universal wash reagent may comprise Tris-HCl (80 mM, pH 8), EDTA (0.4 mM, pH 7.5), NaCl (100 mM), Tween-20 (0.07%). In some cases, this formulation may be referred to as Formulation UWR-AZ.

In some embodiments, a universal wash reagent may comprise Tris-HCl (30 mM, pH 8), EDTA (0.5 mM, pH 7.6), NaCl (50 mM), Tween-20 (0.04%). In some cases, this formulation may be referred to as Formulation UWR-BA.

In some embodiments, a universal wash reagent may comprise Tris-HCl (40 mM, pH 8), EDTA (0.5 mM, pH 7.7), NaCl (750 mM), Tween-20 (0.02%). In some cases, this formulation may be referred to as Formulation UWR-BB.

In some embodiments, a universal wash reagent may comprise Tris-HCl (50 mM, pH 8), EDTA (0.6 mM, pH 7.6), NaCl (1 M), Tween-20 (0.01%). In some cases, this formulation may be referred to as Formulation UWR-BC.

Wash-Removal Reagents and Methods of Use

The present disclosure provides one or more wash-removal reagents, and methods that employ the wash-removal reagents.

In some embodiments, methods that employ the wash-removal reagents include contacting the plurality of concatemers with the wash-removal reagent to remove amplification polymerases and unreacted nucleotides after using the first and second amplification reagents. The wash-removal reagents can be used for the massively parallel sequencing workflow at step (e) as described below.

In some embodiments, methods using the wash-removal reagents include contacting the plurality of immobilized fluorescently-labeled ternary complexes with a wash-removal reagent to remove unbound sequencing polymerases and unbound multivalent molecules. The wash-removal reagent can be used for the massively parallel sequencing workflow at step (k) as described below.

In some embodiments, the wash-removal reagent comprises at least one solvent, a pH buffering agent, a chelating agent, a detergent and a chaotropic agent.

In some embodiments, a wash-removal reagent comprises Tris (50 mM, pH 8.4), EDTA (10 mM, pH 7.2), SDS (0.1%), Tween-20 (0.5%), and KCl (300 mM). In some cases, this formulation may be referred to as Formulation WRR-A.

In some embodiments, a wash-removal reagent comprises Tris (40 mM, pH 8.2), EDTA (50 mM, pH 7.3), SDS (0.5%), Tween-20 (0.5%), and LiCl (250 mM). In some cases, this formulation may be referred to as Formulation WRR-B.

In some embodiments, a wash-removal reagent comprises Tris (30 mM, pH 8.6), EDTA (100 mM, pH 7.4), SDS (1%), Tween-20 (0.4%), and KCl (350 mM). In some cases, this formulation may be referred to as Formulation WRR-C.

In some embodiments, a wash-removal reagent comprises Tris (20 mM, pH 8.4), EDTA (100 mM, pH 7.5), SDS (2%), Tween-20 (0.2%), and LiCl (200 mM). In some cases, this formulation may be referred to as Formulation WRR-D.

In some embodiments, a wash-removal reagent comprises Tris (10 mM, pH 8.2), EDTA (50 mM, pH 7.6), SDS (0.3%), Tween-20 (0.1%), and KCl (300 mM). In some cases, this formulation may be referred to as Formulation WRR-E.

In some embodiments, a wash-removal reagent comprises Tris (50 mM, pH 8.6), EDTA (20 mM, pH 7.3), SDS (1%), Triton™ X-100 (2-[4-(2,4,4-trimethylpentan-2-yl)phenoxy]ethanol) (0.5%), and KCl (250 mM). In some cases, this formulation may be referred to as Formulation WRR-F.

In some embodiments, a wash-removal reagent comprises Tris (40 mM, pH 8.4), EDTA (10 mM, pH 7.4), Triton™ X-100 (2-[4-(2,4,4-trimethylpentan-2-yl)phenoxy]ethanol) (2%), and LiCl (350 mM). In some cases, this formulation may be referred to as Formulation WRR-G.

In some embodiments, a wash-removal reagent comprises Tris (30 mM, pH 8.2), EDTA (50 mM, pH 7.5), SDS (0.3%), Triton™ X-100 (2-[4-(2,4,4-trimethylpentan-2-yl)phenoxy]ethanol) (1%), and KCl (200 mM). In some cases, this formulation may be referred to as Formulation WRR-H.

In some embodiments, a wash-removal reagent comprises Tris (20 mM, pH 8.4), EDTA (20 mM, pH 7.5), SDS (0.5%), Triton™ X-100 (2-[4-(2,4,4-trimethylpentan-2-yl)phenoxy]ethanol) (0.1%), and LiCl (300 mM). In some cases, this formulation may be referred to as Formulation WRR-I.

In some embodiments, a wash-removal reagent comprises Tris (10 mM, pH 8.2), EDTA (200 mM, pH 7.6), SDS (0.3%), Triton™ X-100 (2-[4-(2,4,4-trimethylpentan-2-yl)phenoxy]ethanol) (0.5%), and KCl (350 mM). In some cases, this formulation may be referred to as Formulation WRR-J.

Trap Reagents and Methods of Use

The present disclosure provides one or more trap reagents, and methods that employ the trap reagents where the methods comprise forming a plurality of ternary complexes by contacting the plurality of template molecules (e.g., concatemers or single copy template molecules) with a plurality of sequencing primers that hybridize to a sequencing primer binding site on the template molecules, and the trap reagent. The trap reagent comprises a plurality of first sequencing polymerases and nucleotide reagents (e.g., multivalent molecules) and compounds that promote formation of ternary complexes where polymerase-catalyzed incorporation of nucleotide units is inhibited. The template molecules and sequencing primers form ternary complexes in the presence of the trap reagent. The trap reagents can be used for the massively parallel sequencing workflow at step (g) as described below.

In some embodiments, the trap reagents comprises at least one solvent, a pH buffering agent, a chelating agent, at least one monovalent cation, a non-catalytic divalent cation, a detergent, a plurality of multivalent molecules and a first sequencing polymerase enzyme. The first sequencing polymerases can be labeled with a detectable moiety (e.g., a fluorophore) or can be unlabeled. In some embodiments, the trap reagent further comprises at least one viscosity agent. In some embodiments, the trap reagent further comprises a plurality of sequencing primers which hybridize to at least a portion of a nucleic acid template molecule. The sequencing primer comprises a 3' extendible end or a 3' non-extendible end. In some embodiments, the sequencing primer comprises soluble oligonucleotide primers (e.g., in-solution).

In some embodiments, the trap reagents comprise a plurality of plurality of nucleotide reagents which comprises a plurality of multivalent molecules. A multivalent molecule generally comprises: (1) a core, and (2) a plurality of nucleotide arms which comprise (i) a core attachment moiety, (ii) a spacer comprising a PEG moiety, (iii) a linker, and (iv) a nucleotide unit. See FIGS. 2A to 2D.

In some embodiments, the multivalent molecule comprises a core which is attached to the plurality of nucleotide arms. In some embodiments, the spacer is attached to the linker, wherein the linker is attached to the nucleotide unit. In some embodiments, the nucleotide unit comprises a base, sugar and at least one phosphate group. In some embodiments, the linker is attached to the nucleotide unit through the base. In some embodiments, the linker comprises an aliphatic chain having 2-6 subunits or an oligo ethylene glycol chain having 2-6 subunits and optionally the linker includes an aromatic moiety (FIGS. 2A to 2D). In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP. In some embodiments, the plurality of multivalent molecules comprises a mixture of different types of multivalent molecules having two or more different types of nucleotide units selected from a group consisting of dATP, dGTP, dCTP, dTTP and dUTP. For example, the mixture comprises a plurality of a first type of multivalent molecules each having one type of nucleotide units selected from a group consisting of dATP, dGTP, dCTP, dTTP and dUTP. The mixture also comprises a plurality of a second type of multivalent molecules each having a different type of nucleotide units selected from a group consisting of dATP, dGTP, dCTP, dTTP and dUTP, which differ from the first type of nucleotide units in the first plurality.

In some embodiments, at least one of the multivalent molecules in the plurality is fluorescently-labeled, where the fluorophore is attached to the core or attached to at least one base on a nucleotide unit. In some embodiments, the fluorophore which is attached to the multivalent molecule corresponds to the base of the nucleotide unit to permit distinguishing nucleotide base units of the different fluorescently-labeled multivalent molecules.

In some embodiments, at least one of the multivalent molecules comprises at least one nucleotide arm having a cleavable moiety. In some embodiments, a multivalent molecule comprises 1, 2, 3, 4 or more nucleotide arms where each nucleotide arm includes a cleavable moiety. The cleavable moiety in the nucleotide arm can be cleaved with a cleavable agent to separate the nucleotide arm from the core.

In some embodiments, at least one of the multivalent molecules in the plurality includes a chain terminating moiety which inhibits polymerase-catalyzed incorporation of the nucleotide unit. The chain terminating moiety can be attached to the 2' or 3' sugar position of the nucleotide unit. The chain terminating moiety can be removable from the nucleotide unit by contacting the multivalent molecule with a compound that cleaves/removes the chain terminating moiety to form a nucleotide unit with a 2' or 3' extendible group.

In some embodiments, the trap reagents are formulated to promote formation of a stable ternary complex which comprises a polymerase (e.g., the first sequencing polymerase) bound to a nucleic acid duplex which includes a nucleic acid template molecule (e.g., a concatemer) hybridized to a sequencing primer, and a complementary nucleotide unit of a multivalent molecule. In some embodiments, in the ternary complex, the nucleotide unit is bound to the 3' end of the sequencing primer at a position that is opposite a complementary nucleotide in the template strand. In some embodiments, the trap reagents are formulated to promote formation of a ternary complex without incorporation of the complementary nucleotide unit into the 3' end of the sequencing primer (e.g., no polymerase-catalyzed nucleotide incorporation). In some embodiments, the trap reagent comprises a non-catalytic divalent cation that promotes formation of the ternary complex without incorporation of the complementary nucleotide unit. In some embodiments, the non-catalytic divalent cation comprises strontium ions and/or barium ions. In some embodiments, the trap reagent lacks a catalytic divalent cation that promotes polymerase-catalyzed incorporation of the complementary nucleotide unit. Exemplary catalytic divalent cations include magnesium and/or manganese.

In some embodiments, the trap reagent can also include a monovalent salt which can promote formation of the ternary complex. The monovalent salt may comprise, for example, one or more of Sodium, Potassium, Lithium, Rubidium, Cesium, Silver, or other monovalent cations such as NaCl, KCl, LiCl, CsCl, AgCl, $(NH_4)_2SO_4$ or potassium glutamate or other such monovalent salt solutions. In some embodiments, the monovalent salt comprises NaCl, KCl, $(NH_4)_2SO_4$ or potassium glutamate. In some embodiments, the trap reagent can include a monovalent salt at a concentration of about 25-500 mM, or about 50-250 mM, or about 100-200 mM.

The multivalent molecules used during the sequencing reaction offer many advantages that are not provided by free nucleotides. The multivalent molecules comprise a core attached to multiple arms with each arm tethered to a nucleotide unit. The multivalent molecules increase the local concentration of the nucleotide units in proximity to a polymerase/template binding site which favors formation of the ternary complex. Formation of the ternary complex is conducted under a condition that does not promote incorporation of the nucleotide unit into the sequencing primer. The multivalent molecules also increase the persistence time in forming and preserving a stable ternary complex. When a sequencing reaction is conducted with a multivalent molecule labeled with a detectable moiety (e.g., fluorescent moiety) the longer persistence time of the ternary complex provides shorter imaging time and increases signal intensity during a sequencing reaction. The high signal intensity from the ternary complex remains for the entire binding and imaging step. Strong binding between the polymerase, the primed template strand, and the nucleotide unit also provides a stable ternary complex that remains intact during a subsequent washing step. The high intensity signal is retained when unreacted or non-complementary nucleotide units are removed during a washing step. After the signal imaging step (e.g., see the imaging reagent description below), the ternary complex can be destabilized and the sequencing primer can be extended by one nucleotide base in a subsequent incorporation/extension reaction (e.g., see the nucleotide incorporation reagent description below). After the incorporation/extension reaction, the binding and imaging steps can be repeated again using another cycle of binding with multivalent molecules to determine the identity of the next base in the template molecule.

The persistence time refers to the length of time that a stable complex (e.g., ternary complex) remains intact (e.g., without dissociation), where the complex comprises a nucleic acid template molecule hybridized to a primer, a polymerase, and a free nucleotide or nucleotide unit from a multivalent molecule. The persistence time is indicative of the stability of the complex and strength of the binding interactions between the nucleic acid template molecule hybridized to a primer, the polymerase, and the free nucleotide or nucleotide unit. Persistence time can be measured by observing the onset and/or duration of the complex, for example by observing a signal from a labeled component of the complex. For example, a labeled nucleotide or a labeled multivalent molecule may be present in the complex, thus allowing the signal from the label to be detected during the persistence time of the complex. An exemplary label is a fluorescent label. The stable ternary complex can exhibit a persistence time of more than 0.1, 0.2, 0.3, 0.4, 0.5, 0.6, 0.7, 0.8, 0.9 or 1 second, or longer than 1 second.

The multivalent molecules bind to a polymerase/duplex complex to form a ternary complex with a rate that is time-dependent, though substantially slower than the rate of association known for free nucleotides in solution. The on-rate ($K_{on}$) of a multivalent molecule is substantially slower than the on rate for free nucleotides. Importantly, the off rate ($K_{off}$) of the multivalent molecule is substantially slower than that observed for free nucleotides. Therefore, the multivalent molecules provide a surprising and unexpected beneficial improvement of the persistence time of ternary complexes compared to ternary complexes formed using free nucleotides. Thus, multivalent molecules form stable ternary complexes which do not readily dissociate thereby improving imaging quality of the ternary complex during a sequencing workflow. The ternary complex is stable until exposed to a dissociation condition.

In some embodiments, the first sequencing polymerase can bind a complementary nucleotide unit of a multivalent molecule and nucleic acid duplex to form a ternary complex. The first sequencing polymerase comprises a recombinant wild-type or mutant polymerase comprising an amino acid sequence that is at least 80% identical to a backbone sequence of a polymerase from Candidatus altiarchaeales archaeon (e.g., any of SEQ ID NOS: 2, 3, 4, OR 5.)

In some embodiments, the first sequencing polymerase comprises a recombinant wild-type or mutant polymerase from Candidatus altiarchaeales archaeon. In some embodiments, the first sequencing polymerase comprises a DNA polymerase having an amino acid sequence backbone of a DNA polymerase from a Candidatus Altiarchaeales archaeon. The first sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the first sequencing polymerase comprises the amino acid sequence of any one of SEQ ID NOS: 2, 3, 4, or 5.

In some embodiments, the first sequencing polymerase comprises a DNA polymerase from 9° N which comprises the amino acid sequence of SEQ ID NOS: 6, 7, or 8. In some embodiments, the first sequencing polymerase comprises a mutant 9° N polymerase having a backbone amino acid sequence of a polymerase from 9° N (e.g., SEQ ID NOS: 6, 7, or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

In some embodiments, the first sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the first sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the trap reagents further comprise at least one nucleic acid template molecule which comprises DNA or RNA, or a mixture of RNA and DNA. In some embodiments, the nucleic acid template molecules comprise linear or circularized molecules, or a mixture of linear and circular molecules. In some embodiments, the template molecules comprise a concatemer or a single-copy template molecule. In some embodiments, the nucleic acid template molecules comprise single-stranded molecules, double-stranded molecules or nucleic acid molecules having single- and double-stranded portions. In some embodiments, the nucleic acid template molecules are soluble or immobilized to a support or immobilized to a coating on the support. In some embodiments, the nucleic acid template molecules comprise concatemers each comprising tandem repeat sequences of a sequence of interest and any adaptor sequences operably joined to the sequence of interest. In some embodiments, the nucleic acid template molecules comprise amplified molecules (e.g., clonally amplified molecules).

In some embodiments, the nucleic acid template molecules comprise single copy template molecules (e.g., linear molecules) each comprising one copy of a sequence of interest and any adaptor sequences are operably linked or joined to the sequence of interest. In some embodiments, the nucleic acid template molecules comprise amplified molecules (e.g., clonally amplified molecules).

In some embodiments, the trap reagents further comprise a plurality of sequencing primers that hybridize to a universal sequencing primer binding site on the template molecules.

In some embodiments, the individual nucleic acid template molecules are joined to at least one adaptor, where the adaptor includes a capture primer binding sequence, an amplification primer binding sequence and/or a sequencing primer binding sequence. In some embodiments, individual nucleic acid template molecules are operably linked to at least one adaptor having a sample barcode sequence or a unique molecular tag sequence. In some embodiments, the nucleic acid template molecules are soluble or immobilized to a support or immobilized to a coating on the support.

In some embodiments, the nucleic acid template molecules comprise concatemers each comprising tandem repeat sequences of a sequence of interest and any adaptor sequences operably joined to the sequence of interest. In some embodiments, the nucleic acid template molecules comprise amplified molecules (e.g., clonally amplified molecules).

In some embodiments, the trap reagent further comprises a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule. In some embodiments, the multivalent molecules are labeled with a fluorophore, where the multivalent molecules are part of the ternary complexes.

In some embodiments, the trap reagents further comprise a plurality of ternary complexes immobilized to a support, where the template molecule (e.g., concatemer) within the ternary complex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per $mm^2$.

In some embodiments, the plurality of immobilized ternary complexes are in fluid communication with each other to permit flowing a solution of the trap reagent onto the support so that the plurality of immobilized ternary complexes on the support can be essentially simultaneously reacted with the trap reagent in a massively parallel manner. In some embodiments, the fluid communication of the plurality of immobilized ternary complexes can be used to conduct nucleic acid sequencing reactions (e.g., trapping reactions) in a massively parallel manner on the support.

In some embodiments, the trap reagent comprises HEPES (25 mM, pH 8), EDTA (0.5 mM, pH 7.5), NaCl (25 mM), Sr-acetate (5 mM), Tween-20 (0.02%), Gd-HCl (0.08 M), ethylene glycol (10%), dATP (0.04 μM), dGTP (0.04 μM), dCTP (0.04 μM), dUTP (0.04 μM), and a sequencing polymerase (200 nM). In some cases, this formulation may be referred to as Formulation TR-A.

In some embodiments, the trap reagent comprises Bicine (25 mM, pH 8), EDTA (0.5 mM, pH 7.5), NaCl (50 mM), Ba-acetate (10 mM), Tween-20 (0.02%), Gd-HCl (0.06 M), ethylene glycol (10%), dATP (0.04 μM), dGTP (0.04 μM), dCTP (0.04 μM), dUTP (0.04 μM), and sequencing polymerase (100 nM). In some cases, this formulation may be referred to as Formulation TR-B.

In some embodiments, the trap reagent comprises MOPS (25 mM, pH 8), EDTA (0.5 mM, pH 7.5), KCl (25 mM), Sr-acetate (5 mM), Tween-20 (0.02%), Gd-HCl (0.04 M), ethylene glycol (10%), dATP (0.02 μM), dGTP (0.02 μM), dCTP (0.02 μM), dUTP (0.02 μM), and sequencing polymerase (500 nM). In some cases, this formulation may be referred to as Formulation TR-C.

In some embodiments, the trap reagent comprises BES (25 mM, pH 8), EDTA (0.5 mM, pH 7.5), KCl (50 mM), Ba-acetate (10 mM), Tween-20 (0.02%), Gd-HCl (0.02 M), ethylene glycol (10%), dATP (0.02 μM), dGTP (0.02 μM), dCTP (0.02 μM), dUTP (0.02 μM), and sequencing polymerase (300 nM). In some cases, this formulation may be referred to as Formulation TR-D.

In some embodiments, the trap reagent comprises TES (25 mM, pH 8), EDTA (0.5 mM, pH 7.5), NaCl (25 mM), Sr-acetate (5 mM), Tween-20 (0.02%), Gd-HCl (0.08 M), ethylene glycol (10%), dATP (0.04 μM), dGTP (0.04 μM), dCTP (0.04 μM), dUTP (0.04 μM), and sequencing polymerase (100 nM). In some cases, this formulation may be referred to as Formulation TR-E.

In some embodiments, the trap reagent comprises CAPS (25 mM, pH 8), EDTA (0.5 mM, pH 7.5), KCl (50 mM), Ba-acetate (10 mM), Triton™ X-100 (2-[4-(2,4,4-trimethylpentan-2-yl)phenoxy]ethanol) (0.02%), urea (0.08 M), ethylene glycol (10%), dATP (0.04 μM), dGTP (0.04 μM), dCTP (0.04 μM), dUTP (0.04 μM), and sequencing polymerase (200 nM). In some cases, this formulation may be referred to as Formulation TR-F.

In some embodiments, the trap reagent comprises TAPS (25 mM, pH 8), EDTA (0.5 mM, pH 7.5), KCl (25 mM), Sr-acetate (5 mM), Triton™ X-100 (2-[4-(2,4,4-trimethylpentan-2-yl)phenoxy]ethanol) (0.02%), urea (0.08 M), ethylene glycol (10%), dATP (0.04 μM), dGTP (0.04 μM), dCTP (0.04 μM), dUTP (0.04 μM), and sequencing polymerase (500 nM). In some cases, this formulation may be referred to as Formulation TR-G.

In some embodiments, the trap reagent comprises ACES (25 mM, pH 8), EDTA (0.5 mM, pH 7.5), NaCl (50 mM), Ba-acetate (10 mM), Triton™ X-100 (2-[4-(2,4,4-trimethylpentan-2-yl)phenoxy]ethanol) (0.02%), urea (0.06 M), ethylene glycol (10%), dATP (0.02 μM), dGTP (0.02 μM), dCTP (0.02 μM), dUTP (0.02 μM), and sequencing polymerase (400 nM). In some cases, this formulation may be referred to as Formulation TR-H.

In some embodiments, the trap reagent comprises PIPES (25 mM, pH 8), EDTA (0.5 mM, pH 7.5), KCl (25 mM), Sr-acetate (5 mM), Triton™ X-100 (2-[4-(2,4,4-trimethylpentan-2-yl)phenoxy]ethanol) (0.02%), urea (0.04 M), ethylene glycol (10%), dATP (0.02 μM), dGTP (0.02 μM), dCTP (0.02 μM), dUTP (0.02 μM), and sequencing polymerase (500 nM). In some cases, this formulation may be referred to as Formulation TR-I.

In some embodiments, the trap reagent comprises Tris (25 mM, pH 8), EDTA (0.5 mM, pH 7.5), KCl (50 mM), Ba-acetate (10 mM), Triton™ X-100 (2-[4-(2,4,4-trimethylpentan-2-yl)phenoxy]ethanol) (0.02%), urea (0.02 M), ethylene glycol (10%), dATP (0.04 μM), dGTP (0.04 μM), dCTP (0.04 μM), dUTP (0.04 μM), and sequencing polymerase (200 nM). In some cases, this formulation may be referred to as Formulation TR-J.

Post-Trap Reagents and Methods of Use

The present disclosure provides one or more post-trap reagents, and methods that employ the post-trap reagents where the methods comprise preserving the ternary complexes without polymerase-catalyzed incorporation of the nucleotide units by contacting the plurality of ternary complexes with the post-trap reagent (e.g., step (h) of the methods described herein).

In some embodiments, the post-trap reagents comprises at least one solvent, a pH buffering agent, a chelating agent, at least one monovalent cation, a non-catalytic divalent cation, a detergent and first sequencing polymerase. The post-trap reagents lack a plurality of multivalent molecules.

In some embodiments, the post-trap reagent further comprises at least one viscosity agent. In some embodiments, the post-trap reagent optionally comprises a plurality of sequencing primers which hybridize to at least a portion of a nucleic acid template molecule. The sequencing primer comprises a 3' extendible end or a 3' non-extendible end. In some embodiments, the sequencing primer comprises soluble oligonucleotide primers (e.g., in-solution).

In some embodiments, although the post-trap reagent lacks a plurality of multivalent molecules, the post-trap reagents are formulated to preserve the stable ternary complex which forms when using the trap reagent described above.

In some embodiments, the post-trap reagents are formulated to preserve a ternary complex without incorporation of the complementary nucleotide unit into the 3' end of the sequencing primer (e.g., no polymerase-catalyzed incorporation of the nucleotide unit). In some embodiments, the post-trap reagent comprises a non-catalytic divalent cation that promotes formation of the ternary complex without incorporation of the complementary nucleotide unit. In some embodiments, the non-catalytic divalent cation comprises strontium ions and/or barium ions. In some embodiments, the post-trap reagent lacks a catalytic divalent cation that promotes polymerase-catalyzed incorporation of the complementary nucleotide unit. Exemplary catalytic divalent cations include magnesium and/or manganese.

In some embodiments, the post-trap reagent can also include a monovalent salt which can preserve the ternary complex. The monovalent salt may comprise, for example, one or more of Sodium, Potassium, Lithium, Rubidium, Cesium, Silver, or other monovalent cations and may be supplied as NaCl, KCl, LiCl, CsCl, AgCl, $(NH_4)_2SO_4$ or potassium glutamate or other such monovalent salt solutions. The post-trap reagent can include a monovalent salt at a concentration of about 25-500 mM, or about 50-250 mM, or about 100-200 mM.

In some embodiments, the post-trap reagents contain a first sequencing polymerase which can be the same type or a different type of first sequencing polymerase contained in the trap reagent.

In some embodiments, the first sequencing polymerase comprises a recombinant wild-type or mutant polymerase from Candidatus altiarchaeales archaeon. In some embodiments, the first sequencing polymerase comprises a DNA polymerase having an amino acid sequence backbone of a DNA polymerase from a Candidatus Altiarchaeales archaeon. The first sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the first sequencing polymerase comprises the amino acid sequence of any one of SEQ ID NOS: 2, 3, 4, 5. In some embodiments, the positions of the mutations described herein are with reference to SEQ ID NO: 1. In some embodiments, the positions of the mutations described herein are with reference to any one of SEQ ID NOS: 2, 3, 4, or 5.

In some embodiments, the first sequencing polymerase comprises a DNA polymerase from 9° N which comprises the amino acid sequence of SEQ ID NOS: 6, 7, or 8. In some embodiments, the first sequencing polymerase comprises a mutant 9° N polymerase having a backbone amino acid sequence of a polymerase from 9° N (e.g., SEQ ID NOS: 6, 7, or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NOS: 6, 7, or 8.

In some embodiments, the first sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the first sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the post-trap reagent further comprises a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule. In some embodiments, the multivalent molecules are labeled with a fluorophore, where the multivalent molecules are part of the ternary complexes.

In some embodiments, the post-trap reagents further comprise a plurality of ternary complexes immobilized to a support, where the template molecule (e.g., concatemer) within the ternary complex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per $mm^2$.

In some embodiments, the plurality of immobilized ternary complexes are in fluid communication with each other to permit flowing a solution of the post-trap reagent onto the support so that the plurality of immobilized ternary complexes on the support can be essentially simultaneously reacted with the post-trap reagent in a massively parallel manner. In some embodiments, the fluid communication of the plurality of immobilized ternary complexes can be used to conduct nucleic acid sequencing reactions in a massively parallel manner on the support.

In some embodiments, the stable ternary complex comprises a first sequencing polymerase bound to a nucleic acid duplex which includes a nucleic acid template molecule (e.g., a concatemer) hybridized to a sequencing primer, and a complementary nucleotide unit of a multivalent molecule wherein the multivalent molecule is fluorescently-labeled to permit detection of the stable ternary complex. The stable ternary complex which is preserved by the post-trap reagent is stable enough to be imaged by contacting the stable ternary complex (e.g., fluorescently-labeled) with an imaging reagent (see the imaging reagents described below). The stable ternary complex does not dissociate until contacted with the wash-removal reagent which contains a chaotropic agent (e.g., see the wash-removal reagent described above).

In some embodiments, a post-trap reagent comprises TAPSO (25 mM, pH 8), EDTA (0.5 mM, pH 7.5), NaCl (100 mM), Sr-acetate (5 mM), Triton™ X-100 (2-[4-(2,4,4-trimethylpentan-2-yl)phenoxy]ethanol) (0.01%), sucrose (0.2 M), and a sequencing polymerase (100 nM). In some cases, this formulation may be referred to as Formulation PTR-A.

In some embodiments, a post-trap reagent comprises MES (25 mM, pH 8), EDTA (0.5 mM, pH 7.5), NaCl (100 mM), Ba-acetate (5 mM), Triton™ X-100 (2-[4-(2,4,4-trimethylpentan-2-yl)phenoxy]ethanol) (0.02%), sucrose (0.2 M), and sequencing polymerase (200 nM). In some cases, this formulation may be referred to as Formulation PTR-B.

In some embodiments, a post-trap reagent comprises MOPS (25 mM, pH 8), EDTA (0.5 mM, pH 7.5), KCl (100 mM), Sr-acetate (5 mM), Triton™ X-100 (2-[4-(2,4,4-trimethylpentan-2-yl)phenoxy]ethanol) (0.04%), sucrose (0.2 M), and sequencing polymerase (50 nM). In some cases, this formulation may be referred to as Formulation PTR-C.

In some embodiments, a post-trap reagent comprises MOPSO (25 mM, pH 8), EDTA (0.5 mM, pH 7.5), NaCl (100 mM), Ba-acetate (5 mM), Triton™ X-100 (2-[4-(2,4,4-trimethylpentan-2-yl)phenoxy]ethanol) (0.08%), sucrose (0.2 M), and sequencing polymerase (200 nM). In some cases, this formulation may be referred to as Formulation PTR-D.

In some embodiments, a post-trap reagent comprises Tricine (25 mM, pH 8), EDTA (0.5 mM, pH 7.5), KCl (100 mM), Sr-acetate (5 mM), Triton™ X-100 (2-[4-(2,4,4-trimethylpentan-2-yl)phenoxy]ethanol) (0.2%), sucrose (0.2 M), and sequencing polymerase (50 nM). In some cases, this formulation may be referred to as Formulation PTR-E.

In some embodiments, a post-trap reagent comprises Bicine (10 mM, pH 8), EDTA (0.5 mM, pH 7.5), KCl (50 mM), Ba-acetate (5 mM), Tween-20 (0.01%), sucrose (0.1 M), and a sequencing polymerase (100 nM). In some cases, this formulation may be referred to as Formulation PTR-F.

In some embodiments, a post-trap reagent comprises HEPES (25 mM, pH 8), EDTA (0.5 mM, pH 7.5), NaCl (100 mM), Sr-acetate (5 mM), Tween-20 (0.02%), sucrose (0.2 M), and a sequencing polymerase (200 nM). In some cases, this formulation may be referred to as Formulation PTR-G.

In some embodiments, a post-trap reagent comprises TES (50 mM, pH 8), EDTA (0.5 mM, pH 7.5), NaCl (200 mM), Ba-acetate (5 mM), Tween-20 (0.04%), sucrose (0.4 M), and sequencing polymerase (50 nM). In some cases, this formulation may be referred to as Formulation PTR-H.

In some embodiments, a post-trap reagent comprises ACES (75 mM, pH 8), EDTA (0.5 mM, pH 7.5), KCl (300 mM), Sr-acetate (5 mM), Tween-20 (0.08%), sucrose (0.8 M), and sequencing polymerase (100 nM). In some cases, this formulation may be referred to as Formulation PTR-I.

In some embodiments, a post-trap reagent comprises PIPES (100 mM, pH 8), EDTA (0.5 mM, pH 7.5), KCl (400 mM), Ba-acetate (5 mM), Tween-20 (0.2%), sucrose (2 M), and sequencing polymerase (200 nM). In some cases, this formulation may be referred to as Formulation PTR-J.

Imaging Reagents and Methods of Use

The present disclosure provides one or more imaging reagents, and methods that employ the imaging reagents. In some embodiments, the imaging reagent can be employed after formation of ternary complexes, for example after a trapping step and/or after a stepping step. Formation of ternary complexes can include binding a polymerase, a nucleic acid duplex which comprises a nucleic acid template molecule hybridized to a sequencing primer, and a nucleotide reagent (e.g., a nucleotide unit of a multivalent molecule or a non-conjugated nucleotide), to form a ternary complex. In some embodiments, in a ternary complex, the nucleotide unit or the nucleotide is bound to the 3' end of the sequencing primer at a position that is opposite a complementary nucleotide in the template strand. The imaging reagents can be formulated to preserve (e.g., stabilize) the ternary complexes that were previously formed during a trapping and/or stepping step.

The trapping and/or stepping reagents can be formulated to promote formation of ternary complexes but these reagents may, or may not, be formulated to reduce photo-damage of the ternary complex caused by exposing the ternary complex to excitation illumination during a subsequent imaging/detecting step. Thus, imaging reagent formulations can differ from that of the trapping and stepping reagents. The imaging reagents can be formulated to reduce photo-damage of any of the components of the ternary complexes where the damage may be caused by exposing the ternary complex to excitation illumination during an imaging/detecting step. The imaging reagents can also be formulated to preserve the ternary complex that formed during trapping and/or stepping by reducing dissociation of the components of the ternary complex that would otherwise occur in the absence of the imaging reagent. The imaging reagents preserve a ternary complex thereby increasing the persistence time of an assembled ternary complex. The stable ternary complex can exhibit a persistence time of more than 0.1, 0.2, 0.3, 0.4, 0.5, 0.6, 0.7, 0.8, 0.9 or 1 second, or longer than 1 second. By reducing dissociation of the ternary complex the imaging reagent increases the time period for imaging detectably labeled ternary complexes. The imaging reagents can also be formulated to preserve a ternary complex while inhibiting a polymerase-catalyzed nucleotide incorporation reaction.

The imaging reagent increases the persistence time of an assembled ternary complex, and decreases photo-damage of the template molecule, which effectively reduces the decay in fluorescent signal intensities of ternary complexes formed in a first sequencing cycle and ternary complexes formed in subsequent sequencing cycles, compared to signal intensities detected in subsequent sequencing cycles in the absence of the imaging reagent.

In some embodiments, the imaging reagents can be formulated to preserve (e.g., stabilize) a ternary complex that formed in the presence of any of the trap and/or post-trap reagents described herein. For example, the ternary complex comprises a polymerase (e.g., the first sequencing polymerase) bound to a nucleic acid duplex which includes a nucleic acid template molecule (e.g., a concatemer or single copy template molecule) hybridized to a sequencing primer, and a complementary nucleotide unit of a multivalent molecule. In some embodiments, in the ternary complex, the nucleotide unit is bound to the 3' end of the sequencing primer at a position that is opposite a complementary nucleotide in the template strand. In some embodiments, the multivalent molecule is detectably labeled with a fluorophore. In some embodiments, the imaging reagent is employed to image the signals (e.g., fluorescent signals) emitted by a plurality of ternary complexes.

In some embodiments, the imaging reagents can be formulated to preserve (e.g., stabilize) a ternary complex that formed in the presence of any of the stepping reagents described herein. For example, the ternary complex comprises a polymerase (e.g., the second sequencing polymerase) bound to a nucleic acid duplex which includes a nucleic acid template molecule (e.g., a concatemer or single copy template molecule) hybridized to a sequencing primer, and a complementary nucleotide (e.g., a non-conjugated free nucleotide). In some embodiments, in the ternary complex, the nucleotide is bound to the 3' end of the sequencing primer at a position that is opposite a complementary nucleotide in the template strand. In some embodiments, the nucleotide is detectably labeled with a fluorophore, or the nucleotide is non-labeled. In some embodiments, the nucleotide comprises a chain terminating moiety attached to the 3' sugar position, or the nucleotide lacks a chain terminating moiety. In some embodiments, the imaging reagent is employed to image the signals (e.g., fluorescent signals) emitted by a plurality of ternary complexes.

The present disclosure provides one or more imaging reagents, and methods that employ the imaging reagents where the methods comprise (1) contacting the plurality of stable ternary complexes (e.g., plurality of immobilized fluorescently-labeled ternary complexes) with an imaging reagent under a condition suitable to preserve the ternary complexes; and (2) detecting the presence of at least one of the plurality of ternary complexes by exposing the plurality of ternary complexes to an excitation illumination and detecting a fluorescent signal emitted from the immobilized fluorescently-labeled ternary complexes in response to the excitation illumination (e.g., step (i) of the methods described herein). In some embodiments, the methods further comprise identifying the nucleotide unit of a multivalent molecule that is bound to the sequencing primer, as part of the fluorescently-labeled ternary complex (e.g., step (j) of the methods described herein). The imaging reagents can be used for the massively parallel sequencing workflow at step (i) as described below. In some embodiments, the plurality of ternary complexes comprises a non-conjugated nucleotide that is bound to the sequencing primer, as part of a ternary complex. The imaging reagents can be used for the massively parallel sequencing workflow at step (m) as described below.

In some embodiments, the ternary complexes can be formed in the presence of a trapping or stepping reagent, and the trapping or stepping reagent can be removed from ternary complexes, and the removed reagent can be replaced with an imaging reagent that is formulated to preserve the ternary complexes.

In some embodiments, the ternary complexes can be formed in the presence of a trapping or stepping reagent, and the trapping or stepping reagent is mixed with an imaging reagent, where the imaging reagent is formulated to preserve the ternary complexes.

The imaging reagents can be formulated to include at least one compound for reducing photo-damage caused by exposing the ternary complexes to excitation illumination. The excitation illumination can induce formation of reactive oxygen species which can damage any component of the ternary complexes including the nucleic acid template molecule, the sequencing primer, the sequencing polymerase, the nucleotide unit, the non-conjugated nucleotide, the fluorophore attached to the multivalent molecule and/or the fluorophore attached to a non-conjugated nucleotide.

The inclusion of one or more photo-damage reducing compound in the imaging reagents can reduce formation of the excited triplet state and counteract the damaging effect of reactive oxygen species thereby improving photostability of the fluorophores, reducing photo-bleaching and/or retaining fluorescence intensity. The inclusion of one or more photo-damage reducing compound in the imaging reagents may also reduce non-specific binding of the fluorescent dyes to other biomolecules (e.g., polymerases, nucleic acid template molecules and/or sequencing primer oligonucleotides). In some embodiments, the imaging reagents comprise any one or any combination of two or more photo-damage reducing compounds comprising ascorbic acid (or derivatives thereof), ascorbyl palmitate, D-isoascorbic acid (erythorbic acid), sodium ascorbate, citric acid, coumaric acid, ferulic acid, caffeic acid, chlorogenic acid, sinapic acid, ellagic acid, gallic acid, gentisic acid, salicylic acid, vanillic acid, butylated hydroxytoluene (BTH), butylated hydroxy toluene (BHT), polyphenol antioxidants, polyvinyl alcohols, butylated hydroxy anisol (BHA) and/or Trolox (6-hydroxy-2,5,7,8-tetramethylchroman-2-carboxylic acid). In some embodiments, the Trolox comprises a vitamin E analog including nitrated and nitroalkene Trolox derivatives. In some embodiments, the Trolox comprises Trolox quinone or Trolox hydroquinone. In some embodiments, the imaging reagents comprise Trolox that has been subjected to an aging process. In some embodiments, the imaging reagents comprise 1,3,5,7 cyclo-octatetraene (COT) and/or methyl viologen. In some embodiments, the gallic acid comprises sulfonated forms having 1, 2 or 3 sulfonate groups.

In some embodiments, the imaging reagents can be formulated to include at least one reducing compound which can stabilize any of the photo-damage reducing compound(s) that is/are present in the imaging reagents. For example, an imaging reagent that includes ascorbic acid (e.g., as a photo-damage reducing compound) can further include at least one reducing compound to reduce or inhibit oxidation of ascorbic acid. Oxidized ascorbic acid can form dehydroascorbic acid which can turn color from a clear to yellow. Oxidized ascorbic acid can form crystals. Ascorbic acid can oxidize after exposure to elevated temperatures of 25-65° C. In some embodiments, imaging reagents that contain ascorbic acid can also include at least one reducing compound to inhibit oxidation, inhibit crystallization and/or inhibit oxidation at elevated temperatures. Exemplary reducing compounds include DTT (dithiothreitol), 2-beta mercaptoethanol, TCEP, (tris(2-carboxyethyl)phosphine), formamide, DMSO (dimethylsulfoxide), sodium dithionite ($Na_2S_2O_4$), glutathione, methionine, betaine, Tris(3-hydroxypropyl)phosphine (THPP) and N-acetyl cysteine.

In some embodiments, the imaging reagents can be formulated to include at least one compound that stabilizes ascorbic acid. In some embodiments, an imaging reagent that includes ascorbic acid can further include at least one stabilizing compound to reduce or inhibit degradation of ascorbic acid upon exposure to light. Exemplary stabilizer compounds include boric acid, tartaric acid, citric acid and Tiron (4,5-Dihydroxy-1,3-benzenedisulfonic acid; e.g., disodium salt). The imaging reagents can include a stabilizing compound at a concentration of about 1-20 mM, or about 20-40 mM, or about 40-60 mM, or about 60-100 mM.

In some embodiments, the imaging reagents comprise at least one solvent, a pH buffering agent, a chelating agent, at least one monovalent cation, a non-catalytic divalent cation, a detergent and at least one compound for reducing photo-damage. In some embodiments, the imaging reagents include two, three, four or five photo-damage reducing compounds. In some embodiments, the imaging reagents further comprise, or lack, at least one viscosity agent. In some embodiments, a high viscosity imaging reagent includes one, two, or more viscosity agents. In some embodiments, a low viscosity imaging reagent lacks a viscosity agent.

In some embodiments, the imaging reagents are formulated to preserve the stable ternary complex which forms when using the trap and post-trap reagents described above.

In some embodiments, the imaging reagents are formulated to preserve a ternary complex without incorporation of the complementary nucleotide unit into the 3' end of the sequencing primer (e.g., no polymerase-catalyzed incorporation of the nucleotide unit). In some embodiments, the imaging reagent comprises a non-catalytic divalent cation that promotes formation of the ternary complex without incorporation of the complementary nucleotide unit. In some embodiments, the non-catalytic divalent cation comprises strontium, barium, scandium, titanium, calcium, vanadium, chromium, iron, cobalt, nickel, copper, zinc, gallium, germanium, arsenic, selenium, rhodium, europium, tin, and/or terbium ions. In some embodiments, the imaging reagent lacks a catalytic divalent cation that promotes polymerase-catalyzed incorporation of the complementary nucleotide unit. Exemplary catalytic divalent cations include magnesium and/or manganese.

In some embodiments, the imaging reagent can also include a monovalent salt which can preserve the ternary complex. The monovalent salt may comprise, for example, one or more of Sodium, Potassium, Lithium, Rubidium, Cesium, Silver, or other monovalent cations and may be supplied as NaCl, KCl, LiCl, CsCl, AgCl, $(NH_4)_2SO_4$ or potassium glutamate or other such monovalent salt solutions. In some embodiments, the monovalent salt comprises NaCl, KCl, $(NH_4)_2SO_4$ or potassium glutamate. In some embodiments, the imaging reagent can include a monovalent salt at a concentration of about 25-500 mM, or about 50-250 mM, or about 100-200 mM.

In some embodiments, the imaging reagents comprise at least one solvent, a pH buffering agent, a chelating agent, at least one monovalent cation, a non-catalytic divalent cation, a detergent and at least one compound for reducing photo-damage. In some embodiments, the imaging reagents further comprise at least one reducing agent. In some embodiments, the imaging reagents further comprise at least one stabilizing compound for stabilizing ascorbic acid. In some embodiments, the imaging reagents further comprise one or more compounds for increasing viscosity of the imaging reagents.

In some embodiments, the imaging reagent comprises a pH buffering agent at a pH of about 6.5-9, or a pH of about 7-8.5, or a pH of about 7.5-8. In some embodiments, the imaging reagent comprises a pH buffering agent at a pH of about 7, 7.1, 7.2, 7.3, 7.4, 7.5, 7.6, 7.7, 7.8, 7.9, or a pH of about 8.

In some embodiments, the imaging reagent comprises a chelating agent, for example EDTA (ethylenediaminetetraacetic acid), EGTA (ethylene glycol tetraacetic acid), HEDTA (hydroxyethylethylenediaminetriacetic acid), DPTA (diethylene triamine pentaacetic acid) or NTA (N,N-bis(carboxymethyl)glycine).

In some embodiments, the imaging reagent comprises a monovalent cation comprising sodium, for example as sodium chloride, sodium fluoride, sodium bromide, sodium iodide, sodium sulfate, sodium bicarbonate, sodium carbonate or sodium amide. In some embodiments, the imaging reagent comprises sodium in an amount that does not promote crystal formation in the imaging reagent. In some embodiments, the imaging reagent lacks a monovalent cation comprising sodium.

In some embodiments, the imaging reagent comprises a non-catalytic divalent cation such as for example strontium, barium, calcium and/or tin. In some embodiments, the non-catalytic divalent cation comprises strontium chloride, strontium acetate, barium acetate or nickel chloride.

In some embodiments, the imaging reagent comprises a detergent, for example a non-ionic detergent such as Triton™ X-100 (2-[4-(2,4,4-trimethylpentan-2-yl)phenoxy] ethanol), Tween 20, Tween 80 or Nonidet P-40.

In some embodiments, the imaging reagent comprises a reducing agent, for example DTT (dithiothreitol), TCEP, (tris(2-carboxyethyl)phosphine), or Tris(3-hydroxypropyl) phosphine (THPP). In some embodiments, the imaging reagent lacks a reducing agent.

In some embodiments, the imaging reagents further comprise, or lack, at least one viscosity agent. In some embodiments, a high viscosity imaging reagent includes one, two, or more viscosity agents. In some embodiments, a low viscosity imaging reagent lacks a viscosity agent. In some embodiments, the imaging reagents comprise at least one viscosity agent comprising any one or any combination or two or more of sucrose, ethylene glycol and/or glycerol. In some embodiments, the concentration of the sucrose in the imaging reagents can be about 0.1-0.3 M, or about 0.3-0.6 M, or about 0.6-0.9 M, or about 0.9-1 M, or about 1-2 M. In some embodiments, the concentration of the ethylene glycol in the imaging reagents can be about 1-5%, or about 5-10%, or about 10-20%, or about 20-40%, or about 40-60%, or about 60-80%. In some embodiments, the concentration of the glycerol in the imaging reagents can be about 1-2%, or about 2-4%, or about 4-6%, or about 6-8%, or about 8-10%.

In some embodiments, the imaging reagents include two, three, four or five photo-damage reducing compounds. The photo-damage reducing compounds can be water soluble, for example at a pH of about 6.5-9, or a pH of about 7-8.5, or a pH of about 7.5-8. The imaging reagent includes at least photo-damage reducing compound at a concentration that reduces crystal formation in the imaging reagent.

In some embodiments, the imaging reagents comprise a photo-damage reducing compound including ascorbic acid in any form. Ascorbic acid includes both L-isomer and D-isomer and mixtures of L- and D-isomers, and racemic mixtures. In some embodiments, the ascorbic acid comprises a salt for example sodium L-ascorbate. In some embodiments, the ascorbic acid comprises dehydroascorbic acid (DHA). In some embodiments, includes ascorbate and analogs and derivatives thereof. In some embodiments, derivatives include ascorbate having an esterified 5-hydroxy and/or 6-hydroxy group. In some embodiments, derivatives include ascorbate in which the 5- and/or 6-hydroxy group is replaced with a halo or amino group. In some embodiments, derivatives include ascorbate in which the 5- and/or 6-hydroxy group lacks a hydroxy group such as for example a hydrogen atom replaces the hydroxyl group. In some embodiments, ascorbate derivatives include 5-deoxy-L-ascorbate, 6-bromo-6-deoxy-L-ascorbate, 6-amino-6-deoxy-L-ascorbate, L-ascorbic acid 6-carboxylate, 6-O-tosyl-L-ascorbate, and 6-O-ascorbyl alkanoates such as 6-ascorbyl palmitate (palmitoyl ascorbate). The concentration of the ascorbate in the imaging reagents can be about 1-10 mM, or about 10-20 mM, or about 20-30 mM, or about 30-40 mM, or about 40-50 mM, or about 50-60 mM, or about 60-70 mM, or about 70-80 mM, or about 80-90 mM, or about 90-100 mM.

In some embodiments, the imaging reagents comprise a photo-damage reducing compounds including Trolox (6-hydroxy-2,5,7,8-tetramethylchroman-2-carboxylic acid) or other vitamin E analogs including nitrated and nitroalkene Trolox derivatives. In some embodiments, the Trolox comprises Trolox quinone or Trolox hydroquinone. In some embodiments, the Trolox that has been subjected to an aging process. The concentration of the Trolox or the Trolox derivative in the imaging reagent can be about 0.1-1 mM, or about 1-2 mM, or about 2-3 mM, or about 3-4 mM, or about 4-5 mM, or about 5-10 mM, or about 10-15 mM.

In some embodiments, the imaging reagents comprise a Trolox compound with or without an ascorbate. In some embodiments, the imaging reagents comprise a combination of photo-damage reducing compounds including an ascorbate (e.g., sodium ascorbate) and a Trolox compound (e.g., Trolox or Trolox quinone or Trolox hydroquinone or aged Trolox). In some embodiments, Trolox can be exposed to UV light for minutes or hours to produce aged Trolox which is hydroxylated and can exhibit increased water solubility. For example the Trolox can be exposed to UV light for 15-30 minutes, or 30-45 minutes, or 45-60 minutes. Trolox can be exposed to UV light for 1-4 hours, or 4-8 hours, or 8-12 hours, or 12-16 hours, or 16-20 hours, or up to 60 hours. Conducting a sequencing workflow using imaging reagents that include Trolox (non-aged), Trolox quinone, Trolox hydroquinone or aged Trolox, can reduce sequencing phasing and pre-phasing rates compared to sequencing workflows that do not include these Trolox compounds. The phasing and/or pre-phasing rates can be reduced by about 1-3%, or about 3-6%, or about 6-9%, or more than 9%.

In some embodiments, the imaging reagents comprise an ascorbate (e.g., sodium ascorbate) and a Trolox (or Trolox quinone or Trolox hydroquinone or aged Trolox), and ethylene glycol.

FIGS. 17-18 and FIGS. 35-42 show data of the effects of various imaging reagents on signal intensity of fluorescent dyes with time. The different formulations contain either no compounds that reduce photo damage or different combinations of compounds that reduce photo damage.

In some embodiments, the imaging reagent further comprises a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule. In some embodiments, the multivalent molecules are labeled with a fluorophore, where the multivalent molecules are part of the ternary complexes. In the ternary complex, the nucleotide unit of the multivalent molecule is bound to the 3' end of the sequencing primer at a position that is opposite a complementary nucleotide in the template strand.

In some embodiments, the imaging reagent further comprises a plurality of ternary complexes each comprising a sequencing polymerase (e.g., a second sequencing polymerase) bound to a nucleic acid duplex which includes a nucleic acid template molecule hybridized to a sequencing primer, and a nucleotide reagent (e.g., a complementary non-conjugated nucleotide). In some embodiments, the non-conjugated nucleotide is unlabeled or is labeled with a fluorophore. In some embodiments, in the ternary complex, the non-conjugated nucleotide is bound to the 3' end of the sequencing primer at a position that is opposite a complementary nucleotide in the template strand.

The imaging reagents are formulated to include at least one compound for reducing photo-damage caused by exposing the ternary complexes to excitation illumination. The excitation illumination can induce formation of reactive oxygen species which can damage any component of the ternary complexes including the nucleic acid template molecule, the sequencing primer, the sequencing polymerase and/or the fluorophore attached to the multivalent molecule.

Figure 17:
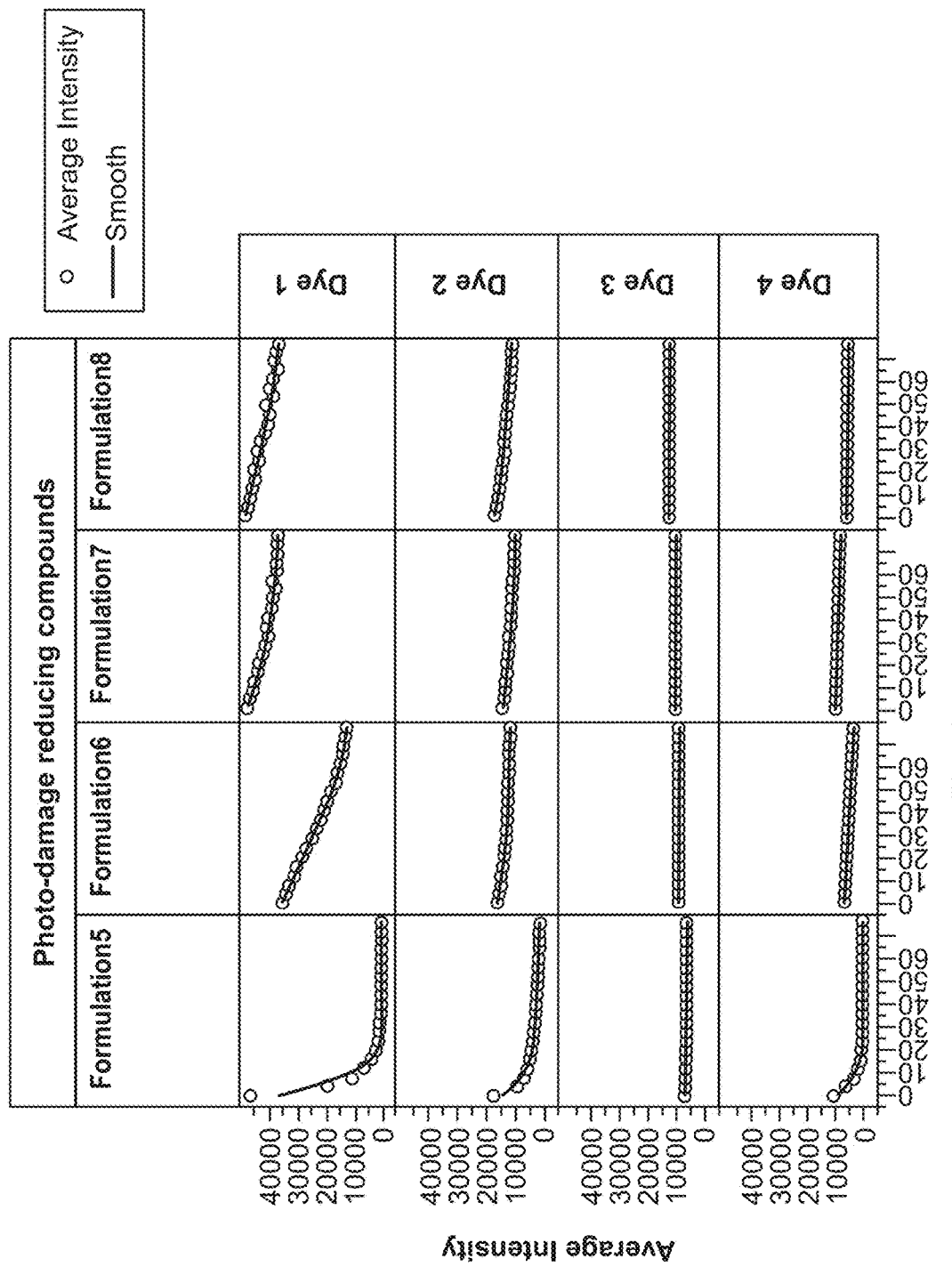
FIG. 17 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 5-8 comprise Tris-HCl (pH 8.8), EDTA, NaCl, Triton™ X-100 (2-[4-(2, 4,4-trimethylpentan-2-yl)phenoxy]ethanol), sucrose, strontium acetate and glycerol. Formulation 5 comprises 1,3,5,7 cyclo-octatetraene (COT) (2 mM). Formulation 6 comprises COT (2 mM) and sodium ascorbate (50 mM). Formulation 7 comprises COT (2 mM), sodium ascorbate (50 mM) and Trolox (2 mM). Formulation 8 comprises sodium ascorbate (50 mM) and Trolox (2 mM).
Figure 18:
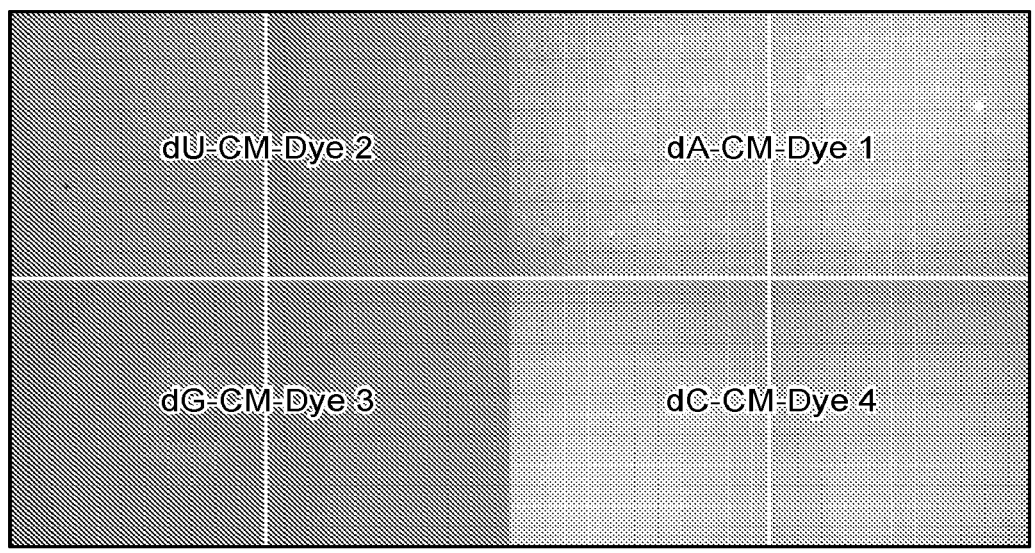
FIG. 18 is a series of images of dye-labeled nucleotides where the nucleotides are joined to a dye via a cleavable moiety (CM). The images show no residual fluorescent signals after a 90 second exposure to high laser power. The imaging reagent comprises Tris-HCl (pH 8.8), EDTA, NaCl, Triton™ X-100 (2-[4-(2,4,4-trimethylpentan-2-yl)phenoxy] ethanol), sucrose, strontium acetate, glycerol, 1,3,5,7 cyclo-octatetraene (COT) (2 mM), sodium ascorbate (50 mM) and Trolox (2 mM).

The inclusion of one or more photo-damage reducing compound in the imaging reagents can reduce formation of the excited triplet state and counteract the damaging effect of reactive oxygen species thereby improving photostability of the fluorophores, reducing photo-bleaching and/or retaining fluorescence intensity (see FIGS. 17 and 18). The inclusion of one or more photo-damage reducing compound in the imaging reagents may also reduce non-specific binding of the fluorescent dyes to other biomolecules (e.g., polymerases, nucleic acid template molecules and/or sequencing primer oligonucleotides).

In some embodiments, the imaging reagents further comprise a plurality of ternary complexes immobilized to a support, where the template molecule (e.g., concatemer or single copy template molecule) within the ternary complex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of about 45-50 degrees. In some embodiments, the plurality of ternary complexes are immobilized to one or more layers of the coatings on the support where the density of the immobilized ternary complexes is about 100-100,000 per $mm^2$. In some embodiments, the plurality of immobilized ternary complexes are in fluid communication with each other to permit flowing a solution of the imaging reagent onto the support so that the plurality of immobilized ternary complexes on the support can be essentially simultaneously reacted with the imaging reagent in a massively parallel manner. In some embodiments, the fluid communication of the plurality of immobilized ternary complexes can be used to conduct imaging reactions in a massively parallel manner on the support.

The inclusion of one or more photo-damage reducing compounds in the imaging reagents can also mitigate/reduce residual signal from a fluorescently-labeled multivalent molecule during an imaging step in one or more subsequent nucleic acid sequencing cycles (e.g., repeated sequencing cycles), or can mitigate/reduce residual signal from a fluorescently-labeled non-conjugated nucleotide during an imaging step in one or more subsequent nucleic acid sequencing cycles (e.g., repeated sequencing cycles). For example, in a first cycle, the imaging step includes detecting the fluorescent signal emitted from the immobilized fluorescently-labeled ternary complexes in the presence of an imaging reagent. In a subsequent step, the fluorescently-labeled ternary complexes are washed to remove the fluorescently-labeled multivalent molecules and sequencing polymerases using a wash-removal reagent that dissociates ternary complexes to generate nucleic acid duplexes of templates (e.g., concatemers) hybridized to sequencing primers. In yet another subsequent step, a plurality of free nucleotides and a second sequencing polymerase are bound to the nucleic acid duplexes under conditions suitable for incorporating a complementary nucleotide into the sequencing primer, thereby advancing the polymerase to the next base position. In a second cycle, the sequencing workflow can be repeated by binding sequencing polymerases and fluorescently-labeled multivalent molecules onto the nucleic acid duplexes using the pre-trap, trap and post-trap reagents. Another imaging step follows in which fluorescent signals from residual fluorescently-labeled multivalent molecules remaining from the first cycle using could increase background signals in the second cycle and interfere with accurate signal detection in the current imaging cycle (See FIGS. 19-21). Thus, the imaging reagents described herein can mitigate residual signals from a fluorescently-labeled multivalent molecule during an imaging step in a subsequent nucleic acid sequencing cycle.

The present disclosure provides methods for inhibiting photo-damage of a ternary complex during a detecting step of a nucleic acid sequencing reaction comprising the steps of: (a) providing a ternary complex comprising a polymerase, a nucleic acid duplex having a nucleic acid template molecule hybridized to a primer, and a nucleotide reagent that is complementary to a next base of the primer-hybridized template molecule, wherein (i) the complementary nucleotide reagent and/or the polymerase is labeled with a fluorescent dye, and (ii) the ternary complex is a stable ternary complex that maintains a persistence time of longer than 1 second without incorporation of the nucleotide reagent; (b) illuminating the ternary complex with light in the presence of an imaging reagent comprising ascorbic acid or a salt thereof; and (c) determining the identity of the complementary nucleotide reagent in the ternary complex.

In some embodiments, in the methods for inhibiting photo-damage of a ternary complex, the fluorescently labelled nucleotide reagent comprises a multivalent molecule which comprises a core attached to a plurality of nucleotide arms where each nucleotide arm comprises (i) a core attachment moiety, (ii) a spacer, (iii) a linker, and (iv) a nucleotide unit.

In some embodiments, in the methods for inhibiting photo-damage of a ternary complex, the fluorescently labelled nucleotide reagent comprises a nucleotide polyphosphate having 3-10 phosphate groups.

In some embodiments, in the methods for inhibiting photo-damage of a ternary complex, the fluorescently labelled nucleotide reagent comprises a nucleotide triphosphate having a removable chain terminating moiety.

In some embodiments, in the methods for inhibiting photo-damage of a ternary complex, (i) the nucleotide reagent is fluorescently labeled and the polymerase lacks a fluorescent label, (ii) the nucleotide reagent lacks a fluorescent label and the polymerase is fluorescently labeled, or (iii) the nucleotide reagent is fluorescently labeled and the polymerase is fluorescently labeled.

In some embodiments, in the methods for inhibiting photo-damage of a ternary complex, the ternary complex is immobilized to a support. In some embodiments, the support is coated with a hydrophilic layer having a water contact angle of less than 50 degrees.

In some embodiments, the methods for inhibiting photo-damage of a ternary complex further comprises providing a plurality of ternary complexes, each complex comprising a polymerase, a nucleic acid duplex having a nucleic acid template molecule hybridized to a primer, and a nucleotide reagent that is complementary to a next base of the primer-hybridized template molecule, wherein the plurality of ternary complexes are immobilized to a support. In some embodiments, the plurality of ternary complexes are immobilized to the support at pre-determined locations on the support. In some embodiments, the plurality of ternary complexes are immobilized to the support at random locations on the support.

In some embodiments, in the methods for inhibiting photo-damage of a ternary complex, the nucleic acid duplex comprises a nucleic acid concatemer template molecule hybridized to a plurality of primers.

In some embodiments, in the methods for inhibiting photo-damage of a ternary complex, the nucleic acid duplex further comprises a cluster of nucleic acid duplexes each duplex in the cluster comprising a single copy template molecule having one copy of an insert sequence and at least one universal adaptor sequence wherein the single copy template molecules are each hybridized to a primer.

In some embodiments, in the methods for inhibiting photo-damage of a ternary complex, the nucleic acid duplex further comprises a plurality of clonally amplified nucleic acid template molecules immobilized to a bead, and wherein each template molecule is hybridized to a primer.

In some embodiments, in the methods for inhibiting photo-damage of a ternary complex, the imaging reagent comprises ascorbic acid or salt thereof at a concentration of at least 10 mM. In some embodiments, the imaging reagent comprises ascorbic acid or salt thereof at a concentration of at least 20 mM. In some embodiments, the imaging reagent comprises ascorbic acid or salt thereof at a concentration of up to 100 mM.

In some embodiments, in the methods for inhibiting photo-damage of a ternary complex, the ascorbic acid comprises sodium ascorbate.

In some embodiments, in the methods for inhibiting photo-damage of a ternary complex, the imaging reagent comprises ascorbic acid or salt thereof and further comprises Trolox and/or Trolox quinone. In some embodiments, the imaging reagent further comprises ethylene glycol.

In some embodiments, in the methods for inhibiting photo-damage of a ternary complex, the imaging reagent comprises a non-catalytic divalent cation that inhibits incorporation of the complementary nucleotide reagent wherein the non-catalytic divalent cation comprises strontium, barium, scandium, titanium, calcium, vanadium, chromium, iron, cobalt, nickel, copper, zinc, gallium, germanium, arsenic, selenium, rhodium, europium, tin or terbium ions.

In some embodiments, the imaging reagent is employed to image the signals (e.g., fluorescent signals) emitted by a plurality of ternary complexes, each ternary complex comprising a first sequencing polymerase bound to a nucleic acid duplex which includes a nucleic acid template molecule (e.g., a concatemer) hybridized to a sequencing primer, and a complementary nucleotide unit of a multivalent molecule. In some embodiments, the multivalent molecules are labeled with a fluorophore, where the multivalent molecules are part of the ternary complexes. In the ternary complex, the nucleotide unit of the multivalent molecule is bound to the 3' end of the sequencing primer at a position that is opposite a complementary nucleotide in the template strand.

In some embodiments, a multivalent molecule generally comprises: (1) a core, and (2) a plurality of nucleotide arms which comprise (i) a core attachment moiety, (ii) a spacer comprising a PEG moiety, (iii) a linker, and (iv) a nucleotide unit. See FIGS. 2A and B.

In some embodiments, the multivalent molecule comprises a core which is attached to the plurality of nucleotide arms. In some embodiments, the spacer is attached to the linker, wherein the linker is attached to the nucleotide unit. In some embodiments, the nucleotide unit comprises a base, sugar and at least one phosphate group. In some embodiments, the linker is attached to the nucleotide unit through the base. In some embodiments, the linker comprises an aliphatic chain having 2-6 subunits or an oligo ethylene glycol chain having 2-6 subunits and optionally the linker includes an aromatic moiety (FIGS. 2A and 2B). In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP. In some embodiments, the plurality of multivalent molecules comprises a mixture of different types of multivalent molecules having two or more different types of nucleotide units selected from a group consisting of dATP, dGTP, dCTP, dTTP and dUTP. For example, the mixture comprises a plurality of a first type of multivalent molecules each having one type of nucleotide units selected from a group consisting of dATP, dGTP, dCTP, dTTP and dUTP. The mixture also comprises a plurality of a second type of multivalent molecules each having a different type of nucleotide units selected from a group consisting of dATP, dGTP, dCTP, dTTP and dUTP, which differ from the first type of nucleotide units in the first plurality.

In some embodiments, at least one of the multivalent molecules in the plurality is fluorescently-labeled, where the fluorophore is attached to the core or attached to at least one base on a nucleotide unit. In some embodiments, the fluorophore which is attached to the multivalent molecule corresponds to the base of the nucleotide unit to permit distinguishing nucleotide base units of the different fluorescently-labeled multivalent molecules.

In some embodiments, at least one of the multivalent molecules comprises at least one nucleotide arm having a cleavable moiety. In some embodiments, a multivalent molecule comprises 1, 2, 3, 4 or more nucleotide arms where each nucleotide arm includes a cleavable moiety. The cleavable moiety in the nucleotide arm can be cleaved with a cleavable agent to separate the nucleotide arm from the core.

In some embodiments, at least one of the multivalent molecules in the plurality includes a chain terminating moiety which inhibits polymerase-catalyzed incorporation of the nucleotide unit. The chain terminating moiety can be attached to the 2' or 3' sugar position of the nucleotide unit. The chain terminating moiety can be removable from the nucleotide unit by contacting the multivalent molecule with a compound that cleaves/removes the chain terminating moiety to form a nucleotide unit with a 2' or 3' extendible group.

In some embodiments, the first sequencing polymerase comprises a recombinant wild-type or mutant polymerase from Candidatus altiarchaeales archaeon. In some embodiments, the first sequencing polymerase comprises a DNA polymerase having an amino acid sequence backbone of a DNA polymerase from a Candidatus Altiarchaeales archaeon. The first sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the first sequencing polymerase comprises the amino acid sequence of any one of SEQ ID NOS: 2, 3, 4, or 5. In some embodiments, the positions of the mutations described herein are with reference to SEQ ID NO: 1. In some embodiments, the positions of the mutations described herein are with reference to any one of SEQ ID NOS: 2, 3, 4, or 5.

In some embodiments, the first sequencing polymerase comprises a DNA polymerase from 9° N which comprises the amino acid sequence of SEQ ID NOS: 6, 7, or 8. In some embodiments, the first sequencing polymerase comprises a mutant 9° N polymerase having a backbone amino acid sequence of a polymerase from 9° N (e.g., SEQ ID NOS: 6, 7, or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NOS: 6, 7, or 8.

In some embodiments, the first sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the first sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the nucleic acid template molecules comprise concatemers each comprising tandem repeat sequences of a sequence of interest and one or more adaptor sequences operably joined to a sequence of interest. In some embodiments, the sequence of interest is operably joined to any one or any combination of two or more adaptor sequence(s) including a surface capture primer binding sequence, an amplification primer binding sequence, a sequencing primer binding sequence, a sample barcode sequence, unique molecular tag sequence. In some embodiments, the nucleic acid template molecules comprise amplified molecules (e.g., clonally amplified molecules).

In some embodiments, the imaging reagent further comprises a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule. In some embodiments, the multivalent molecules are labeled with a fluorophore, where the multivalent molecules are part of the ternary complexes.

In some embodiments, the imaging reagents further comprise a plurality of ternary complexes immobilized to a support, where the template molecule (e.g., concatemer) within the ternary complex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per mm$^2$.

In some embodiments, the plurality of immobilized ternary complexes are in fluid communication with each other to permit flowing a solution of the imaging reagent onto the support so that the plurality of immobilized ternary complexes on the support can be essentially simultaneously reacted with the imaging reagent in a massively parallel manner. In some embodiments, the fluid communication of the plurality of immobilized ternary complexes can be used to conduct imaging reactions in a massively parallel manner on the support.

In some embodiments, an imaging reagent may comprise Tris-HCl (10 mM; pH 8.8), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), sucrose (1 M), glycerol (5%), Trolox (2 mM), and ascorbic acid (50 mM). In some cases, this formulation may be referred to as Formulation IR-A.

In some embodiments, an imaging reagent may comprise Tris-HCl (10 mM; pH 8.8), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), sucrose (1 M), glycerol (5%), Trolox (2 mM), ascorbic acid (50 mM), and methyl viologen (2 mM). In some cases, this formulation may be referred to as Formulation IR-B.

In some embodiments, an imaging reagent may comprise Tris-HCl (10 mM; pH 8.8), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), sucrose (1 M), glycerol (5%), Trolox (2 mM), ascorbic acid (50 mM), and 1,3,5,7 cyclo-octatetraene (2 mM). In some cases, this formulation may be referred to as Formulation IR-C.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), sucrose (1 M), glycerol (5%), Trolox (2 mM), and ascorbic acid (50 mM). In some cases, this formulation may be referred to as Formulation IR-D.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), glycerol (5%), Trolox (8 mM), and ascorbic acid (25 mM). In some cases, this formulation may be referred to as Formulation IR-E.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), glycerol (5%), Trolox (5 mM), and ascorbic acid (25 mM). In some cases, this formulation may be referred to as Formulation IR-F.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), glycerol (5%), Trolox (2 mM), and ascorbic acid (25 mM). In some cases, this formulation may be referred to as Formulation IR-G.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), Trolox (8 mM), and ascorbic acid (25 mM). In some cases, this formulation may be referred to as Formulation IR-H.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), Trolox (5 mM), and ascorbic acid (25 mM). In some cases, this formulation may be referred to as Formulation IR-I.

In some embodiments, an imaging reagent may comprise Tris-HCl (10 mM; pH 8.0), EDTA (0.5 mM; pH 7.5), NaCl (100 mM), Sr-acetate (5 mM), Triton™ X-100 (2-[4-(2,4,4-trimethylpentan-2-yl)phenoxy]ethanol) (0.1%), Trolox (2 mM), and ascorbic acid (25 mM). In some cases, this formulation may be referred to as Formulation IR-J.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), sucrose (0.5 M), glycerol (5%), aged Trolox (2 mM), and ascorbic acid (25 mM). In some cases, this formulation may be referred to as Formulation IR-K.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), glycerol (5%), aged Trolox (2 mM), and ascorbic acid (25 mM). In some cases, this formulation may be referred to as Formulation IR-L.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), sucrose (0.5 M), glycerol (5%), Trolox quinone (2 mM), and ascorbic acid (25 mM). In some cases, this formulation may be referred to as Formulation M.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), glycerol (5%), Trolox quinone (2 mM), and ascorbic acid (25 mM). In some cases, this formulation may be referred to as Formulation IR-N.

In some embodiments, an imaging reagent may comprise Tris-HCl (20 mM; pH 7.2-7.5), EDTA (0.5 mM; pH 7.5), NaCl (75 mM), Sr-acetate (5 mM), Tween-20 (0.02%), ethylene glycol (30%), glycerol (5%), Trolox (2 mM), and ascorbic acid (50 mM). In some cases, this formulation may be referred to as Formulation IR-O.

In some embodiments, an imaging reagent may comprise Tris-HCl (20 mM; pH 7.2), EDTA (0.5 mM; pH 7.5), NaCl (75 mM), Sr-acetate (5 mM), Tween-20 (0.02%), ethylene glycol (30%), glycerol (5%), Trolox (2 mM), and ascorbic acid (50 mM). In some cases, this formulation may be referred to as Formulation IR-P.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), Trolox (2 mM), and ascorbic acid (25 mM). In some cases, this formulation may be referred to as Formulation IR-Q.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), aged Trolox (2 mM), and ascorbic acid (25 mM). In some cases, this formulation may be referred to as Formulation IR-R.

In some embodiments, an imaging reagent may comprise Tris-HCl (10 mM; pH 8.0), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), Trolox quinone (2 mM), and ascorbic acid (25 mM). In some cases, this formulation may be referred to as Formulation IR-S.

In some embodiments, an imaging reagent may comprise Tris-HCl (10 mM; pH 7.2-7.5), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), Trolox (2 mM), and ascorbic acid (25 mM). In some cases, this formulation may be referred to as Formulation IR-T.

In some embodiments, an imaging reagent may comprise Tris-HCl (10 mM; pH 7.2-7.5), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), aged Trolox (2 mM), and ascorbic acid (25 mM). In some cases, this formulation may be referred to as Formulation IR-U.

In some embodiments, an imaging reagent may comprise Tris-HCl (10 mM; pH 7.2-7.5), EDTA (0.5 mM; pH 7.5), NaCl (75 mM), Sr-acetate (5 mM), Triton™ X-100 (2-[4-(2,4,4-trimethylpentan-2-yl)phenoxy]ethanol) (0.1%), ethylene glycol (30%), glycerol (5%), Trolox quinone (2 mM), and ascorbic acid (25 mM). In some cases, this formulation may be referred to as Formulation IR-V.

In some embodiments, an imaging reagent may comprise Tris-HCl (20 mM; pH 7.2), EDTA (0.5 mM; pH 7.5), NaCl (25 mM), Sr-acetate (5 mM), Tween-20 (0.02%), ethylene glycol (30%), glycerol (5%), Trolox (2 mM, fresh Trolox), and ascorbic acid (50 mM). In some cases, this formulation may be referred to as Formulation IR-W.

In some embodiments, an imaging reagent may comprise Tris-HCl (20 mM; pH 7.2), EDTA (0.5 mM; pH 7.5), NaCl (25 mM), Sr-acetate (5 mM), Tween-20 (0.02%), TCEP (0.5 mM), ethylene glycol (30%), glycerol (5%), Trolox (2 mM, fresh Trolox), and ascorbic acid (50 mM). In some cases, this formulation may be referred to as Formulation IR-X.

In some embodiments, an imaging reagent may comprise Tris-HCl (20 mM; pH 7.2), EDTA (0.5 mM; pH 7.5), Sr-acetate (5 mM), Tween-20 (0.02%), TCEP (0.5 mM), ethylene glycol (30%), glycerol (5%), Trolox (2 mM, fresh Trolox), and ascorbic acid (50 mM). In some cases, this formulation may be referred to as Formulation IR-Y.

Stepping Reagents and Methods of Use

The present disclosure provides one or more stepping reagents, and methods that employ the stepping reagents where the methods comprise contacting the plurality of immobilized nucleic acid duplexes with the stepping reagent (e.g., step (m) of the methods described herein) under a condition suitable for promoting polymerase-catalyzed nucleotide incorporation. The stepping reagents can be used for the massively parallel sequencing workflow at step (m) as described below.

In some embodiments, the stepping reagents comprise: at least one solvent, at least one pH buffering agent, at least one monovalent cation, a catalytic divalent cation, a detergent, a second sequencing polymerase enzyme and a plurality of nucleotides (e.g., free nucleotides). In some embodiments, the second sequencing polymerases can be labeled with a detectable moiety (e.g., a fluorophore) or can be unlabeled. In some embodiments, the catalytic divalent cation comprises magnesium and/or manganese. In some embodiments, the stepping reagent lacks a non-catalytic divalent cation. Exemplary non-catalytic divalent cations include strontium and/or barium. In some embodiments, the monovalent salt which can promote formation of the ternary complex. The monovalent salt may comprise, for example, one or more of Sodium, Potassium, Lithium, Rubidium, Cesium, Silver, or other monovalent cations as, and may be supplied as NaCl, KCl, LiCl, CsCl, AgCl, $(NH_4)_2SO_4$ or potassium glutamate or other such monovalent salt solutions. In some embodiments, the monovalent salt comprises NaCl, KCl, (NH4)2SO4 or potassium glutamate. In some embodiments, the catalytic divalent cation comprises magnesium and/or manganese. In some embodiments, the stepping reagent lacks a non-catalytic divalent cation. Exemplary non-catalytic divalent cations include strontium and/or barium. In some embodiments, the monovalent salt which can promote formation of the ternary complex. In some embodiments, the monovalent salt comprises NaCl, KCl, (NH4)2SO4 or potassium glutamate.

In some embodiments, the stepping reagent further comprises at least one viscosity agent.

In some embodiments, the stepping reagent can optionally include a plurality of sequencing primers which hybridize to at least a portion of a nucleic acid template molecule. The plurality of sequencing primers comprise a 3' extendible end or a 3' non-extendible end. In some embodiments, the plurality of sequencing primers comprise soluble oligonucleotide primers (e.g., in-solution).

In some embodiments, individual nucleotides in the plurality of nucleotides comprise an aromatic base, a five carbon sugar (e.g., ribose or deoxyribose), and at least one phosphate group. In some embodiments, the nucleotides comprise a polyphosphate chain having 1-10 phosphate groups.

In some embodiments, the plurality of nucleotide comprises at least one type of nucleotide selected from a group consisting of dATP, dGTP, dCTP, dTTP and dUTP. In some embodiments, the plurality of nucleotide comprises a mixture of two or more, in any combination of nucleotides, selected from a group consisting of dATP, dGTP, dCTP, dTTP and dUTP.

In some embodiments, at least one of the nucleotides in the plurality is fluorescently-labeled. The fluorophore can be attached to the base of the nucleotide. In some embodiments, the fluorophore corresponds to the base of the nucleotide to permit distinguishing nucleotide base of the different fluorescently-labeled nucleotides. In some embodiments, the labeled nucleotide comprises a fluorophore is attached to the base of the nucleotide via a cleavable linker that is cleavable with a compound that cleaves/removes the cleavable linker thereby removing the fluorophore label from the nucleotide.

In some embodiments, at least one of the nucleotides in the plurality of nucleotides includes a chain terminating moiety which inhibits nucleotide incorporation in a subsequent polymerase-catalyzed nucleotide incorporation reaction. The chain terminating moiety can be attached to the 2' or 3' sugar position of the nucleotide. The chain terminating moiety can be removable from the nucleotide by contacting the chain terminating nucleotide with a compound that cleaves/removes the chain terminating moiety to form a nucleotide with a 2' or 3' extendible group. For example, a chain terminating nucleotide comprising a chain terminating moiety attached to its 3' sugar position, can be converted to a nucleotide having an extendible 3'OH sugar group by contacting the chain terminating nucleotide with a compound that cleaves/removes the chain terminating moiety.

In some embodiments, the stepping reagents are formulated to promote formation of a stable ternary complex which comprises a polymerase (e.g., the second sequencing polymerase) bound to a nucleic acid duplex which includes a nucleic acid template molecule (e.g., a concatemer) hybridized to a sequencing primer, and a complementary nucleotide. In some embodiments, in the ternary complex, the nucleotide is bound to the 3' end of the sequencing primer at a position that is opposite a complementary nucleotide in the template strand. In some embodiments, the stepping reagents are formulated to promote incorporation of the complementary nucleotide unit into the 3' end of the sequencing primer (e.g., polymerase-catalyzed nucleotide incorporation) to generate a plurality of nucleic acid duplexes each having a template molecule (e.g., concatemer) hybridized to a nascent strand (e.g., extended sequencing primer) where the nascent strand is extended by one nucleotide. In some embodiments, the catalytic divalent cation comprises magnesium and/or manganese.

In some embodiments, the stepping reagent can also include a monovalent salt which can promote formation of the ternary complex. The monovalent salt may comprise, for example, one or more of Sodium, Potassium, Lithium, Rubidium, Cesium, Silver, or other monovalent cations as are known in the art, and may be supplied as NaCl, KCl, LiCl, CsCl, AgCl, $(NH_4)_2SO_4$ or potassium glutamate or other such monovalent salt solutions as are known in the art. In some embodiments, the monovalent salt comprises NaCl, KCl, (NH4)2SO4 or potassium glutamate. The stepping reagent can include a monovalent salt at a concentration of about 5-200 mM, or about 25-100 mM.

Figure 16:
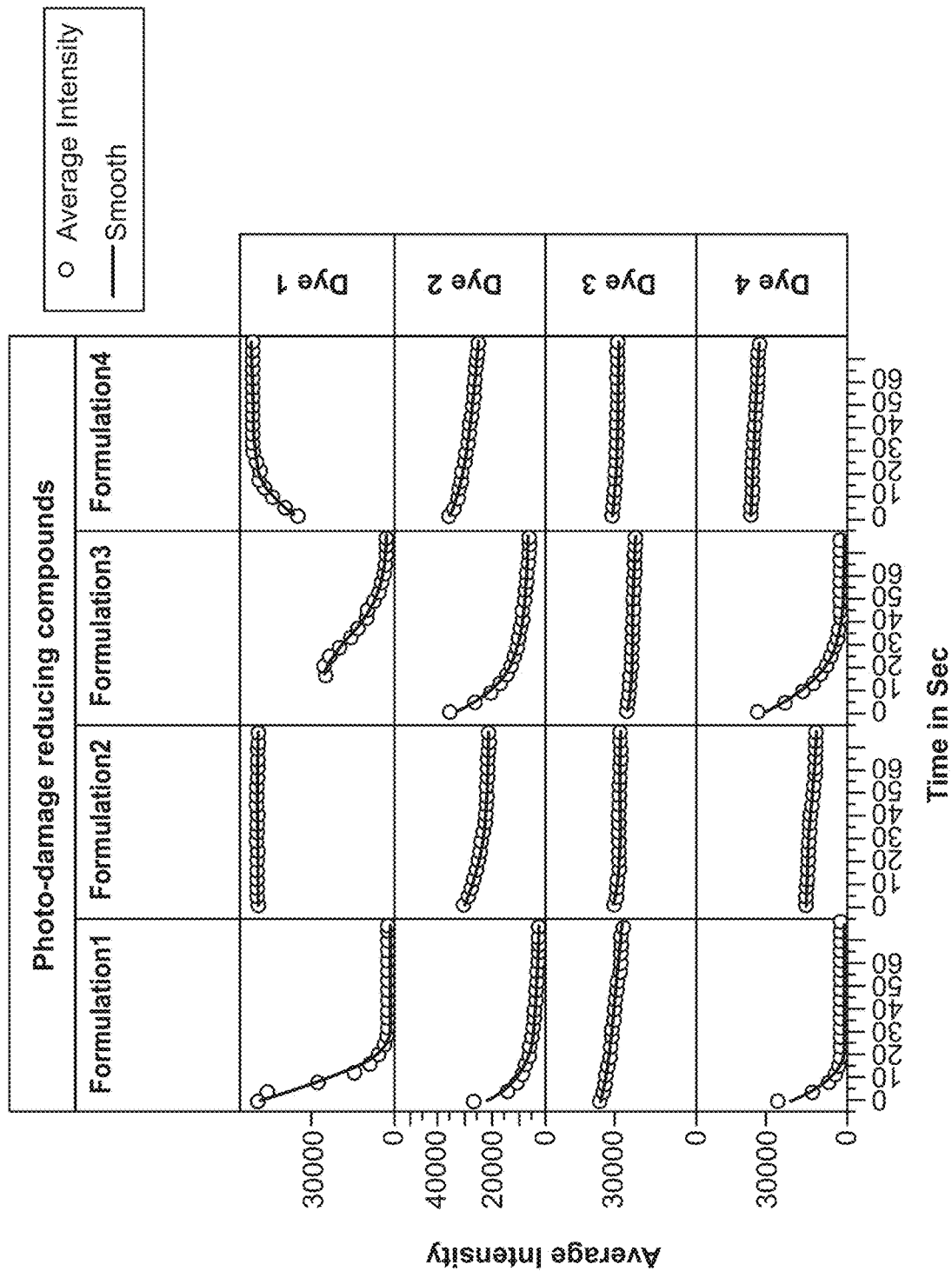
FIG. 16 is a series of graphs showing the effects of imaging reagents comprising different formulations on average signal intensity with time. The different formulations contain either no compounds that reduce photo damage or different combinations of compounds that reduce photo damage. Dye 1 is AF647, dye 2 is CF532, dye 3 is CF570 and dye 4 is CD680. Formulations 1-4 comprise Tris-HCl (pH 8.8), EDTA, NaCl, Triton™ X-100 (2-[4-(2,4,4-trimethylpentan-2-yl)phenoxy]ethanol), sucrose, strontium acetate and glycerol. Formulation 1 contains no photo-damage reducing compound. Formulation 2 comprises Trolox (2 mM) and sodium ascorbate (50 mM). Formulation 3 comprises Trolox (2 mM) and methyl viologen (2 mM). Formulation 4 comprises Trolox (2 mM), methyl viologen (2 mM) and sodium ascorbate (50 mM).

In some embodiments, the second sequencing polymerase can bind a complementary nucleotide and nucleic acid duplex to form a ternary complex. The second sequencing polymerase comprises a recombinant wild-type or mutant polymerase comprising an amino acid sequence that is at least 80% identical to a backbone sequence of a polymerase from Candidatus altiarchaeales archaeon (e.g., any of SEQ ID NOS:221-225), or from 9° N (e.g., SEQ ID NOS:226 or 227), or from Therminator (e.g., SEQ ID NO:228), or from Vent (e.g., SEQ ID NO:229), or from Deep Vent (e.g., SEQ ID NO:230), or from Pfu (e.g., SEQ ID NO:231), or from *Pyrococcus abyssi* (e.g., SEQ ID NO:232), or from RB69 (SEQ ID NO:233). FIGS. 16A and 16B list exemplary positionally equivalent mutations for various polymerases.

In some embodiments, the stepping reagents further comprise at least one nucleic acid template molecule which comprises DNA or RNA, or a mixture of RNA and DNA. In some embodiments, the nucleic acid template molecules comprise concatemer or single-copy template molecules, or a mixture of concatemer and single-copy template molecules. In some embodiments, the nucleic acid template molecules comprise single-stranded molecules, double-stranded molecules or nucleic acid molecules having single- and double-stranded portions. In some embodiments, individual nucleic acid template molecules include at least one adaptor, where the adaptor includes a capture primer binding sequence, an amplification primer binding sequence and/or a sequencing primer binding sequence. In some embodiments, individual nucleic acid template molecules are operably linked to at least one adaptor having a sample barcode sequence or a unique molecular tag sequence. In some embodiments, the nucleic acid template molecules are soluble or immobilized to a support or immobilized to a coating on the support.

In some embodiments, the nucleic acid template molecules comprise concatemers each comprising tandem repeat sequences of a sequence of interest and any adaptor sequences operably joined to the sequence of interest. In some embodiments, the nucleic acid template molecules comprise amplified molecules (e.g., clonally amplified molecules).

In some embodiments, the second sequencing polymerase comprises a recombinant wild-type or mutant polymerase from Candidatus altiarchaeales archaeon. In some embodiments, the second sequencing polymerase comprises a DNA polymerase having an amino acid sequence backbone of a DNA polymerase from a Candidatus Altiarchaeales archaeon. The second sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the second sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the second sequencing polymerase comprises the amino acid sequence of any one of SEQ ID NOS: 2, 3, 4, or 5. In some embodiments, the positions of the mutations described herein are with reference to SEQ ID NO: 1. In some embodiments, the positions of the mutations described herein are with reference to any one of SEQ ID NOS: 2, 3, 4, or 5.

In some embodiments, the second sequencing polymerase comprises a DNA polymerase from 9° N which comprises the amino acid sequence of SEQ ID NOS: 6, 7 or 8. In some embodiments, the second sequencing polymerase comprises a mutant 9° N polymerase having a backbone amino acid sequence of a polymerase from 9° N (e.g., SEQ ID NOS: 6, 7 or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NOS: 6, 7, or 8.

In some embodiments, the second sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the second sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the second sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the second sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the stepping reagent further comprises a plurality of ternary complexes each comprising a second sequencing polymerase bound to a nucleic acid duplex which includes a nucleic acid template molecule (e.g., a concatemer) hybridized to a sequencing primer, and a complementary nucleotide. In some embodiments, the nucleotide is labeled with a fluorophore, where the nucleotide is part of the ternary complex. In the ternary complex, the nucleotide is bound to the 3' end of the sequencing primer at a position that is opposite a complementary nucleotide in the template strand.

In some embodiments, the stepping reagents further comprise a plurality of ternary complexes immobilized to a support, where the template molecule (e.g., concatemer) within the ternary complex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per mm$^2$.

In some embodiments, the plurality of immobilized ternary complexes are in fluid communication with each other to permit flowing a solution of the stepping reagent onto the support so that the plurality of immobilized ternary complexes on the support can be essentially simultaneously reacted with the stepping reagent in a massively parallel manner. In some embodiments, the fluid communication of the plurality of immobilized ternary complexes can be used to conduct stepping reactions in a massively parallel manner on the support.

In some embodiments, a stepping reagent comprises Bis-Tris propane (25 mM, pH 8.8), KCl (40 mM), NH$_4$SO$_4$ (10 mM), MgSO$_4$ (10 mM), Tween-20 (0.2%), Betaine (250 mM), sucrose (200 mM), N3-dATP (2 µM), N3-dGTP (2 µM), N3-dCTP (2 µM), N3-dTTP (2 µM), DMSO (0.5%), and a sequencing polymerase (0.24 µM). In some cases, this formulation may be referred to as Formulation SR-A.

In some embodiments, a stepping reagent comprises HEPES (25 mM, pH 8.6), KCl (40 mM), NH$_4$SO$_4$ (10 mM), MgSO$_4$ (20 mM), Triton™ X-100 (2-[4-(2,4,4-trimethyl-pentan-2-yl)phenoxy]ethanol) (0.5%), glutathione (250 mM), sucrose (200 mM), N3-dATP (2 µM), N3-dGTP (2 µM), N3-dCTP (2 µM), N3-dTTP (2 µM), DMSO (0.5%), and a sequencing polymerase (0.37 µM). In some cases, this formulation may be referred to as Formulation SR-B.

In some embodiments, a stepping reagent comprises MES (25 mM, pH 8.4), KCl (40 mM), NH$_4$SO$_4$ (40 mM), MgSO$_4$ (30 mM), Tween-20 (1%), tris(2-carboxyethyl)phosphine (250 mM), sucrose (200 mM), N3-dATP (2 µM), N3-dGTP (2 µM), N3-dCTP (2 µM), N3-dTTP (2 µM), DMSO (0.5%), and a sequencing polymerase (0.48 µM). In some cases, this formulation may be referred to as Formulation SR-C.

In some embodiments, a stepping reagent comprises MOPS (25 mM, pH 8.2), KCl (40 mM), NH$_4$SO$_4$ (10 mM), MgSO$_4$ (10 mM), Triton™ X-100 (2-[4-(2,4,4-trimethyl-pentan-2-yl)phenoxy]ethanol) (1%), TCEP (250 mM), sucrose (200 mM), N3-dATP (2 µM), N3-dGTP (2 µM), N3-dCTP (2 µM), N3-dTTP (2 µM), DMSO (0.5%), and a sequencing polymerase (0.2 µM). In some cases, this formulation may be referred to as Formulation SR-D.

In some embodiments, a stepping reagent comprises MOPSO (25 mM, pH 8.0), KCl (40 mM), NH$_4$SO$_4$ (40 mM), MgSO$_4$ (20 mM), Triton™ X-100 (2-[4-(2,4,4-trimethylpentan-2-yl)phenoxy]ethanol) (1%), sodium dithionite (250 mM), sucrose (200 mM), N3-dATP (2 µM), N3-dGTP (2 µM), N3-dCTP (2 µM), N3-dTTP (2 µM), DMSO (0.5%), and a sequencing polymerase (1.20 µM). In some cases, this formulation may be referred to as Formulation SR-E.

In some embodiments, a stepping reagent comprises Bis-Tris propane (25 mM, pH 8.8), NaCl (40 mM), NH$_4$SO$_4$ (10 mM), MgSO$_4$ (10 mM), Tween-20 (0.2%), 2-beta mercaptoethanol (50 mM), sucrose (200 mM), N3-dATP (2 µM), N3-dGTP (2 µM), N3-dCTP (2 µM), N3-dTTP (2 µM), DMSO (2%), and a sequencing polymerase (0.88 µM). In some cases, this formulation may be referred to as Formulation SR-F.

In some embodiments, a stepping reagent comprises BES (25 mM, pH 8.6), NaCl (40 mM), NH$_4$SO$_4$ (40 mM), MgSO$_4$ (20 mM), Triton™ X-100 (2-[4-(2,4,4-trimethyl-pentan-2-yl)phenoxy]ethanol) (0.5%), DTT (50 mM), sucrose (200 mM), N3-dATP (2 µM), N3-dGTP (2 µM), N3-dCTP (2 µM), N3-dTTP (2 µM), DMSO (2%), and a sequencing polymerase (0.44 µM). In some cases, this formulation may be referred to as Formulation SR-G.

In some embodiments, a stepping reagent comprises TES (25 mM, pH 8.4), NaCl (40 mM), NH$_4$SO$_4$ (10 mM), MgSO$_4$ (30 mM), Tween-20 (1%), formamide (50 mM), sucrose (200 mM), N3-dATP (2 µM), N3-dGTP (2 µM), N3-dCTP (2 µM), N3-dTTP (2 µM), and a sequencing polymerase (0.42 µM). In some cases, this formulation may be referred to as Formulation SR-H.

In some embodiments, a stepping reagent comprises Bis-Tris propane (25 mM, pH 8.2), NaCl (40 mM), NH$_4$SO$_4$ (40 mM), MgSO$_4$ (10 mM), Triton™ X-100 (2-[4-(2,4,4-trimethylpentan-2-yl)phenoxy]ethanol) (1%), glutathione (50 mM), sucrose (200 mM), N3-dATP (2 µM), N3-dGTP (2 µM), N3-dCTP (2 µM), N3-dTTP (2 µM), and a sequencing polymerase (0.52 µM). In some cases, this formulation may be referred to as Formulation SR-I.

In some embodiments, a stepping reagent comprises CAPS (25 mM, pH 8.0), NaCl (40 mM), NH$_4$SO$_4$ (10 mM), MgSO$_4$ (20 mM), Triton™ X-100 (2-[4-(2,4,4-trimethyl-pentan-2-yl)phenoxy]ethanol) (1%), Betaine (50 mM), sucrose (200 mM), N3-dATP (2 µM), N3-dGTP (2 µM), N3-dCTP (2 µM), N3-dTTP (2 µM), DMSO (2%), and a sequencing polymerase (0.88 µM). In some cases, this formulation may be referred to as Formulation SR-J.

Cleaving Reagents and Methods of Use

The present disclosure provides one or more cleaving reagents, and methods that employ the cleaving reagents where the methods comprise cleaving a chain terminating moiety from the terminal nucleotide on a nascent strand (e.g., extended sequencing primer) thereby generating an extended sequencing primer with a 3' extendible end (e.g., step (p) of the methods described herein).

In some embodiments, the cleaving reagent comprises: at least one solvent, a pH buffering agent, at least one monovalent cation, a detergent, a cleaving agent and a cleaving catalyst.

The cleaving reagents are formulated to retain the plurality of nucleic acid duplexes each having a template molecule (e.g., concatemer) hybridized to a nascent strand (e.g., extended sequencing primer).

In some embodiments, when the cleaving reagent includes at least one nucleotide having a chain terminating moiety at the 2' or 3' sugar position, then the cleaving reagents are formulated to include a cleaving agent that cleaves the chain terminating moiety from the terminal nucleotide on the nascent strand (e.g., on the extended sequencing primer) to generate an extended sequencing primer with a 3' extendible end.

In some embodiments, when the stepping reagent includes at least one nucleotide having a fluorophore attached to its base via a cleavable linker, then the cleaving reagents are formulated to include a cleaving agent that cleaves the cleavable linker to generate a nucleotide that lacks a fluorophore.

In some embodiments, the cleaving reagent further comprise a plurality of nucleic acid duplexes each having a template molecule (e.g., concatemer) hybridized to a nascent strand (e.g., extended sequencing primer) where the nascent strand is extended by one nucleotide. In some embodiments, the one nucleotide is a terminal nucleotide on the nascent strand and the nucleotide comprises a chain terminating moiety. In some embodiments, the one nucleotide is a terminal nucleotide on the nascent strand and the nucleotide comprises an extendible 3' OH group. In some embodiments, the nucleic acid duplexes are each bound to a polymerase (e.g., a second sequencing polymerase).

In some embodiments, the cleaving reagents further comprise a plurality of nucleic acid duplexes immobilized to a support, where the template molecule (e.g., concatemer) within the nucleic acid duplex is immobilized to a support or is immobilized to a coating (e.g., polymer coating) on the support. In some embodiments, the support can be coated with at least one hydrophilic polymer coating. In some embodiment, the hydrophilic polymer coating has a water contact angle of no more than 45-50 degrees. In some embodiments, the plurality of nucleic acid duplexes are immobilized to one or more layers of the coatings on the support where the density of the immobilized nucleic acid duplexes is about 100-100,000 per mm$^2$.

In some embodiments, the plurality of immobilized nucleic acid duplexes are in fluid communication with each other to permit flowing a solution of the cleaving reagent onto the support so that the plurality of immobilized nucleic acid duplexes on the support can be essentially simultaneously reacted with the cleaving reagent in a massively parallel manner. In some embodiments, the fluid communication of the plurality of immobilized nucleic acid duplexes can be used to conduct cleaving reactions in a massively parallel manner on the support.

In some embodiments, the cleaving reagent comprises HEPES (50 mM, pH 9.2), $MgCl_2$ (4 mM), NaCl (500 mM), Triton™ X-100 (2-[4-(2,4,4-trimethylpentan-2-yl)phenoxy] ethanol) (0.1%), Trolox (2 mM), ascorbic acid (50 mM), TCEP (50 mM). In some cases, this formulation may be referred to as Formulation CR-A.

In some embodiments, the cleaving reagent comprises MES (50 mM, pH 9.2), $MgCl_2$ (4 mM), KCl (500 mM), CHAPS (0.1%), Trolox (2 mM), ascorbyl palmitate (50 mM), THPP (50 mM). In some cases, this formulation may be referred to as Formulation CR-B.

In some embodiments, the cleaving reagent comprises Bis Tris propane (50 mM, pH 9.2), $MgCl_2$ (4 mM), NaCl (500 mM), 3-[(3-cholamidopropyl)dimethylammonio-]-1-propanesulfonate (CHAPS) (0.1%), Trolox (2 mM), ascorbic acid (50 mM), THPP (50 mM). In some cases, this formulation may be referred to as Formulation CR-C.

In some embodiments, the cleaving reagent comprises MOPS (50 mM, pH 9.2), $MgCl_2$ (4 mM), KCl (500 mM), CHAPS (0.1%), Trolox (2 mM), citric acid (50 mM), betaine (50 mM). In some cases, this formulation may be referred to as Formulation CR-D.

In some embodiments, the cleaving reagent comprises MOPSO (50 mM, pH 9.2), $MgCl_2$ (4 mM), NaCl (500 mM), CHAPS (0.1%), Trolox (2 mM), butylated hydroxytoluene (50 mM), 2-beta mercaptoethanol (50 mM). In some cases, this formulation may be referred to as Formulation CR-E.

In some embodiments, the cleaving reagent comprises BES (50 mM, pH 9.2), $MgCl_2$ (4 mM), KCl (500 mM), Tween-20 (0.1%), Trolox (2 mM), Trolox (50 mM), N-acetyl cysteine (50 mM). In some cases, this formulation may be referred to as Formulation CR-F.

In some embodiments, the cleaving reagent comprises TES (50 mM, pH 9.2), $MgCl_2$ (4 mM), NaCl (500 mM), Tween-20 (0.1%), Trolox (2 mM), butylated hydroxy toluene (50 mM), glutathione (50 mM). In some cases, this formulation may be referred to as Formulation CR-G.

In some embodiments, the cleaving reagent comprises CAPS (50 mM, pH 9.2), $MgCl_2$ (4 mM), KCl (500 mM), Tween-20 (0.1%), Trolox (2 mM), butylated hydroxy anisol (50 mM), THPP (50 mM). In some cases, this formulation may be referred to as Formulation CR-H.

In some embodiments, the cleaving reagent comprises TAPS (50 mM, pH 9.2), $MgCl_2$ (4 mM), NaCl (500 mM), Triton™ X-100 (2-[4-(2,4,4-trimethylpentan-2-yl)phenoxy] ethanol) (0.1%), Trolox (2 mM), coumaric acid (50 mM), betaine (50 mM). In some cases, this formulation may be referred to as Formulation CR-I.

In some embodiments, the cleaving reagent comprises TAPSO (50 mM, pH 9.2), $MgCl_2$ (4 mM), KCl (500 mM), Triton™ X-100 (2-[4-(2,4,4-trimethylpentan-2-yl)phenoxy] ethanol) (0.1%), Trolox (2 mM), caffeic acid (50 mM), THPP (50 mM). In some cases, this formulation may be referred to as Formulation CR-J.

Methods

The present disclosure provides methods for conducting a nucleic acid sequencing workflow. In some embodiments, a method may comprise contacting a plurality of nucleic acid template molecules with a plurality of amplification primers in the presence of a nucleic acid hybridization reagent under a condition suitable to form a plurality of nucleic acid duplexes each duplex comprising a template molecule hybridized to an amplification primer. In some embodiments, the amplification primers are soluble primers or are immobilized to a support. In some embodiments, the plurality of nucleic acid duplexes comprises at least a first nucleic acid template molecule hybridized to a first amplification primer to form at least a first nucleic acid duplex, and at least a second nucleic acid template molecule hybridized to a second amplification primer to form a second nucleic acid duplex.

In some embodiments, the nucleic acid hybridization reagent comprises at least one solvent, a pH buffering agent, and at least one monovalent cation. In some embodiments, the hybridization reagent further comprises any one or any combination of two or more of a detergent, a reducing agent, a chaotropic agent, a chelating agent, an alcohol, a zwitterion, a sugar alcohol and/or a crowding agent.

In some embodiments, the contacting is conducted at a temperature of about 20-25° C., or about 25-35° C., or about 35-45° C., or about 45-55° C., or about 55-65° C., or about 65-75° C., or higher temperatures.

In some embodiments, the plurality of nucleic acid template molecules comprises DNA, RNA, or a mixture of RNA and DNA. In some embodiments, the plurality of nucleic acid template molecules comprises linear or circularized molecules, or a mixture of linear and circular molecules. In some embodiments, the plurality of nucleic acid template molecules comprises single-stranded molecules, double-stranded molecules or nucleic acid molecules having single- and double-stranded portions. In some embodiments, individual nucleic acid template molecules in the plurality of nucleic acid template molecules are operably linked to at least one adaptor sequence, where the adaptor sequence includes a capture primer binding sequence, an amplification primer binding sequence and/or a sequencing primer binding sequence. In some embodiments, individual nucleic acid template molecules in the plurality of nucleic acid template molecules are operably linked to at least one adaptor sequence having a sample barcode sequence or a unique molecular tag sequence.

In some embodiments, the amplification primers can hybridize to at least a portion of the nucleic acid template molecules. The amplification primer comprises a 3' extendible end or the 3' end comprises a chain terminating moiety.

In some embodiments, the amplification primers comprise soluble oligonucleotide primers (e.g., in-solution), or the amplification primers are immobilized to a support or immobilized to a coating on the support. In some embodiments, the density of the immobilized amplification primers on the support is about $10^4$-$10^{12}$ per $mm^2$.

In some embodiments, the plurality of nucleic acid duplexes are immobilized to a support, where the template molecules (e.g., circularized template molecules) and/or the amplification primers are immobilized to a support or are immobilized to a coating on the support. In some embodiments, the support can be coated with at least one hydrophilic polymer coating. In some embodiment, the hydrophilic polymer coating has a water contact angle of no more than 45-50 degrees. In some embodiments, a plurality of amplification primers are immobilized to one or more layers of the coating on the support where the density of the immobilized amplification primers is about 100-100,000 amplification primers per $mm^2$.

In some embodiment, the plurality of immobilized amplification primers on the support are in fluid communication with each other to permit flowing a solution of the reagents (e.g., hybridization reagent) onto the support so that the plurality of immobilized amplification primers on the support can be essentially simultaneously reacted with the reagents in a massively parallel manner. In some embodiments, the fluid communication of the plurality of immobilized amplification primers can be used to conduct nucleic acid hybridization reactions in a massively parallel manner on the support.

In some embodiments, when the amplification primers are immobilized to a support or immobilized to a coating on the support, prior to forming the plurality of nucleic acid duplexes, the methods for conducting a nucleic acid sequencing workflow may comprise (i) providing a plurality of amplification primers that are immobilized to a support or immobilized to a coating on the support, and (ii) washing the immobilized amplification primers with a wash reagent. In some embodiments, the wash reagent comprises at least one solvent, a pH buffering agent, a chelating agent, at least one monovalent cation, and a detergent. In some embodiments, the wash reagent comprises at least one solvent, a pH buffering agent, a chelating agent, at least one monovalent cation, or a detergent. In some embodiments, the washing is conducted at a temperature of about 20-45° C., or at a temperature of about 20-30° C.

In some embodiments, the methods for conducting a nucleic acid sequencing workflow may comprise: washing the plurality of immobilized nucleic acid duplexes with a universal wash reagent. In some embodiments, the wash reagent comprises at least one solvent, a pH buffering agent, a chelating agent, at least one monovalent cation, and a detergent. In some embodiments, the wash reagent comprises at least one solvent, a pH buffering agent, a chelating agent, at least one monovalent cation, or a detergent. In some embodiments, the washing is conducted at a temperature of about 20-45° C., or at a temperature of about 20-30° C.

In some embodiments, the methods for conducting a nucleic acid sequencing workflow may comprise a two-stage amplification reaction employing a first and second amplification reagent where the pH of the first amplification reagent is formulated to inhibit nucleic acid amplification and the pH of the second amplification reagent is formulated to promote nucleic acid amplification.

In some embodiments, the methods for conducting a nucleic acid sequencing workflow may comprise: contacting the plurality of nucleic acid duplexes with a first amplification reagent which comprises at least one solvent, a pH buffering agent, at least one monovalent cation, ammonium ions, a plurality of nucleotides, and/or an amplification polymerase enzyme. In some embodiments, the first amplification reagent further comprises any one or any combination of two or more of a detergent, a reducing agent, and/or a viscosity agent. In some embodiments, the pH of the first amplification reagent is suitable for binding the amplification polymerase to a nucleic acid duplex which comprises a nucleic acid template molecule hybridized to an amplification oligonucleotide primer. In some embodiments, the pH of the first amplification reagent can reduce/inhibit activity of the amplification polymerase. In some embodiments, the pH of the first amplification reagent can be about pH 8 or lower (e.g., pH 7-8).

In some embodiments, the contacting is conducted under a condition suitable for forming a plurality of complexed amplification polymerases each comprising an amplification polymerase and a nucleotide bound to a nucleic acid duplex. In some embodiments, the condition is not suitable for conducting nucleic acid amplification reactions.

In some embodiments, the plurality of nucleic acid duplexes are immobilized to the support, where the template molecules comprise circularized template molecules that are hybridizes to the amplification primers. In some embodiments, the amplification primers are immobilized to the support or are immobilized to a coating on the support.

In some embodiments, the amplification polymerase has strand displacement activity and comprise phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In some embodiments, the plurality of nucleotides comprise a mixture of two or more nucleotides selected from a group consisting of dATP, dGTP, dCTP and dTTP. In some embodiments, the plurality of nucleotides comprise a mixture of three or more nucleotides selected from a group consisting of dATP, dGTP, dCTP and dTTP. In some embodiments, the plurality of nucleotides comprise a mixture of four types of nucleotides including dATP, dGTP, dCTP and dTTP.

In some embodiments, the methods for conducting a nucleic acid sequencing workflow may comprise: contacting the plurality of complexed amplification polymerases with a second amplification reagent which comprises at least one solvent, a pH buffering agent, at least one monovalent cation, ammonium ions, and/or a plurality of nucleotides. In some embodiments, the second amplification reagent lacks an amplification polymerase enzyme. In some embodiments, the second amplification reagent further comprises any one or any combination of two or more of a detergent, a reducing agent, and/or a viscosity agent. In some embodiments, the first amplification reagent and the second amplification reagent have a different pH. In some embodiments, the pH of the second amplification reagent is suitable for retaining a complex having the amplification polymerase (e.g., from the first amplification reagent) bound to a nucleic acid duplex which comprises a nucleic acid template molecule hybridized to an amplification oligonucleotide primer. In some embodiments, the pH of the second amplification reagent can be suitable for promoting activity of the amplification polymerase. For example, the pH of the second amplification reagent can be about pH 8.5 or higher (e.g., pH 8.5-8.8).

In some embodiments, the contacting is conducted under a condition suitable for retaining the plurality of complexed amplification polymerases from each comprising an amplification polymerase and a nucleotide bound to a nucleic acid duplex, and the condition is suitable for conducting a plurality of nucleic acid amplification reactions to form a plurality of clonally amplified template molecules (e.g., concatemers or single copy template molecules).

In some embodiments, the plurality of concatemers comprises at least a first concatemer and a second concatemer. In some embodiments, the first concatemer is immobilized to a first location on the support (or a first location on the coating on the support). In some embodiments, the second concatemer is immobilized to a second location on the support (or a second location on the coating on the support) which differs from the location of the first immobilized concatemer.

In some embodiments, the second amplification reaction comprises a rolling circle amplification reaction to generate a plurality of concatemers each containing tandem repeat sequences of the circular template molecule and any adaptor sequences present in the original circularized nucleic acid template molecule. In some embodiments, the rolling circle amplification reaction can be conducted under isothermal amplification conditions at a constant temperature such as, for example about 20° C., about 25° C., about 30° C., about 35° C., about 37° C., about 40° C., about 42° C., about 50° C., about 60° C., about 65° C., about 70° C., about 75° C. or at a higher temperature, or within a temperature range defined by any two of the foregoing temperatures.

In some embodiments, the plurality of nucleotides comprise a mixture of two or more nucleotides selected from a group consisting of dATP, dGTP, dCTP and dTTP. In some embodiments, the plurality of nucleotides comprise a mixture of three or more nucleotides selected from a group consisting of dATP, dGTP, dCTP and dTTP. In some embodiments, the plurality of nucleotides comprise a mixture of four types of nucleotides including dATP, dGTP, dCTP and dTTP.

In some embodiments, the methods for conducting a nucleic acid sequencing workflow may comprise: contacting the plurality of concatemers with a wash-removal reagent under a condition suitable to retain the immobilized concatemers, and the condition is suitable to remove (e.g., wash away) components of a first reaction (e.g., a first amplification reaction) and/or the second reaction (e.g., a second amplification reaction), including removing the amplification polymerase and the nucleotides. In some embodiments, the wash-removal reagent comprises at least one solvent, a pH buffering agent, a chelating agent, a detergent, and/or a chaotropic agent. In some embodiments, the contacting is conducted at a temperature of about 20-60° C., or at a temperature of about 25-45° C.

In some embodiments, the methods for conducting a nucleic acid sequencing workflow may comprise: washing the plurality of concatemers with a universal wash reagent. In some embodiments, the washing can remove the chaotropic agent from the wash-removal reagent. In some embodiments, the universal wash reagent comprises at least one solvent, a pH buffering agent, a chelating agent, at least one monovalent cation, and/or a detergent. In some embodiments, the washing is conducted at a temperature of about 20-65° C., or at a temperature of about 25-45° C.

In some embodiments, the methods for conducting a nucleic acid sequencing workflow may comprise: contacting the plurality of concatemers (e.g., immobilized concatemers) with a trap reagent, wherein the trap reagent comprises at least one solvent, a pH buffering agent, a chelating agent, at least one monovalent cation, a non-catalytic divalent cation, a detergent, a plurality of multivalent molecules, a plurality of sequencing primers, and/or a first sequencing polymerase enzyme. In some embodiments, the trap reagent further comprises at least one viscosity agent. In some embodiments, the non-catalytic divalent cations comprise strontium and/or barium.

In some embodiments, the contacting is conducted under a condition suitable for forming a plurality of immobilized ternary complexes by binding the immobilized concatemers to sequencing primers, the first sequencing polymerases and a plurality of multivalent molecules, thereby forming a plurality of immobilized ternary complexes.

In some embodiments, the immobilized template molecule comprises an immobilized concatemer molecule comprising tandem repeat sequences of a sequence-of-interest and any adaptor sequences present in the original circularized nucleic acid template molecule. The contacting of step (g) can generate multiple ternary complexes along the same concatemer molecule, wherein individual ternary complexes comprise a sequencing primer, a first sequencing polymerase and a nucleotide unit of a multivalent molecule.

In some embodiments, the trap reagent further comprises a monovalent salt which can promote formation of the ternary complex. The monovalent salt may comprise, for example, one or more of Sodium, Potassium, Lithium, Rubidium, Cesium, Silver, or other monovalent cations as are known in the art, and may be supplied as NaCl, KCl, LiCl, CsCl, AgCl, (NH$_4$)$_2$SO$_4$ or potassium glutamate or other such monovalent salt solutions as are known in the art. In some embodiments, the monovalent salt comprises NaCl, KCl, (NH4)2SO4, or potassium glutamate.

In some embodiments, the trap reagent further comprises a plurality of sequencing primers which hybridize to at least a portion of a nucleic acid template molecule. In some embodiments, the sequencing primer comprises a 3' extendible end or a 3' non-extendible end. In some embodiments, the sequencing primer comprises soluble oligonucleotide primers (e.g., in-solution).

In some embodiments, the contacting is conducted at a temperature of about 20-65° C., or at a temperature of about 25-45° C.

In some embodiments, the plurality of immobilized concatemers are contacted with the trap reagent and the plurality of sequencing primers under a condition suitable for forming at least a first immobilized ternary complex by binding the first immobilized concatemer (e.g., first immobilized template) to a sequencing primer, at least one of the first sequencing polymerases and at least one of the multivalent molecules, thereby forming the first immobilized ternary complex.

In some embodiments, the plurality of immobilized concatemers are contacted with the trap reagent and the plurality of sequencing primers under a condition suitable for forming at least a second immobilized ternary complex by binding the second immobilized concatemer (e.g., second immobilized template) to a sequencing primer, at least one of the first sequencing polymerases and at least one of the multivalent molecules, thereby forming the second immobilized ternary complex.

In some embodiments, in an individual ternary complex in the plurality of ternary complexes, the nucleotide unit from the multivalent molecule is bound to the 3' end of the sequencing primer at a position that is opposite a complementary nucleotide in the template strand.

In some embodiments, the plurality of immobilized concatemers are contacted with the trap reagent under a condition suitable for forming a plurality of ternary complexes, (e.g., at least a first and second ternary complex), and in the plurality of ternary complexes the suitable condition inhibits incorporation of a nucleotide unit from a multivalent molecule into a sequencing primer.

In some embodiments, the plurality of immobilized concatemers are contacted with the trap reagent under a condition suitable for forming a plurality of stable ternary complexes, (e.g., at least a first and second stable ternary complex) wherein the plurality of stable ternary complexes have a longer persistence time (e.g., little or no dissociation) compared to a plurality of ternary complexes formed by binding template molecules to the sequencing primer, the sequencing polymerase and a free nucleotide.

In some embodiments, individual multivalent molecule in the plurality comprise (a) a core, and (b) a plurality of nucleotide arms which comprise (i) a core attachment moiety, (ii) a spacer comprising a PEG moiety, (iii) a linker, and (iv) a nucleotide unit. See FIGS. 2A to 2D.

In some embodiments, the multivalent molecule comprises a core which is attached to the plurality of nucleotide arms. In some embodiments, the spacer is attached to the linker, wherein the linker is attached to the nucleotide unit. In some embodiments, the nucleotide unit comprises a base, sugar and at least one phosphate group. In some embodiments, the linker is attached to the nucleotide unit through the base. In some embodiments, the linker comprises an aliphatic chain having 2-6 subunits or an oligo ethylene glycol chain having 2-6 subunits and optionally the linker includes an aromatic moiety In some embodiments, the multivalent molecule comprises a core which is attached to the plurality of nucleotide arms. In some embodiments, the spacer is attached to the linker, wherein the linker is attached to the nucleotide unit. In some embodiments, the nucleotide unit comprises a base, sugar and at least one phosphate group. In some embodiments, the linker is attached to the nucleotide unit through the base. In some embodiments, the linker comprises an aliphatic chain having 2-6 subunits or an oligo ethylene glycol chain having 2-6 subunits and optionally the linker includes an aromatic moiety (FIGS. 2A to 2D). In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP. In some embodiments, the plurality of multivalent molecules comprises a mixture of multivalent molecules having two or more different types of nucleotides selected from a group consisting of dATP, dGTP, dCTP, dTTP and dUTP. In some embodiments, at least one of the multivalent molecules in the plurality is fluorescently-labeled, where the fluorophore is attached to the core or attached to at least one base on a nucleotide unit. In some embodiments, the fluorophore corresponds to the base of the nucleotide unit to permit distinguishing nucleotide base units of the different fluorescently-labeled multivalent molecules.

In some embodiments, the first sequencing polymerase can bind a complementary nucleotide unit of a multivalent molecule and nucleic acid duplex to form a ternary complex. The first sequencing polymerase comprises a recombinant wild-type or mutant polymerase comprising an amino acid sequence that is at least 80% identical to a backbone sequence of a polymerase from Candidatus altiarchaeales archaeon (e.g., any of SEQ ID NOS:221-225), or from 9° N (e.g., SEQ ID NOS:226 or 227), or from Therminator (e.g., SEQ ID NO:228), or from Vent (e.g., SEQ ID NO:229), or from Deep Vent (e.g., SEQ ID NO:230), or from Pfu (e.g., SEQ ID NO:231), or from *Pyrococcus abyssi* (e.g., SEQ ID NO:232), or from RB69 (SEQ ID NO:233).

In some embodiments, the first sequencing polymerase comprises a recombinant wild-type or mutant polymerase from Candidatus altiarchaeales archaeon. In some embodiments, the first sequencing polymerase comprises a DNA polymerase having an amino acid sequence backbone of a DNA polymerase from a Candidatus Altiarchaeales archaeon. In some embodiments, the first sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the first sequencing polymerase comprises the amino acid sequence of any one of SEQ ID NOS: 2, 3, 4, or 5. In some embodiments, the positions of the mutations described herein are with reference to SEQ ID NO: 1. In some embodiments, the positions of the mutations described herein are with reference to any one of SEQ ID NOS: 2, 3, 4, or 5.

In some embodiments, the first sequencing polymerase comprises a DNA polymerase from 9° N which comprises the amino acid sequence of SEQ ID NOS: 6, 7 or 8. In some embodiments, the first sequencing polymerase comprises a mutant 9° N polymerase having a backbone amino acid sequence of a polymerase from 9° N (e.g., SEQ ID NOS: 6, 7 or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NOS: 6, 7, or 8.

In some embodiments, the first sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the first sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the plurality of ternary complexes are immobilized to a support. In some embodiments, the template molecule (e.g., concatemer) within the ternary complex is immobilized to a support or is immobilized to a coating (e.g., polymer coating) on the support. In some embodiments, the support can be coated with at least one hydrophilic polymer coating. In some embodiments, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per $mm^2$. In some embodiments, at least one of the plurality of immobilized ternary complexes is a fluorescently-labeled ternary complex which comprises a nucleic acid duplex having a template molecule (e.g., a concatemer) hybridized to a sequencing primer, where the duplex is bound to a first sequencing polymerase and a fluorescently-labeled multivalent molecule.

In some embodiments, the plurality of immobilized ternary complexes are in fluid communication with each other to permit flowing a solution of the trap reagent onto the support so that the plurality of immobilized ternary complexes on the support can be essentially simultaneously reacted with the trap reagent in a massively parallel manner. In some embodiments, the fluid communication of the plurality of immobilized ternary complexes can be used to conduct nucleic acid sequencing reactions in a massively parallel manner on the support.

In some embodiments, the methods for conducting a nucleic acid sequencing workflow may comprise: contacting the plurality of stable ternary complexes (e.g., immobilized ternary complexes) with a post-trap reagent, where the post-trap reagent comprises at least one solvent, a pH buffering agent, a chelating agent, at least one monovalent cation, a non-catalytic divalent cation, a detergent and a first sequencing polymerase. In some embodiments, the post-trap reagents lack a plurality of multivalent molecules. In some embodiments, the post-trap reagent further comprises at least one viscosity agent. In some embodiments, the non-catalytic divalent cations comprise strontium and/or barium.

In some embodiments, the post-trap reagent further comprises a monovalent salt which can promote formation of the ternary complex. The monovalent salt may comprise, for example, one or more of Sodium, Potassium, Lithium, Rubidium, Cesium, Silver, or other monovalent cations as are known in the art, and may be supplied as NaCl, KCl, LiCl, CsCl, AgCl, $(NH_4)_2SO_4$ or potassium glutamate or other such monovalent salt solutions as are known in the art. In some embodiments, the monovalent salt comprises NaCl, KCl, (NH4)2SO4 or potassium glutamate.

In some embodiments, the post-trap reagent optionally comprises a plurality of sequencing primers which hybridize to at least a portion of a nucleic acid template molecule. In some embodiments, the sequencing primer comprises a 3' extendible end or a 3' non-extendible end. In some embodiments, the sequencing primer comprises soluble oligonucleotide primers (e.g., in-solution).

In some embodiments, the plurality of immobilized ternary complexes (e.g., at least the first and second ternary complexes) that formed during step (g) are contacted with the post-trap reagent of step (h) under a condition suitable for preserving the ternary complexes without polymerase-catalyzed incorporation of the nucleotide units. In some embodiments, the post-trap reagent lacks a plurality of multivalent molecules. In some embodiments, the post-trap reagent reduces or eliminates dissociation of the existing polymerase from the multivalent molecules and nucleic acid duplexes so that the ternary complexes remain intact.

In some embodiments, the plurality of stable ternary complexes have a longer persistence time (e.g., little or no dissociation) compared to a plurality of ternary complexes formed by binding template molecules to the sequencing primer, the sequencing polymerase and a free nucleotide.

In some embodiments, the contacting is conducted at a temperature of about 20-65° C., or at a temperature of about 25-45° C.

In some embodiments, the post-trap reagents contain a first sequencing polymerase which can be the same type or a different type of first sequencing polymerase contained in the trap reagent.

In some embodiments, the first sequencing polymerase comprises a recombinant wild-type or mutant polymerase from Candidatus altiarchaeales archaeon. In some embodiments, the first sequencing polymerase comprises a DNA polymerase having an amino acid sequence backbone of a DNA polymerase from a Candidatus Altiarchaeales archaeon. In some embodiments, the first sequencing polymerase comprises an amino acid sequence that is at least 80% identical to SEQ ID NO: 1, where the mutant DNA polymerase comprises an amino acid substitution at one or more positions selected from a group consisting of Leu416, Tyr417, Pro418, Ala493, Arg515, Ile529 and Asn567. In some embodiments, the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the positions of the mutations described herein are with reference to SEQ ID NO: 1. In some embodiments, the positions of the mutations described herein are with reference to any one of SEQ ID NOS: 2, 3, 4, or 5.

In some embodiments, the first sequencing polymerase comprises a DNA polymerase from 9° N which comprises the amino acid sequence of SEQ ID NOS: 6, 7, or 8. In some embodiments, the first sequencing polymerase comprises a mutant 9° N polymerase having a backbone amino acid sequence of a polymerase from 9° N (e.g., SEQ ID NOS: 6, 7, or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NO: 6, 7, or 8.

In some embodiments, the first sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO: 9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 9.

In some embodiments, the first sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, the plurality of ternary complexes are immobilized to a support. In some embodiments, the template molecule (e.g., concatemer) within the ternary complex is immobilized to a support or is immobilized to a coating (e.g., polymer coating) on the support. In some embodiments, the support can be coated with at least one hydrophilic polymer coating. In some embodiments, the hydrophilic polymer coating has a water contact angle of no more than 45-50 degrees. In some embodiments, the plurality of ternary complexes are immobilized to one or more layers of the coatings on the support where the density of the immobilized ternary complexes is about 100-100,000 per $mm^2$. In some embodiments, at least one of the plurality of immobilized ternary complexes is a fluorescently-labeled ternary complex which comprises a nucleic acid duplex having a template molecule (e.g., a concatemer) hybridized to a sequencing primer, where the duplex is bound to a first sequencing polymerase and a fluorescently-labeled multivalent molecule.

In some embodiments, the plurality of immobilized ternary complexes are in fluid communication with each other to permit flowing a solution of the post-trap reagent onto the support so that the plurality of immobilized ternary complexes on the support can be essentially simultaneously reacted with the post-trap reagent in a massively parallel manner. In some embodiments, the fluid communication of the plurality of immobilized ternary complexes can be used to conduct nucleic acid sequencing reactions in a massively parallel manner on the support.

In some embodiments, the methods for conducting a nucleic acid sequencing workflow may comprise: (i) contacting the plurality of stable ternary complexes (e.g., plurality of immobilized fluorescently-labeled ternary complexes) with an imaging reagent, and (ii) detecting the presence of at least one of the plurality of ternary complexes by exposing the plurality of ternary complexes to an excitation illumination and detecting a fluorescent signal emitted from the immobilized fluorescently-labeled ternary complexes in response to the excitation illumination.

In some embodiments, the imaging reagent comprises at least one solvent, a pH buffering agent, a chelating agent, at least one monovalent cation, a non-catalytic divalent cation, a detergent, and/or at least one compound for reducing photo-damage. In some embodiments, the imaging reagents further comprise at least one viscosity agent.

In some embodiments, the imaging reagent preserves (e.g., stabilizes) the ternary complexes that were formed in the presence of a trap reagent. In some embodiments, the imaging reagent inhibits polymerase-catalyzed nucleotide incorporation reaction. In some embodiments, the imaging reagent reduces or inhibits photo-damage of the ternary complex by exposure to excitation illumination.

In some embodiments, the fluorescent signal emitted from the immobilized fluorescently-labeled ternary complexes can be detected by employing a system comprising a excitation illumination source, a detector and an optical train. In some embodiments, the system can be configured in a manner that directs the excitation illumination to the immobilized fluorescently-labeled ternary complexes immobilized on the support, and the detector can detect the fluorescent signal emitted from the immobilized fluorescently-labeled ternary complexes in response to the excitation illumination.

In some embodiments, the excitation illumination comprises electromagnetic radiation including infrared, visible light and ultraviolet light. In some embodiments, the electromagnetic radiation can be provided by a laser. In some embodiments, the laser can have characteristics including intensity, radiance (e.g., brightness), directionality, coherence, polarization and/or mono-chromaticity. In some embodiments, the laser can be a continuous-wave laser that emits a continuous laser uninterrupted beam of light. In some embodiments, the laser can be a pulsed laser such as a Q-switching, mode-locking or pulsed pumping laser. In some embodiments, the laser can be an ultrafast laser that can produce pulses in a time range of about 5 femtoseconds to 100 picoseconds. In some embodiments, the laser can be employed in a one-photon or multi-photon excitation mode.

In some embodiments, the fluorescently-labeled ternary complexes can be exposed to an appropriate excitation wavelength which is dependent on the fluorophore attached to the multivalent molecule. In some embodiments, the wavelength of the excitation illumination can be at any wavelength in the range of about 488-752 nm.

In some embodiments, the laser power can about 50-250 mW, or about 75-200 mW.

In some embodiments, the imaging of step (i) can be conducted at a temperature of about 20-65° C., or at a temperature of 25-45° C.

In some embodiments, the methods for conducting a nucleic acid sequencing workflow may comprise: identifying the nucleotide unit (e.g., fluorescently labeled nucleotide unit) of a multivalent molecule that is bound to the sequencing primer, as part of the fluorescently-labeled ternary complex detected. In some embodiments, the nucleotide unit that is bound to the sequencing primer is not incorporated into the 3' end of the sequencing primer. In some embodiments, in the fluorescently-labeled ternary complex which is undergoing detection, the fluorophore that is attached to the multivalent molecule corresponds to the base of the nucleotide unit to permit identification of the nucleotide base unit.

In some embodiments, the identifying can be conducted at a temperature of about 20-65° C., or at a temperature of about 25-45° C.

In some embodiments, the methods for conducting a nucleic acid sequencing workflow may comprise: contacting the plurality of immobilized fluorescently-labeled ternary complexes with a wash-removal reagent under a condition suitable for dissociating the ternary complex (e.g., fluorescently labeled ternary complex) by removing the fluorescently-labeled multivalent molecules and the first sequencing polymerases from the nucleic acid duplexes. In some embodiments, the wash-removal reagent retains the nucleic acid duplex which comprises the sequencing primer hybridized to the template molecule (e.g., concatemer), and duplex remains immobilized to the support.

In some embodiments, the wash-removal reagent comprises at least one solvent, a pH buffering agent, a chelating agent, a detergent, and/or a chaotropic agent. In some embodiments, the contacting is conducted at a temperature of about 20-65° C., or at a temperature of about 25-45° C.

In some embodiments, the methods for conducting a nucleic acid sequencing workflow may comprise: conducting a pre-step reaction by washing the plurality of immobilized nucleic acid duplexes with the universal wash reagent under a condition that retains the nucleic acid duplexes (e.g., nucleic acid template molecules hybridized to sequencing primers) immobilized to the support. In some embodiments, the washing can remove the chaotropic agent from the wash-removal reagent. In some embodiments, the universal wash reagent comprises at least one solvent, a pH buffering agent, a chelating agent, at least one monovalent cation and a detergent. In some embodiments, the washing is conducted at a temperature of about 20-65° C., or at a temperature of about 25-45° C.

In some embodiments, the methods for conducting a nucleic acid sequencing workflow may comprise: conducting a stepping reaction by contacting the plurality of immobilized nucleic acid duplexes with the stepping reagent comprising at least one solvent, at least one pH buffering agent, at least one monovalent cation, a catalytic divalent cation, a detergent, a second sequencing polymerase enzyme, and/or a plurality of nucleotides (e.g., free nucleotides). In some embodiments, the catalytic divalent cation can promote polymerase-catalyzed nucleotide incorporation. In some embodiments, the catalytic divalent cation comprises magnesium and/or manganese. In some embodiments, the monovalent salt can promote formation of the ternary complex. The monovalent salt may comprise, for example, one or more of Sodium, Potassium, Lithium, Rubidium, Cesium, Silver, or other monovalent cations as are known in the art, and may be supplied as NaCl, KCl, LiCl, CsCl, AgCl, $(NH_4)_2SO_4$ or potassium glutamate or other such monovalent salt solutions as are known in the art. In some embodiments, the monovalent salt comprises NaCl, KCl, (NH4)2SO4 or potassium glutamate.

In some embodiments, the stepping reagent further comprises at least one viscosity agent. In some embodiments, the stepping reagent optionally comprises a plurality of sequencing primers which hybridize to at least a portion of a nucleic acid template molecule. In some embodiments, the sequencing primer comprises a 3' extendible end or a 3' non-extendible end. In some embodiments, the sequencing primer comprises soluble oligonucleotide primers (e.g., in-solution).

In some embodiments, the stepping reagent retains the nucleic acid duplex which comprises the sequencing primer hybridized to the template molecule (e.g., concatemer), and duplex remains immobilized to the support.

In some embodiments, the contacting of step (m) is conducted under a condition suitable for forming a plurality of immobilized ternary complexes by binding the immobilized nucleic acid duplexes from step (l) with the second sequencing polymerases and a plurality of nucleotides (free non-conjugated nucleotides), thereby forming a plurality of immobilized ternary complexes.

In some embodiments, the second sequencing polymerase can bind a complementary nucleotide and nucleic acid duplex to form a ternary complex. The second sequencing polymerase comprises a recombinant wild-type or mutant polymerase comprising an amino acid sequence that is at least 80% identical to a backbone sequence of a polymerase from Candidatus altiarchaeales archaeon (e.g., any of SEQ ID NOS:221-225), or from 9° N (e.g., SEQ ID NOS:226 or 227), or from Therminator (e.g., SEQ ID NO:228), or from Vent (e.g., SEQ ID NO:229), or from Deep Vent (e.g., SEQ ID NO:230), or from Pfu (e.g., SEQ ID NO:231), or from *Pyrococcus abyssi* (e.g., SEQ ID NO:232), or from RB69 (SEQ ID NO:233).

In some embodiments, the plurality of nucleotide comprises a mixture of two or more nucleotides selected from a group consisting of dATP, dGTP, dCTP, dTTP and dUTP. In some embodiments, the plurality of nucleotide comprises a mixture of three or more nucleotides selected from a group consisting of dATP, dGTP, dCTP, dTTP and dUTP. In some embodiments, the plurality of nucleotide comprises a mixture of four or more nucleotides selected from a group consisting of dATP, dGTP, dCTP, dTTP and dUTP. In some embodiments, the plurality of nucleotide comprises a mixture of dATP, dGTP, dCTP, dTTP and dUTP.

In some embodiments, at least one of the nucleotides in the plurality of nucleotides comprises a chain terminating moiety attached to the 2' and/or 3' sugar moiety. The chain terminator moiety can be an azide, azido or azidomethyl group. In some embodiments, the azide, azido or azidomethyl group is cleavable/removable with a chemical agent. In some embodiments, the chemical agent comprises a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, at least one of the nucleotides in the plurality of nucleotides can be attached to a detectable reporter moiety. In some embodiments, the detectable reporter moiety can be a fluorophore. In some embodiments, the fluorophore can be attached to the base of the nucleotide. In some embodiments, the fluorophore corresponds to the base of the nucleotide to permit distinguishing nucleotide base of the different fluorescently-labeled nucleotides.

In some embodiments, the contacting is conducted at a temperature of about 20-75° C., or at a temperature of about 30-65° C., or at a temperature of about 40-50° C.

In some embodiments, the plurality of immobilized nucleic acid duplexes are contacted with the stepping reagent under a condition suitable for forming a plurality of immobilized ternary complexes by binding individual duplexes to the second sequencing polymerase and a complementary nucleotide, thereby forming immobilized ternary complexes. In some embodiments, in an individual ternary complex in the plurality, the complementary nucleotide is bound to the 3' end of the sequencing primer at a position that is opposite a complementary nucleotide in the template strand. In some embodiments, the condition is also suitable for promoting polymerase-catalyzed nucleotide incorporation thereby advancing the second sequencing polymerase to the next base position on the nucleic acid duplex to generate a plurality of nucleic acid duplexes each having a template molecule (e.g., concatemer) hybridized to a nascent strand (e.g., extended sequencing primer) where the nascent strand is extended by one nucleotide. In some embodiments, when the incorporated nucleotide includes a 2' or 3' chain terminator moiety, the terminal 3' ends of the nascent strands cannot undergo nucleotide incorporation in a subsequent stepping reaction without removal of the chain terminating moiety.

In some embodiments, the methods for conducting a nucleic acid sequencing workflow may comprise: contacting the plurality of immobilized nucleic acid duplexes having extended sequencing primers that are formed with a wash-removal reagent under a condition suitable to remove (e.g., wash away) components of the stepping reaction, including removing the second sequencing polymerases and unreacted nucleotides. In some embodiments, the wash-removal reagent retains the nucleic acid duplex which comprises the sequencing primer hybridized to the template molecule (e.g., concatemer), and duplex remains immobilized to the support. In some embodiments, the wash-removal reagent comprises at least one solvent, a pH buffering agent, a chelating agent, a detergent and a chaotropic agent. In some embodiments, the contacting is conducted at a temperature of about 20-65° C., or at a temperature of about 25-45° C.

In some embodiments, the methods for conducting a nucleic acid sequencing workflow may comprise: washing the plurality of immobilized nucleic acid duplexes having extended sequencing primers with the universal wash reagent under a condition to remove the chaotropic agent from the wash-removal reagent. In some embodiments, the washing condition is suitable to retain the plurality of immobilized nucleic acid duplexes. In some embodiments, the universal wash reagent comprises at least one solvent, a pH buffering agent, a chelating agent, at least one monovalent cation, and/or a detergent. In some embodiments, the washing is conducted at a temperature of about 20-65° C., or at a temperature of about 25-45° C.

In some embodiments, the methods for conducting a nucleic acid sequencing workflow may comprise: contacting the plurality of immobilized nucleic acid duplexes with a cleaving reagent under a condition suitable for cleaving the chain terminating moiety from the terminal nucleotide on the nascent strand (e.g., extended sequencing primer) thereby generating an extended sequencing primer with a 3' extendible end. In some embodiments, the cleaving reaction is suitable to retain the plurality of immobilized nucleic acid duplexes. In some embodiments, the cleaving reagent comprises at least one solvent, a pH buffering agent, at least one monovalent cation, a detergent, a cleaving agent and a cleaving catalyst. In some embodiments, the washing is conducted at a temperature of about 20-65° C., or at a temperature of about 25-45° C.

In some embodiments, the methods for conducting a nucleic acid sequencing workflow may comprise: washing the plurality of immobilized nucleic acid duplexes having extended sequencing primers with the universal wash reagent under a condition to remove the cleaving agent and cleaving catalyst. In some embodiments, the universal wash reagent retains the nucleic acid duplexes (e.g., nucleic acid template molecules hybridized to extended sequencing primers) immobilized to the support. In some embodiments, the universal wash reagent comprises at least one solvent, a pH buffering agent, a chelating agent, at least one monovalent cation, and/or a detergent. In some embodiments, the washing is conducted at a temperature of about 20-65° C., or at a temperature of about 25-45° C.

In some embodiments, the methods for conducting a nucleic acid sequencing workflow may comprise: repeating any one of: (a) contacting the plurality of immobilized concatemers with a trap reagent, (b) contacting the plurality of immobilized concatemers with a post-trap reagent, (c) contacting the plurality of immobilized fluorescently-labeled ternary complexes with an imaging reagent, (d) identifying the fluorescently-labeled nucleotide unit of the multivalent molecule that is bound to the sequencing primer, (e) contacting the plurality of immobilized fluorescently-labeled ternary complexes with a wash-removal reagent, (f) washing the plurality of immobilized nucleic acid duplexes with a universal wash reagent, (g) contacting the plurality of immobilized nucleic acid duplexes with a stepping reagent, (h) contacting the plurality of immobilized extended nucleic acid duplexes with a wash-removal reagent, (i) washing the plurality of immobilized extended nucleic acid duplexes with a universal wash reagent, or (j) contacting the plurality of immobilized extended nucleic acid duplexes with a cleaving reagent. In some embodiments, the plurality of immobilized concatemers are contacted with the trap reagent in the absence of sequencing primers.

Pairwise Sequencing Reagents and Methods of Use

The present disclosure provides one or more pairwise sequencing reagents, and methods that employ the pairwise sequencing reagents where the methods comprise obtaining a first sequencing read of a first region of a first nucleic acid strand (e.g., sense strand), and obtaining a second sequencing read of a second region of a second nucleic acid strand that is complementary to the first stand (e.g., anti-sense strand), wherein the first and second strands correspond to two complementary strands of the same double stranded template molecule. The first sequencing read of the first sequenced region and the second sequencing read of the second sequenced region can having overlapping sequences which correspond to complementary sequences from the first and second strands of the double stranded template molecule. The first and second sequencing reads can be aligned so that the overlapping sequencing reads can yield sequence information of a paired region in the original double stranded nucleic acid source (e.g., a paired region in the genome), and the accuracy of the sequence information can be ascertained from the first and second sequencing reads with a high level of confidence. The first sequencing read of the first sequenced region and the second sequencing read of the second sequenced region do not necessarily have overlapping sequences in which case sequence information of a paired region in the original double stranded nucleic acid source cannot be ascertained with a high level of confidence. The first and second sequencing reads can initiate at one end of their respective template molecules, or can initiate at an internal position.

In some embodiments, the first nucleic acid strand comprises at least one nucleotide having a scissile moiety that can be cleaved to generate at least one abasic site in the first nucleic acid strand. Exemplary nucleotides having a scissile moiety include uridine, 8-oxo-7,8-dihydroquinine and deoxyinosine. In some embodiments, the first nucleic acid strand that includes one or more nucleotides having a scissile moiety can be hybridized with at least one soluble forward sequencing primer and the first strand can be sequenced to generate at least one extended forward sequencing primer strand, thereby sequencing the first nucleic acid strand. The at least one forward sequencing primer strand can be replaced by conducting a primer extension reaction using a second strand synthesis reagent and the first nucleic acid strand as a template molecule to generate a forward extension strand which is the second nucleic acid strand.

In some embodiments, the first nucleic acid strand can be removed using a strand degradation reagent which generates abasic sites at the nucleotides having the scissile moiety. The strand degradation reagent can generate gaps at the abasic sites to generate a gap-containing first strand while retaining the forward extension strand (second strand). The gap-containing first strand(s) can be removed while retaining the forward extension strand (second strand). The second strand can be hybridized with at least one soluble reverse sequencing primer and sequenced to generate at least one extended reverse sequencing primer strand, thereby sequencing the second nucleic acid strand. In some embodiments, the first nucleic acid strand lacks a nucleotide having a scissile moiety.

In some embodiments, the second strand synthesis reagent comprises at least one solvent, a pH buffering agent, ammonium ions (e.g., $(NH_4)_2SO_4$), potassium ions (e.g., KCl), magnesium ions (e.g., $MgCl_2$), at least one detergent, at least one reducing agent, a viscosity agent, a crowding agent, a mixture of nucleotides, and a primer extension polymerase. In some embodiments, the mixture of nucleotides comprises any combination of dATP, dGTP, dCTP, dTTP and/or dUTP. In some embodiments, the primer extension polymerase has strand displacing activity. In some embodiments, the second strand synthesis reagent further comprises (or lacks) a plurality of soluble amplification primers that can hybridize to a universal adaptor sequence in the first strand. In some embodiments, the second strand synthesis reagent further comprises at least one compaction oligonucleotide. The compaction oligonucleotide comprises the sequence (SEQ ID NO: 215)
`5-CATGTAATGCACGTACTTTCAGGGTAAACATGTAATGCACG TACTTTCAGGGTUUU-3
or the sequence (SEQ ID NO: 216)
5'-GATCAGGTGAGGCTGCGACGACTAAAGATCAGGTGAGGCTG

CGACGACTUUU-3'.

In some embodiments, the strand degradation reagent comprises at least one solvent, a pH buffering agent, a potassium ion, a magnesium ion, and an enzyme stabilizing agent. For example, the strand degradation reagent comprises Tris-acetate (pH about 7.9), potassium acetate, magnesium acetate and an albumin such as bovine serum albumin. In some embodiments, the strand degradation reagent further comprises at least enzyme that releases uracil from deoxyuridine-containing DNA molecules. For example the at least one uracil-releasing enzymes comprise uracil DNA glycosylase, DNA glycosylase-lyase and endonuclease VIII. In some embodiments, the strand degradation reagent further comprises T7 exonuclease.

In some embodiments, a second strand synthesis reagent comprises Tris-HCl (40 mM, pH 7.5), $(NH_4)SO_4$ (15 mM), KCl (200 mM), $MgSO_4$ (5 mM), Tween-80 (0.1%), DTT (5 mM), betaine (400 mM), sucrose (400 mM), PEG 32K (5%), dATP (3 mM), dGTP (3 mM), dCTP (3 mM), dTTP (3 mM), an amplification polymerase (0.37 µM). In some cases, this formulation may be referred to as Formulation SSR-A.

In some embodiments, a second strand synthesis reagent comprises HEPES (20 mM, pH 7.8), $(NH_4)SO_4$ (25 mM), NaCl (200 mM), $MgSO_4$ (5 mM), Tween-80 (0.1%), DTT (5 mM), betaine (400 mM), sucrose (400 mM), PEG 16K (5%), dATP (2 mM), dGTP (2 mM), dCTP (2 mM), dTTP (2 mM), an amplification polymerase (0.57 µM). In some cases, this formulation may be referred to as Formulation SSR-A.

In some embodiments, a second strand synthesis reagent comprises PIPES (50 mM, pH 8), $(NH_4)SO_4$ (35 mM), KCl (200 mM), $MgSO_4$ (5 mM), Tween-80 (0.1%), DTT (5 mM), betaine (400 mM), sucrose (400 mM), PEG 8K (5%), dATP (1 mM), dGTP (1 mM), dCTP (1 mM), dTTP (1 mM), an amplification polymerase (1.22 µM). In some cases, this formulation may be referred to as Formulation SSR-A.

In some embodiments, a second strand synthesis reagent comprises Tris (200 mM, pH 8.2), $(NH_4)SO_4$ (50 mM), NaCl (200 mM), $MgSO_4$ (5 mM), Tween-80 (0.1%), DTT (5 mM), betaine (400 mM), sucrose (400 mM), PEG 32K (5%), dATP (5 mM), dGTP (5 mM), dCTP (5 mM), dTTP (5 mM), an amplification polymerase (0.83 µM). In some cases, this formulation may be referred to as Formulation SSR-A.

In some embodiments, a second strand synthesis reagent comprises HEPES (150 mM, pH 7), $(NH_4)SO_4$ (50 mM), KCl (200 mM), $MgSO_4$ (5 mM), Tween-80 (0.1%), DTT (5 mM), betaine (400 mM), sucrose (400 mM), PEG 16K (5%), dATP (4 mM), dGTP (4 mM), dCTP (4 mM), dTTP (4 mM), an amplification polymerase (0.60 µM). In some cases, this formulation may be referred to as Formulation SSR-A.

In some embodiments, a second strand synthesis reagent comprises MOPS (100 mM, pH 7.5), $(NH_4)SO_4$ (10 mM), NaCl (200 mM), $MgSO_4$ (5 mM), Tween-80 (0.1%), DTT (5 mM), betaine (400 mM), sucrose (400 mM), PEG 8K (5%), dATP (3 mM), dGTP (3 mM), dCTP (3 mM), dTTP (3 mM), an amplification polymerase (0.42 µM). In some cases, this formulation may be referred to as Formulation SSR-A.

In some embodiments, a second strand synthesis reagent comprises Tris-HCl (75 mM, pH 7.5), $(NH_4)SO_4$ (10 mM), KCl (200 mM), $MgSO_4$ (5 mM), Tween-80 (0.1%), DTT (5 mM), betaine (400 mM), sucrose (400 mM), PEG 16K (5%), dATP (2 mM), dGTP (2 mM), dCTP (2 mM), dTTP (2 mM), an amplification polymerase (0.33 µM). In some cases, this formulation may be referred to as Formulation SSR-A.

In some embodiments, a second strand synthesis reagent comprises Tris-HCl (50 mM, pH 7), $(NH_4)SO_4$ (5 mM), KCl (200 mM), $MgSO_4$ (5 mM), Tween-80 (0.1%), DTT (5 mM), betaine (400 mM), sucrose (400 mM), PEG 8K (5%), dATP (1 mM), dGTP (1 mM), dCTP (1 mM), dTTP (1 mM), an amplification polymerase (0.24 µM). In some cases, this formulation may be referred to as Formulation SSR-A.

In some embodiments, a second strand synthesis reagent comprises HEPES (20 mM, pH 7), $(NH_4)SO_4$ (50 mM), NaCl (200 mM), MgSO$_4$ (5 mM), Tween-80 (0.1%), DTT (5 mM), betaine (400 mM), sucrose (400 mM), PEG 16K (5%), dATP (1 mM), dGTP (1 mM), dCTP (1 mM), dTTP (1 mM), an amplification polymerase (0.15 µM). In some cases, this formulation may be referred to as Formulation SSR-A.

In some embodiments, a second strand synthesis reagent comprises MOPS (40 mM, pH 7.3), (NH$_4$)SO$_4$ (40 mM), KCl (200 mM), MgSO$_4$ (5 mM), Tween-80 (0.1%), DTT (5 mM), betaine (400 mM), sucrose (400 mM), PEG 8K (5%), dATP (1 mM), dGTP (1 mM), dCTP (1 mM), dTTP (1 mM), an amplification polymerase (0.1 µM). In some cases, this formulation may be referred to as Formulation SSR-A.

In some embodiments, a second strand synthesis reagent comprises MES (100 mM, pH 7.3), (NH$_4$)SO$_4$ (30 mM), NaCl (200 mM), MgSO$_4$ (5 mM), Tween-80 (0.1%), DTT (5 mM), betaine (400 mM), sucrose (400 mM), PEG 16K (5%), dATP (1 mM), dGTP (1 mM), dCTP (1 mM), dTTP (1 mM), an amplification polymerase (0.6 µM). In some cases, this formulation may be referred to as Formulation SSR-A.

In some embodiments, a synthesis degradation reagent comprises K acetate (10 mM), Tris acetate (20 mM, pH 7.9), Mg acetate (10 mM), BSA (100 µg/mL), and T7 exonuclease. Formulation SDR-A.

In some embodiments, a synthesis degradation reagent comprises K acetate (50 mM), Tris acetate (20 mM, pH 7.9), Mg acetate (10 mM), BSA (100 µg/mL), T7 exonuclease, and uracil DNA glycosylase. Formulation SDR-B.

In some embodiments, a synthesis degradation reagent comprises K acetate (50 mM), Tris acetate (20 mM, pH 7.9), Mg acetate (10 mM), BSA (100 µg/mL), T7 exonuclease, uracil DNA glycosylase, and DNA glycosylases-lyase. Formulation SDR-C.

In some embodiments, a synthesis degradation reagent comprises K acetate (50 mM), Tris acetate (20 mM, pH 7.9), Mg acetate (10 mM), BSA (100 µg/mL), T7 exonuclease, uracil DNA glycosylase, and endonuclease VIII. Formulation SDR-D.

In some embodiments, a synthesis degradation reagent comprises K acetate (50 mM), Tris acetate (20 mM, pH 7.9), Mg acetate (10 mM), BSA (100 µg/mL), T7 exonuclease, uracil DNA glycosylase, DNA glycosylase-lyase, and endonuclease VIII. Formulation SDR-E.

In some embodiments, a synthesis degradation reagent comprises K acetate (50 mM), Tris acetate (20 mM, pH 7.9), Mg acetate (10 mM), recombinant albumin (100 µg/mL), and T7 exonuclease. Formulation SDR-F.

In some embodiments, a synthesis degradation reagent comprises K acetate (50 mM), Tris acetate (20 mM, pH 7.9), Mg acetate (10 mM), recombinant albumin (100 µg/mL), T7 exonuclease, and uracil DNA glycosylase. Formulation SDR-G.

In some embodiments, a synthesis degradation reagent comprises K acetate (50 mM), Tris acetate (20 mM, pH 7.9), Mg acetate (10 mM), recombinant albumin (100 µg/mL), T7 exonuclease, uracil DNA glycosylase, and DNA glycosylase-lyase. Formulation SDR-H.

In some embodiments, a synthesis degradation reagent comprises K acetate (50 mM), Tris acetate (20 mM, pH 7.9), Mg acetate (10 mM), recombinant albumin (100 µg/mL), T7 exonuclease, uracil DNA glycosylase, and endonuclease VIII. Formulation SDR-I.

In some embodiments, a synthesis degradation reagent comprises K acetate (50 mM), Tris acetate (20 mM, pH 7.9), Mg acetate (10 mM), recombinant albumin (100 µg/mL), T7 exonuclease, uracil DNA glycosylase, DNA glycosylase-lyase, and endonuclease VIII. Formulation SDR-J.

Cartridges Containing Reagents

The present disclosure provides one or more cartridges each containing one or more reagents used for conducting a nucleic acid sequencing workflow. A cartridge can contain any combination of the reagents described herein. A cartridge can be sub-divided into two or more separate reservoirs where each reservoir contains a reagent for conducting one or more steps of the nucleic acid sequencing workflow described herein. Examples of reagents that can be contained in a cartridge include any combination of reagents for preparing a linear nucleic acid library, circularizing linear library molecules, hybridizing library molecules to surface primers, rolling circle amplification (e.g., first and second amplification reagents), nucleic acid sequencing (e.g., trapping, post-trapping and/or stepping reagents), imaging reagents, cleaving reagents, wash-removal reagent and/or washing reagent. The cartridge can also contain any of the reagents for conducting pairwise sequencing, including second strand synthesis reagent, and strand degradation reagent. In some embodiments, the cartridge contains at least one fluid reagent. In some embodiments, the cartridge is configured to fit into a nucleic acid sequencing apparatus. In some embodiments, the cartridge is connected to at least one capillary that is configured to deliver the contents of the cartridge to one or more supports that are integrated or assembled on a microfluidic flow cell.

Compositions

Disclosed herein, in some embodiments, are compositions useful for sequencing a nucleic acid library. Some compositions are useful for hybridizing a nucleic acid library with oligonucleotides. Some compositions are useful for performing amplifying nucleic acid libraries. Some compositions are useful for washing a surface comprising nucleic acids functionalized or hybridized thereon. Some compositions are useful for binding fluorescently-labeled multivalent molecules with nucleic acids. Some compositions are useful for imaging a surface comprising fluorescently-labeled multivalent molecules. Some compositions are useful for extending a oligonucleotide by one nucleotide.

Solvents

In some embodiments, any of the reagents described herein, can include at least one solvent. In some embodiments, the solvent comprises water. In some embodiments, the solvent comprises an alcohol comprising a short chain alcohol having 1-6 carbon backbone, including linear or branched alcohols. In some embodiments, the short chain alcohol can be methanol, ethanol, propanol, butanol, pentanol, hexanol, or structural isomers thereof (e.g., isopropanol, tert-butanol, n-pentanol, 2-pentanol, 3-pentanol, etc.). In some embodiments, the solvent comprises a polar aprotic solvent including acetonitrile, diethylene glycol, N,N-dimethylacetamide, dimethyl formamide, dimethyl sulfoxide, ethylene glycol, formamide, glycerin, methanol, N-methyl-2-pyrrolidinone, hexamethylphosphoramide, nitrobenzene, or nitromethane. In some embodiments, the solvent may comprise a mixture of two or more solvents described herein (e.g., a mixture of water and methanol). In some embodiments, a solvent may comprise acetonitrile. In some embodiments, a solvent may comprise formamide. In some embodiments, a solvent may comprise pyridine. In some embodiments a solvent may comprise formamide and acetonitrile. In some embodiments, a solvent may comprise ethanol and water.

Reagents that can include at least one solvent include the universal wash reagents, nucleic acid hybridization reagents, first amplification reagents, second amplification reagents, wash removal reagents, trap reagents, post-trap reagents, imaging reagents, stepping reagents and cleaving reagents.

pH Buffering Agents

In some embodiments, any of the reagents described herein can include a pH buffering agent which can maintain the pH of the reagent in a range that is suitable for nucleic acid hybridization. In some embodiments, the pH buffering agent comprises any one or any combination of two or more of Tris, Tris-HCl, Tricine, Bicine, Bis-Tris propane, HEPES, MES, MOPS, MOPSO, BES, TES, CAPS, TAPS, TAPSO, ACES, PIPES, ethanolamine (a.k.a 2-amino methanol; MEA), a citrate compound, a citrate mixture, NaOH, and/or KOH. In some embodiments, the pH buffering agent can be present in any of the reagents described herein at a concentration of about 1-100 mM, or about 10-50 mM, or about 10-25 mM. In some embodiments, the pH of the pH buffering agent which is present in any of the reagents described herein can be adjusted to a pH of about 4-9, or a pH of about 5-9, or a pH of about 5-8.

In some embodiments, in the hybridization reagent and in hybridization methods, the hybridization reagent comprises a pH buffering agent which comprises a saline sodium citrate (SSC) which include sodium citrate and sodium chloride. In some embodiments, the SSC can be at a concentration of 20×SSC (e.g., 3 M NaCl and 0.3 M sodium citrate), or at 10×SSC (e.g., 1.5 M NaCl and 0.15 M sodium citrate), or at 5×SSC (e.g., 0.75 M NaCl and 0.075 M sodium citrate), or at 2×SSC (e.g., 0.30 M NaCl and 0.003 M sodium citrate), or at 1×SSC (e.g., 0.15 M NaCl and 0.015 M sodium citrate). In some embodiments in the hybridization reagent and in hybridization methods, the hybridization reagent comprises at least one pH buffering agent having a pH range of about 4-9 or about 5-8 or about 6-7. In some embodiments, the hybridization reagent comprises at least one pH buffering agent at a concentration of about 1 mM-1 M, or about 5 mM-0.5 M, or about 10 mM-0.25 M.

Reagents that can include at least one pH buffering agent include the universal wash reagents, nucleic acid hybridization reagents, first amplification reagents, second amplification reagents, wash removal reagents, trap reagents, post-trap reagents, imaging reagents, stepping reagents and cleaving reagents.

Monovalent Cations

In some embodiments, any of the reagents described herein can include a monovalent cation. In some embodiments, the monovalent cation is sodium or potassium. In some embodiments, the monovalent cation is in the form of NaCl or KCl. In some embodiments, the hybridization reagent comprises NaCl at a concentration of about 25-200 mM, or about 50-150 mM. In some embodiments, the hybridization reagent comprises KCl at a concentration of about 1-200 mM, or about 25-150 mM, or about 50-100 mM.

Reagents that can include at least one monovalent cation include the universal wash reagents, nucleic acid hybridization reagents, first amplification reagents, second amplification reagents, trap reagents, post-trap reagents, imaging reagents, stepping reagents and cleaving reagents.

In some embodiments, any of the reagents described herein can include at least one salt which comprises potassium acetate (e.g., $KCH_3CO_2$) and/or $MgCl_2$. In some embodiments, the annealing reagent for forming any of the library-splint complexes (e.g., (300) and (800)) described herein, or reagents for generating abasic sites in a concatemer, comprises potassium acetate at a concentration of about 10-50 mM, or about 50-100 mM, or about 100-150 mM, or about 150-200 mM. In some embodiments, the ligation reagent for forming any of the covalently closed circular molecules (e.g., (400) and (900)) described herein comprises $MgCl_2$ at a concentration of about 1-10 mM, or about 10-25 mM, or about 25-50 mM, or about 50-100 mM.

Ammonium Ions

In some embodiments, any of the reagents described herein can include ammonium ions, for example, in the form of ammonium sulfate. In some embodiments, the reagent comprises ammonium ions at a concentration of about 1-50 mM, or about 10-25 mM. In some embodiments, the reagent comprises ammonium sulfate at a concentration of about 1-50 mM, or about 10-25 mM.

Reagents that can include a source of ammonium ions include the first amplification reagents and second amplification reagents.

Detergents

In some embodiments, any of the reagents described herein can include a detergent. In some embodiments, the detergent comprises an ionic detergent such as SDS (sodium dodecyl sulfate). In some embodiments, the detergent comprises a non-ionic detergent such as Triton™ X-100 (2-[4-(2,4,4-trimethylpentan-2-yl)phenoxy]ethanol), Tween 20, Tween 80 or Nonidet P-40. In some embodiments, the detergent comprises a zwitterionic detergent such as CHAPS (3-[(3-cholamidopropyl)dimethylammonio]-1-propanesulfonate) or N-Dodecyl-N,N-dimethyl-3-ammonio-1-propanesulfate (DetX). In some embodiments, the detergent comprises LDS (lithium dodecyl sulfate), sodium taurodeoxycholate, sodium taurocholate, sodium glycocholate, sodium deoxycholate, or sodium cholate. In some embodiments, the detergent is included in a reagent at a concentration of about 0.01-0.05%, or about 0.05-0.1%, or about 0.1-0.15%, or about 0.15-0.2%, or about 0.2-0.25%.

Reagents that can include a detergent include the universal wash reagents, first amplification reagents, second amplification reagents, wash removal reagents, trap reagents, post-trap reagents, imaging reagents, stepping reagents, and cleaving reagents.

Reducing Agents

In some embodiments, any of the reagents described herein can include at least one reducing agent comprising DTT (dithiothreitol), 2-beta mercaptoethanol, TCEP, (tris(2-carboxyethyl)phosphine), formamide, DMSO (dimethylsulfoxide), sodium dithionite ($Na_2S_2O_4$), glutathione, methionine, or betaine, Tris(3-hydroxypropyl)phosphine (THPP) and/or N-acetyl cysteine. In some embodiments, the reagents can include the reducing agent at a concentration of about 0.1-0.5 M, or about 0.5-1 M, or about 1-2 M. In some embodiments, the reagents can include the reducing agent at a concentration of about 0.1-1 mM, or about 1-2.5 mM, or about 2.5-5 mM, or about 5-7.5 mM, or about 7.5-9 mM, or about 9-12 mM. The reagents can include the reducing agent at a concentration of about 0.01-0.1 mM, or about 0.1-1 mM, or about 1-2.5 mM, or about 2.5-5 mM, or about 5-7.5 mM, or about 7.5-9 mM, or about 9-12 mM, or about 12-25 mM, or about 25-50 mM.

Reagents that can include a reducing agent include the first amplification reagents, second amplification reagents, wash removal reagents, trap reagents, post-trap reagents, imaging reagents, stepping reagents, and cleaving reagents.

Viscosity Agents

In some embodiments, any of the reagents described herein can include a viscosity agent comprising a saccharide such as trehalose, sucrose, cellulose, xylitol, mannitol, sorbitol or inositol. In some embodiments, the viscosity agent comprises glycerol or a glycol compound such as ethylene glycol or propylene glycol. In some embodiments, the reagents can include the viscosity agent at a concentration of about 0.1-1%, or about 1-5%, or about 5-10%, or about 10-15% based on volume. In some embodiments, the reagents can include the viscosity agent at a concentration of about 1-50 mM, or about 50-100 mM, or about 100-150 mM, or about 150-200 mM. In some embodiments, the reagents can include the viscosity agent at a concentration of about 0.1-0.5 M, or about 0.5-1 M, or about 1-2 M, or about 2-3 M, or about 3-5 M.

Reagents that can include at least one solvent include the first amplification reagents, second amplification reagents, trap reagents, post-trap reagents, imaging reagents and stepping reagents.

Chaotropic Agents

In some embodiments, any of the reagents described herein can include a chaotropic agent that can disrupt non-covalent bonds such as hydrogen bonds or van der Waals forces. In some embodiments, the chaotropic agent comprises SDS (sodium dodecyl sulfate), urea, thiourea, guanidinium chloride, guanidine hydrochloride, guanidine thiocyanate, guanidine isothionate, potassium thiocyanate, lithium chloride, sodium iodide or sodium perchlorate. In some embodiments, the reagents can include a chaotropic agent at a concentration of about 0.1-1 M, or about 1-2 M, or about 2-3 M, or about 3-4 M, or about 4-5 M.

Reagents that can include at least one chaotropic agent include the nucleic acid hybridization reagents and wash removal reagents.

Chelating Agents

In some embodiments, any of the reagents described herein can include a chelating agent that binds metal ions by chelation, coordination or covalent bonding. In some embodiments, the chelating agent comprises EDTA (ethylenediaminetetraacetic acid), EGTA (ethylene glycol tetraacetic acid), HEDTA (hydroxyethylethylenediaminetriacetic acid), DPTA (diethylene triamine pentaacetic acid), NTA (N,N-bis(carboxymethyl)glycine), citrate anhydrous, sodium citrate, calcium citrate, ammonium citrate, ammonium bicitrate, citric acid, potassium citrate, or magnesium citrate. In some embodiments, the hybridization region comprises a chelating agent at a concentration of about 0.01-50 mM, or about 0.1-20 mM, or about 0.2-10 mM.

Reagents that can include at least one chelating agent include the universal wash reagents, wash removal reagents, trap reagents, post-trap reagents and imaging reagents.

Zwitterions

In some embodiments, any of the reagents described herein can include a source of zwitterions. In some embodiments, the zwitterionic comprises a cationic zwitterionic compound such as a betaine including N,N,N-trimethylglycine and cocamidopropyl betaine. In some embodiments, the zwitterion comprises an albuminoids including ovalbumin, and the serum albumins derived from bovine, equine, or human. In some embodiments, the reagent can include a zwitterion at a concentration of about 0.1-0.5 M, or about 0.5-1 M, or about 1-2 M.

Reagents that can include at least one source of zwitterions include the first amplification reagents and second amplification reagents.

Sugar Alcohols

In some embodiments, any of the reagents described herein can include a sugar alcohol, comprising a sugar alcohol comprising sucrose, trehalose, maltose, rhamnose, arabinose, fucose, mannitol, sorbitol or adonitol. In some embodiments, the reagents can include the sugar alcohol at a concentration of about 1-50 mM, or about 50-100 mM, or about 100-150 mM, or about 150-200 mM. In some embodiments, the reagents can include the sugar alcohol agent at a concentration of about 0.1-0.5 M, or about 0.5-1 M, or about 1-2 M, or about 2-3 M, or about 3-5 M.

Reagents that can include at least one sugar alcohol include the first amplification reagents, second amplification reagents, trap reagents, post-trap reagents, imaging reagents, and stepping reagents.

Crowding Agents

In some embodiments, any of the reagents described herein can include a crowding agent that increases molecular crowding. In some embodiments, the crowding agent comprises polyethylene glycol (PEG, e.g., 1-50K molecular weight), dextran, dextran sulfate, hydroxypropyl methyl cellulose (HPMC), hydroxyethyl methyl cellulose (HEMC), hydroxybutyl methyl cellulose, hydroxypropyl cellulose, methylcellulose, and hydroxyl methyl cellulose. In some embodiments, the crowding agent can be present in the hybridization reagent at about 1-10%, or about 10-25%, or about 25-50%, or higher percentages by volume based on the total volume of the hybridization reagent.

Reagents that can include at least one crowding agent include the nucleic acid hybridization reagents, first amplification reagents and second amplification reagents.

Amplification Polymerases

In some embodiments, any of the reagents described herein can include an amplification polymerase. In some embodiments, the amplification polymerase has strand displacement activity. In some embodiments, the amplification polymerase comprises a phi29 DNA polymerase, large fragment of Bst DNA polymerase, large fragment of Bsu DNA polymerase, and Bca (exo-) DNA polymerase, Klenow fragment of *E. coli* DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), variant EquiPhi29 DNA polymerase (e.g., from Thermo Fisher Scientific), or chimeric QualiPhi DNA polymerase (e.g., from 4basebio). In some embodiments, the reagent can include the amplification polymerase at a concentration of about 10-50 nM, or about 50-100 nM, or about 100-150 nM, or about 150-200 nM, or about 200-250 nM.

Reagents that can include at least one amplification polymerase include the first amplification reagents and/or second amplification reagents.

Condenser Oligonucleotides

In some embodiments, any of the reagents described herein can include a condenser oligonucleotide. In some embodiments, the condenser oligonucleotides comprise single-stranded DNA. In some embodiments, the condenser oligonucleotides comprise three regions: a 5' region that binds a portion of a first adaptor sequence which is operably linked to a template molecule, an internal region that does not bind to a portion of the template molecule or an adaptor sequence, and a 3' region that binds a portion of a second adaptor sequence which is operably linked to a template molecule. In some embodiments, the condenser oligonucleotides can be 20-150 nucleotides in length. In some embodiments, the 3' terminal end of the condenser oligonucleotide is not extendible. In some embodiments, the 3' end of the condenser oligonucleotide can include at least one dideoxynucleotide, at least one 2' O-methyl RNA base, or an inverted dT. In some embodiments, the condenser oligonucleotide includes a moiety that increases the rigidity of the condenser oligonucleotide. In some embodiments, the condenser oligonucleotide comprises an internal PEG moiety which increases rigidity. In some embodiments, the reagent can include the condenser oligonucleotides at a concentration of about 1-10 nm, or about 10-50 nM, or about 50-100 nM, or about 100-150 nM, or about 150-200 nM.

Reagents that can include a plurality of condenser oligonucleotides include the first amplification reagents and/or second amplification reagents.

Non-Catalytic Divalent Cations

In some embodiments, any of the reagents described herein can include a non-catalytic divalent cation. In some embodiments, the non-catalytic divalent cation can promote formation of a ternary complex. In some embodiments, the non-catalytic divalent cation can promote binding of a complementary nucleotide (e.g., free nucleotide) or a complementary nucleotide unit (e.g., of a multivalent molecule) to the 3' end of a primer that is hybridized to a template molecule in the presence of a polymerase. In some embodiments, the non-catalytic divalent cation does not promote polymerase-catalyzed incorporation of the nucleotide or the nucleotide unit into the primer. In some embodiments, the non-catalytic divalent cation comprises strontium, barium, scandium, titanium, calcium, vanadium, chromium, iron, cobalt, nickel, copper, zinc, gallium, germanium, arsenic, selenium, rhodium, europium, tin, or terbium ion. In some embodiments, the non-catalytic divalent cation may be provided in the form of strontium chloride, strontium acetate, or nickel chloride. In some embodiments, the trap reagent, post-trap reagent and imaging reagent include a non-catalytic divalent cation at a concentration of about 0.1-50 mM, about 1-25 mM, or about 5-10 mM.

Reagents that can include at least one non-catalytic divalent cation include the trap reagents, post-trap reagents and imaging reagents.

Catalytic Divalent Cations

In some embodiments, any of the reagents described herein can include a catalytic divalent cation. In some embodiments, the catalytic divalent cation can promote formation of a ternary complex. In some embodiments, the catalytic divalent cation can promote binding of a complementary nucleotide (e.g., free nucleotide) or a complementary nucleotide unit (e.g., of a multivalent molecule) to the 3' end of a primer that is hybridized to a template molecule in the presence of a polymerase. In some embodiments, the catalytic divalent cation promotes polymerase-catalyzed incorporation of the nucleotide or the nucleotide unit into the primer. In some embodiments, the catalytic divalent cation comprises magnesium and manganese. In some embodiments, the catalytic divalent cation can be present in a reagent at a concentration of about 0.1-50 mM, or about 1-25 mM, or about 5-10 mM.

Reagents that can include at least one catalytic divalent cation include the first amplification reagents, second amplification reagents, stepping reagents, and cleaving reagents.

Multivalent Molecules

In some embodiments, any of the reagents described herein can include a plurality of multivalent molecules. In some embodiments, the multivalent molecule comprises a plurality of nucleotide arms attached to a core and having any configuration including a starburst, helter skelter, or bottle brush configuration (e.g., FIG. 2B). In some embodiments, individual multivalent molecules in the plurality comprise: (1) a core, and (2) a plurality of nucleotide arms which comprise (i) a core attachment moiety, (ii) a spacer comprising a PEG moiety, (iii) a linker, and (iv) a nucleotide unit e.g., see FIGS. 2A to 2D).

In some embodiments, the multivalent molecule comprises a core which is attached to the plurality of nucleotide arms. In some embodiments, the spacer is attached to the linker, wherein the linker is attached to the nucleotide unit. For example, see FIGS. 2A and 2B.

In some embodiments, the multivalent molecule comprises a core which can be an avidin-like moiety and the core attachment moiety can be a biotin moiety. In some embodiments, the avidin-like moiety comprises streptavidin, N-acyl avidins, e.g., N-acetyl, N-phthalyl, or N-succinyl avidin. In some embodiments, the avidin-like moiety comprises commercially-available products such as ExtrAvidin™, Captavidin™, Neutravidin™, or Neutralite Avidin™.

In some embodiments, the nucleotide unit comprises a base, a five-carbon sugar (e.g., a ribose) and at least one phosphate group. In some embodiments, the linker is attached to the nucleotide unit through the base. In some embodiments, the linker comprises an aliphatic chain having 2-6 subunits or an oligo ethylene glycol chain having 2-6 subunits and optionally the linker includes an aromatic moiety (e.g., see FIGS. 2A and 2B). In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP. In some embodiments, the plurality of multivalent molecules comprises a mixture of multivalent molecules having two or more different types of nucleotides selected from a group consisting of dATP, dGTP, dCTP, dTTP and dUTP. In some embodiments, the plurality of multivalent molecules comprises a mixture of multivalent molecules having three or more different types of nucleotides selected from a group consisting of dATP, dGTP, dCTP, dTTP and dUTP. In some embodiments, the plurality of multivalent molecules comprises a mixture of multivalent molecules having four or more different types of nucleotides selected from a group consisting of dATP, dGTP, dCTP, dTTP and dUTP. In some embodiments, the mixture comprises a plurality of a first type of multivalent molecules each having one type of nucleotide units selected from a group consisting of dATP, dGTP, dCTP, dTTP and dUTP. In some embodiments, the mixture also comprises a plurality of a second type of multivalent molecules each having a different type of nucleotide units selected from a group consisting of dATP, dGTP, dCTP, dTTP and dUTP, which differ from the first type of nucleotide units in the first plurality.

In some embodiments, at least one of the multivalent molecules is labeled with a detectable reporter moiety. In some embodiments, the labeled multivalent molecule comprises a core attached to multiple nucleotide arms, wherein the core is labeled with detectable reporter moiety or at least one nucleotide unit is labeled with a detectable reporter moiety. In some embodiments, the detectable reporter moiety can be a fluorophore. In some embodiments, the fluorophore which is attached to the multivalent molecule corresponds to the base of the nucleotide unit to permit distinguishing nucleotide base units of the different fluorescently-labeled multivalent molecules. In some embodiments, a fluorescently labeled multivalent molecule comprises a core or a nucleotide base that is attached to a fluorophore, where the fluorophore corresponds to the base of the nucleotide unit to permit distinguishing which nucleotide base is bound to a sequencing polymerase in a ternary complex.

In some embodiments, at least one of the multivalent molecules comprises at least one nucleotide arm having a cleavable moiety. In some embodiments, a multivalent molecule comprises 1, 2, 3, 4 or more nucleotide arms where each nucleotide arm includes a cleavable moiety. In some embodiments, the cleavable moiety in the nucleotide arm can be cleaved with a cleavable agent to separate the nucleotide arm from the core.

In some embodiments, the multivalent molecule comprises at least one nucleotide arm having a linker with a cleavable moiety which is selected from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the cleavable moiety in the linker is reactive with a chemical reagent. In some embodiments, the cleavable moieties alkyl, alkenyl, alkynyl and allyl are reactive with tetrakis(triphenylphosphine)palladium(0) (Pd (PPh$_3$)$_4$) with piperidine, or with 2,3-Dichloro-5,6-dicyano-1,4-benzo-quinone (DDQ). In some embodiments, the cleavable moieties aryl and benzyl are reactive with H2 Pd/C. In some embodiments, the cleavable moieties amine, amide, keto, isocyanate, phosphate, thio, disulfide are reactive with phosphine or with a thiol group including beta-mercaptoethanol or dithiothreitol (DTT). In some embodiments, the cleavable moiety carbonate is reactive with potassium carbonate (K$_2$CO$_3$) in MeOH, with triethylamine in pyridine, or with Zn in acetic acid (AcOH). In some embodiments, the cleavable moieties urea and silyl are reactive with tetrabutylammonium fluoride, pyridine-HF, with ammonium fluoride, or with triethylamine trihydrofluoride.

In some embodiments, the cleavable moiety in the linker comprises an azide, azido or azidomethyl group. In some embodiments, the azide, azido or azidomethyl group in the linker is reactive with a chemical agent. In some embodiments, the chemical agent comprises a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, at least one of the multivalent molecules in the plurality includes a chain terminating moiety which inhibits polymerase-catalyzed incorporation of a subsequent nucleotide unit or free nucleotide in a nascent strand. In some embodiments, the multivalent molecule comprises a core attached to multiple nucleotide arms, wherein individual nucleotide arms comprise a nucleotide unit having a chain terminating moiety (e.g., blocking moiety) at the sugar 2' position, at the sugar 3' position, or at the sugar 2' and 3' position. In some embodiments, the chain terminating moiety can be removable from the nucleotide unit by contacting the multivalent molecule with a compound that cleaves/removes the chain terminating moiety to form a nucleotide unit with a 2' or 3' extendible group.

In some embodiments, the multivalent molecule comprises a chain terminating moiety which is selected from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the multivalent molecule comprises a chain terminating moiety which comprises a 3'-O-alkyl hydroxylamino group, a 3'-phosphorothioate group, a 3'-O-malonyl group, or a 3'-O-benzyl group.

In some embodiments, the multivalent molecule comprises a chain terminating moiety which is selected from a group consisting of 3'-deoxy nucleotides, 2',3'-dideoxy-nucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydryl, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof. In some embodiments, the chain-terminating moiety comprises an azide, azido or azidomethyl group.

In some embodiments, the multivalent molecule comprises a chain terminating moiety which is cleavable/removable from the nucleotide arm, for example with a chemical compound, light or heat. In some embodiments, the chain terminating moiety comprises an alkyl, alkenyl, alkynyl or allyl group which are cleavable with tetrakis(triphenylphosphine)palladium(0) (Pd(PPh$_3$)$_4$), with piperidine, or with 2,3-Dichloro-5,6-dicyano-1,4-benzo-quinone (DDQ). In some embodiment, the chain terminating moiety comprises an aryl or benzyl group which are cleavable with Pd/C. In some embodiments, the chain terminating moiety comprises an amine, amide, keto, isocyanate, phosphate, thio or disulfide group which are cleavable with phosphine or with a thiol group including beta-mercaptoethanol or dithiothreitol (DTT). In some embodiments, the chain terminating moiety comprises a carbonate group which is cleavable with potassium carbonate (K$_2$CO$_3$) in MeOH, with triethylamine in pyridine, or with Zn in acetic acid (AcOH). In some embodiments, the chain terminating moiety comprises a urea or silyl group which are cleavable with tetrabutylammonium fluoride, pyridine-HF, with ammonium fluoride, or with triethylamine trihydrofluoride. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

The reagents can include the multivalent molecules at a concentration of about 1-25 nM, or about 25-50 nM, or about 50-75 nM, or about 75-100 nM. Reagents that can include at least or a plurality of multivalent molecules include the trap reagents and/or post-trap reagents.

First and Second Sequencing Polymerases

In some embodiments, any of the reagents described herein can include a first or a second sequencing polymerase. In some embodiments, the first and second sequencing polymerases comprise a recombinant mutant DNA polymerase that exhibits reduced mismatch and/or reduced misincorporation rates (e.g., increased fidelity) of nucleotide analogs compared to a wild type polymerase. In some embodiments, the mutant polymerases comprise polypeptides, or fragments thereof, derived from recombinantly engineered novel B-family and A-family polymerases, wherein the mutant polymerases exhibit improvements in their specificity while maintaining high discrimination for the correct Watson-crick base-pairing, which yields exceptionally high fidelity.

In some embodiments, the first and second sequencing polymerases comprise a recombinant mutant polymerase derived from a wild-type polymerase from Candidatus altiarchaeales archaeon where the mutant polymerases exhibit nucleotide binding and incorporation activity at a temperature range of about 45-75° C. In some embodiments, the engineered Candidatus altiarchaeales archaeon polymerases exhibits optimal nucleotide binding and incorporation activity at a temperature range of about 65-75° C. In some embodiments, the Candidatus altiarchaeales archaeon polymerase is a moderately thermostable polymerase (e.g., mesothermal polymerase). In some embodiments, engineered polymerases having Candidatus altiarchaeales archaeon sequence backbone with one or more mutations can be used for conducting nucleotide binding, nucleotide incorporation, and/or nucleic acid sequencing reactions at a temperature range of about 45-75° C., or about 50-65° C., or about 50-60° C.

In some embodiments, the first and/or second sequencing polymerase comprises a DNA polymerase having an amino acid sequence backbone of a DNA polymerase from a Candidatus Altiarchaeales archaeon. In some embodiments, the first and/or second sequencing polymerase comprises an amino acid sequence that is at least 80% identical to SEQ ID NO: 1, wherein the mutant DNA polymerase comprises an amino acid substitution at one or more positions selected from a group consisting of Leu416, Tyr417, Pro418, Ala493, Arg515, Ile529 and Asn567. In some embodiments, the first and/or second sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the positions of the mutations described herein are with reference to SEQ ID NO: 1. In some embodiments, the positions of the mutations described herein are with reference to any one of SEQ ID NOS: 2, 3, 4, or 5. In some embodiments, the first and/or second sequencing polymerases comprise the amino acid sequence of any one of SEQ ID NOS: 2, 3, 4, or 5.

In some embodiments, the first and/or second sequencing polymerase comprises a DNA polymerase from 9° N which comprises the amino acid sequence of SEQ ID NOS: 6, 7 or 8. In some embodiments, the first and/or second sequencing polymerase comprises a mutant 9° N polymerase having a backbone amino acid sequence of a polymerase from 9° N (e.g., SEQ ID NOS: 6, 7 or 8) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to any one of SEQ ID NOS: 6, 7, or 8.

In some embodiments, the first and/or second sequencing polymerase comprises a DNA polymerase comprising the amino acid sequence of SEQ ID NO: 9 (Vent polymerase). In some embodiments, the first and/or second sequencing polymerase comprises a mutant Vent polymerase having a backbone amino acid sequence of a polymerase from Vent (e.g., SEQ ID NO:9) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID No: 9.

In some embodiments, the first and/or second sequencing polymerase comprises a DNA polymerase comprising the amino acid sequence of SEQ ID NO: 10 (Deep Vent polymerase). In some embodiments, the first and/or second sequencing polymerase comprises a mutant Deep Vent polymerase having a backbone amino acid sequence of a polymerase from Vent (e.g., SEQ ID NO: 10) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 10.

In some embodiments, the first and/or second sequencing polymerase comprises a DNA polymerase comprising the amino acid sequence of SEQ ID NO: 11 (Pfu polymerase). In some embodiments, the first and/or second sequencing polymerase comprises a mutant Pfu polymerase having a backbone amino acid sequence of a polymerase from Pfu (e.g., SEQ ID NO: 11) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 11.

In some embodiments, the first and/or second sequencing polymerase comprises a DNA polymerase comprising the amino acid sequence of SEQ ID NO: 12 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO: 12) with mutations at positions that are equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567. In some embodiments, the positions of the mutations described herein are with reference to SEQ ID NO: 12.

In some embodiments, any of the first and/or second sequencing polymerases can be labeled with at least one detectable reporter moiety (e.g., fluorophore).

In some embodiments, the first sequencing polymerases are capable of binding a complementary nucleotide unit of a multivalent molecule and a nucleic acid duplex to form a ternary complex.

In some embodiments, the second sequencing polymerases are binding a complementary nucleotide and a nucleic acid duplex to form a ternary complex. The second polymerases are also capable of catalyzing incorporation of the complementary nucleotide.

Examples of suitable first and/or second sequencing polymerases for use in sequencing with multivalent molecules and nucleotides include but are not limited to: Klenow DNA polymerase; *Thermus aquaticus* DNA polymerase I (Taq polymerase); KlenTaq polymerase; Candidatus altiarchaeales archaeon; Candidatus Hadarchaeum Yellowstonense; Hadesarchaea archaeon; Euryarchaeota archaeon; Thermoplasma archaeon; *Thermococcus polymerases* such as *Thermococcus litoralis*, bacteriophage T7 DNA polymerase; human alpha, delta and epsilon DNA polymerases; bacteriophage polymerases such as T4, RB69 and phi29 bacteriophage DNA polymerases; *Pyrococcus furiosus* DNA polymerase (Pfu polymerase); *Bacillus subtilis* DNA polymerase III; *E. coli* DNA polymerase III alpha and epsilon; 9 degree N polymerase; reverse transcriptases such as HIV type M or O reverse transcriptases; avian myeloblastosis virus reverse transcriptase; Moloney Murine Leukemia Virus (MMLV) reverse transcriptase; or telomerase. Further non-limiting examples of DNA polymerases include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus*, and *Vulcanisaeta* and the like or variants thereof, including such polymerases as are known in the art such as 9 degrees N, VENT, DEEP VENT, THERMINATOR, Pfu, KOD, Pfx, Tgo and RB69 polymerases.

The reagents can include the first or second polymerase at a concentration of about 1-50 nM, or about 50-100 nM, or about 100-150 nM, or about 150-200 nM, or about 200-250 nM. Reagents that can include a first sequencing polymerase or a second sequencing polymerase include the trap reagents, post-trap reagents and stepping reagents.

In some embodiments, the first and/or second sequencing polymerase comprises a recombinant wild-type or mutant DNA polymerase having an amino acid sequence backbone of a DNA polymerase from a Candidatus Altiarchaeales archaeon. The first and/or second sequencing polymerase comprises an amino acid sequence that is at least 80% identical to SEQ ID NO:221, where the mutant DNA polymerase comprises an amino acid substitution at one or more positions selected from a group consisting of Leu416, Tyr417, Pro418, Ala493, Arg515, Ile529 and Asn567. In some embodiments, the first and/or second sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp. In some embodiments, the first and/or second sequencing polymerases comprise the amino acid sequence of any one of SEQ ID NOS:221-225.

In some embodiments, the first and/or second sequencing polymerase comprises a DNA polymerase from 9° N which comprises the amino acid sequence that is at least 80% identical to SEQ ID NOS:226 or 227. In some embodiments, the first and/or second sequencing polymerase comprises a mutant 9° N polymerase having a backbone amino acid sequence of a polymerase from 9° N (e.g., SEQ ID NOS:226 or 227) with mutations at positions that are positionally equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

In some embodiments, the first and/or second sequencing polymerase comprises a DNA polymerase comprising the amino acid sequence that is at least 80% identical to SEQ ID NO:229 (Vent polymerase). In some embodiments, the first and/or second sequencing polymerase comprises a mutant Vent polymerase having a backbone amino acid sequence of a polymerase from Vent (e.g., SEQ ID NO:229) with mutations at positions that are positionally equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

In some embodiments, the first and/or second sequencing polymerase comprises a DNA polymerase comprising the amino acid sequence that is at least 80% identical to SEQ ID NO:230 (Deep Vent polymerase). In some embodiments, the first and/or second sequencing polymerase comprises a mutant Deep Vent polymerase having a backbone amino acid sequence of a polymerase from Vent (e.g., SEQ ID NO:230) with mutations at positions that are positionally equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

In some embodiments, the first and/or second sequencing polymerase comprises a DNA polymerase comprising the amino acid sequence that is at least 80% identical to SEQ ID NO:231 (Pfu polymerase). In some embodiments, the first and/or second sequencing polymerase comprises a mutant Pfu polymerase having a backbone amino acid sequence of a polymerase from Pfu (e.g., SEQ ID NO:231) with mutations at positions that are positionally equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

In some embodiments, the first and/or second sequencing polymerase comprises a DNA polymerase comprising the amino acid sequence that is at least 80% identical to SEQ ID NO:232 (*Pyrococcus abyssi* polymerase). In some embodiments, the first and/or second sequencing polymerase comprises a mutant *Pyrococcus abyssi* polymerase having a backbone amino acid sequence of a polymerase from Vent (e.g., SEQ ID NO:232) with mutations at positions that are positionally equivalent to amino acid positions in a mutant polymerase from a Candidatus Altiarchaeales archaeon, such as, for example, one or more mutations at positions Leu416, Tyr417, Pro418, Ala493, Arg515, Ile529 and Asn567.

Nucleotides

In some embodiments, any of the reagents described herein can include a plurality of nucleotides. In some embodiments, the nucleotides include native nucleotides and nucleotide analogs. In some embodiments, a nucleotide comprises an aromatic base, a five carbon sugar (e.g., ribose or deoxyribose), and at least one phosphate group. In some embodiments, the plurality of nucleotides comprise a mixture of two or more different types of nucleotides selected from a group consisting of dATP, dGTP, dCTP, dTTP and dUTP. In some embodiments, the plurality of nucleotides comprise a mixture of three or more different types of nucleotides selected from a group consisting of dATP, dGTP, dCTP, dTTP and dUTP. In some embodiments, the plurality of nucleotides comprise a mixture of four or more different types of nucleotides selected from a group consisting of dATP, dGTP, dCTP, dTTP and dUTP.

In some embodiments, the nucleotide can lack a chain terminating moiety, or can be attached to a chain terminating moiety. In some embodiments, the chain terminating moiety (e.g., blocking moiety) can be attached to the sugar 2' position, the sugar 3' position, or the sugar 2' and 3' position.

In some embodiments, the chain terminating moiety is selected from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the chain terminating moiety comprises a 3'-O-alkyl hydroxylamino group, a 3'-phosphorothioate group, a 3'-O-malonyl group, or a 3'-O-benzyl group.

In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydryl, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof. In some embodiments, the chain-terminating moiety comprises an azide, azido or azidomethyl group.

In some embodiments, the chain terminating moiety is cleavable/removable from the nucleotide, for example with a chemical compound, light or heat. In some embodiments, the chain terminating moiety comprises an alkyl, alkenyl, alkynyl or allyl group which are cleavable with tetrakis(triphenylphosphine)palladium(0) (Pd(PPh$_3$)$_4$), with piperidine, or with 2,3-Dichloro-5,6-dicyano-1,4-benzo-quinone (DDQ). In some embodiment, the chain terminating moiety comprises an aryl or benzyl group which are cleavable with Pd/C. In some embodiments, the chain terminating moiety comprises an amine, amide, keto, isocyanate, phosphate, thio or disulfide group which are cleavable with phosphine or with a thiol group including beta-mercaptoethanol or dithiothreitol (DTT). In some embodiments, the chain terminating moiety comprises a carbonate group which is cleavable with potassium carbonate (K$_2$CO$_3$) in MeOH, with triethylamine in pyridine, or with Zn in acetic acid (AcOH). In some embodiments, the chain terminating moiety comprises a urea or silyl group which are cleavable with tetrabutylammonium fluoride, pyridine-HF, with ammonium fluoride, or with triethylamine trihydrofluoride. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the nucleotide can be unlabeled, or can be attached to a detectable reporter moiety. The detectable reporter moiety can be a fluorophore. In some embodiments, the labeled nucleotide comprises a detectable moiety (e.g., a fluorophore) attached to the base of the nucleotide via a cleavable linker that connects the base to the fluorophore. In some embodiments, the fluorophore which is attached to the nucleotide corresponds to the base of the nucleotide to permit distinguishing a nucleotide base of the different fluorescently-labeled nucleotides.

In some embodiments, the cleavable linker on the nucleotide comprises cleavable moiety which is selected from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the cleavable moiety in the cleavable linker is reactive with a chemical reagent. For example, the cleavable moieties alkyl, alkenyl, alkynyl and allyl are reactive with tetrakis(triphenylphosphine)palladium(0) (Pd(PPh$_3$)$_4$) with piperidine, or with 2,3-Dichloro-5,6-dicyano-1,4-benzo-quinone (DDQ). In some embodiments, the cleavable moieties aryl and benzyl are reactive with H2 Pd/C. In some embodiments, the cleavable moieties amine, amide, keto, isocyanate, phosphate, thio, disulfide are reactive with phosphine or with a thiol group including beta-mercaptoethanol or dithiothreitol (DTT). In some embodiments, the cleavable moiety carbonate is reactive with potassium carbonate (K$_2$CO$_3$) in MeOH, with triethylamine in pyridine, or with Zn in acetic acid (AcOH). In some embodiments, the cleavable moieties urea and silyl are reactive with tetrabutylammonium fluoride, pyridine-HF, with ammonium fluoride, or with triethylamine trihydrofluoride.

In some embodiments, the cleavable moiety in the cleavable linker comprises an azide, azido or azidomethyl group. In some embodiments, the azide, azido or azidomethyl group is reactive/cleavable with a chemical agent. In some embodiments, the chemical agent comprises a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the nucleotides can be included in a reagent at a concentration of about 0.1-100 uM, or about 0.1-1 uM, or about 1-10 uM, or about 10-20 uM, or about 20-30 uM, or about 30-40 uM, or about 40-50 uM.

Reagents that can include at least one or a plurality of nucleotides include the first amplification reagents, second amplification reagents and stepping reagents.

Compounds for Reducing Photo-Damage

In some embodiments, any of the reagents described herein can include one or more compounds for reducing photo-damage. In some embodiments, compounds that can reduce photo-damage include antioxidants, triplet state quenchers, singlet oxygen quenchers, oxygen scavengers, electron scavengers, anti-fade formulations. Some of these compounds can be classified as more than one type of photo-damage reducing compound. In some embodiments, the compounds that can reduce photo-damage comprise chemical compounds or enzymes.

In some embodiments, antioxidants include ascorbic acid or derivatives thereof, ascorbyl palmitate, D-isoascorbic acid (erythorbic acid), sodium ascorbate, butylated hydroxytoluene (BTH), butylated hydroxy toluene (BHT), polyphenol antioxidants, polyvinyl alcohols, butylated hydroxy anisol (BHA), Trolox (6-hydroxy-2,5,7,8-tetramethylchroman-2-carboxylic acid) or other vitamin E analogs including nitrated and nitroalkene Trolox derivates (see U.S. Pat. No. 9,994,541, the entire contents of which are expressly incorporated by reference in its entirety).

In some embodiments, the Trolox comprises Trolox quinone or Trolox hydroquinone. In some embodiments, the imaging reagents comprise Trolox that has been subjected to an aging process.

In some embodiments, the antioxidants comprise water soluble compounds, including ascorbic acid, citric acid, coumaric acid, ferulic acid, caffeic acid, chlorogenic acid, sinapic acid, ellagic acid, gallic acid, gentisic acid, salicylic acid, vanillic acid, Trolox (6-hydroxy-2,5,7,8-tetramethylchroman-2-carboxylic acid) and nitroalkene derivatives of Trolox. In some embodiments, the gallic acid comprises sulfonated forms having 1, 2 or 3 sulfonate groups.

The ascorbic acid includes both L-isomer and D-isomer and mixtures of L- and D-isomers, and racemic mixtures. In some embodiments, the ascorbic acid comprises a salt for example sodium L-ascorbate. In some embodiments, the ascorbic acid comprises dehydroascorbic acid (DHA). In some embodiments, includes ascorbate and analogs and derivatives thereof. In some embodiments, derivatives include ascorbate having an esterified 5-hydroxy and/or 6-hydroxy group. In some embodiments, derivatives include ascorbate in which the 5- and/or 6-hydroxy group is replaced with a halo or amino group. In some embodiments, derivatives include ascorbate in which the 5- and/or 6-hydroxy group lacks a hydroxy group such as for example a hydrogen atom replaces the hydroxyl group. In some embodiments, ascorbate derivatives include 5-deoxy-L-ascorbate, 6-bromo-6-deoxy-L-ascorbate, 6-amino-6-deoxy-L-ascorbate, L-ascorbic acid 6-carboxylate, 6-O-tosyl-L-ascorbate, and 6-O-ascorbyl alkanoates such as 6-ascorbyl palmitate (palmitoyl ascorbate).

In some embodiments, the triplet state quenchers include ascorbic acid, 1,4-diazobicyclo[2.2.2]octane (DABCO), 1,3,5,7, cyclo-octatetraene (COT), dithiothreitol (DTT), mercaptoethylamine (MEA), β-mercaptoethanol (BME), n-propyl gallate, p-phenylenediamine (PPD), hydroquinone, sodium azide ($NaN_3$), TEMPO (2,2,6,6-tetramethyl1-1-piperidinyloxyl), HTEMPO (4-hydroxy derivative of TEMPO), DTBN (di-t-butylnitroxide), or 3-nitrobenzoic acid (NBA).

In some embodiments, singlet oxygen quenchers include thiol-based quenchers such as glutathione, dithiothreitol, ergothioneine, methionine, cysteine, beta-dimethyl cysteine (penicillamine), mercaptopropionylglycine, MESNA, imidazole, or N-acetyl cysteine and captopril.

In some embodiments, oxygen scavengers include glutathione, and N-acetylcysteine, histidine, tryptophan, hydrazine ($N_2H_4$), sodium sulfite ($Na_2SO_3$), hydroxylamine and cystamine.

In some embodiments, electron scavengers include methyl viologen (e.g., 1,1'-dimethyl-4,4'-bipyridinium dichloride).

In some embodiments, the anti-fade formulations include commercially-available products including Fluoroguard Antifade Reagent (e.g., from BioRad), SlowFade Antifade Kit (e.g., includes DABCO, from Molecular Probes-Invitrogen), ProLong Gold Antifade Reagent (e.g., from Invitrogen), and CitiFluor (e.g., from CitiFluor).

The reagents can include at least one of the compounds for reducing photo damage at a concentration of about 0.1-1 mM, or about 1-10 mM, or about 10-25 mM, or about 25-50 mM, or about 50-75 mM, or about 75-100 mM. Reagents that can include at least one compound for reducing photo damage include the imaging reagents.

Cleaving Agents and Cleaving Catalysts

In some embodiments, any of the reagents described herein can include a cleaving agent and/or a cleaving catalyst.

In some embodiments, the cleaving agent and/or a cleaving catalyst can be selected to react with a fluorescently-labeled nucleotide. In some embodiments, the cleaving agent and/or a cleaving catalyst can cleave/remove a cleavable linker which connects a nucleotide base and a fluorophore, thereby removing the fluorophore label from the nucleotide.

In some embodiments, the cleaving agent and/or a cleaving catalyst can be selected to react with a chain terminating nucleotide. In some embodiments, the cleaving agent and/or a cleaving catalyst can cleave/remove a chain terminating moiety which is attached to the 2' or 3' sugar position of a nucleotide. In some embodiments, the cleaving agent and/or a cleaving catalyst can cleave/remove the chain terminating moiety from the 2' or 3' sugar position to convert to a nucleotide having an extendible 3'OH sugar group.

In some embodiments, the cleaving agent comprises piperidine, 2,3-Dichloro-5,6-dicyano-1,4-benzo-quinone (DDQ), or tetrakis(triphenylphosphine)palladium(0) (Pd($PPh_3$)$_4$), with piperidine.

In some embodiment, the cleaving agent comprises a palladium catalyst, for example palladium-on-carbon (Pd/C).

In some embodiments, the cleaving agent comprises beta-mercaptoethanol or dithiothreitol (DTT).

In some embodiments, the cleaving agent comprise potassium carbonate ($K_2CO_3$) in MeOH, triethylamine in pyridine, or Zn in acetic acid (AcOH).

In some embodiments, the cleaving agent comprises tetrabutylammonium fluoride, pyridine-HF, ammonium fluoride, or triethylamine trihydrofluoride.

In some embodiments, the cleaving agent comprises a phosphine compound, including for example a phosphine having a derivatized tri-alkyl phosphine moiety or a derivatized tri-aryl phosphine moiety. In some embodiments, the phosphine cleaving compound comprises Tris(2-carboxyethyl)phosphine (TCEP) or bis-sulfo triphenyl phosphine (BS-TPP). In some embodiments, the phosphine cleaving compound comprises Tri(hydroxyprolyl)phosphine (THPP). In some embodiments, the phosphine cleaving compound comprises Tri(hydroxymethyl)phosphine (THMP).

In some embodiments, the cleaving agent comprises ethanolamine (also known as 2-aminoethanol).

In some embodiments, the cleaving catalyst comprises 4-dimethylaminopyridine (4-DMAP).

In some embodiments, the reagents can include a cleaving agent and/or a cleaving catalyst at a concentration of about 1-10 mM, or about 10-25 mM, or about 25-50 mM, or about 50-75 mM, or about 75-100 mM, or about 100-150 mM, or about 150-200 mM. The reagents can include a cleaving agent having a pH of about 7-9.5, or a pH of about 8-9. Reagents that can include at least one cleaving agent include the cleaving reagents.

In some embodiments, the cleaving agent can be formulated to include a salt, for example NaCl and/or $MgCl_2$. The cleaving agent can include at least one salt at a concentration of about 1-25 mM, or about 25-100 mM, or about 100-250 mM, or about 250-400 mM, or about 400-500 mM.

Hydrophilic Polymer Coatings on a Support

In some embodiments, the hydrophilic polymer coatings described herein enable improved nucleic acid hybridization and amplification performance. In some embodiments, a support may comprise a substrate (or support structure), one or more layers of a covalently or non-covalently attached low-binding, chemical modification layers, e.g., silane layers, polymer films, and/or one or more covalently attached or non-covalently attached primer sequences that may be used for tethering single-stranded target nucleic acid(s) to the support surface. In some embodiments, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. In some embodiments, the formulation of the surface may be varied such that non-specific hybridization on the support surface is minimized or reduced relative to a comparable monolayer. In some embodiments, the formulation of the surface may be varied such that non-specific amplification on the support surface is minimized or reduced relative to a comparable monolayer. In some embodiments, the formulation of the surface may be varied such that specific amplification rates and/or yields on the support surface are maximized. In some embodiments, amplification levels suitable for detection are achieved in no more than 2, 3, 4, 5, 6, 7, 8, 9, 10, 15, 20, 25, 30, or more than 30 amplification cycles.

In some embodiments, the substrate or support structure that comprises the one or more chemically-modified layers, e.g., layers of a low non-specific binding polymer, may be independent or be integrated into another structure or assembly. In some embodiments, the substrate or support structure may comprise one or more surfaces within an integrated or assembled microfluidic flow cell. In some embodiments, the substrate or support structure may comprise one or more surfaces within a microplate format, e.g., the bottom surface of the wells in a microplate. In some embodiments, the substrate or support structure comprises the interior surface (such as the lumen surface) of a capillary. In some embodiments, the substrate or support structure comprises the interior surface (such as the lumen surface) of a capillary etched into a planar chip.

In some embodiments, the attachment chemistry used to graft a first chemically-modified layer to a surface may be dependent on both the material from which the surface is fabricated and the chemical nature of the layer. In some embodiments, the first layer may be covalently attached to the surface. In some embodiments, the first layer may be non-covalently attached, e.g., adsorbed to the surface through non-covalent interactions such as electrostatic interactions, hydrogen bonding, or van der Waals interactions between the surface and the molecular components of the first layer. In some embodiments, the substrate surface may be treated prior to attachment or deposition of the first layer. Various surface preparation techniques may be used to clean or treat the surface. For example, glass or silicon surfaces may be acid-washed using a Piranha solution (a mixture of sulfuric acid ($H_2SO_4$) and hydrogen peroxide ($H_2O_2$)), base treatment in KOH and NaOH, and/or cleaned using an oxygen plasma treatment method.

In some embodiments, silane chemistries can covalently modify silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. In some embodiments, silanes that may be used in creating any of the low binding surfaces include any one of, but are not limited to, (3-Aminopropyl) trimethoxysilane (APTMS), (3-Aminopropyl) triethoxysilane (APTES), any one of various PEG-silanes (e.g., comprising molecular weights of at least 1K, at least 2K, at least 5K, at least 10K, at least 20K, etc.), amino-PEG silane (i.e., comprising a free amino functional group), maleimide-PEG silane, biotin-PEG silane, and the like.

Various molecules including any one of, but not limited to, amino acids, peptides, nucleotides, oligonucleotides, other monomers or polymers, or combinations thereof may be used in creating the one or more chemically-modified layers on the surface. In some embodiments, the choice of components used may be varied to alter one or more properties of the surface, e.g., the surface density of functional groups and/or tethered oligonucleotide primers, the hydrophilicity/hydrophobicity of the surface, or the three three-dimensional nature (e.g., "thickness") of the surface. In some embodiments, a polymer may be used to create one or more layers of low non-specific binding material on a surface. In some embodiments, the polymer can be any one of, but is not limited to, polyethylene glycol (PEG) of various molecular weights and branching structures, streptavidin, polyacrylamide, polyester, dextran, poly-lysine, and poly-lysine copolymers, or any combination thereof. In some embodiments, a conjugate chemistry may be used to graft one or more layers of material to the surface and/or to cross-link the layers. In some embodiments, conjugation chemistries that may be used include any one of, but are not limited to, biotin-streptavidin interactions (or variations thereof), His tag-Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, or silane.

In some embodiments, the low non-specific binding surface coating may be applied uniformly across the substrate. In some embodiments, the surface coating may be patterned, such that the chemical modification layers are confined to one or more discrete regions of the substrate. In some embodiments, the surface may be patterned using photolithographic techniques to create an ordered array or random pattern of chemically-modified regions on the surface. In some embodiments, the substrate surface may be patterned using, e.g., contact printing and/or ink-jet printing techniques. In some embodiments, an ordered array or random patter of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In some embodiments, in order to achieve low nonspecific binding surfaces, hydrophilic polymers may be nonspecifically adsorbed or covalently grafted to the surface. In some embodiments, passivation is performed utilizing poly(ethylene glycol) (PEG, also known as polyethylene oxide (PEO) or polyoxyethylene) or other hydrophilic polymers with different molecular weights and end groups that are linked to a surface using, for example, silane chemistry. In some embodiments, the end groups distal from the surface can include, but are not limited to, biotin, methoxy ether, carboxylate, amine, NHS ester, maleimide, and bis-silane. In some embodiments, two or more layers of a hydrophilic polymer, e.g., a linear polymer, branched polymer, or multi-branched polymer, may be deposited on the surface. In some embodiments, two or more layers may be covalently coupled to each other or internally cross-linked to improve the stability of the resulting surface. In some embodiments, oligonucleotide primers with different base sequences and base modifications (or other biomolecules, e.g., enzymes or antibodies) may be tethered to the resulting surface layer at various surface densities. In some embodiments, for example, both surface functional group density and oligonucleotide concentration may be varied to target a certain primer density range. In some embodiments, primer density can be controlled by diluting oligonucleotide with other molecules that carry the same functional group. In some embodiments, amine-labeled oligonucleotide can be diluted with amine-labeled polyethylene glycol in a reaction with an NHS-ester coated surface to reduce the final primer density. In some embodiments, primers with different lengths of linker between the hybridization region and the surface attachment functional group can also be applied to control surface density. In some embodiments, suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). In some embodiments, to measure the primer density, fluorescently-labeled primers may be tethered to the surface and a fluorescence reading then may be compared with that of a dye solution of known concentration.

In some embodiments, in order to scale primer surface density and add additional dimensionality to hydrophilic or amphoteric surfaces, surfaces comprising multi-layer coatings of PEG and other hydrophilic polymers may be used. In some embodiments, by using hydrophilic and amphoteric surface layering approaches that include any one of, but are not limited to, the polymer/co-polymer materials described below, primer loading density on the surface may be increased significantly. Traditional PEG coating approaches use monolayer primer deposition, which have been generally reported for single molecule applications, but do not yield high copy numbers for nucleic acid amplification applications. As described herein, "layering" can be accomplished using traditional crosslinking approaches with any compatible polymer or monomer subunits such that a surface comprising two or more highly crosslinked layers can be built sequentially. In some embodiments, the polymer may include any one of, but are not limited to, streptavidin, poly acrylamide, polyester, dextran, poly-lysine, or copolymers of poly-lysine and PEG. In some embodiments, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some embodiments, high primer density materials may be constructed in solution and subsequently layered onto the surface in multiple steps.

In some embodiments, the low non-specific binding coatings of the present disclosure exhibit reduced non-specific binding of proteins, nucleic acids, and other components of the hybridization and/or amplification formulation used for solid-phase nucleic acid amplification. In some embodiments, the degree of non-specific binding exhibited by a given support surface may be assessed either qualitatively or quantitatively. In some embodiments, exposure of the surface to fluorescent dyes (e.g., cyanine dyes such as Cy3, or Cy5, etc., fluoresceins, coumarins, rhodamines, etc. or other dyes disclosed herein), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some embodiments, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under a condition where fluorescence signal is linearly related (or related in a predictable manner) to the number of fluorophores on the support surface (e.g., under a condition where signal saturation and/or self-quenching of the fluorophore is not an issue) and suitable calibration standards are used. In some embodiments, other techniques, for example, radioisotope labeling and counting methods may be used for quantitative assessment of the degree to which non-specific binding is exhibited by the different support surface formulations of the present disclosure.

In some embodiments, a surface exhibits a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some embodiments, a surface exhibits a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

In some embodiments, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed by detection of the amount of label remaining on the surface and comparison of the signal resulting therefrom to an appropriate calibration standard. In some embodiments, the label may comprise a fluorescent label. In some embodiments, the label may comprise a radioisotope. In some embodiments, the label may comprise any other detectable label. In some embodiments, the degree of non-specific binding exhibited by a given support surface formulation may thus be assessed in terms of the number of non-specifically bound protein molecules (or other molecules) per unit area. In some embodiments, the low-binding supports of the present disclosure may exhibit non-specific protein binding (or non-specific binding of other specified molecules, (e.g., cyanine dyes such as Cy3, or Cy5, etc., fluoresceins, coumarins, rhodamines, etc. or other dyes disclosed herein)) of less than 0.001 molecule per µm², less than 0.01 molecule per µm², less than 0.1 molecule per µm², less than 0.25 molecule per µm², less than 0.5 molecule per µm², less than 1 molecule per µm², less than 10 molecules per µm², less than 100 molecules per µm², or less than 1,000 molecules per µm². In some embodiments, a support surface of the present disclosure may exhibit non-specific binding falling anywhere within this range, for example, of less than 86 molecules per µm². In some embodiments, some modified surfaces disclosed herein exhibit nonspecific protein binding of less than 0.5 molecule/µm² following contact with a 1 µM solution of Cy3 labeled streptavidin (GE Amersham) in phosphate buffered saline (PBS) buffer for 15 minutes, followed by 3 rinses with deionized water. In some embodiments, modified surfaces disclosed herein exhibit nonspecific binding of Cy3 dye molecules of less than 0.25 molecules per µm².

In independent nonspecific binding assays, 1 µM labeled Cy3 SA (ThermoFisher), 1 µM Cy5 SA dye (ThermoFisher), 10 µM Aminoallyl-dUTP—ATTO-647N (Jena Biosciences), 10 µM Aminoallyl-dUTP—ATTO-Rho11 (Jena Biosciences), 10 µM Aminoallyl-dUTP—ATTO-Rho11 (Jena Biosciences), 10 µM 7-Propargylamino-7-deaza-dGTP—Cy5 (Jena Biosciences, and 10 µM 7-Propargylamino-7-deaza-dGTP—Cy3 (Jena Biosciences) were each incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, Pa.) with a total internal reflectance fluorescence (TIRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75 W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, N.Y.), e.g., 405, 488, 532, or 633 nm dichroic reflectors/beamsplitters, and band pass filters were chosen as 532 LP or 645 LP concordant with the appropriate excitation wavelength. In some embodiments, modified surfaces disclosed herein exhibit nonspecific binding of dye molecules of less than 0.25 molecules per µm².

In some embodiments, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some embodiments, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

In some embodiments, the low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. In some embodiments, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some embodiments, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some embodiments, a static contact angle may be determined. In some embodiments, an advancing or receding contact angle may be determined. In some embodiments, the water contact angle for the hydrophilic, low-binding support surfaced disclosed herein may range from about 0 degrees to about 30 degrees. In some embodiments, the water contact angle for the hydrophilic, low-binding support surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. In some embodiments, a given hydrophilic, low-binding support surface of the present disclosure may exhibit a water contact angle having a value of anywhere within this range.

In some embodiments, the hydrophilic surfaces disclosed herein facilitate reduced wash times for bioassays, often due to reduced nonspecific binding of biomolecules to the low-binding surfaces. In some embodiments, adequate wash steps may be performed in less than 60, 50, 40, 30, 20, 15, 10, or less than 10 seconds. In some embodiments, adequate wash steps may be performed in less than 30 seconds.

In some embodiments, the low-binding surfaces of the present disclosure exhibit significant improvement in stability or durability to prolonged exposure to solvents and elevated temperatures, or to repeated cycles of solvent exposure or changes in temperature. In some embodiments, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some embodiments, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some embodiments, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some embodiments, the surfaces disclosed herein may exhibit a high ratio of specific signal to nonspecific signal or other background. In some embodiments, when used for nucleic acid amplification, surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. In some embodiments, surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

In some embodiments, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In some embodiments, one or more types of primer (e.g., capture oligonucleotides and/or circularization oligonucleotides) may be attached or tethered to the support surface. In some embodiments, the one or more types of adapters or primers may comprise spacer sequences, adapter sequences for hybridization to adapter-ligated target library nucleic acid sequences, forward amplification primers, reverse amplification primers, sequencing primers, and/or molecular barcoding sequences, or any combination thereof. In some embodiments, 1 primer or adapter sequence may be tethered to at least one layer of the surface. In some embodiments, at least 2, 3, 4, 5, 6, 7, 8, 9, 10, or more than 10 different primer or adapter sequences may be tethered to at least one layer of the surface.

In some embodiments, the tethered adapter and/or primer sequences may range in length from about 10 nucleotides to about 100 nucleotides. In some embodiments, the tethered adapter and/or primer sequences may be at least 10, at least 20, at least 30, at least 40, at least 50, at least 60, at least 70, at least 80, at least 90, or at least 100 nucleotides in length. In some embodiments, the tethered adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some embodiments the length of the tethered adapter and/or primer sequences may range from about 20 nucleotides to about 80 nucleotides. The tethered adapter and/or primer sequences may have any value within this range, e.g., about 24 nucleotides.

In some embodiments, the resultant surface density of primers on the low binding support surfaces of the present disclosure may range from about 100 primer molecules per $\mu m^2$ to about 100,000 primer molecules per $\mu m^2$. In some embodiments, the resultant surface density of primers on the low binding support surfaces of the present disclosure may range from about 100,000 primer molecules per $\mu m^2$ to about $10^{15}$ primer molecules per $\mu m^2$. In some embodiments, the surface density of primers may be at least 1,000, at least 10,000, at least 100,000, or at least $10^{15}$ primer molecules per $\mu m^2$. In some embodiments, the surface density of primers may be at most 10,000, at most 100,000, at most 1,000,000, or at most $10^{15}$ primer molecules per $\mu m^2$. Any of the lower and upper values described in this paragraph may be combined to form a range included within the present disclosure, for example, in some embodiments the surface density of primers may range from about 10,000 molecules per $\mu m^2$ to about $10^{15}$ molecules per $\mu m^2$. The surface density of primer molecules may have any value within this range, e.g., about 455,000 molecules per $\mu m^2$. In some embodiments, the surface density of target library nucleic acid sequences initially hybridized to adapter or primer sequences on the support surface may be less than or equal to that indicated for the surface density of tethered primers. In some embodiments, the surface density of clonally-amplified target library nucleic acid sequences hybridized to adapter or primer sequences on the support surface may span the same range as that indicated for the surface density of tethered primers.

In some embodiments, local densities as listed above do not preclude variation in density across a surface, such that a surface may comprise a region having an oligo density of, for example, 500,000 per $\mu m^2$, while also comprising at least a second region having a substantially different local density.

In some embodiments, the low non-specific binding coating comprise one or more layers of a multi-layered surface coating may comprise a branched polymer or may be linear. In some embodiments, suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly(N-isopropylacrylamide) (branched PNIPAM), branched poly(methyl methacrylate) (branched PMA), branched poly(-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

In some embodiments, linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkages per molecule and about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. In some embodiments, when an amine coupling chemistry is used to attach a new material layer to the previous one, any residual amine groups may subsequently be acetylated or deactivated by coupling with a small amino acid such as glycine.

In some embodiments, the number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiment, all of the layers may comprise a branched polymer.

In some embodiments, one or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some embodiments, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. In some embodiments, the pH of the solvent mixture used may be less than 6, about 6, 6.5, 7, 7.5, 8, 8.5, 9, or greater than pH 9.

Various compositions and methods for preparing, testing, and using the low non-specific binding coatings, including methods for immobilizing to the coating any type of primer (e.g., capture oligonucleotides, amplification oligonucleotides and/or circularization oligonucleotides) are described in U.S. application Ser. No. 16/363,842, filed Mar. 25, 2019; Ser. No. 16/740,355, filed Jan. 10, 2020; Ser. No. 16/740,357, filed Jan. 10, 2020; and U.S. Pat. No. 16,855,877, filed Apr. 22, 2020, the contents of the aforementioned patent applications are hereby expressly incorporated by reference in their entireties.

Kits

Disclosed herein, in some embodiments, are kits for preparing a nucleic acid sequencing library and/or sequence the nucleic acid sequencing library. In some embodiments, the kits comprise compositions described herein, such as reagents and substrates for circularizing a nucleic acid molecule and/or sequencing the nucleic acid molecule following circularization.

The kit may include enzymes, nucleic acids, nucleotides, supports with functionalized surfaces, reagents, or instructions. In some embodiments, the enzymes may be ligating enzymes, proteases, transposases, any one of enzymes described herein and combination thereof. In some embodiments, the nucleic acids may be oligonucleotides, splint oligonucleotides, any oligonucleotides or nucleic acids described herein, or any combinations thereof. In some embodiments, nucleotides may comprise nucleotides with blocking moieties. In some embodiments, nucleotides may comprise nucleotides without blocking moieties. In some embodiments, nucleotides may comprise fluorescently-labeled multivalent molecules. In some embodiments, supports with functionalized surfaces may comprise a plastic, metal, glass, or any combinations thereof for the support. In some embodiments, supports with functionalized surfaces may comprise hydrophilic, hydrophobic, polymeric, primed, or any combinations thereof for the functionalizations. In some embodiments, the reagents may comprise any one of the reagents described herein.

Figure 22A:
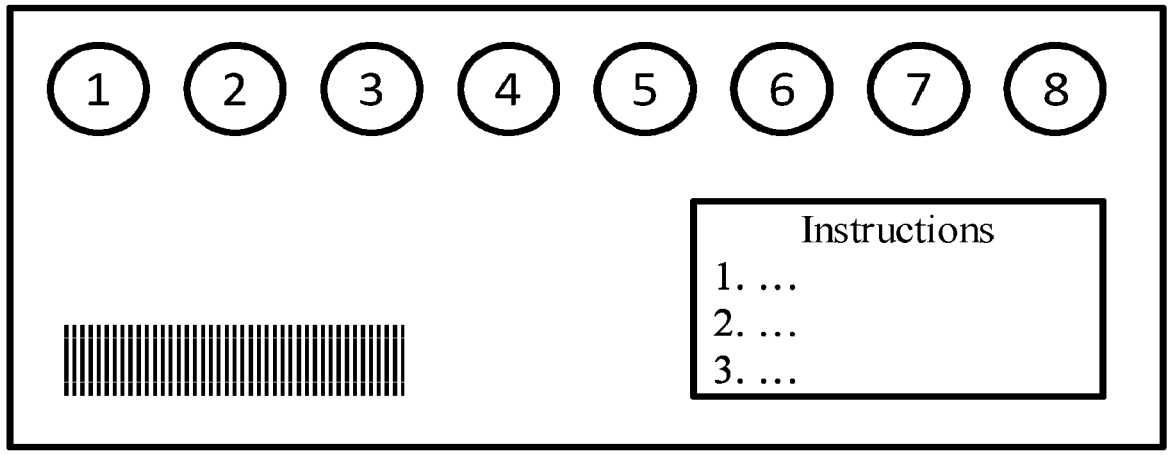
FIGS. 22A-22B illustrates kits comprising reagents of the present disclosure, in accordance with some embodiments.
Figure 22B:
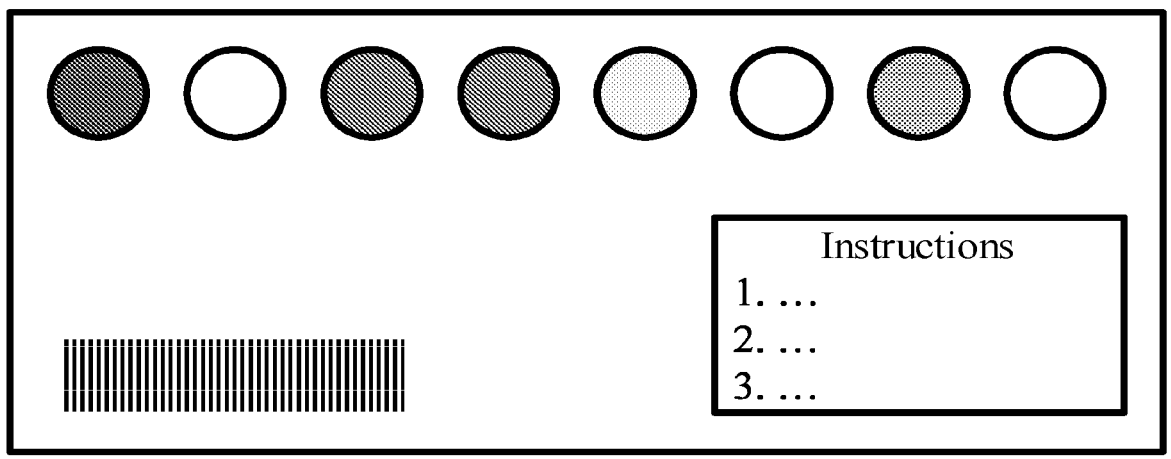

In some embodiments, each reagent in the kit may be labeled. In some embodiments, each reagent in the kit may be labeled with different numbers or different letters, for example, as shown in FIG. 22A. In some embodiments, reagents in the kit may be contained in differently colored containers, for example, as shown in FIG. 22B. In some embodiments, reagents in the kit may be contained in containers having flat bottom surfaces. In some embodiments, reagents in the kit may be contained in containers having non-flat bottom surfaces. In some embodiments, a container may comprise a light-blocking material. In some embodiments, a container may comprise a material that blocks UV light. In some embodiments, a container may comprise plastic. In some embodiments, a container may comprise glass. In some embodiments, a container may comprise an identifier, such as a barcode, for example, as shown in FIG. 22A. In some embodiments, containers may comprise differently colored caps. In some embodiments, a container may be a 96 well plate. In some embodiments, a container may be 384 well plate. In some embodiments, a container may comprise a 96 well plate. In some embodiments, a container may comprise a 384 well plate. In some embodiments, a container may be a tube.

In some embodiments, the instructions may comprise a description for a method of circularizing single stranded nucleic acid, single stranded DNA, single stranded RNA, double stranded nucleic acid, double stranded DNA, double stranded RNA, any nucleic acid described herein and combinations thereof. In some embodiments, the instructions may further comprise a description for a method of attaching nucleic acid adapters or primers before circularization, simultaneously with circularization, or after circularization. In some embodiments, the instructions may further comprise a description for processing the genetic material from a biological source. In some embodiments, the instructions may comprise a description for detecting nucleic acid sequences. In some embodiments, the instructions may comprise a description for planning multiple stages, each stage employing one of the methods described herein. In some embodiments, such a description may describe one or more steps for using any one of the reagent compositions described herein. In some embodiments, such a description may describe the steps for using any one of the reagent compositions described herein in combination with other reagent compositions.

In some embodiments, the instructions may describe a step for preparing a nucleic acid library. In some embodiments, the instructions may describe a step for preprocessing a biological sample. In some embodiments, the instructions may describe a step for extracting nucleic acids from a biological sample. In some embodiments, the instructions may describe a step for purifying nucleic acids from other chemicals. In some embodiments, the instructions may describe a step for isolating one kind of nucleic acid (e.g., DNA, RNA, plasmid, etc.) from other kinds of nucleic acids. In some embodiments, the instructions may describe a step for adding one or more primers or one or more adapters to the nucleic acids. In some embodiments, the instructions may describe a step for circularizing the nucleic acids.

In some embodiments, the instructions may describe a step for hybridizing nucleic acids from a nucleic acid library to oligonucleotides functionalized onto a surface. In some embodiments, the step may describe using a hybridizing reagent. In some embodiments, the step may describe using the hybridizing reagent at a variety of compositions. In some embodiments, the step may describe mixing the hybridizing reagent with an appropriate amount of solvent. In some embodiments, the step may describe using the hybridizing reagent within a predetermined temperature range. In some embodiments, the step may describe using the hybridizing reagent for a predetermined duration of time.

In some embodiments, the instructions may describe a step for washing a surface. In some embodiments, the step may describe using a universal washing reagent. In some embodiments, the step may describe using a wash-removal reagent. In some embodiments, the step may describe using the universal washing reagent or the wash-removal reagent at a variety of compositions. In some embodiments, the step may describe mixing the universal washing reagent or the wash-removal reagent with an appropriate amount of solvent. In some embodiments, the step may describe using the universal washing reagent or the wash-removal reagent within a predetermined temperature range. In some embodiments, the step may describe using the universal washing reagent or the wash-removal reagent for a predetermined duration of time.

In some embodiments, the instructions may describe a step for amplifying nucleic acids. In some embodiments, the nucleic acids may be hybridized with oligonucleotides functionalized onto a surface. In some embodiments, the step may describe using an amplifying reagent. In some embodiments, the step may describe using the amplifying reagent at a variety of compositions. In some embodiments, the step may describe mixing the amplifying reagent with an appropriate amount of solvent. In some embodiments, the step may describe using the amplifying reagent within a predetermined temperature range. In some embodiments, the step may describe using the amplifying reagent for a predetermined duration of time.

In some embodiments, the instructions may describe a step for binding fluorescently-labeled multivalent molecules. In some embodiments, the step may describe using a trapping reagent. In some embodiments, the step may describe using the trapping reagent at a variety of compositions. In some embodiments, the step may describe mixing the trapping reagent with an appropriate amount of solvent. In some embodiments, the step may describe using the trapping reagent within a predetermined temperature range. In some embodiments, the step may describe using the trapping reagent for a predetermined duration of time.

In some embodiments, the instructions may describe a step for binding fluorescently-labeled multivalent molecules onto oligonucleotides functionalized onto a surface. In some embodiments, the step may describe using a trapping reagent. In some embodiments, the step may describe using the trapping reagent at a variety of compositions. In some embodiments, the step may describe mixing the trapping reagent with an appropriate amount of solvent. In some embodiments, the step may describe using the trapping reagent within a predetermined temperature range. In some embodiments, the step may describe using the trapping reagent for a predetermined duration of time.

In some embodiments, the instructions may describe a step for washing a surface while retaining fluorescently-labeled multivalent molecules bound to oligonucleotides functionalized onto a surface. In some embodiments, the step may describe using a post-trapping reagent. In some embodiments, the step may describe using the post-trapping reagent at a variety of compositions. In some embodiments, the step may describe mixing the post-trapping reagent with an appropriate amount of solvent. In some embodiments, the step may describe using the post-trapping reagent within a predetermined temperature range. In some embodiments, the step may describe using the post-trapping reagent for a predetermined duration of time.

In some embodiments, the instructions may describe a step for imaging a surface. In some embodiments, the step may describe using an imaging reagent. In some embodiments, the step may describe using the imaging reagent at a variety of compositions. In some embodiments, the step may describe mixing the imaging reagent with an appropriate amount of solvent. In some embodiments, the step may describe using the imaging reagent within a predetermined temperature range. In some embodiments, the step may describe using the imaging reagent for a predetermined duration of time.

In some embodiments, the instructions may describe a step extending an oligonucleotide functionalized on a surface. In some embodiments, the step may describe using a stepping reagent. In some embodiments, the step may describe using the stepping reagent at a variety of compositions. In some embodiments, the step may describe mixing the stepping reagent with an appropriate amount of solvent. In some embodiments, the step may describe using the stepping reagent within a predetermined temperature range. In some embodiments, the step may describe using the stepping reagent for a predetermined duration of time. In some embodiments, the step may describe using a cleaving reagent. In some embodiments, the step may describe using the cleaving reagent at a variety of compositions. In some embodiments, the step may describe mixing the cleaving reagent with an appropriate amount of solvent. In some embodiments, the step may describe using the cleaving reagent within a predetermined temperature range. In some embodiments, the step may describe using the cleaving reagent for a predetermined duration of time.

In some embodiments, a kit may comprise separate tubes for each enzyme. In some embodiments, a tube of reaction buffer may be provided for each step. In some embodiments, reaction buffers may be supplied as concentrates. In some embodiments, oligonucleotides may be provided with the kit.

EXAMPLES

These examples are provided for illustrative purposes only and not to limit the scope of the claims provided herein.

Example 1. Photo Bleaching Measurements of Immobilized Ternary Complexes with Trapping Reagents and Imaging Reagents A comparison of various imaging reagents was conducted to assess their ability to reduce photo-damage of ternary complexed immobilized on a support. A glass coverslip was attached to the bottom of 384-well plates. The coverslip included immobilized surface primers. Circularized DNA libraries were hybridized to the immobilized surface primers on the coverslip and subjected to a rolling circle amplification reaction to generate concatemers template molecules (e.g., polonies) immobilized to the coverslip. Sequencing primers were added to the wells to hybridize to the concatemer template molecules and form ternary complexes on the coverslip. 20 uL of trap reagent was added to each well and incubated for 45 seconds at 42° C. The wells were washed five times with 40 uL of imaging reagent to remove unbound first sequencing polymerases and unbound multivalent molecules. For the imaging step, 40 uL of imaging reagent was added to the wells. The immobilized ternary complexes were subjected to photo-bleaching conditions by illumination with a laser for 3 seconds followed by a 1 second delay for 90 seconds. Approximately 90% of the green laser power was used to excite labeled multivalent molecules dU-CF532 and dG-CF570. Approximately 70% of the red laser power was used to excite labeled multivalent molecules dA-CF647 and dC-CF680. Fluorescent imaging was conducted on a custom-built Olympus inverted microscope with a 20×0.7 numerical aperture (NA) objective. The fluorescent images were taken with an ANDOR Zyla cMOS camera with 0.5 second exposure. Curves representing photo-bleaching of the immobilized ternary complexes were plotted using the average intensity or P90 intensity of the duration of the green or red laser excitation time in seconds. Representative photo-bleaching data are shown in FIGS. 17-18, 35-36, 38-42, and 45.

Trap reagent: A solvent, a pH buffering agent, a chelating agent, at least one monovalent cation, a non-catalytic divalent cation, a detergent, a plurality of nucleotide reagents (e.g., a plurality of fluorophore-labeled multivalent molecules) and a plurality of a first sequencing polymerase enzyme (non-labeled polymerases). An exemplary multivalent molecule is shown in FIG. 2B.

Imaging reagents: The imaging reagents included at least one solvent, a pH buffering agent, a chelating agent, at least one monovalent cation, a non-catalytic divalent cation, a detergent, at least one compound for increasing viscosity, and at least one compound for reducing photo-damage. In some embodiments, the compounds for reducing photo-damage included one compound or a combination of two or more compounds, including ascorbic acid, a Trolox compound (e.g., non-aged Trolox, aged Trolox, Trolox quinone, methyl viologen, 1,3,5,7 cyclo-octatetraene (COT), cystamine, 3-nitrobenzoic acid (NBA) and/or P-phenyl diamine (PPD).

Figure 40:
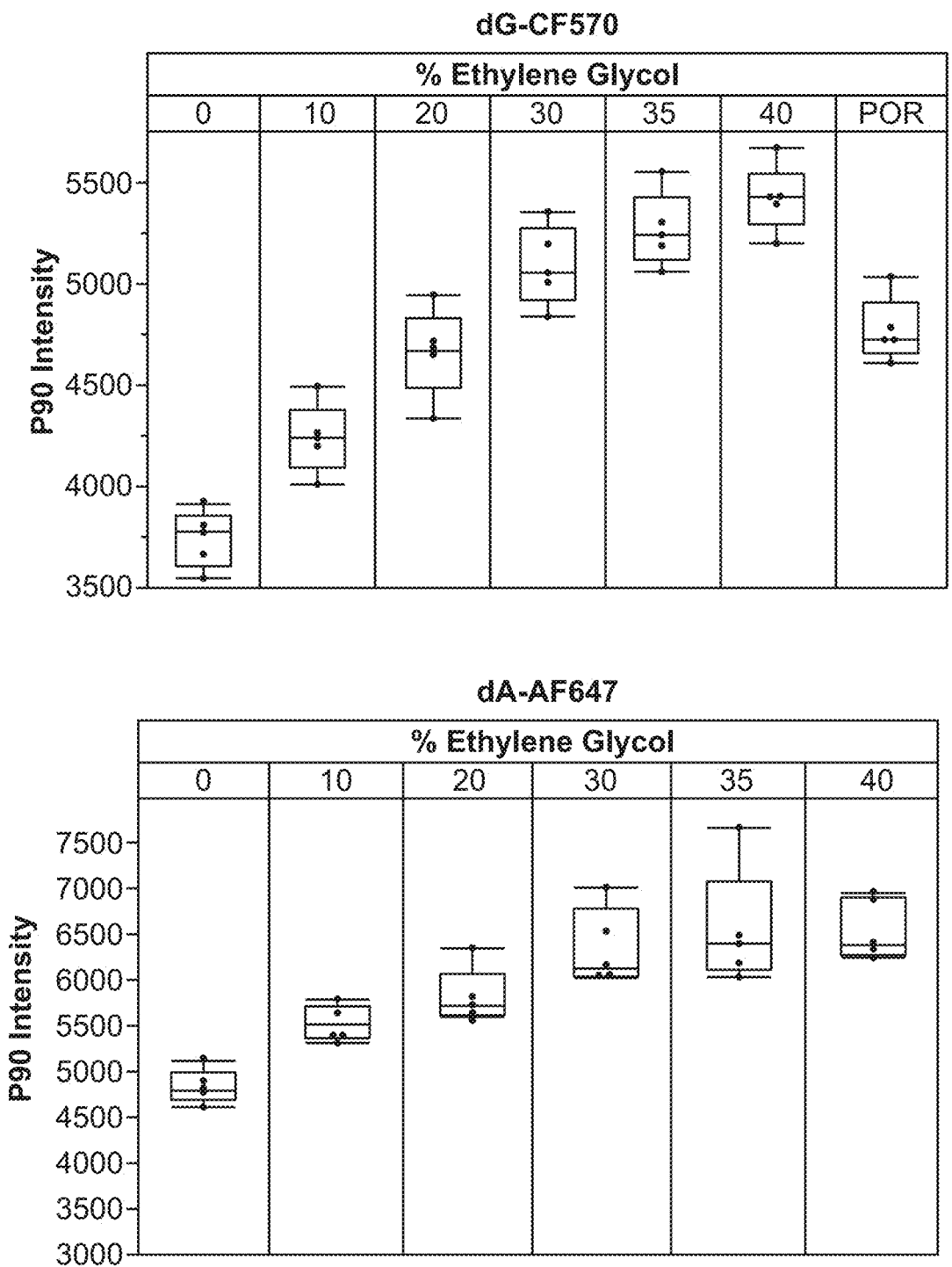
FIG. 40 is a series of box plots showing the effects of imaging reagents comprising different formulations (with varying concentrations of ethylene glycol) on signal intensity of labeled multivalent molecules. Labeled multivalent molecules: dG-CF57 (top) and dA-AF647 (bottom). The imaging reagents comprise Tris-HCl (pH 8), EDTA, NaCl (reduced from 100 mM to 75 mM), Triton™ X-100 (2-[4-(2,4,4-trimethylpentan-2-yl)phenoxy]ethanol), strontium acetate, glycerol, varying concentrations of ethylene glycol, Trolox (2 mM), and sodium ascorbate (25 mM) (and no sucrose).
Figure 41:
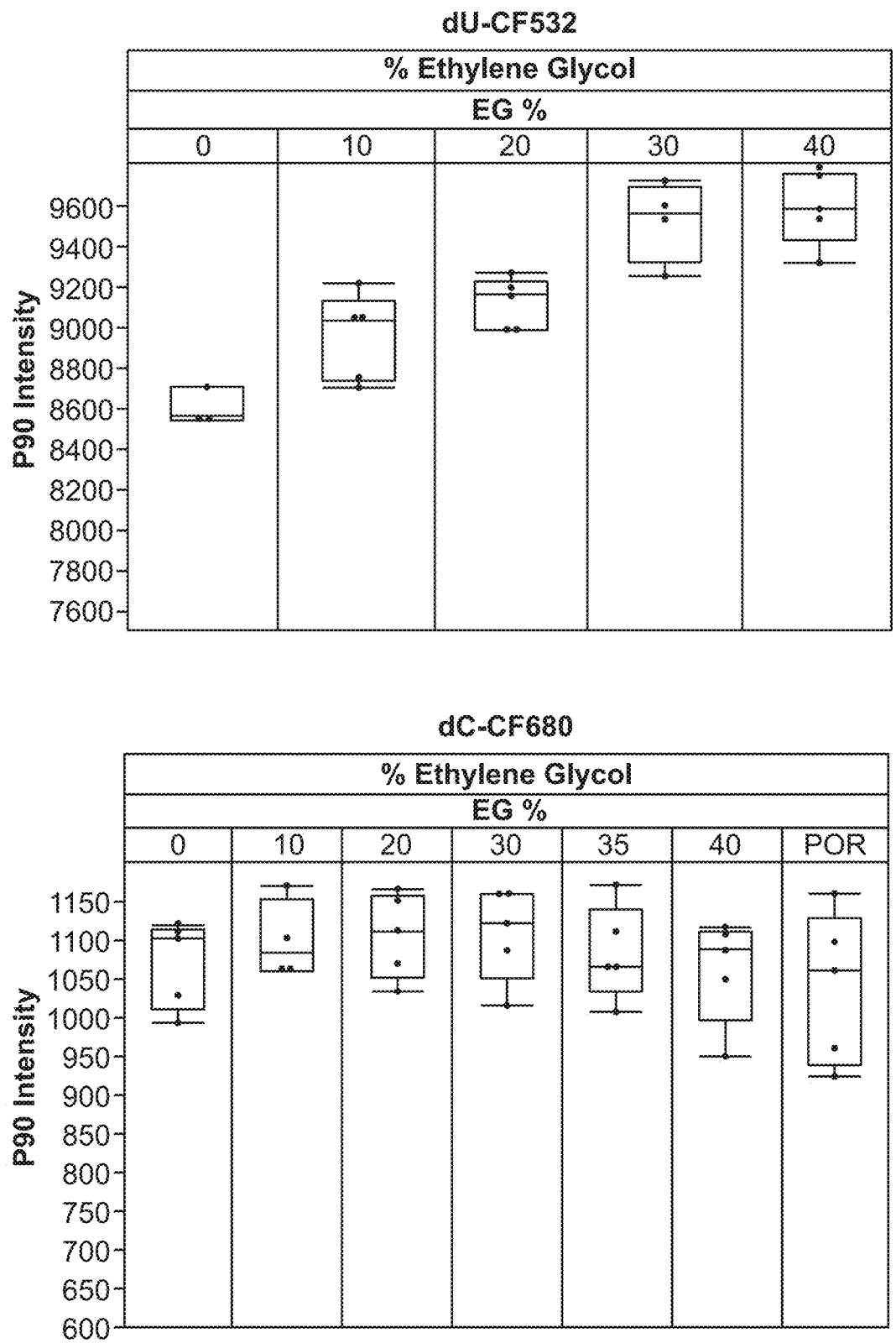
FIG. 41 is a series of box plots showing the effects of imaging reagents comprising different formulations (with varying concentrations of ethylene glycol) on signal intensity of labeled multivalent molecules. Labeled multivalent molecules: dU-CF532 (top) and dC-CF680 (bottom). The imaging reagents comprise Tris-HCl (pH 8), EDTA, NaCl (reduced from 100 mM to 75 mM), Triton™ X-100 (2-[4-(2,4,4-trimethylpentan-2-yl)phenoxy]ethanol), strontium acetate, glycerol, varying concentrations of ethylene glycol, Trolox (2 mM), and sodium ascorbate (25 mM) (and no sucrose).
Figure 42:
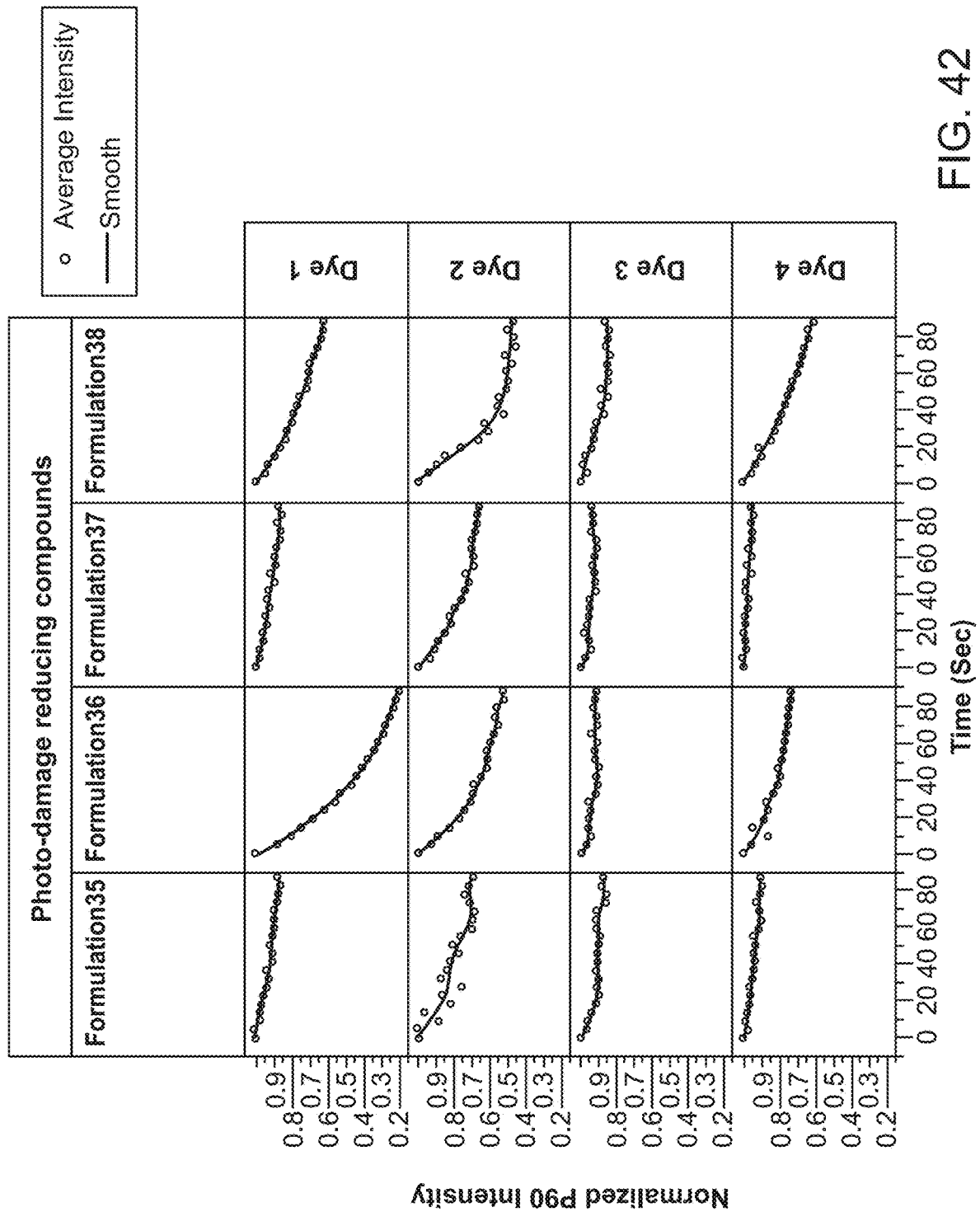
FIG. 42 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 35 and 36 comprise Tris-HCl (pH 7.2-7.5), EDTA, NaCl (reduced from 100 mM to 75 mM), Triton™ X-100 (2-[4-(2,4,4-trimethylpentan-2-yl)phenoxy]ethanol), strontium acetate, glycerol, ethylene glycol (30%), and no sucrose. Formulation 35 comprises Tris-HCl (pH 7.5), Trolox (aged) (2 mM) and sodium ascorbate (25 mM). Formulation 36 comprises Tris-HCl (pH 7.5), Trolox (non-aged) (2 mM) and sodium ascorbate (25 mM). Formulation 37 comprises Tris-HCl (pH 8), EDTA, NaCl (reduced from 100 mM to 75 mM), Triton™ X-100 (2-[4-(2,4,4-trimethylpentan-2-yl)phenoxy] ethanol), strontium acetate, glycerol, ethylene glycol (30%), no sucrose, Trolox (aged) (2 mM), and sodium ascorbate (25 mM). Formulation 38 comprises Tris-HCl (pH 8.8), EDTA, NaCl (100 mM), Triton™ X-100 (2-[4-(2,4,4-trimethylpentan-2-yl)phenoxy]ethanol), sucrose (1 M), strontium acetate, glycerol, Trolox (non-aged) (2 mM), and sodium ascorbate (25 mM).
Figure 43:
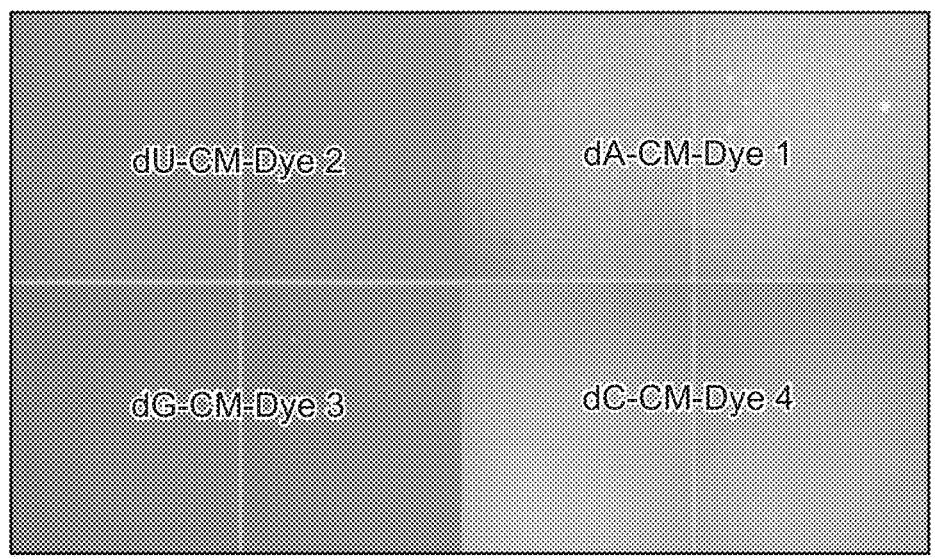
FIG. 43 is a series of images of dye-labeled nucleotides where the nucleotides are joined to a dye via a cleavable moiety (CM). The images show no residual fluorescent signals after a 90 second exposure to high laser power. The imaging reagent comprises Tris-HCl (pH 8.8), EDTA, NaCl, Triton™ X-100 (2-[4-(2,4,4-trimethylpentan-2-yl)phenoxy] ethanol), sucrose, strontium acetate, glycerol, 1,3,5,7 cyclooctatetraene (COT) (2 mM), sodium ascorbate (50 mM) and Trolox (2 mM).

Example 2: Intensity Measurements of Immobilized Ternary Complexes with Imaging Reagents Comprising Ethylene Glycol A comparison of various imaging reagents was conducted to assess their ability to improve fluorescent intensity of ternary complexes immobilized on a support. Glass flowcells were treated to immobilize surface primers thereon. Circularized DNA libraries were hybridized to the immobilized surface primers on the flowcells and subjected to a rolling circle amplification reaction to generate concatemers template molecules (e.g., polonies) immobilized to the flowcells. Sequencing primers were flowed onto the flowcell to permit hybridization to the concatemer template molecules and form ternary complexes on the flowcells. 200 uL of trap reagent was flowed onto the flowcells and incubated for 45 seconds at 42° C. The flowcells were washed with imaging reagent to remove unbound first sequencing polymerases and unbound multivalent molecules. For the imaging step, 400 uL of imaging reagent was flowed onto the flowcells. The imaging reagent contained varying amounts of ethylene glycol (e.g., 0, 10, 20, 30, 35 or 40%). The same flowcell was reused to test the imaging reagents containing a particular concentration of ethylene glycol. Images were obtained using the same inverted microscope described in Example 1. Approximately 30% of the green laser power was used to excite labeled multivalent molecules dU-CF532 and dG-CF570. Approximately 13% of the red laser power was used to excite labeled multivalent molecules dA-CF647 and dC-CF680. The intensity data is shown in FIG. 40 and FIG. 41.

Trap reagent: A solvent, a pH buffering agent, a chelating agent, at least one monovalent cation, a non-catalytic divalent cation, a detergent, a plurality of nucleotide reagents (e.g., a plurality of fluorophore-labeled multivalent molecules) and a plurality of a first sequencing polymerase enzyme (non-labeled polymerases). An exemplary multivalent molecule is shown in FIG. 2B.

Imaging reagents: The imaging reagents included at least one solvent, a pH buffering agent, a chelating agent, at least one monovalent cation, a non-catalytic divalent cation, a detergent, at least one compound for increasing viscosity, and at least one compound for reducing photo-damage. In some embodiments, the compounds for reducing photo-damage included one compound or a combination of compounds including ascorbic acid and/or a Trolox compound (e.g., non-aged Trolox, aged Trolox or Trolox quinone).

Example 3: Preparing Aged Trolox

Trolox (6-hydroxy-2,5,7,8-tetramethylchroman-2-carboxylic acid) can be subjected to UV light exposure and/or aeration to generate hydroxylated derivatives which exhibit increased water solubility. Several methods for preparing hydroxylated Trolox derivatives (aged Trolox) were tested (see Methods A-E below). The aged Trolox were included in various imaging reagents and tested in photo-bleaching assays.

Method A: A solution of Trolox (1.25 g, 5 mmol) dissolved in MeOH (25 mL) and water (25 mL) in a 250 mL beaker was illuminated with UV light (254 nm, 15 W) for 3 hours. The solution was analyzed by RP-HPLC (C-18 column) to establish its chromatographic profile. The RP-HPLC results showed that in addition to the starting Trolox (9.70 min) there are three major new peaks (10.35 min, 11.33 min and 14.44 min) together with a few minor peaks observed in the HPLC chromatogram. It is noted that all the newly formed peaks are less polar than Trolox itself and are eluted at longer migration times than Trolox (data not shown).

Method B: To a suspended solution of Trolox (1.25 gram, 5 mmol) in MeOH (5 mL) was added NaOH solution (1 N, 12 mL). The solution turned clear after vortexing for 2 minutes and then diluted with water (10% methanol in the final solution) to a total volume of 50 mL. The pH measured 12.5. The solution was transferred to a 250 mL beaker and illuminated under UV light (254 nm, 15 W) for 3 hours. The solution was analyzed by RP-HPLC (C-18 column). In addition to the starting Trolox (9.70 min) and two of the previously observed peaks (10.35 min, 11.33 min), there are several other peaks observed in the HPLC chromatogram. In particular, the two major peaks with migration times at 8.12 min and 8.82 min are noteworthy since they are more polar than Trolox and potentially more water solvable than Trolox itself. The solution was left in the hood under ambient condition for 60 hours to increase the aging process while samples were monitored with RP-HPLC. The conversion of Trolox was a slow process. After 60 hours incubation at room temperature, there was a significant amount of unmodified Trolox remaining in solution.

Method C: An attempt to speed up the aging process was tested. A 100 mM solution of Trolox solution (pH 12.5) was treated with UV irradiation for 3 hours, then stirred at 600 rpm in a flask opened to the air. Analysis of the solution with RP-HPLC analysis showed that Trolox peak was almost all consumed after 16 hours of stirring, which suggested that the stirring method helps oxygen uptake and speeds up the oxidation process.

Method D: In another procedure, Trolox (pH 12.5) was prepared as described in Method C above with stirring but UV irradiation was omitted. RP-HPLC analysis showed similar results after stirring the Trolox solution overnight.

Method E: To further investigate the base treated oxidation process, a solution of 30% $H_2O_2$ (5 mL) was added to the 100 mM Trolox solution at pH 12.5. Bubbles quickly released from the solution, and the pH quickly dropped to 9.5. RP-HPLC chromatograms showed the formation of Trolox quinone (11.33 min) and a major peak of unmodified Trolox remained after 16 hours.

Figure 32:
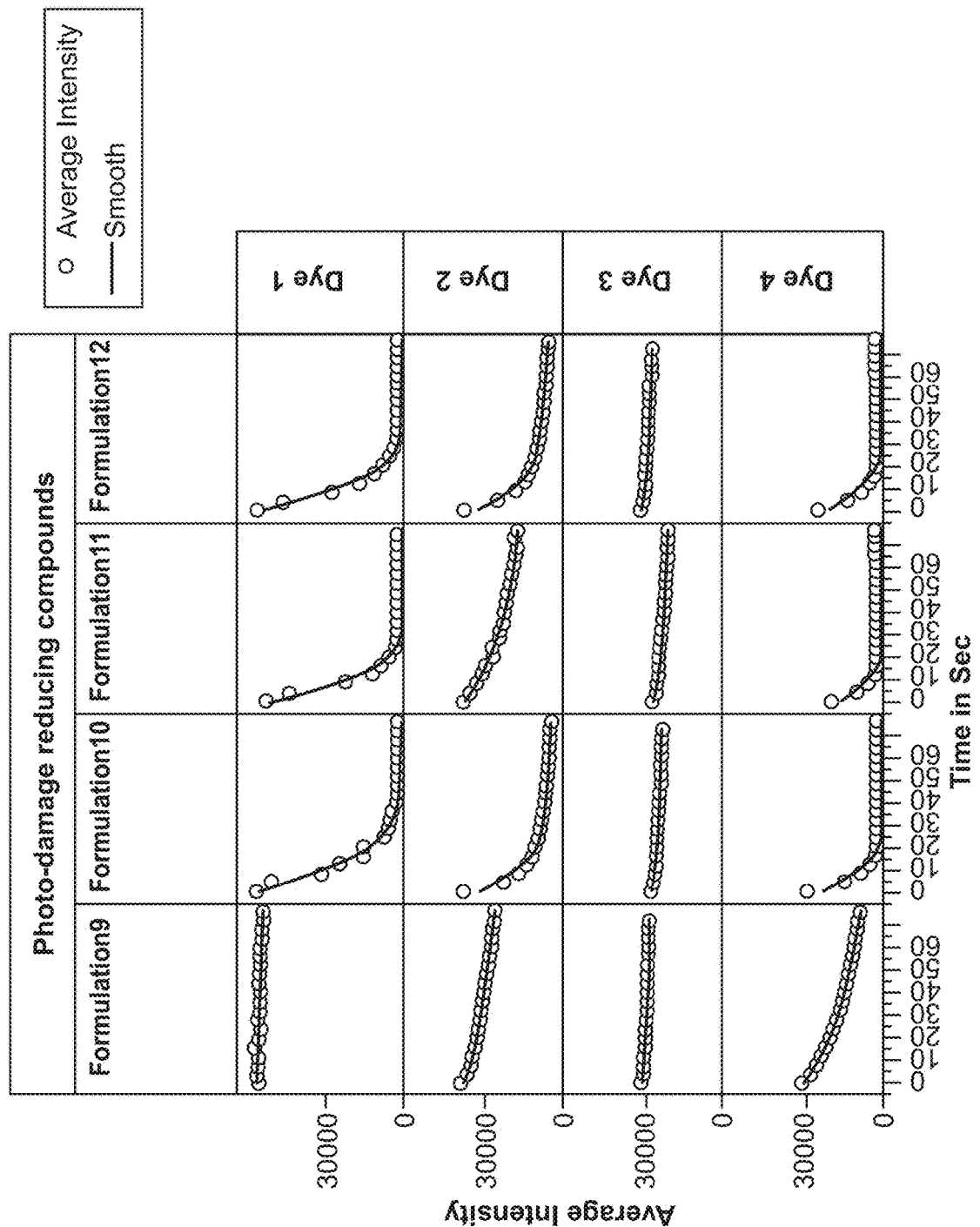
FIG. 32 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 9-12 comprise Tris-HCl (pH 8.8), EDTA, NaCl, Triton™ X-100 (2-[4-(2,4,4-trimethylpentan-2-yl)phenoxy]ethanol), sucrose, strontium acetate and glycerol. Formulation 9 comprises sodium ascorbate (50 mM). Formulation 10 comprises Trolox aged for 3 hours (2 mM). Formulation 11 comprises no photodamage reducing compound. Formulation 12 comprises Trolox (non-aged) (2 mM).
Figure 33:
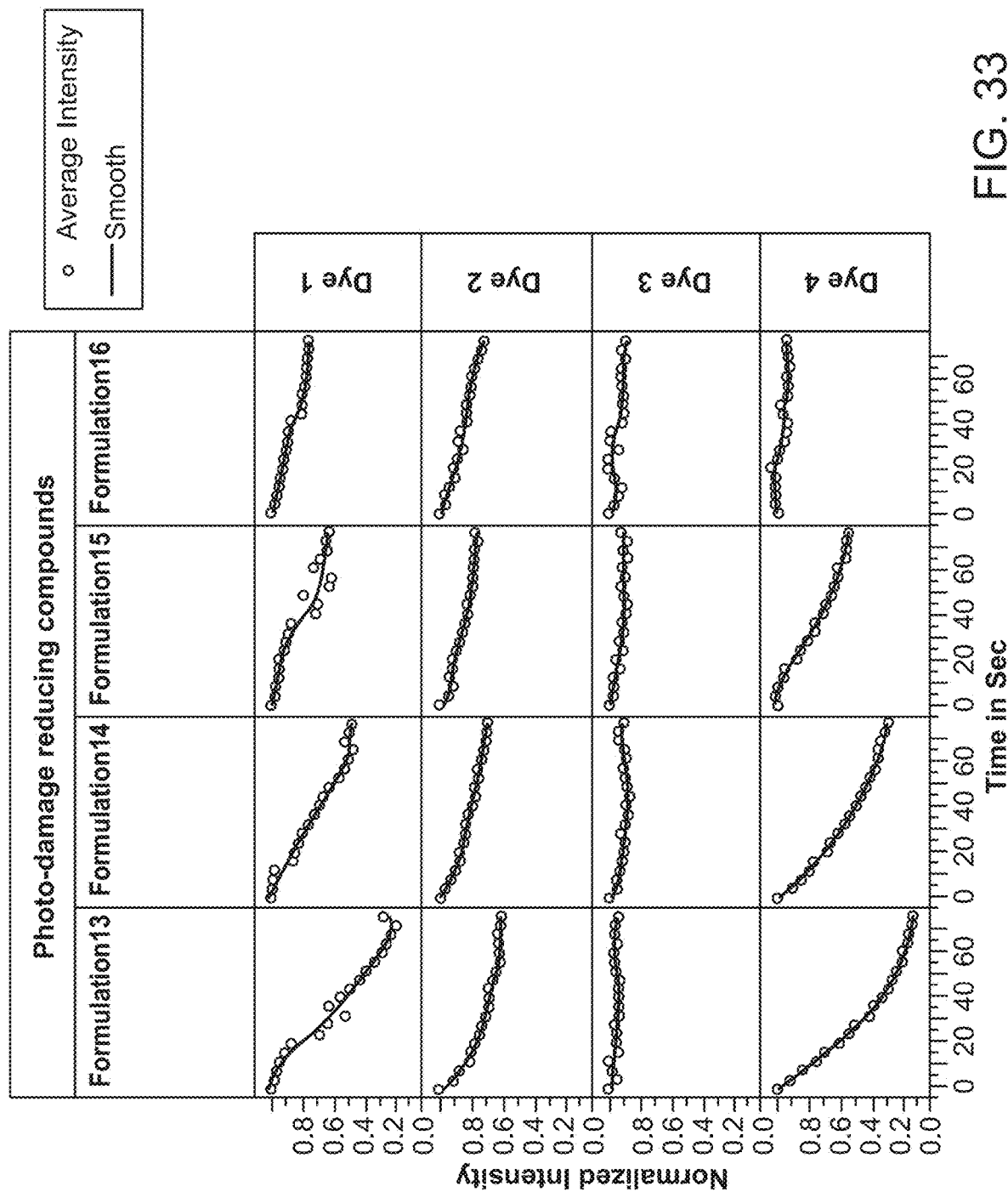
FIG. 33 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 13-16 comprise Tris-HCl (pH 8 or 8.8), EDTA, NaCl, Triton™ X-100 (2-[4-(2,4,4-trimethylpentan-2-yl)phenoxy]ethanol), strontium acetate and glycerol (and no sucrose). Formulation 13 comprises Tris-HCl (pH 8), Trolox (2 mM) and sodium ascorbate (10 mM). Formulation 14 comprises Tris-HCl (pH 8), Trolox (2 mM) and sodium ascorbate (20 mM). Formulation 15 comprises Tris-HCl (pH 8), Trolox (2 mM) and sodium ascorbate (50 mM). Formulation 16 comprises Tris-HCl (pH 8.8), Trolox (2 mM) and sodium ascorbate (50 mM).
Figure 34:
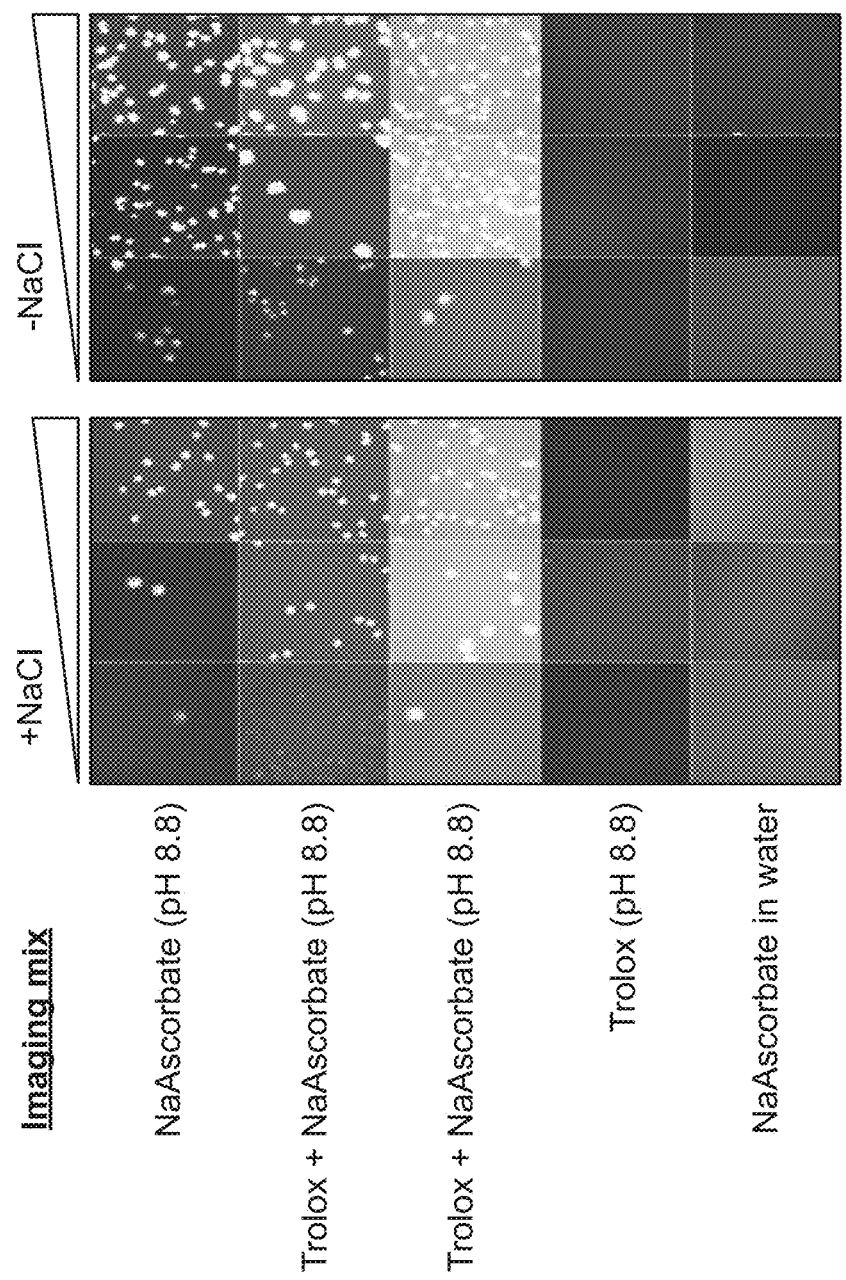
FIG. 34 is a series of images of micro crystal formation of sodium ascorbate (pH 8.8) with an increasing titration of NaCl. The micro crystal formation can be an indication of instability of sodium ascorbate. The formulation tested for all of the images comprises Tris-HCl (pH 8), EDTA, NaCl, Triton™ X-100 (2-[4-(2,4,4-trimethylpentan-2-yl)phenoxy]ethanol), sucrose, strontium acetate and glycerol (and no sucrose).
Figure 35:
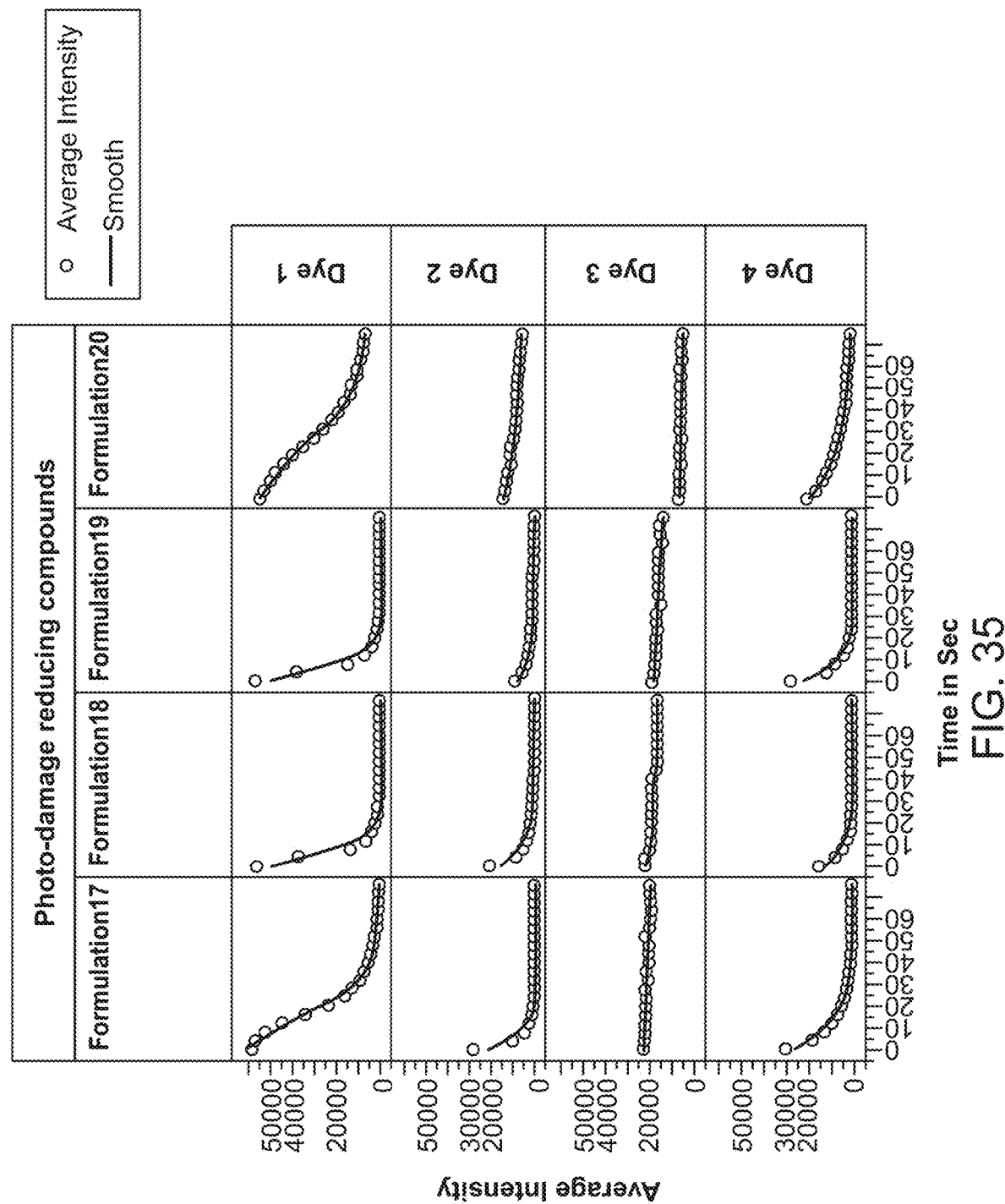
FIG. 35 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 17-20 comprise Tris-HCl (pH 8.8), EDTA, NaCl, Triton™ X-100 (2-[4-(2,4,4-trimethylpentan-2-yl)phenoxy]ethanol), sucrose, strontium acetate and glycerol. Formulation 17 comprises cystamine (10 mM). Formulation 18 comprises 3-nitrobenzoic acid (NBA) (2 mM). Formulation 19 comprises no photodamage reducing compound. Formulation 20 comprises P-phenyl diamine (PPD) (1 mM).
Figure 36:
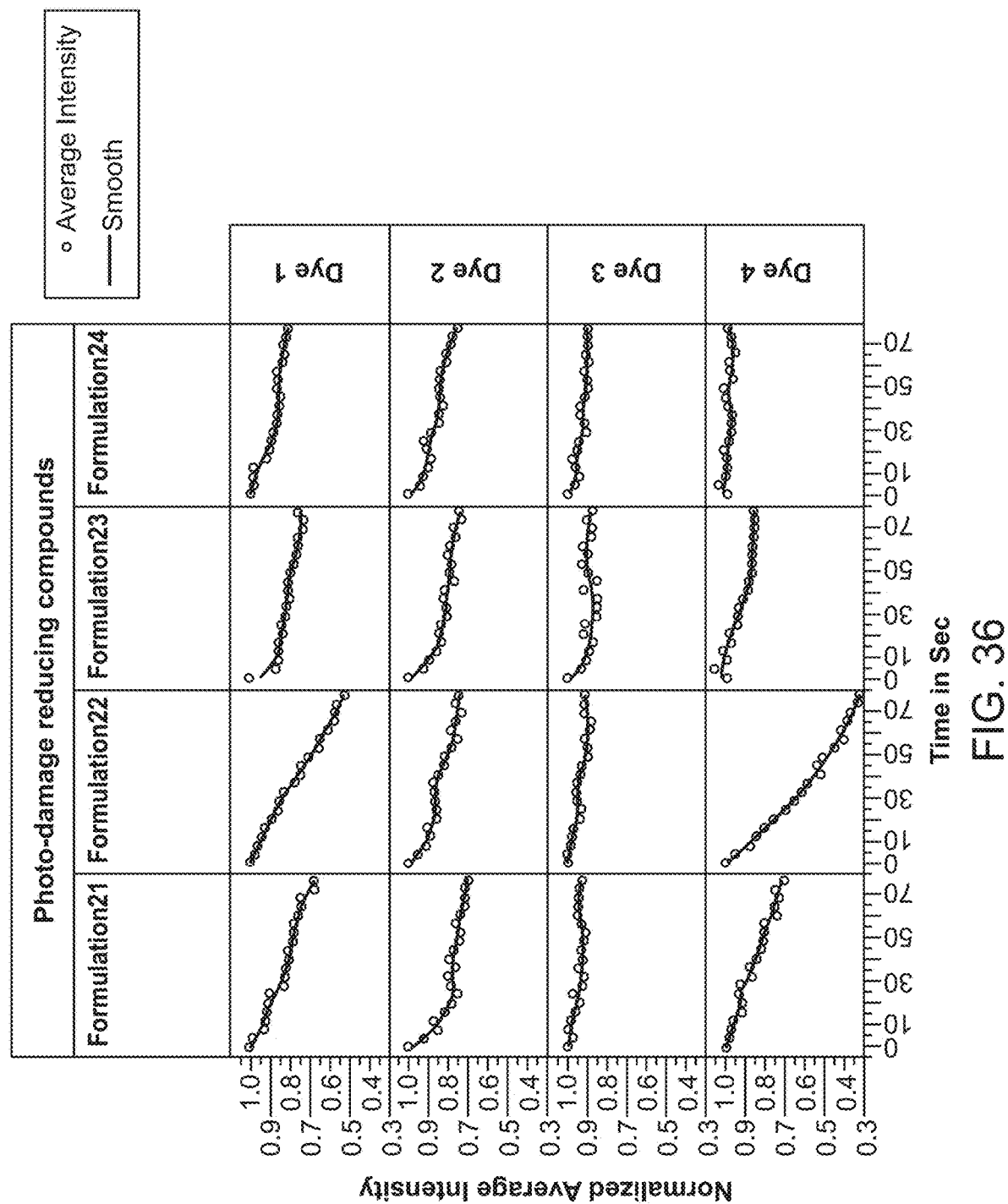
FIG. 36 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 21-24 comprise Tris-HCl (pH 8), EDTA, NaCl, Triton™ X-100 (2-[4-(2,4,4-trimethylpentan-2-yl)phenoxy]ethanol), strontium acetate and glycerol (and with or without sucrose). Formulation 21 comprises sucrose (1 M), Trolox (2 mM) and sodium ascorbate (50 mM). Formulation 22 comprises no sucrose, Trolox (2 mM) and sodium ascorbate (50 mM). Formulation 23 comprises no sucrose, Trolox (5 mM) and sodium ascorbate (50 mM). Formulation 24 comprises no sucrose, Trolox (8 mM) and sodium ascorbate (50 mM).
Figure 37:
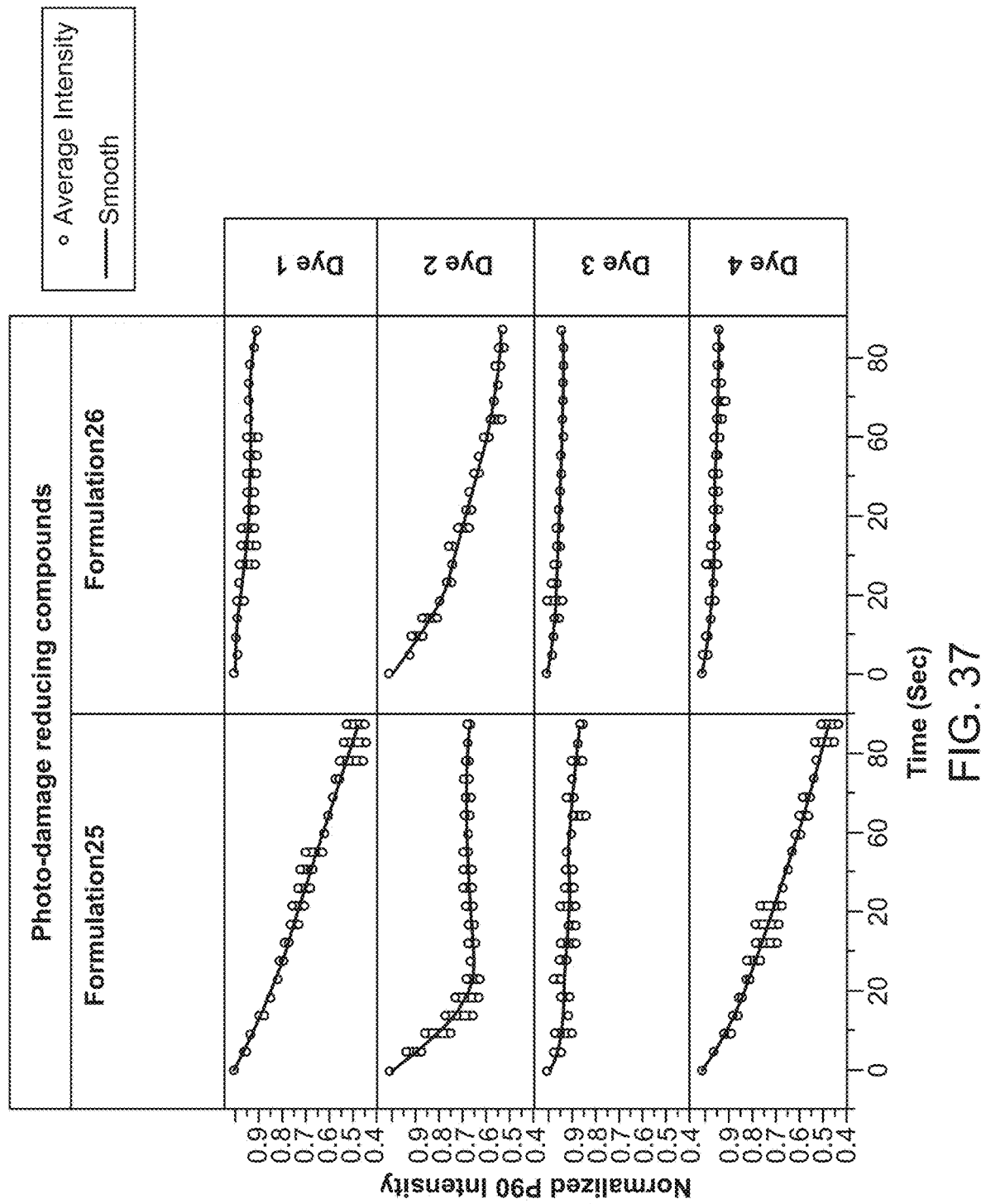
FIG. 37 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 25 and 26 comprise Tris-HCl (pH 8), EDTA, NaCl (reduced from 100 mM to 75 mM), Triton™ X-100 (2-[4-(2,4,4-trimethylpentan-2-yl)phenoxy]ethanol), sucrose (reduced from 1 M to 0.5 M), strontium acetate and glycerol. Formulation 25 comprises Trolox (2 mM) and sodium ascorbate (50 mM). Formulation 26 comprises Trolox quinone (2 mM) and sodium ascorbate (50 mM).
Figure 38:
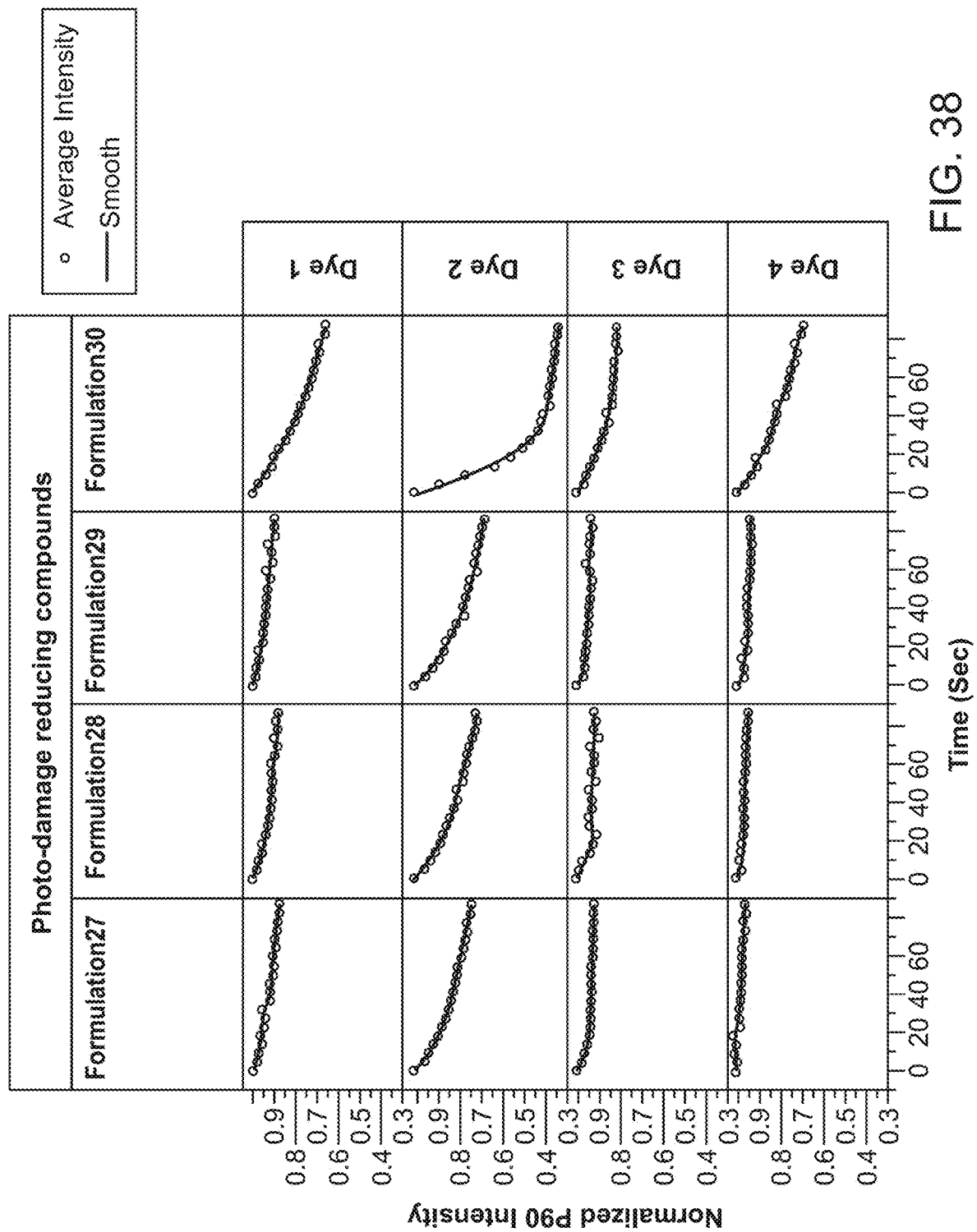
FIG. 38 is a series of graphs showing the effects of imaging reagents comprising different formulations on average signal intensity with time. The different formulations contain different combinations compounds that reduce photo damage. Dye 1 is AF647, dye 2 is CF532, dye 3 is CF570 and dye 4 is CD680. Formulations 27-30 comprise Tris-HCl (pH 8), EDTA, NaCl (reduced from 100 mM to 75 mM), Triton™ X-100 (2-[4-(2,4,4-trimethylpentan-2-yl)phenoxy]ethanol), strontium acetate and glycerol (and with or without sucrose). Formulation 27 comprises Trolox quinone (1 mM), Trolox (3 mM), sodium ascorbate (25 mM) and no sucrose. Formulation 28 comprises Trolox quinone (2 mM), sodium ascorbate (25 mM) and no sucrose. Formulation 29 comprises Trolox quinone (3 mM), sodium ascorbate (25 mM) and no sucrose. Formulation 30 comprises Trolox (2 mM), sodium ascorbate (50 mM) and sucrose (1M).
Figure 39:
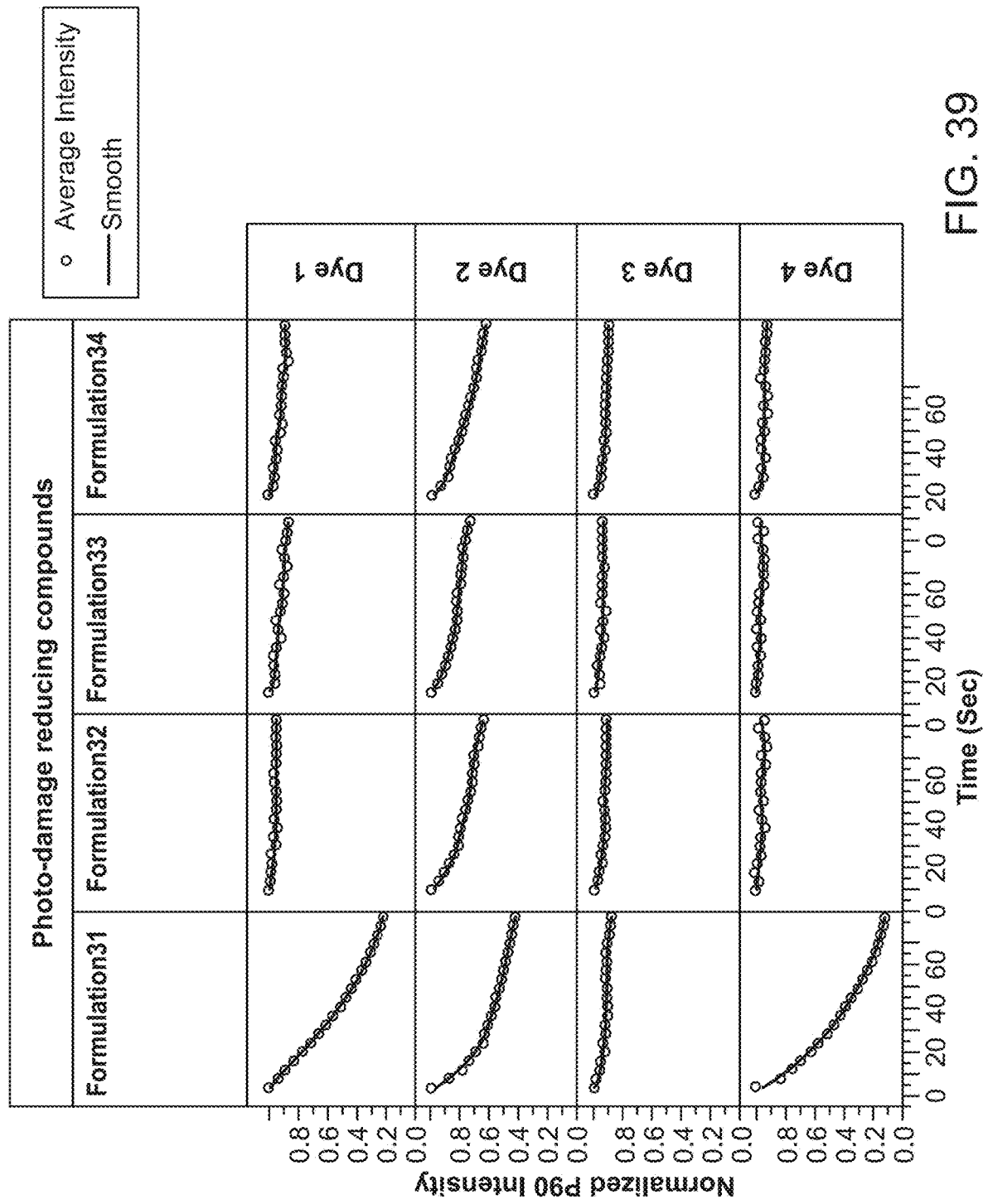
FIG. 39 is a series of graphs showing the effects of imaging reagents comprising different formulations on average signal intensity with time. The different formulations contain different combinations of compounds that reduce photo damage. Dye 1 is AF647, dye 2 is CF532, dye 3 is CF570 and dye 4 is CD680. Formulations 31-34 comprise Tris-HCl (pH 8), EDTA, NaCl (reduced from 100 mM to 75 mM), Triton™ X-100 (2-[4-(2,4,4-trimethylpentan-2-yl)phenoxy]ethanol), sucrose (reduced from 1 M to 0.5 M), strontium acetate and glycerol. Formulation 31 comprises Trolox (2 mM) and sodium ascorbate (25 mM). Formulation 32 comprises Trolox quinone (2 mM) and sodium ascorbate (25 mM). Formulation 33 comprises Trolox (aged for 16 hours) (2 mM) and sodium ascorbate (25 mM). Formulation 34 comprises Trolox (aged for 3 hours) (2 mM) and sodium ascorbate (25 mM).

Various imaging reagents were prepared using the different aged Trolox solutions described herein, and these imaging reagents were tested for their ability to reduce photo-damage of ternary complexes (e.g., reduce photo-damage of fluorophores). The ranked order of photo-damage protection, ranked in order from best to worst, were as follows: Trolox at pH 12.5 with stirring, aged Trolox at pH 12.5 with UV irradiation>Trolox in 50% MeOH with UV irradiation>Trolox. Exemplary data showing protection from photo-bleaching using imaging reagents containing aged Trolox are shown in FIGS. 32 (Formulation 10), 39 (Formulations 33 and 34), and 42 (Formulations 35 and 37).

Imaging reagents: The imaging reagents included at least one solvent, a pH buffering agent, a chelating agent, at least one monovalent cation, a non-catalytic divalent cation, a detergent, at least one compound for increasing viscosity, and at least one compound for reducing photo-damage. In some embodiments, the compounds for reducing photo-damage included one compound or a combination of compounds including ascorbic acid and/or a Trolox compound (e.g., non-aged Trolox, aged Trolox or Trolox quinone).

FIG. 18 shows a series of images of dye-labeled nucleotides where the nucleotides are joined to a dye via a cleavable moiety (CM). The images show no residual fluorescent signals after a 90 second exposure to high laser power. The imaging reagent comprises Tris-HCl (pH 8.8), EDTA, NaCl, Triton™ X-100 (2-[4-(2,4,4-trimethylpentan-2-yl)phenoxy]ethanol), sucrose, strontium acetate, glycerol, 1,3,5,7 cyclo-octatetraene (COT) (2 mM), sodium ascorbate (50 mM) and Trolox (2 mM).

Figure 19:
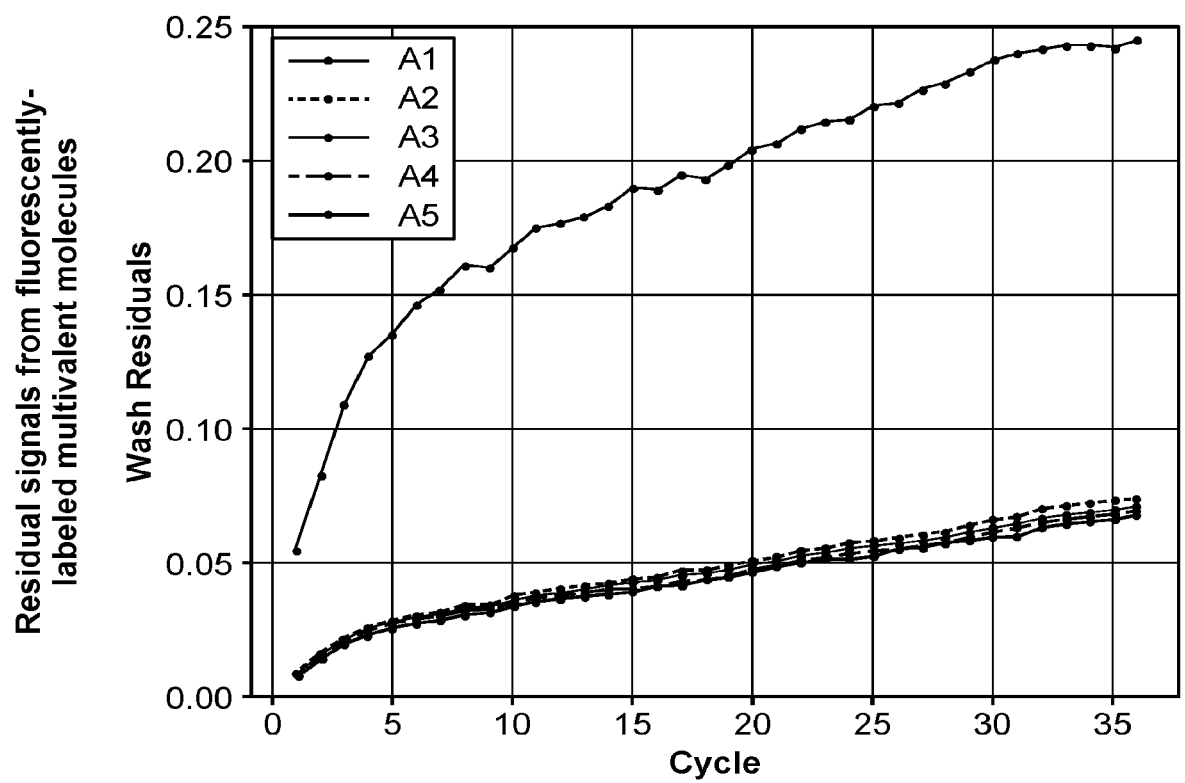
FIG. 19 is a graph showing the effect of various imaging reagents on residual signals from fluorescently-labeled multivalent molecules with repeat cycles. The imaging reagent comprises Tris-HCl (pH 8.8), EDTA, NaCl (100 mM), Triton™ X-100 (2-[4-(2,4,4-trimethylpentan-2-yl)phenoxy] ethanol), sucrose (1 M), strontium acetate, and glycerol.

FIG. 19 shows a graph showing the effect of an imaging reagent on residual signals from fluorescently-labeled multivalent molecules with repeat cycles. The imaging reagent comprises Tris-HCl (pH 8.8), EDTA, NaCl (100 mM), Triton™ X-100 (2-[4-(2,4,4-trimethylpentan-2-yl)phenoxy]ethanol), sucrose (1 M), strontium acetate, and glycerol.

Figure 20:
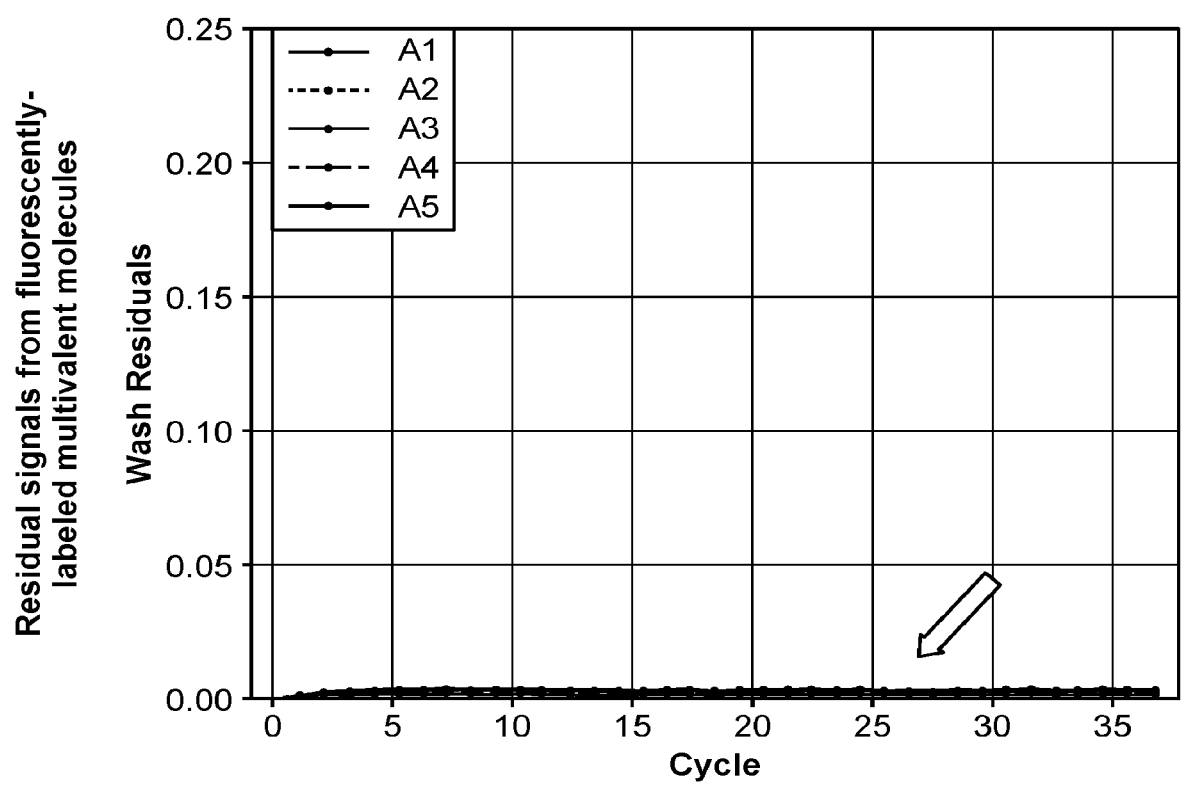
FIG. 20 is a graph showing the effect of various imaging reagents on residual signals from fluorescently-labeled multivalent molecules with repeat cycles. The imaging reagent comprises Tris-HCl (pH 8.8), EDTA, NaCl (100 mM), Triton™ X-100 (2-[4-(2,4,4-trimethylpentan-2-yl)phenoxy] ethanol), sucrose (1 M), strontium acetate, glycerol, Trolox (2 mM) and sodium ascorbate (50 mM). Compare with the results shown in FIG. 19.

FIG. 20 shows a graph showing the effect of an imaging reagent on residual signals from fluorescently-labeled multivalent molecules with repeat cycles. The imaging reagent comprises Tris-HCl (pH 8.8), EDTA, NaCl (100 mM), Triton™ X-100 (2-[4-(2,4,4-trimethylpentan-2-yl)phenoxy]ethanol), sucrose (1 M), strontium acetate, glycerol, Trolox (2 mM) and sodium ascorbate (50 mM). Compare with the results shown in FIG. 19

Example 4. Prophetic Sequencing Workflow Example

The following describes an example procedure for nucleic acid sequencing using some reagents of the present disclosure. This example describes (a) the formation of hydrophilic coatings having primed oligonucleotides on a support, (b) the generation of circular nucleic acid libraries, (c) performing rolling circle amplification to generate concatemers from the circular nucleic acid library, and (d) sequencing of the concatemers to determine the sequences of nucleic acids comprising the circular nucleic acid library. However, it shall be understood that the various reagents of the present disclosure may similarly be applied in other nucleic acid processing, reacting, or sequencing procedures and/or steps.

Forming Hydrophilic Polymer Coatings on a Support

Method for preparing a 2-layer polyethylene glycol (PEG) surface with thiol-maleimide chemistry: A glass slide is cleaned using a 2M KOH treatment of 30 minutes at room temperature. The glass slide is washed, and then surface silanol groups of the glass are activated using an oxygen plasma. Silane-PEGSK-Thiol (Creative PEGWorks, Inc., Durham, N.C.) is applied at a concentration of 0.1% in ethanol. After a 2-hour coating reaction, the slide is washed thoroughly with ethanol and water, and is then reacted with 2.5 mM of Maleimide-PEG-Succinimidyl Valerate (MW=20K) in dimethylformamide (DMF) for 30 minutes. The resulting surface is washed and promptly reacted with 5'-amine-labeled oligonucleotide primer at room temperature for 2 hours. Excess succinimidyl esters on the surface are deactivated by reacting with 100 mM glycine at pH=9 following the primer immobilization.

Method for preparing a multi-layer PEG surface with NHS ester-amine chemistry: A glass slide is cleaned by 2M KOH treatment of 30 minutes at room temperature, washed, and then surface silanol groups are activated using an oxygen plasma. Silane-PEG2K-amine (Nanocs, Inc., New York, N.Y.) is applied at a concentration of 0.5% in ethanol solution. After a 2-hour coating reaction, the slide is washed thoroughly with ethanol and water. 100 uM of 8-arm PEG NHS (MW=10K, Creative PEGWorks, Inc., Durham, N.C.) is introduced at room temperature for 20 minute in a solvent composition that can include 5, 10, 20, 30, 40, 50, 60, 70, 80 or 90 percent organic solvent and 5, 10, 20, 30, 40, 50, 60, 70, 80 or 90 percent low ionic strength buffer. The resulting surface is washed and reacted with 20 μM multi-arm PEG amine (MW=10K, Creative PEGWorks, Inc., Durham, N.C.) for 2 hours. The resulting amine-PEG surface is then reacted with a mixture of multi-arm PEG-NHS and amine-labeled oligonucleotide primer at varying concentrations. This process is be repeated to generate additional PEG layers on the surface.

Method for preparing a other NSB surfaces: A glass slide is physically- or chemically-treated (e.g., using a plasma treatment, a piranha cleaning step, an acid wash, a base wash, high temperature glass annealing, or any combination thereof) to remove organic contaminants and activate surface hydroxyl groups for silane coupling. The prepared glass surface is then reacted with a silane to covalently attached a first layer of functional groups (e.g., primary amines) and/or a hydrophilic polymer layer. In some instances, for example, a silane such as (3-aminopropyl)trimethoxysilane (APTMS) or (3-aminopropyl)triethoxysilane (APTES) 3 (3-acrylopropyl) trimethoxysilane is reacted with the surface using standard protocols to covalently attach primary amine functional groups to the surface. In other instances, a silane-modified polymer, e.g., a hydrophilic, heterobifunctional polymer comprising a silyl group at one end and a second functional group (e.g., a primary amine, carboxyl group, etc.) at the other end may be reacted directly with the surface (e.g., by contacting the clean glass surface with the silane-modified polymer at concentration of 0.1%-2% in ethanol for about 1 to 2 hours followed by rinsing with ethanol and water). Examples of suitable silane-modified polymers include, but are not limited to, silane-PEG-NH2 (having a polyethylene glycol (PEG) molecular weight of, for example, 1000, 2000, 3400, 5000, or 10K Daltons), silane-PEG-COOH (having a PEG molecular weight of, for example, 1000, 2000, 3400, 5000, or 10K Daltons), silane-PEG-maleimide (having a PEG molecular weight of, for example, 1000, 2000, 3400, 5000, or 10K Daltons), silane-PEG-biotin (having a PEG molecular weight of, for example, 1000, 2000, 3400, 5000, or 10K Daltons), silane-PEG-acrylate (having a PEG molecular weight of, for example, 1000, 2000, 3400, 5000, or 10K Daltons), silane-PEG-silane (having a PEG molecular weight of, for example, 1000, 2000, 3400, 5000, or 10K Daltons), silane-modified polypropylene glycols (PPGs) of various molecular weights that comprise an additional functional group, silane-modified poly(vinyl alcohols) (PVAs) of various molecular weights that comprise an additional reactive functional group, silane-modified polyethylenimine (PEIs) of various molecular weights that comprise an additional reactive functional group, silane-modified poly(lysine) of various molecular weights that comprise an additional reactive functional group, and the like, or any combination thereof.

In some instances, at least one additional layer of a hydrophilic polymer layer is coupled to, or deposited on, the glass surface following the initial reaction of the surface with a silane or silane-modified polymer. Any of a number of hydrophilic polymers including, but not limited to, polyethylene glycol (PEG), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(-hydroxylethyl methacrylate) (PHEMA), poly(oligo(ethylene glycol) methyl ether methacrylate) (POEGMA), polyglutamic acid (PGA), poly-lysine, poly-glucoside, streptavidin, dextran, or any combination thereof may be used where, in the case of covalent coupling, polymer(s) comprising the appropriate monofunctional, homobifunctional, and/or heterobifunctional reactive groups are selected for compatibility with the chosen conjugation chemistry. In some cases, a derivatized polymer is used, such as a PEG-amine, a PEG-NHS, or a PEG-Acrylate. In some cases, a bifunctional PEG derivative is used, such as an acrylate-PEG-NHS. In some cases, these additional hydrophilic polymer layers may be coupled to, or deposited on, the previous layer by contacting the surface with a 0.1%-2% polymer in ethanol or an ethanol/aqueous buffer solution for about 5 minutes to about 1 hour at room temperature, followed by rinsing with ethanol or an ethanol/aqueous buffer.

In some instances, a second, third, fourth, fifth, or more additional layers of a hydrophilic polymer may be coupled to, or deposited on, the initial layer of the support surface. In some instances, the polymer molecules within a layer may be cross-linked with each other using appropriate homo-functional or heterofunctional cross-linking reagents. In some instances, the polymer molecules in different layers may be cross-linked with each other. In some instances, one or more of the hydrophilic polymer layers may comprise a branched polymer, e.g., a branched PEG, branched poly (vinyl alcohol) (branched PVA), branched poly(vinyl pyridine), branched poly(vinyl pyrrolidone) (branched PVP), branched), poly(acrylic acid) (branched PAA), branched polyacrylamide, branched poly(N-isopropylacrylamide) (branched PNIPAM), branched poly(methyl methacrylate) (branched PMA), branched poly(2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, branched dextran, or any combination thereof.

One of more of the hydrophilic polymer layers may comprise a plurality of covalently-attached oligonucleotide adapter or primer molecules, wherein the oligonucleotide molecules are covalently coupled to the polymer using any of a variety of suitable conjugation chemistries. In some instances, the oligonucleotide adapter or primer molecules are covalently coupled to the polymer in solution, i.e., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

The choice of polymer(s) used, the number of layers, the degree of cross-linking within and between layers, the number of layers comprising covalently-attached oligonucleotide adapter or primer molecules, and the local concentration or surface density of oligonucleotide adapter or primer molecules may be individually or collectively adjusted to "tune" the properties of the surface to achieve a desired surface wettability (as indicated, for example, by a water contact angle of less than 50 degrees), a desired surface stability under prolonged exposure to sequencing/genotyping reagents and repeated thermocycling, which often require temperature ramps at a peak temperature of at least 95 degrees C. and held for at least 5 minutes and cycled multiple times of at least 30 cycles, and a desired surface density of oligonucleotide adapter or primer molecules (e.g., at least 1,000 adapter or primer molecules per $\mu m^2$), which in turn provide for extremely low non-specific binding of dye molecules or other labeled sequencing/genotyping reagents, improved hybridization efficiency, improved amplification efficiency and specificity, optimal densities of clonally-amplified target sequences (in terms of the number of clonal colonies per unit area, the number of copies of target sequence per unit area, or the number of amplified target molecules per unit area), higher contrast-to-noise ratios (CNRs) in images (e.g., fluorescence images) of the support surface (e.g., CNR >20), and ultimately, improved detection accuracy or base-calling accuracy in genotyping and sequencing applications.

In some cases, the oligonucleotide primer may comprise a sequence that is complementary to the sequence of primers of nucleic acids in a nucleic acid library. In some cases, the oligonucleotide primer may comprise a sequence that is complementary to a sequencing primer.

Nucleic Acid Library Generation

A double-stranded nucleic acid molecule is sheared mechanically or enzymatically into a plurality of double-stranded nucleic acid fragments. The plurality of double-stranded nucleic acid fragments are 100-5000 bp fragments.

The plurality of double-stranded nucleic acid fragments are modified. The modification comprises repairing and A-tailing by polymerase. The process of A tailing is performed by adding adenine to 3' end of each of the plurality of double-stranded nucleic acid fragments.

One or more adapters are ligated onto the A-tailed double-stranded nucleic acid fragments. The one or more adapters are ligated onto the both ends of A-tailed double-stranded nucleic acid fragments. The one or more adapters comprise a sequence complementary to the oligonucleotide primer sequence of the NSB surface. The one or more adapters may also comprise a universal primer site, a surface binding site, a P5 site, a P7 site, or an index site.

PCR is used to amplify the modified double-stranded nucleic acid molecules comprising the one or more adapters.

To circularize the library, a splint oligonucleotide is used to hybridize to library outer adapters. DNA ligase is used to seal the nick formed by linear library and splint oligo. After ligation, non-circular DNA molecules are digested with exonucleases, followed by a SPRI beads clean-up. Final product contained only circular libraries ready for loading onto Flow Cells and Amp/Sequencing.

Figure 23:
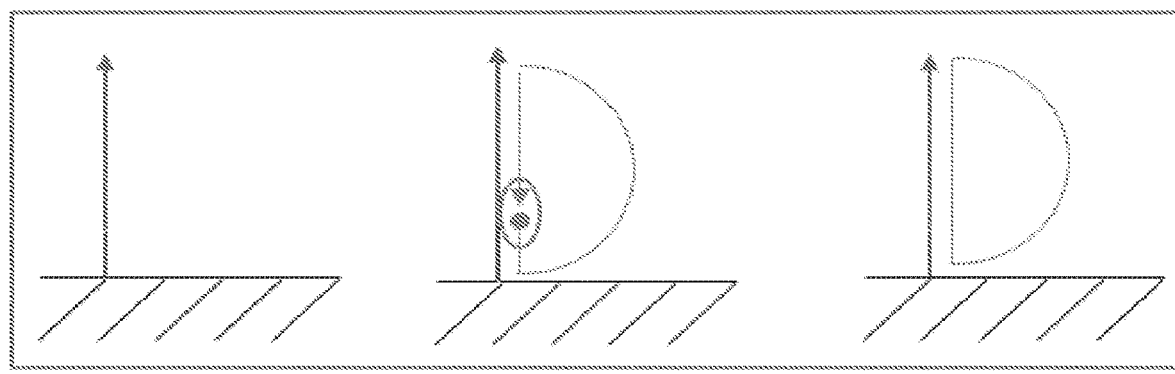
FIG. 23 schematically illustrates on-surface splint ligation, in accordance with some embodiments.
Figure 24:
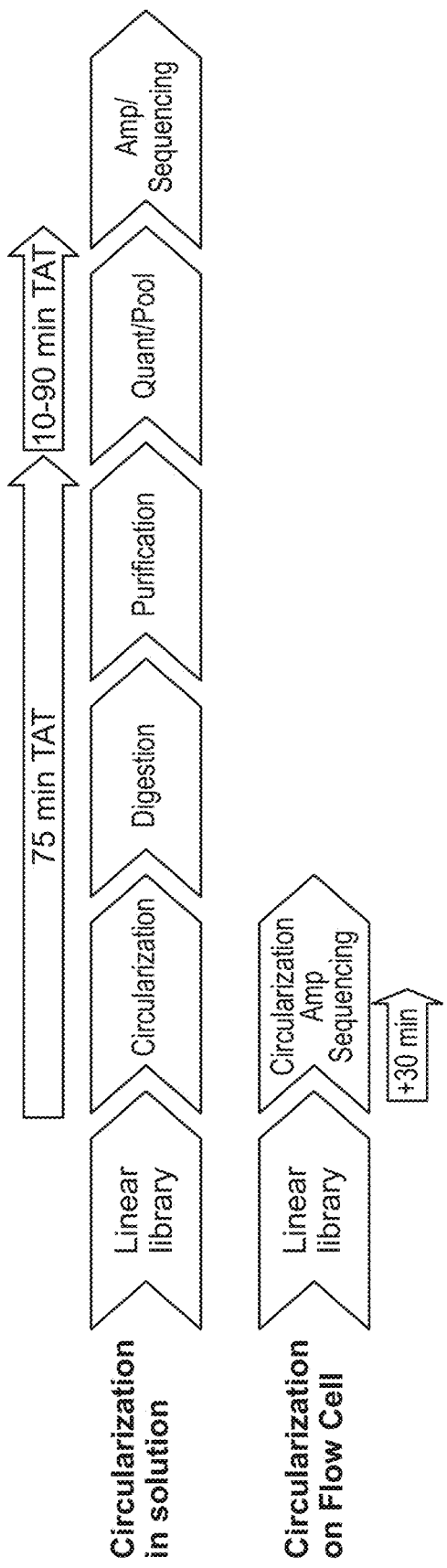
FIG. 24 shows process diagrams for circularizing a nucleic acid library, in accordance with some embodiments.
Figure 31:
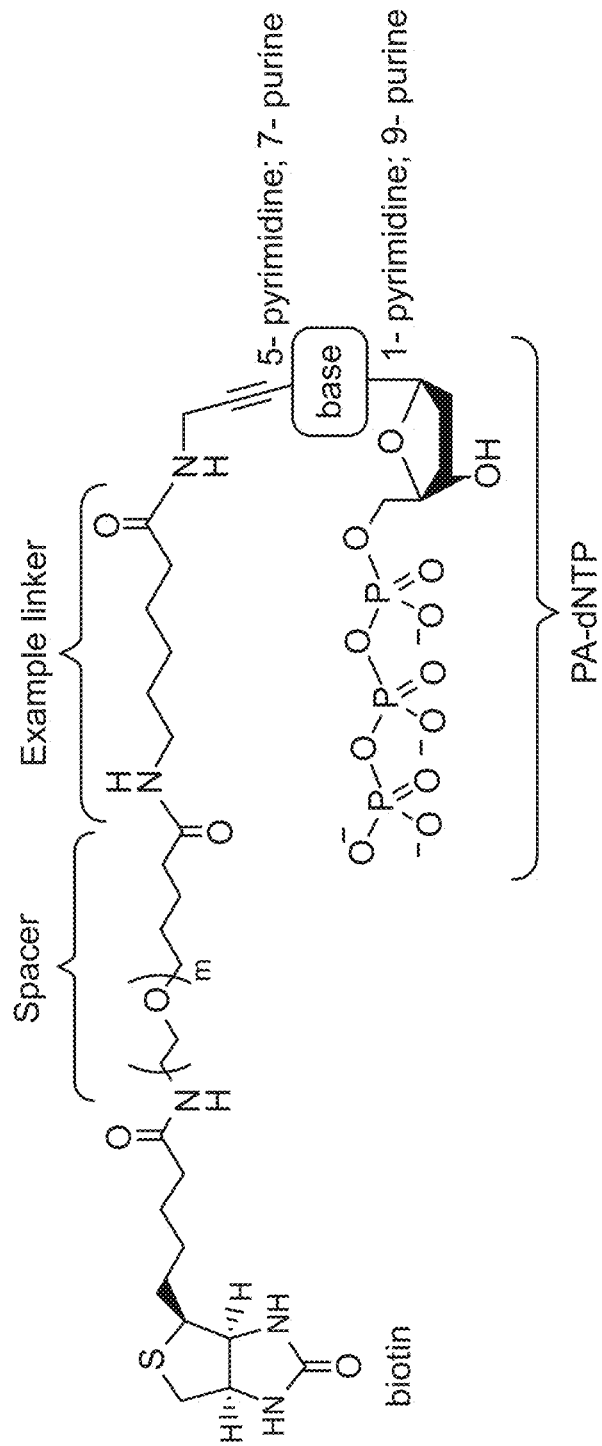
FIG. 31 shows the chemical structure of an exemplary biotinylated nucleotide-arm. In this example, the nucleotide unit is connected to the linker via a propargyl amine attachment at the 5 position of a pyrimidine base or the 7 position of a purine base.

Alternatively, the nucleic acid library may be circularized using flow cells. With flow cells containing splint oligonucleotides as surface primers, linear libraries are loaded directly. The splint oligonucleotides on flow cell are used to hybridize to library outer adapters and DNA ligase seals the nick formed by linear library and splint oligonucleotides. After ligation, non-circular DNA molecules and DNA ligase are washed away by universal wash buffer without the need for exonuclease digestion. Circularized libraries on flow cells are ready for amplification and sequencing. A non-limiting schematic of on-surface splint ligation is provided in FIG. 23. FIG. 24 shows a non-limiting schematic of in-solution splint ligation compared with on-surface splint ligation, and shows that on-surface splint ligation can reduce the reaction time by at least 75 minutes because it obviates a need for digestion, purification, and quantification/pooling.

Binding and Amplifying Template Nucleic Acid

Figure 21A:
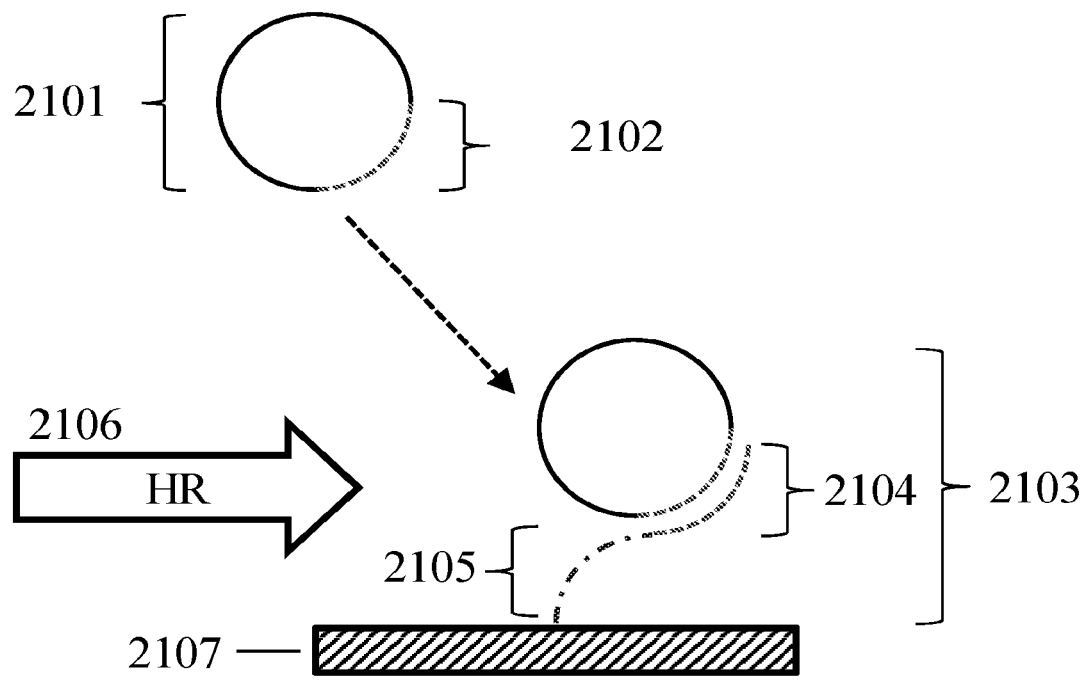
FIGS. 21A-21H schematically illustrates a method for sequencing a nucleic acid using reagents of the present disclosure, in accordance with some embodiments.

The purified circular nucleic acid library, comprising primed circular nucleic acids (2101), is contacted with the NSB surface (2107) in the presence of a hybridizing reagent (HR, 2106). In some cases, the HR comprises a solvent, a buffer, a monovalent cation, and a chaotrope. In some cases, the HR comprises a formulation selected from any one of Formulation HR-A to HR-J. The one or more adapters (2102) of the primed circular nucleic acids, which comprise a sequence complementary to a primer sequence (2104) of the oligonucleotide primers of the NSB surface, hybridize with the oligonucleotide primers of the NSB surface. This step is schematically illustrated in FIG. 21A.

The NSB surface, now having the primed circular nucleic acids hybridized to the oligonucleotide primers, are washed with a universal washing reagent (UWR). In some cases, the UWR comprises a solvent, a buffer, a chelator, a monovalent cation, and a detergent. In some cases, the UWR comprises a formulation selected from any one of Formulation UWR-A to UWR-BC. As a result, any unhybridized primed circular nucleic acids or remaining contaminants from the purification process are washed from the NSB.

Figure 21B:
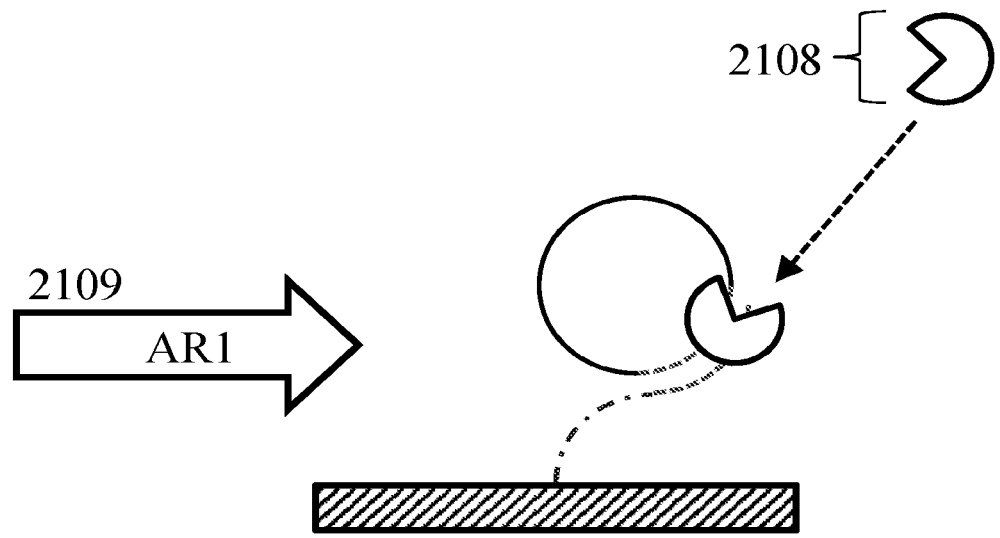

The NSB is contacted with a first amplification reagent (AR1). In some cases, the AR1 comprises a solvent, a buffer, a monovalent cation, ammonium ions, nucleotides (ACGT for DNA, ACUG for RNA), detergent, reducing agent, viscosity modifier, condenser oligonucleotide, an amplification polymerase (which may be one of a polymerase disclosed herein). In some cases, the AR1 comprises a formulation selected from any one of Formulation AR1-A to AR1-H. The pH of the AR1 is designed so that any amplification reaction (i.e., appending of nucleotides onto a 3' end of the nucleic acid molecule) is inhibited. The amplification polymerase (2108) binds to form a ternary complex with the primed circular nucleic acids and the primed oligonucleotides of the NSB. This step is schematically illustrated in FIG. 21B.

Figure 21C:
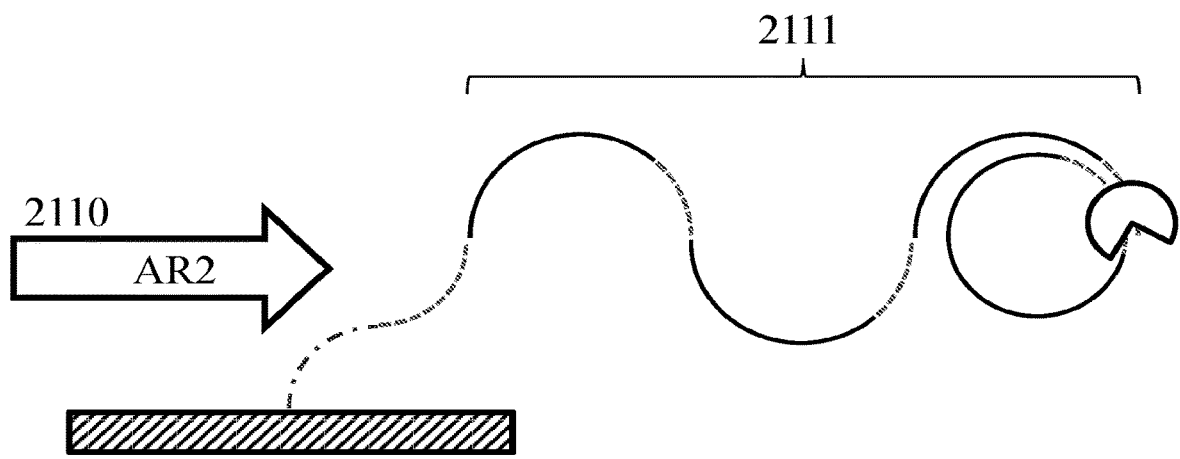

The NSB is then contacted with a second amplification reagent (AR2, 2110). In some cases, the AR2 comprises a solvent, a buffer, a monovalent cation, ammonium ions, nucleotides (ACGT for DNA, ACUG for RNA), detergent, reducing agent, viscosity modifier, condenser oligonucleotide. In some cases, the AR2 comprises a formulation selected from any one of Formulation AR2-A to AR2-I. In this case, AR2 does not comprise the amplification polymerase. The AR2 is formulated such that a majority, most, or all of the amplification polymerase remains complexed with the primed circular nucleic acids and the primed oligonucleotides of the NSB. The pH of the AR2 is designed so that amplification reactions are promoted. The amplification polymerase carries out a rolling circle amplification reaction, creating a series (one or more) of concatemers (2111) extending from the oligonucleotide of the NSB, wherein the concatemers each have a sequence complementary to the circular nucleic acids. This step is schematically illustrated in FIG. 21C.

The NSB is then washed with a wash-removal agent to remove chemicals from the NSB except the primed oligonucleotides comprising the concatemers. In some cases, the wash-removal reagent (WRR) comprises a solvent, a buffer, a chelator, a detergent, and a chaotrope. In some cases, the WRR comprises a formulation selected from any one of Formulation WRR-A to WRR-J. The NSB is then washed with the UWR.

Sequencing Nucleic Acids

Figure 21D:
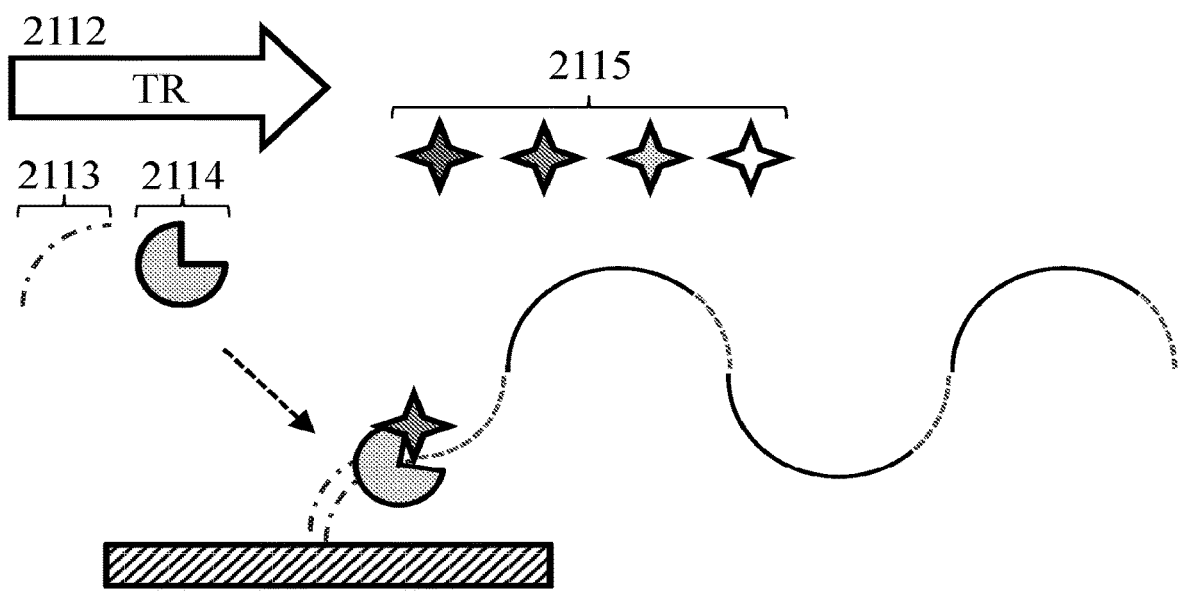

The NSB is contacted with a trapping reagent (TR). In some cases, the TR comprises a solvent, a buffer, a chelator, a monovalent cation, a non-catalytic divalent cation, a detergent, sequencing primers (2113), sequencing polymerases (2114), and fluorescently labeled multivalent molecules (2115). In some cases, the TR comprises a formulation selected from any one of Formulation TR-A to TR-J. Recall that the oligonucleotide of the NSB comprises a sequence that is complementary to the sequencing primer sequence. Therefore, the sequencing primer hybridizes with the oligonucleotide of the NSB. The sequencing polymerase binds with the sequencing primer and the oligonucleotide of the NSB to form a ternary complex. The fluorescently-labeled multivalent molecules reversibly bind to the first unpaired base from the 3' end of the oligonucleotide of the NSB (i.e., the fluorescently-labeled multivalent molecules are not incorporated into the oligonucleotide of the NSB). This step is schematically illustrated in FIG. 21D.

The NSB is washed with a post-trap reagent (PTR). In some cases, the PTR comprises a solvent, a buffer, a chelator, a monovalent cation, a non-catalytic divalent cation, a detergent, a viscosity modifier, sequencing primers, and sequencing polymerases. In some cases, the PTR comprises a formulation selected from any one of Formulation PTR-A to PTR-J. The PTR does not comprise the fluorescently-labeled multivalent molecules, so any unbound fluorescently-labeled multivalent molecules are washed from the NSB.

Figure 21E:
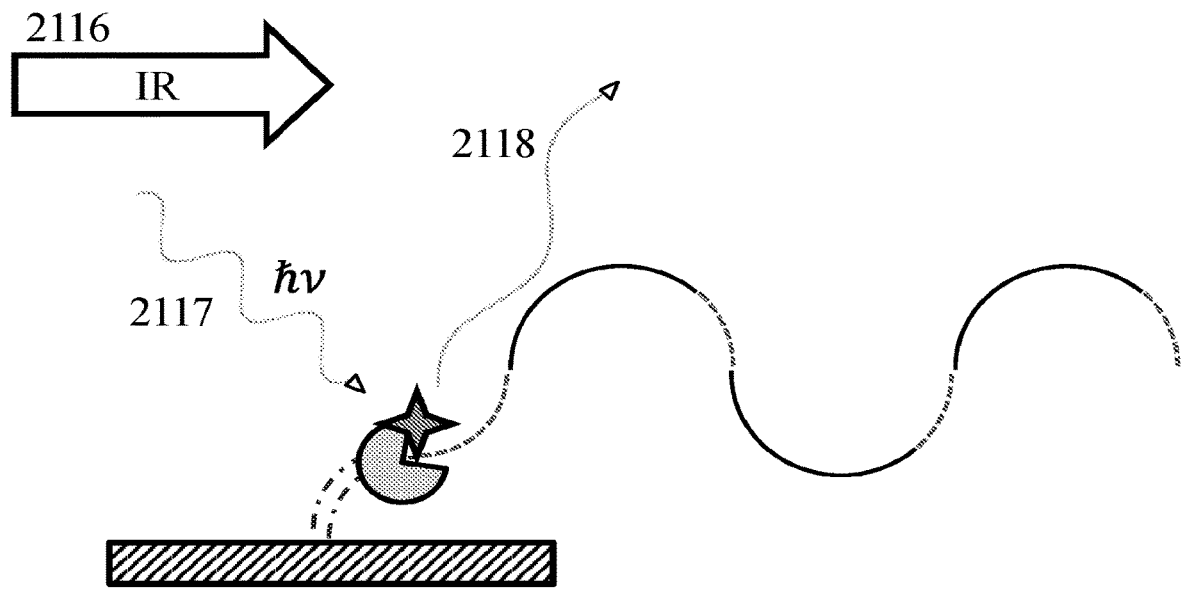

The NSB is contacted with an imaging reagent (IR). In some cases, the IR comprises a solvent, a buffer, chelator, a monovalent cation, a non-catalytic divalent cation, a detergent, a viscosity modifier, and a photo-damage reducing compound. In some cases, the IR comprises a formulation selected from any one of Formulation IR-A to IR-Y. The NSB is irradiated with light (2117), having a wavelength configured to excite fluorescing moieties of the fluorescently-labeled multivalent molecules to higher energy levels, which creates fluorescent signals (2118) that can be detected. This step is schematically illustrated in FIG. 21E. The fluorescent signal may be used to determine the chemical identity of the fluorescently-labeled multivalent molecules.

The NSB is washed with the WRR and then with the UWR. In some cases, the WRR comprises a formulation selected from any one of Formulation WRR-A to WRR-J. In some cases, the UWR comprises a formulation selected from any one of Formulation UWR-A to UWR-BC. This removes chemicals except sequencing primer and the oligonucleotide of the NSB.

Figure 21F:
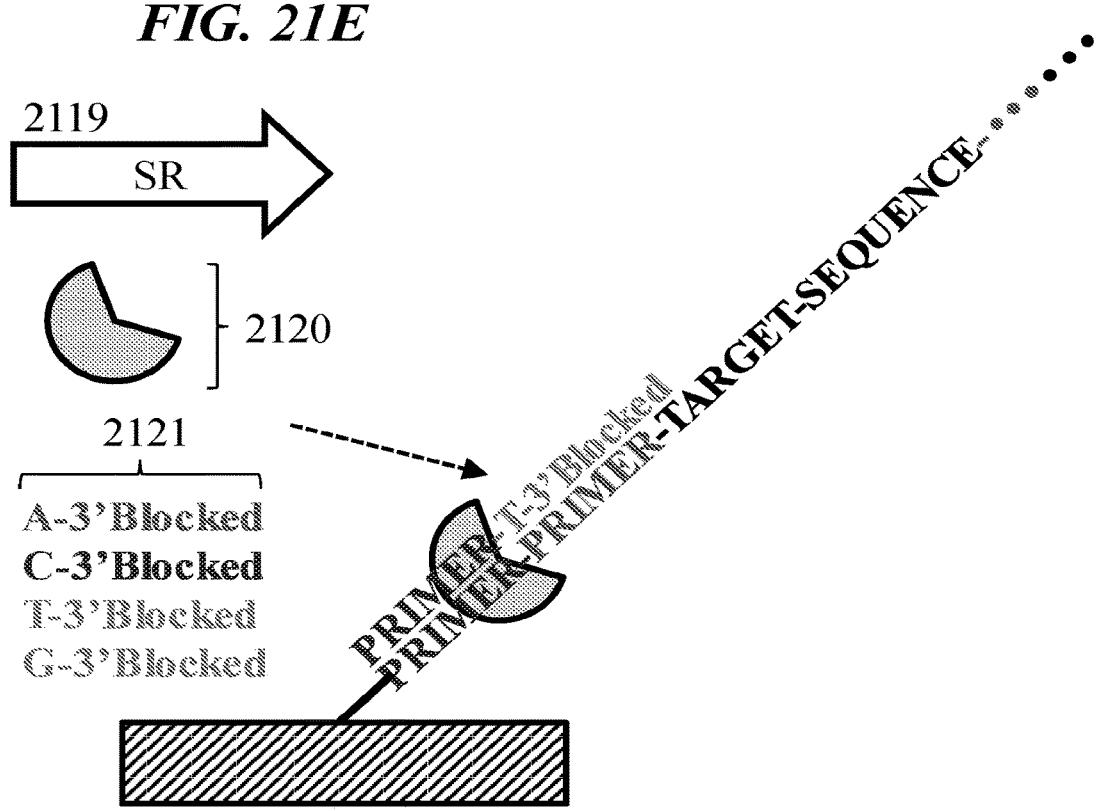

The NSB is contacted with a stepping reagent (SR, 2119). In some cases, the SR comprises a solvent, a buffer, a monovalent cation, a catalytic divalent cation, a detergent, a sequencing polymerase enzyme (2120) and a plurality of nucleotides (2121) each having a cleavable chain terminating moiety attached to the 3' sugar position. In some cases, the SR comprises a formulation selected from any one of Formulation SR-A to SR-J. The sequencing polymerase enzyme forms a ternary complex with the sequencing primer and the oligonucleotide of the NSB. A nucleotide (having a cleavable chain terminating moiety attached to the 3' sugar position) binds to the first unpaired base from the 3' end of the oligonucleotide of the NSB. The sequencing polymerase appends the nucleotide to the 3' end of the oligonucleotide of the NSB, extending the oligonucleotide of the NSB. Only a single nucleotide is added; the plurality of nucleotides have a cleavable chain terminating moiety. This step is schematically illustrated in FIG. 21F.

The NSB is washed with the WRR and then with the UWR. This removes chemicals except sequencing primer and the oligonucleotide of the NSB.

Figure 21G:
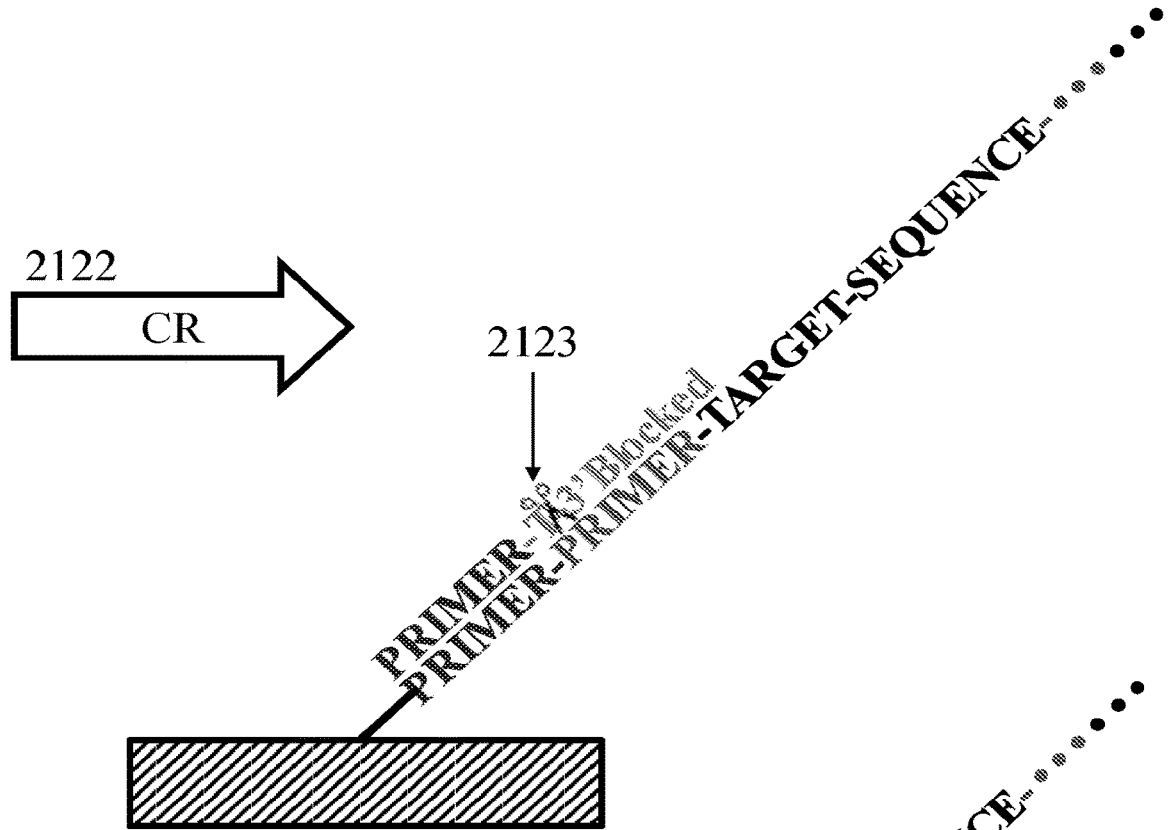

The NSB is contacted with a cleaving reagent (CR, 2122). In some cases, the CR comprises a solvent, a buffer, a monovalent cation, a detergent, a cleaving agent (2123), and a cleaving catalyst. In some cases, the CR comprises a formulation selected from any one of Formulation CR-A to CR-J. The cleavable chain terminating moiety at the 3' end is cleaved by the cleaving agent. This step is schematically illustrated in FIG. 21G.

Figure 21H:
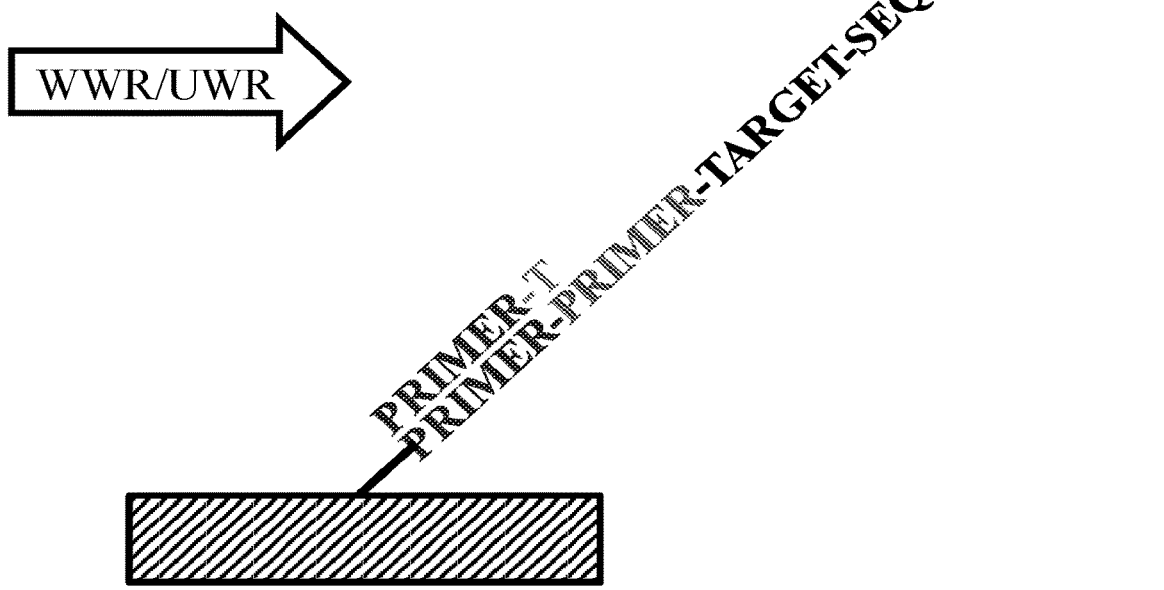

The NSB is washed with the WRR and then with the UWR. In some cases, the WRR comprises a formulation selected from any one of Formulation WRR-A to WRR-J. In some cases, the UWR comprises a formulation selected from any one of Formulation UWR-A to UWR-BC. This removes chemicals except sequencing primer and the oligonucleotide of the NSB. This step is schematically illustrated in FIG. 21H.

The oligonucleotide of the NSB may subsequently be identified at the next exposed nucleotide position following some of the steps above.

NUMBERED EMBODIMENTS

Embodiments contemplated herein include the following numbered embodiments:

Embodiment 1. A nucleic acid hybridization reagent, comprising: at least one solvent, a pH buffering agent, and at least one monovalent cation.

Embodiment 2. The nucleic acid hybridization reagent of Embodiment 1, further comprising: any one or any combination of two or more of a detergent, a reducing agent, a chaotropic agent, a chelating agent, an alcohol, a zwitterion, a sugar alcohol and/or a crowding agent.

Embodiment 3. The nucleic acid hybridization reagent of Embodiment 1, further comprising: at least one nucleic acid template molecule which comprises DNA or RNA, or a mixture of RNA and DNA.

Embodiment 4. The nucleic acid hybridization reagent of Embodiment 3, wherein the nucleic acid template molecules comprises a linear or circularized molecule.

Embodiment 5. The nucleic acid hybridization reagent of Embodiment 3, wherein the nucleic acid template molecule is operably linked to at least one adaptor, wherein the adaptor includes a capture primer binding sequence, an amplification primer binding sequence and/or a sequencing primer binding sequence.

Embodiment 6. The nucleic acid hybridization reagent of Embodiment 3, wherein the nucleic acid template molecule is operably linked to at least one adaptor, and wherein the adaptor includes a sample barcode sequence or a unique molecular tag sequence.

Embodiment 7. The nucleic acid hybridization reagent of Embodiment 3, wherein the nucleic acid template molecule is operably linked to at least one adaptor, and wherein the adaptor includes a sequence that binds to a portion of a condenser oligonucleotide.

Embodiment 8. The nucleic acid hybridization reagent of Embodiment 1, further comprising: at least one nucleic acid amplification duplex which comprises a nucleic acid template molecule hybridized to an amplification primer.

Embodiment 9. The nucleic acid hybridization reagent of Embodiment 8, wherein the amplification primer comprises a soluble oligonucleotide primer (e.g., in-solution), or the amplification primer is immobilized to a support or is immobilized to a polymer coating on the support.

Embodiment 10. The nucleic acid hybridization reagent of Embodiment 1, further comprising at least one nucleic acid duplex immobilized to a support, wherein the nucleic acid duplex comprise a nucleic acid template molecule hybridized to an amplification primer, and wherein the template molecule and/or the amplification primer is immobilized to a support or is immobilized to a polymer coating on the support.

Embodiment 11. The nucleic acid hybridization reagent of Embodiment 10, wherein the polymer coating on the support comprises a hydrophilic polymer coating having a water contact angle of no more than 45-50 degrees.

Embodiment 12. The nucleic acid hybridization reagent of Embodiment 10, wherein the support or the polymer coating on the support comprises a plurality of amplification primers immobilized thereon, and wherein the density of the immobilized amplification primers is about 100-100,000 amplification primers per mm2.

Embodiment 13. The nucleic acid hybridization reagent of Embodiment 12, wherein the plurality of immobilized amplification primers are in fluid communication with each other to permit flowing a solution of the nucleic acid hybridization reagent onto the support so that the plurality of immobilized amplification primers on the support can be essentially simultaneously reacted with the nucleic acid hybridization reagent in a massively parallel manner.

Embodiment 14. A first nucleic acid amplification reagent, comprising: at least one solvent, a pH buffering agent, at least one monovalent cation, ammonium ions, a plurality of nucleotides and an amplification polymerase enzyme.

Embodiment 15. The first nucleic acid amplification reagent of Embodiment 14, further comprising: any one or any combination of two or more of a detergent, a reducing agent, a viscosity agent, and/or a plurality of condenser oligonucleotides.

Embodiment 16. The first nucleic acid amplification reagent of Embodiment 14, having a pH of about pH 7-8 that reduces/inhibits activity of the amplification polymerase.

Embodiment 17. The first nucleic acid amplification reagent of Embodiment 14, wherein the amplification polymerase has strand displacement activity.

Embodiment 18. The first nucleic acid amplification reagent of Embodiment 14, wherein the plurality of nucleotides comprise a mixture of four types of nucleotides including dATP, dGTP, dCTP and dTTP.

Embodiment 19. The first nucleic acid amplification reagent of Embodiment 14, further comprising: at least one nucleic acid amplification duplex which comprises a nucleic acid template molecule hybridized to an amplification primer.

Embodiment 20. The first nucleic acid amplification reagent of Embodiment 19, wherein the amplification primer comprises a soluble oligonucleotide primer (e.g., in-solution), or the amplification primer is immobilized to a support or is immobilized to a polymer coating on the support.

Embodiment 21. The first nucleic acid amplification reagent of Embodiment 19, further comprising at least one nucleic acid duplex immobilized to a support, wherein the nucleic acid duplex comprise a nucleic acid template molecule hybridized to an amplification primer, and wherein the template molecule and/or the amplification primer is immobilized to a support or is immobilized to a polymer coating on the support.

Embodiment 22. The first nucleic acid amplification reagent of Embodiment 21, wherein the polymer coating on the support comprises a hydrophilic polymer coating having a water contact angle of no more than 45-50 degrees.

Embodiment 23. The first nucleic acid amplification reagent of Embodiment 21, wherein the support or the polymer coating on the support comprises a plurality of amplification primers immobilized thereon, and wherein the density of the immobilized amplification primers is about 100-100,000 amplification primers per mm2.

Embodiment 24. The first nucleic acid amplification reagent of Embodiment 23, wherein the plurality of immobilized amplification primers are in fluid communication with each other to permit flowing a solution of the first nucleic acid amplification reagent onto the support so that the plurality of immobilized amplification primers on the support can be essentially simultaneously reacted with the nucleic acid hybridization reagent in a massively parallel manner.

Embodiment 25. A second nucleic acid amplification reagent, comprising: at least one solvent, a pH buffering agent, at least one monovalent cation, ammonium ions and a plurality of nucleotides.

Embodiment 26. The second nucleic acid amplification reagent of Embodiment 25 which lacks an amplification polymerase.

Embodiment 27. The second nucleic acid amplification reagent of Embodiment 25, further comprising: any one or any combination of two or more of a detergent, a reducing agent, a viscosity agent, and/or a plurality of condenser oligonucleotides.

Embodiment 28. The second nucleic acid amplification reagent of Embodiment 25, having a pH of about pH 8.5-8.8 that is suitable for promoting activity of the amplification polymerase.

Embodiment 29. The second nucleic acid amplification reagent of Embodiment 25, wherein the plurality of nucleotides comprise a mixture of four types of nucleotides including dATP, dGTP, dCTP and dTTP.

Embodiment 30. The second nucleic acid amplification reagent of Embodiment 29, further comprising at least one nucleic acid duplex immobilized to a support, wherein the nucleic acid duplex comprise a nucleic acid template molecule hybridized to an amplification primer, and wherein the template molecule and/or the amplification primer is immobilized to a support or is immobilized to a polymer coating on the support.

Embodiment 31. The second nucleic acid amplification reagent of Embodiment 30, wherein the polymer coating on the support comprises a hydrophilic polymer coating having a water contact angle of no more than 45-50 degrees.

Embodiment 32. The second nucleic acid amplification reagent of Embodiment 30, wherein the support or the polymer coating on the support comprises a plurality of amplification primers immobilized thereon, and wherein the density of the immobilized amplification primers is about 100-100,000 amplification primers per mm2.

Embodiment 33. The second nucleic acid amplification reagent of Embodiment 32, wherein the plurality of immobilized amplification primers are in fluid communication with each other to permit flowing a solution of the second nucleic acid amplification reagent onto the support so that the plurality of immobilized amplification primers on the support can be essentially simultaneously reacted with the nucleic acid hybridization reagent in a massively parallel manner.

Embodiment 34. The second nucleic acid amplification reagent of Embodiment 23, further comprising at least one concatemer containing tandem repeat sequences of a circular template molecule and any adaptor sequences present in the original circularized nucleic acid template molecule, and wherein the at least one concatemer is immobilized to the support or is immobilized to a polymer coating on the support.

Embodiment 35. The second nucleic acid amplification reagent of Embodiment 34, wherein the support is coated with at least one hydrophilic polymer coating having a water contact angle of no more than 45-50 degrees.

Embodiment 36. The second nucleic acid amplification reagent of Embodiment 35, wherein the support or the polymer coating on the support comprises a plurality of concatemers immobilized thereon, and wherein the density of the immobilized concatemers is about 100-100,000 amplification primers per mm2.

Embodiment 37. The second nucleic acid amplification reagent of Embodiment 36, wherein the plurality of immobilized concatemers are in fluid communication with each other to permit flowing a solution of the second nucleic acid amplification reagent onto the support so that the plurality of immobilized concatemers on the support can be essentially simultaneously reacted with the nucleic acid hybridization reagent in a massively parallel manner.

Embodiment 38. A wash-removal reagent comprising: at least one solvent, a pH buffering agent, a chelating agent, a detergent and a chaotropic agent.

Embodiment 39. A trap reagent comprising: at least one solvent, a pH buffering agent, a chelating agent, at least one monovalent cation, a non-catalytic divalent cation, a detergent, a plurality of multivalent molecules and a first sequencing polymerase enzyme.

Embodiment 40. The trap reagent of Embodiment 39, further comprising a plurality of sequencing primers each comprising a 3' extendible end or a 3' non-extendible end.

Embodiment 41. The trap reagent of Embodiment 39, further comprising: at least one viscosity agent.

Embodiment 42. The trap reagent of Embodiment 39, wherein individual multivalent molecules in the plurality comprises: (1) a core, and (2) a plurality of nucleotide arms which comprise (i) a core attachment moiety, (ii) a spacer comprising a PEG moiety, (iii) a linker, and (iv) a nucleotide unit.

Embodiment 43. The trap reagent of Embodiment 42, wherein the multivalent molecule comprises a core which is attached to the plurality of nucleotide arms, Embodiment 44. The trap reagent of Embodiment 42, wherein in the nucleotide arm, the spacer is attached to the linker, and the linker is attached to the nucleotide unit.

Embodiment 45. The trap reagent of Embodiment 42, wherein the linker comprises an aliphatic chain having 2-6 subunits or an oligo ethylene glycol chain having 2-6 subunits.

Embodiment 46. The trap reagent of Embodiment 42, wherein individual multivalent molecules in the plurality comprise a core attached to multiple nucleotide arms, wherein the multiple nucleotide arms have the same type of nucleotide unit which is selected from a group consisting of dATP, dGTP, dCTP, dTTP and dUTP.

Embodiment 47. The trap reagent of Embodiment 42, wherein the plurality of multivalent molecules comprises a mixture of multivalent molecules having two or more different types of nucleotides selected from a group consisting of dATP, dGTP, dCTP, dTTP and dUTP.

Embodiment 48. The trap reagent of Embodiment 42, wherein at least one of the multivalent molecules in the plurality is fluorescently-labeled, wherein the fluorophore is attached to the core or attached to at least one base on a nucleotide unit.

Embodiment 49. The trap reagent of Embodiment 42, wherein at least one of the multivalent molecules comprises at least one nucleotide arm having a cleavable moiety, wherein the cleavable moiety in the nucleotide arm can be cleaved with a cleavable agent to separate the nucleotide arm from the core.

Embodiment 50. The trap reagent of Embodiment 42, wherein at least one of the multivalent molecules in the plurality includes a chain terminating moiety which is attached to the 2' or 3' sugar position of at least one nucleotide unit, wherein the chain terminating moiety can be removed from the nucleotide unit by contacting the multivalent molecule with a compound that cleaves/removes the chain terminating moiety.

Embodiment 51. The trap reagent of Embodiment 39, wherein the first sequencing polymerase comprises a recombinant mutant polymerase from Candidatus altiarchaeales archaeon having an amino acid sequence that is at least 80% identical to SEQ ID NO: 1, where the first sequencing polymerase comprises an amino acid substitution at one or more positions selected from a group consisting of Leu416, Tyr417, Pro418, Ala493, Arg515, Ile529 and Asn567.

Embodiment 52. The trap reagent of Embodiment 39, wherein the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp.

Embodiment 53. The trap reagent of Embodiment 39, wherein the first sequencing polymerase comprises the amino acid sequence of any one of SEQ ID NOS: 2, 3, 4, or 5.

Embodiment 54. The trap reagent of Embodiment 39, further comprising: at least one nucleic acid template molecule which comprises a concatemer template molecule.

Embodiment 55. The trap reagent of Embodiment 54, wherein the concatemer template molecule comprises an amplified molecule (e.g., a clonally amplified molecule).

Embodiment 56. The trap reagent of Embodiment 54, wherein the concatemer template molecule includes at least one adaptor, wherein the adaptor includes a capture primer binding sequence, an amplification primer binding sequence and/or a sequencing primer binding sequence.

Embodiment 57. The trap reagent of Embodiment 54, wherein the concatemer template molecule includes at least one adaptor, and wherein the adaptor includes a sample barcode sequence or a unique molecular tag sequence.

Embodiment 58. The trap reagent of Embodiment 39, further comprising a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule.

Embodiment 59. The trap reagent of Embodiment 58, wherein the plurality of ternary complexes are immobilized to a support, wherein the template molecule (e.g., concatemer) within the ternary complex is immobilized to a support or is immobilized to a coating (e.g., polymer coating) on the support.

Embodiment 60. The trap reagent of Embodiment 59, wherein the support is coated with at least one hydrophilic polymer coating having a water contact angle of no more than 45-50 degrees.

Embodiment 61. The trap reagent of Embodiment 59, wherein the plurality of ternary complexes are immobilized to one or more layers of the coatings on the support and wherein the density of the immobilized ternary complexes is about 100-100,000 per mm2.

Embodiment 62. The trap reagent of Embodiment 59, wherein the plurality of immobilized ternary complexes are in fluid communication with each other to permit flowing a solution of the trap reagent onto the support so that the plurality of immobilized ternary complexes on the support can be essentially simultaneously reacted with the trap reagent in a massively parallel manner.

Embodiment 63. A post-trap reagent, comprising: at least one solvent, a pH buffering agent, a chelating agent, at least one monovalent cation, a non-catalytic divalent cation, a detergent and a first sequencing polymerase enzyme.

Embodiment 64. The post-trap reagent of Embodiment 63 further comprising at least one viscosity agent.

Embodiment 65. The post-trap reagent of Embodiment 63 which lacks a plurality of multivalent molecules.

Embodiment 66. The trap reagent of Embodiment 63, wherein the first sequencing polymerase comprises a recombinant mutant polymerase from Candidatus altiarchaeales archaeon having an amino acid sequence that is at least 80% identical to SEQ ID NO: 1, where the first sequencing polymerase comprises an amino acid substitution at one or more positions selected from a group consisting of Leu416, Tyr417, Pro418, Ala493, Arg515, Ile529 and Asn567.

Embodiment 67. The trap reagent of Embodiment 63, wherein the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp.

Embodiment 68. The trap reagent of Embodiment 63, wherein the first sequencing polymerase comprises the amino acid sequence of any one of SEQ ID NOS: 2, 3, 4, or 5.

Embodiment 69. The post-trap reagent of Embodiment 63, further comprising a plurality of sequencing primers each comprising a 3' extendible end or a 3' non-extendible end.

Embodiment 70. The post-trap reagent of Embodiment 63, further comprising a plurality of ternary complexes each comprising the first sequencing polymerase bound to a nucleic acid duplex which includes a nucleic acid template molecule (e.g., a concatemer) hybridized to a sequencing primer, and a complementary nucleotide unit of a multivalent molecule.

Embodiment 71. The post-trap reagent of Embodiment 70, wherein the plurality of ternary complexes are immobilized to a support, wherein the template molecule (e.g., concatemer) within the ternary complex is immobilized to a support or is immobilized to a coating (e.g., polymer coating) on the support.

Embodiment 72. The post-trap reagent of Embodiment 71, wherein the support is coated with at least one hydrophilic polymer coating having a water contact angle of no more than 45-50 degrees.

Embodiment 73. The post-trap reagent of Embodiment 71, wherein the plurality of ternary complexes are immobilized to one or more layers of the coatings on the support and wherein the density of the immobilized ternary complexes is about 100-100,000 per mm2.

Embodiment 74. The post-trap reagent of Embodiment 71, wherein the plurality of immobilized ternary complexes are in fluid communication with each other to permit flowing a solution of the post-trap reagent onto the support so that the plurality of immobilized ternary complexes on the support can be essentially simultaneously reacted with the post-trap reagent in a massively parallel manner.

Embodiment 75. An imaging reagent, comprising: at least one solvent, a pH buffering agent, a chelating agent, at least one monovalent cation, a non-catalytic divalent cation, a detergent and at least one compound for reducing photo-damage.

Embodiment 76. The imaging reagent of Embodiment 75, comprising 2-5 photo-damage reducing compounds.

Embodiment 77. The imaging reagent of Embodiment 75, further comprising at least one viscosity agent, or the imaging reagent lacks a viscosity agent.

Embodiment 78. The imaging reagent of Embodiment 75, wherein the monovalent salt comprises NaCl, KCl, (NH4)2SO4 or potassium glutamate.

Embodiment 79. The imaging reagent of Embodiment 75, wherein the non-catalytic divalent cation comprises strontium ions and/or barium ions.

Embodiment 80. The imaging reagent of Embodiment 75, which lacks a catalytic divalent cation which comprises magnesium and/or manganese.

Embodiment 81. The imaging reagent of Embodiment 75, further comprising a plurality of ternary complexes each comprising a first sequencing polymerase bound to a nucleic acid duplex which includes a nucleic acid template molecule (e.g., a concatemer) hybridized to a sequencing primer, and a complementary nucleotide unit of a multivalent molecule, wherein the multivalent molecule is labeled with a fluorophore, and the nucleotide unit of the multivalent molecule is bound to the 3' end of the sequencing primer at a position that is opposite a complementary nucleotide in the template strand.

Embodiment 82. The imaging reagent of Embodiment 81, wherein the imaging reagent comprises at least one compound for reducing photo-damage, wherein the compound (i) reduces formation of an excited triplet state of the fluorophores attached to the multivalent molecules, (ii) counteracts the damaging effect of an reactive oxygen species thereby improving photostability of the fluorophores that are attached to the multivalent molecules, (iii) reduces photo-bleaching of the fluorophores attached to the multivalent molecules, (iv) retains fluorescence intensity of the fluorophores attached to the multivalent molecules, and/or (v) reduces non-specific binding of the fluorophores (which are attached to the multivalent molecules) to other biomolecules (e.g., polymerases, nucleic acid template molecules and/or sequencing primer oligonucleotides).

Embodiment 83. The imaging reagent of Embodiment 81, wherein the imaging reagent comprises at least one compound for reducing photo-damage, where the compound mitigates residual signal from a fluorescently-labeled multivalent molecule during an imaging step in a subsequent sequencing cycle.

Embodiment 84. The imaging reagent of Embodiment 81, wherein the multivalent molecule comprises: (1) a core, and (2) a plurality of nucleotide arms which comprise (i) a core attachment moiety, (ii) a spacer comprising a PEG moiety, (iii) a linker, and (iv) a nucleotide unit.

Embodiment 85. The imaging reagent of Embodiment 84, wherein the multivalent molecule comprises a core which is attached to the plurality of nucleotide arms, Embodiment 86. The imaging reagent of Embodiment 84, wherein in the nucleotide arm, the spacer is attached to the linker, and the linker is attached to the nucleotide unit.

Embodiment 87. The imaging reagent of Embodiment 84, wherein the linker comprises an aliphatic chain having 2-6 subunits or an oligo ethylene glycol chain having 2-6 subunits.

Embodiment 88. The imaging reagent of Embodiment 84, wherein the multivalent molecule comprises a core attached to multiple nucleotide arms, wherein the multiple nucleotide arms have the same type of nucleotide unit which is selected from a group consisting of dATP, dGTP, dCTP, dTTP and dUTP.

Embodiment 89. The imaging reagent of Embodiment 84, wherein the multivalent molecule comprises a mixture of multivalent molecules having two or more different types of nucleotides selected from a group consisting of dATP, dGTP, dCTP, dTTP and dUTP.

Embodiment 90. The imaging reagent of Embodiment 84, wherein the multivalent molecule is fluorescently-labeled, wherein the fluorophore is attached to the core or attached to at least one base on a nucleotide unit.

Embodiment 91. The imaging reagent of Embodiment 84, wherein the multivalent molecule comprises at least one nucleotide arm having a cleavable moiety, wherein the cleavable moiety in the nucleotide arm can be cleaved with a cleavable agent to separate the nucleotide arm from the core.

Embodiment 92. The imaging reagent of Embodiment 84, wherein the multivalent molecule comprises a chain terminating moiety which is attached to the 2' or 3' sugar position of at least one nucleotide unit, wherein the chain terminating moiety can be removed from the nucleotide unit by contacting the multivalent molecule with a compound that cleaves/removes the chain terminating moiety.

Embodiment 93. The imaging reagent of Embodiment 81, wherein the first sequencing polymerase comprises a recombinant mutant polymerase from Candidatus altiarchaeales archaeon having an amino acid sequence that is at least 80% identical to SEQ ID NO: 1, where the first sequencing polymerase comprises an amino acid substitution at one or more positions selected from a group consisting of Leu416, Tyr417, Pro418, Ala493, Arg515, Ile529 and Asn567.

Embodiment 94. The imaging reagent of Embodiment 81, wherein the first sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp.

Embodiment 95. The imaging reagent of Embodiment 81, wherein the first sequencing polymerase comprises the amino acid sequence of any one of SEQ ID NOS: 2, 3, 4, or 5.

Embodiment 96. The imaging reagent of Embodiment 81, wherein the nucleic acid template molecule comprises a concatemer template molecule.

Embodiment 97. The imaging reagent of Embodiment 96, wherein the concatemer template molecule comprises an amplified molecule (e.g., a clonally amplified molecule).

Embodiment 98. The imaging reagent of Embodiment 96, wherein the concatemer template molecule includes at least one adaptor sequence comprising at least one surface capture primer binding sequence, an amplification primer binding sequence and/or a sequencing primer binding sequence.

Embodiment 99. The imaging reagent of Embodiment 96, wherein the concatemer template molecule includes at least one adaptor sequence comprising at least one sample barcode sequence or a unique molecular tag sequence.

Embodiment 100. The imaging reagent of Embodiment 96, wherein the concatemer template molecule includes an adaptor sequence that binds at least a portion of a condenser oligonucleotide Embodiment 101. The imaging reagent of Embodiment 81, wherein the plurality of ternary complexes are immobilized to a support or the plurality of ternary complexes are immobilized to a coating (e.g., hydrophilic polymer coating) on the support.

Embodiment 102. The imaging reagent of Embodiment 101, wherein the hydrophilic polymer coating has a water contact angle of no more than 45-50 degrees.

Embodiment 103. The imaging reagent of Embodiment 101, wherein the plurality of ternary complexes are immobilized to one or more layers of the polymer coating on the support and wherein the density of the immobilized ternary complexes is about 100-100,000 per mm2.

Embodiment 104. The imaging reagent of Embodiment 101, where the plurality of immobilized ternary complexes are in fluid communication with each other to permit flowing a solution of the imaging reagent onto the support so that the plurality of immobilized ternary complexes on the support can be essentially simultaneously reacted with the imaging reagent in a massively parallel manner.

Embodiment 105. A stepping reagent, comprising: at least one solvent, at least one pH buffering agent, at least one monovalent cation, a catalytic divalent cation, a detergent, a second sequencing polymerase enzyme and a plurality of nucleotides (e.g., free nucleotides).

Embodiment 106. The stepping reagent of Embodiment 105, wherein the catalytic divalent cation comprises magnesium and/or manganese.

Embodiment 107. The stepping reagent of Embodiment 105, which lacks a non-catalytic divalent cation which comprises strontium and/or barium.

Embodiment 108. The stepping reagent of Embodiment 105, wherein the monovalent salt comprises NaCl, KCl, (NH4)2SO4 or potassium glutamate.

Embodiment 109. The stepping reagent of Embodiment 105, further comprising at least one viscosity agent.

Embodiment 110. The stepping reagent of Embodiment 105, optionally including a plurality of sequencing primers which hybridize to at least a portion of a nucleic acid template molecule, wherein the plurality of sequencing primers comprise a 3' extendible end or a 3' non-extendible end.

Embodiment 111. The stepping reagent of Embodiment 105, wherein the plurality of nucleotides comprises at least one type of nucleotide selected from a group consisting of dATP, dGTP, dCTP, dTTP and dUTP.

Embodiment 112. The stepping reagent of Embodiment 105, wherein the plurality of nucleotides comprises a mixture of two or more, in any combination of nucleotides, selected from a group consisting of dATP, dGTP, dCTP, dTTP and dUTP.

Embodiment 113. The stepping reagent of Embodiment 105, wherein at least one of the nucleotides in the plurality is fluorescently-labeled.

Embodiment 114. The stepping reagent of Embodiment 113, wherein the plurality of fluorescently-labeled nucleotides each comprise a fluorophore attached to the base of the nucleotide, wherein the attached fluorophore corresponds to the base of the nucleotide to permit distinguishing the nucleotide base of the different fluorescently-labeled nucleotides.

Embodiment 115. The stepping reagent of Embodiment 114, wherein the plurality of the fluorescently-labeled nucleotides each comprise a fluorophore attached to the base of the nucleotide via a cleavable linker that is cleavable with a compound that cleaves the cleavable linker to remove the fluorophore from the nucleotides.

Embodiment 116. The stepping reagent of Embodiment 105, wherein at least one of the nucleotides in the plurality of nucleotides includes a chain terminating moiety attached to the 2' or 3' sugar position of the nucleotide.

Embodiment 117. The stepping reagent of Embodiment 116, wherein the at least one chain terminating nucleotide comprises a chain terminating moiety attached to the 2' or 3' sugar position of nucleotide unit, and wherein the chain terminating moiety can be removed from the nucleotide by contacting the chain terminating nucleotide with a compound that cleaves/removes the chain terminating moiety.

Embodiment 118. The stepping reagent of Embodiment 105, wherein the second sequencing polymerase comprises a recombinant mutant polymerase from Candidatus altiarchaeales archaeon having an amino acid sequence that is at least 80% identical to SEQ ID NO: 1, where the second sequencing polymerase comprises an amino acid substitution at one or more positions selected from a group consisting of Leu416, Tyr417, Pro418, Ala493, Arg515, Ile529 and Asn567.

Embodiment 119. The stepping reagent of Embodiment 105, wherein the second sequencing polymerase comprises (i) an amino acid substitution selected from a group consisting of Leu416Ser, Leu416Phe and Leu416Tyr; and (ii) the amino acid substitutions of Tyr417Ala, Pro418Gly, Ala493Ser, Ile529His, Arg515Leu and Asn567Asp.

Embodiment 120. The stepping reagent of Embodiment 105, wherein the second sequencing polymerase comprises the amino acid sequence of any one of SEQ ID NOS: 2, 3, 4, or 5.

Embodiment 121. The stepping reagent of Embodiment 105, further comprising a plurality of ternary complexes each comprising a second sequencing polymerase bound to a nucleic acid duplex which includes a nucleic acid template molecule (e.g., a concatemer) hybridized to a sequencing primer, and a complementary nucleotide, wherein the nucleotide is labeled with a fluorophore, and the nucleotide is bound to the 3' end of the sequencing primer at a position that is opposite a complementary nucleotide in the template strand.

Embodiment 122. The stepping reagent of Embodiment 121, wherein the plurality of ternary complexes are immobilized to a support or the plurality of ternary complexes are immobilized to a coating (e.g., hydrophilic polymer coating) on the support.

Embodiment 123. The stepping reagent of Embodiment 122, wherein the hydrophilic polymer coating has a water contact angle of no more than 45-50 degrees.

Embodiment 124. The stepping reagent of Embodiment 122, wherein the plurality of ternary complexes are immobilized to one or more layers of the polymer coating on the support and wherein the density of the immobilized ternary complexes is about 100-100,000 per mm2.

Embodiment 125. The stepping reagent of Embodiment 122, where the plurality of immobilized ternary complexes are in fluid communication with each other to permit flowing a solution of the stepping reagent onto the support so that the plurality of immobilized ternary complexes on the support can be essentially simultaneously reacted with the stepping reagent in a massively parallel manner.

Embodiment 126. A cleaving reagent, comprising: at least one solvent, a pH buffering agent, at least one monovalent cation, a detergent, a cleaving agent and a cleaving catalyst.

Embodiment 127. The cleaving reagent of Embodiment 126, wherein the cleaving agent can react with a fluorescently-labeled nucleotide by cleaving/removing a cleavable linker which joins a nucleotide base and a fluorophore, thereby removing the fluorophore label from the fluorescently-labeled nucleotide.

Embodiment 128. The cleaving reagent of Embodiment 126, wherein the cleaving agent can react with a chain terminating nucleotide by cleaving/removing a chain terminating moiety which is attached to the 2' or 3' sugar position of a nucleotide to convert the chain terminating nucleotides to a nucleotide having an extendible 3'OH sugar group.

Embodiment 129. The cleaving reagent of Embodiment 126, further comprising a plurality of nucleic acid duplexes immobilized to a support, where the template molecule (e.g., concatemer) within the nucleic acid duplex is immobilized to a support or is immobilized to a coating (e.g., polymer coating) on the support.

Embodiment 130. The cleaving reagent of Embodiment 129, wherein the hydrophilic polymer coating has a water contact angle of no more than 45-50 degrees.

Embodiment 131. The cleaving reagent of Embodiment 129, wherein the plurality of nucleic acid duplexes that are immobilized to one or more layers of the coatings on the support and wherein the density of the immobilized nucleic acid duplexes is about 100-100,000 per mm2.

Embodiment 132. The cleaving reagent of Embodiment 129, wherein the plurality of immobilized nucleic acid duplexes are in fluid communication with each other to permit flowing a solution of the cleaving reagent onto the support so that the plurality of immobilized nucleic acid duplexes on the support can be essentially simultaneously reacted with the cleaving reagent in a massively parallel manner.

Embodiment 133. A method for conducting a nucleic acid sequencing workflow, comprising: (a) contacting a plurality of nucleic acid template molecules with a plurality of amplification primers in the presence of a nucleic acid hybridization reagent under a condition suitable to form a plurality of nucleic acid duplexes each duplex comprising a template molecule hybridized to an amplification primer, wherein the amplification primers are immobilized to a support, and wherein the nucleic acid hybridization reagent comprises at least one solvent, a pH buffering agent, at least one monovalent cation, and a chaotropic agent, wherein the nucleic acid hybridization reagent optionally includes any one or any combination of two or more of a detergent, a reducing agent, a chelating agent, an alcohol, a zwitterion, a sugar alcohol and/or a crowding agent; (b) optionally washing the plurality of immobilized nucleic acid duplexes formed in step (a) with a universal wash reagent under a condition suitable to retain the nucleic acid duplexes formed in step (a), wherein the universal wash reagent comprises at least one solvent, a pH buffering agent, a chelating agent, at least one monovalent cation and a detergent; (c) contacting the plurality of nucleic acid duplexes with a first amplification reagent which comprises at least one solvent, a pH buffering agent, at least one monovalent cation, ammonium ions, a plurality of nucleotides and an amplification polymerase enzyme, and wherein the first amplification reagent optionally further comprises any one or any combination of two or more of a detergent, a reducing agent, a viscosity agent, and/or a plurality of condenser oligonucleotides, wherein the pH of the first amplification reagent inhibits activity of the amplification polymerase, wherein the contacting of step (c) is conducted under a condition that is suitable for forming a plurality of complexed amplification polymerases each comprising an amplification polymerase and a nucleotide bound to a nucleic acid duplex; (d) contacting the plurality of concatemers from step (c) with a second amplification reagent under a condition suitable for retaining the plurality of complexed amplification polymerases and the condition is suitable for conducting a plurality of nucleic acid amplification reactions to form a plurality of concatemers that are immobilized to the support, wherein the second amplification reagent comprises at least one solvent, a pH buffering agent, at least one monovalent cation, ammonium ions and a plurality of nucleotides, wherein the second amplification reagent optionally includes any one or any combination of two or more of a detergent, a reducing agent, a viscosity agent, and/or a plurality of condenser oligonucleotides, wherein the second amplification reagent has a pH that is suitable for promoting activity of the amplification polymerase, and wherein the second amplification reagent lacks an amplification polymerase enzyme; (e) contacting the plurality of immobilized concatemers formed in step (d) with a wash-removal reagent under a condition suitable to retain the immobilized concatemers and suitable to remove (e.g., wash away) amplification polymerase and the nucleotides from steps (c) and (d), wherein the wash-removal reagent comprises at least one solvent, a pH buffering agent, a chelating agent, a detergent and a chaotropic agent; (f) optionally washing the plurality of immobilized concatemers formed in step (d) with a universal wash reagent under a condition suitable to retain the plurality of immobilized concatemers, wherein the universal wash reagent comprises at least one solvent, a pH buffering agent, a chelating agent, at least one monovalent cation and a detergent; (g) contacting the plurality of immobilized concatemers with a trap reagent which comprises at least one solvent, a pH buffering agent, a chelating agent, at least one monovalent cation, a non-catalytic divalent cation, a detergent, a plurality of fluorescently-labeled multivalent molecules, a plurality of sequencing primers, and a first sequencing polymerase enzyme, and the trap reagent optionally includes at least one viscosity agent, wherein the non-catalytic divalent cations comprise strontium and/or barium, wherein individual multivalent molecules in the plurality comprise (1) a core, and (2) a plurality of nucleotide arms wherein each arm comprises (i) a core attachment moiety, (ii) a spacer comprising a PEG moiety, (iii) a linker, and (iv) a fluorescently-labeled nucleotide unit, and wherein the contacting of step (g) is conducted under a condition suitable for forming a plurality of immobilized fluorescently-labeled ternary complexes by binding the immobilized concatemers to the sequencing primers, the first sequencing polymerases and a plurality of fluorescently-labeled multivalent molecules, and wherein the in the immobilized fluorescently-labeled ternary complex the nucleotide unit does not incorporate into the sequencing primer; (h) contacting the plurality of immobilized concatemers with a post-trap reagent under a condition suitable for preserving the plurality of immobilized fluorescently-labeled ternary complexes without polymerase-catalyzed incorporation of the fluorescently-labeled nucleotide units, wherein the post-trap reagent comprises at least one solvent, a pH buffering agent, a chelating agent, at least one monovalent cation, a non-catalytic divalent cation, a detergent and a first sequencing polymerase, wherein the non-catalytic divalent cations comprise strontium and/or barium, wherein the post-trap reagent lacks a plurality of multivalent molecules, and wherein the post-trap reagent optionally comprises at least one viscosity agent; (i) contacting the plurality of immobilized fluorescently-labeled ternary complexes with an imaging reagent and detecting the presence of at least one of the plurality of immobilized fluorescently-labeled ternary complexes by exposing the plurality of ternary complexes to an excitation illumination and detecting a fluorescent signal emitted from the immobilized fluorescently-labeled ternary complexes in response to the excitation illumination, wherein the imaging reagent comprises at least one solvent, a pH buffering agent, a chelating agent, at least one monovalent cation, a non-catalytic divalent cation, a detergent and at least one compound for reducing photo-damage, and the imaging reagent optionally includes at least one viscosity agent; (j) identifying the fluorescently-labeled nucleotide unit of the multivalent molecule that is bound to the sequencing primer, as part of the fluorescently-labeled ternary complex detected in step (i); (k) contacting the plurality of immobilized fluorescently-labeled ternary complexes with a wash-removal reagent under a condition suitable for dissociating the fluorescently-labeled ternary complexes by removing the fluorescently-labeled multivalent molecules and the first sequencing polymerases from the immobilized nucleic acid duplexes, and under a condition suitable for retaining the immobilized nucleic acid duplexes, wherein the wash-removal reagent comprises at least one solvent, a pH buffering agent, a chelating agent, a detergent and a chaotropic agent; (l) optionally washing the plurality of immobilized nucleic acid duplexes with a universal wash reagent under a condition suitable to retain the plurality of immobilized nucleic acid duplexes, wherein the universal wash reagent comprises at least one solvent, a pH buffering agent, a chelating agent, at least one monovalent cation and a detergent; (m) contacting the plurality of immobilized nucleic acid duplexes with a stepping reagent comprising at least one solvent, at least one pH buffering agent, at least one monovalent cation, a catalytic divalent cation, a detergent, a second sequencing polymerase enzyme and a plurality of nucleotides each having a cleavable chain terminating moiety attached to the 3' sugar position, wherein the catalytic divalent cation comprises magnesium and/or manganese, wherein the stepping reagent optionally includes at least one viscosity agent, wherein the contacting of step (m) is conducted under a condition suitable for forming a plurality of immobilized ternary complexes by binding individual immobilized duplexes to the second sequencing polymerase and a complementary nucleotide and the condition is suitable for promoting polymerase-catalyzed nucleotide incorporation thereby generating a plurality of immobilized extended nucleic acid duplexes each comprising an immobilized template concatemer hybridized to an extended sequencing primer; (n) contacting the plurality of immobilized extended nucleic acid duplexes with a wash-removal reagent under a condition suitable for removing the second sequencing polymerases and chain terminating nucleotides, and under a condition to retain the plurality of immobilized extended nucleic acid duplexes, wherein the wash-removal reagent comprises at least one solvent, a pH buffering agent, a chelating agent, a detergent and a chaotropic agent; (o) optionally washing the plurality of immobilized extended nucleic acid duplexes under a condition suitable to retain the plurality of immobilized extended nucleic acid duplexes, wherein the universal wash reagent comprises at least one solvent, a pH buffering agent, a chelating agent, at least one monovalent cation and a detergent; (p) contacting the plurality of immobilized extended nucleic acid duplexes with a cleaving reagent under a condition suitable for cleaving the chain terminating moiety from the nucleotide incorporated on the extended sequencing primer thereby generating a plurality of immobilized extended nucleic acid duplexes each having an extended sequencing primer with a 3' extendible end, wherein the cleaving reagent comprises at least one solvent, a pH buffering agent, at least one monovalent cation, a detergent, a cleaving agent that cleaves the chain terminating moiety from the incorporated nucleotide, and a cleaving catalyst; (q) optionally washing the plurality of immobilized extended nucleic acid duplexes under a condition suitable to retain the plurality of immobilized extended nucleic acid duplexes, wherein the universal wash reagent comprises at least one solvent, a pH buffering agent, a chelating agent, at least one monovalent cation and a detergent; and (r) repeating steps (g)-(q) except that in the repeated step (g) the plurality of immobilized concatemers are contacted with the trap reagent in the absence of sequencing primers.

Embodiment 134. The method of Embodiment 133, wherein the first sequencing polymerase comprises a recombinant wild-type or mutant polymerase from Candidatus altiarchaeales archaeon which comprises an amino acid sequence that is at least 80% identical to SEQ ID NO: 1.

Embodiment 135. The method of Embodiment 134, wherein the mutant DNA polymerase comprises an amino acid substitution at one or more positions selected from a group consisting of Leu416, Tyr417, Pro418, Ala493, Arg515, Ile529 and Asn567.

Embodiment 136. The method of Embodiment 133, wherein the second sequencing polymerase comprises a recombinant wild-type or mutant polymerase from Candidatus altiarchaeales archaeon which comprises an amino acid sequence that is at least 80% identical to SEQ ID NO: 1.

Embodiment 137. The method of Embodiment 136, wherein the mutant DNA polymerase comprises an amino acid substitution at one or more positions selected from a group consisting of Leu416, Tyr417, Pro418, Ala493, Arg515, Ile529 and Asn567.

```
                              SEQUENCE LISTING

Sequence total quantity: 233
SEQ ID NO: 1            moltype = AA  length = 773
FEATURE                 Location/Qualifiers
REGION                  1..773
                        note = Description of Unknown:Candidatus altiarchaeales
                        archaeon sequence
source                  1..773
                        mol_type = protein
                        organism = unidentified
SEQUENCE: 1
MKKTLLDADY ITREEKAVVR LFYKTEEGRE IQEVADFRPY MYVLPEEHDL KKLQREIKEL   60
KNITNVEIKR MIEGDREVEV LKVMVNQPRD VPNLRGLIKE LEGCKEVREA HIPFAERYLI  120
DSGLIPMQDC ENFDLRIAAF DMEVYNPRGE PKAERDPIII ISYADNRGLR RVWTYKTVEN  180
LNLDYMEVLK DEREIIRRFI DTIREREIDI IVTYNGDNFD FPYLKERAEK HRIPVSLGVD  240
GSPLRLERRG MNLGARVTGR PHIDMYPVCR QIFNLSRYTL EDVYLEITGR EKKDIRVGEM  300
AGIWDNPEKE KFKELIEYAM SDAESTLEIA ITLLPLHYEI SRITRELIYQ SSRAGSGQRV  360
ESLLIKKAFE KSILVPNRPS DRVVNERQRK TYIGAYVVEP KRGIHDNILL FDFRSLYPSI  420
IISHNIDPST IDCECCPEDS YRSPTGHYFC KKKRGLIPET LNELVQRRIE VKKGLKNEKN  480
PERRRFLDVK QQALKLLANS MYGYFGFPRA RWYCRECAES ITALGRKYIL HTIDIVPKFG  540
FDVIYGDTDS VYLIKPNITD RERVMKNAEH FLDKINSELP EAMELEFEGF YPRGIFITKK  600
RYALIDERGK LIVKGLETKR RDWANIAKDT QEKVLDALLK DKNPEKAASI VKDVIRNIKT  660
GKIPLKDLAI NTQITRGMAE YKTEGPHIVA AKKAMKRGLE FKQGNIVTYV VTKKGKSISD  720
KARVIDFVEE GDYDPDYYIN NQVLPSVLRI LEALGYSEDE LKGLGKQMKL GGF         773

SEQ ID NO: 2            moltype = AA  length = 774
FEATURE                 Location/Qualifiers
REGION                  1..774
                        note = Description of Unknown:Candidatus altiarchaeales
                        archaeon sequence
source                  1..774
                        mol_type = protein
                        organism = unidentified
SEQUENCE: 2
MMKKTLLDAD YITREEKAVV RLFYKTEEGR EIQEVADFRP YMYVLPEEHD LKKLQREIKE   60
LKNITNVEIK RMIEGDREVE VLKVMVNQPR DVPNLRGLIK ELEGCKEVRE AHIPFAERYL  120
IDSGLIPMQD CENFDLRIAA FAMAVYNPRG EPKAERDPII IISYADNRGL RRVWTYKTVE  180
NLNLDYMEVL KDEREIIRRF IDTIREREID IIVTYNGDNF DFPYLKERAE KHRIPVSLGV  240
DGSPLRLERR GMNLGARVTG RPHIDMYPVC RQIFNLSRYT LEDVYLEITG REKKDIRVGE  300
MAGIWDNPEK EKFKELIEYA MSDAESTLEI AITLLPLHYE ISRITRELIY QSSRAGSGQR  360
VESLLIKKAF EKSILVPNRP SDRVVNERQR KTYIGAYVVE PKRGIHDNIL LFDFRSSAGS  420
IIISHNIDPS TIDCECCPED SYRSPTGHYF CKKKRGLIPE TLNELVQRRI EVKKGLKNEK  480
NPERRRFLDV KQQSLKLLAN SMYGYFGFPR ARWYCLECAE SITALGRKYH LHTIDIVPKF  540
GFDVIYGDTD SVYLIKPNIT DRERVMKNAE HFLDKINSEL PEAMELEFEG FYPRGIFITK  600
KRYALIDERG KLIVKGLETK RRDWANIAKD TQEKVLDALL KDKNPEKAAS IVKDVIRNIK  660
TGKIPLKDLA INTQITRGMA EYKTEGPHIV AAKKAMKRGL EFKQGNIVTY VVTKKGKSIS  720
DKARVIDFVE EGDYDPDYYI NNQVLPSVLR ILEALGYSED ELKGLGKQMK LGGF        774

SEQ ID NO: 3            moltype = AA  length = 774
FEATURE                 Location/Qualifiers
REGION                  1..774
                        note = Description of Unknown:Candidatus altiarchaeales
                        archaeon sequence
source                  1..774
                        mol_type = protein
                        organism = unidentified
SEQUENCE: 3
MMKKTLLDAD YITREEKAVV RLFYKTEEGR EIQEVADFRP YMYVLPEEHD LKKLQREIKE   60
LKNITNVEIK RMIEGDREVE VLKVMVNQPR DVPNLRGLIK ELEGCKEVRE AHIPFAERYL  120
IDSGLIPMQD CENFDLRIAA FAMAVYNPRG EPKAERDPII IISYADNRGL RRVWTYKTVE  180
NLNLDYMEVL KDEREIIRRF IDTIREREID IIVTYNGDNF DFPYLKERAE KHRIPVSLGV  240
DGSPLRLERR GMNLGARVTG RPHIDMYPVC RQIFNLSRYT LEDVYLEITG REKKDIRVGE  300
MAGIWDNPEK EKFKELIEYA MSDAESTLEI AITLLPLHYE ISRITRELIY QSSRAGSGQR  360
VESLLIKKAF EKSILVPNRP SDRVVNERQR KTYIGAYVVE PKRGIHDNIL LFDFRSSAGS  420
IIISHNIDPS TIDCECCPED SYRSPTGHYF CKKKRGLIPE TLNELVQRRI EVKKGLKNEK  480
NPERRRFLDV KQQSLKLLAN SMYGYFGFPR ARWYCLECAE SITALGRKYH LHTIDIVPKF  540
GFDVIYGDTD SVYLIKPNIT DRERVMKDAE HFLDKINSEL PEAMELEFEG FYPRGIFITK  600
KRYALIDERG KLIVKGLETK RRDWANIAKD TQEKVLDALL KDKNPEKAAS IVKDVIRNIK  660
```

```
TGKIPLKDLA INTQITRGMA EYKTEGPHIV AAKKAMKRGL EFKQGNIVTY VVTKKGKSIS  720
DKARVIDFVE EGDYDPDYYI NNQVLPSVLR ILEALGYSED ELKGLGKQMK LGGF        774

SEQ ID NO: 4            moltype = AA  length = 774
FEATURE                 Location/Qualifiers
REGION                  1..774
                        note = Description of Unknown:Candidatus altiarchaeales
                        archaeon sequence
source                  1..774
                        mol_type = protein
                        organism = unidentified
SEQUENCE: 4
MMKKTLLDAD YITREEKAVV RLFYKTEEGR EIQEVADFRP YMYVLPEEHD LKKLQREIKE   60
LKNITNVEIK RMIEGDREVE VLKVMVNQPR DVPNLRGLIK ELEGCKEVRE AHIPFAERYL  120
IDSGLIPMQD CENFDLRIAA FAMAVYNPRG EPKAERDPII IISYADNRGL RRVWTYKTVE  180
NLNLDYMEVL KDEREIIRRF IDTIREREID IIVTYNGDNF DFPYLKERAE KHRIPVSLGV  240
DGSPLRLERR GMNLGARVTG RPHIDMYPVC RQIFNLSRYT LEDVYLEITG REKKDIRVGE  300
MAGIWDNPEK EKFKELIEYA MSDAESTLEI AITLLPLHYE ISRITRELIY QSSRAGSGQR  360
VESLLIKKAF EKSILVPNRP SDRVVNERQR KTYIGAYVVE PKRGIHDNIL LFDFRSFAGS  420
IIIISHNIDPS TIDCECCPED SYRSPTGHYF CKKKRGLIPE TLNELVQRRI EVKKGLKNEK  480
NPERRRFLDV KQQSLKLLAN SMYGYFGFPR ARWYCLECAE SITALGRKYH LHTIDIVPKF  540
GFDVIYGDTD SVYLIKPNIT DRERVMKDAE HFLDKINSEL PEAMELEFEG FYPRGIFITK  600
KRYALIDERG KLIVKGLETK RRDWANIAKD TQEKVLDALL KDKNPEKAAS IVKDVIRNIK  660
TGKIPLKDLA INTQITRGMA EYKTEGPHIV AAKKAMKRGL EFKQGNIVTY VVTKKGKSIS  720
DKARVIDFVE EGDYDPDYYI NNQVLPSVLR ILEALGYSED ELKGLGKQMK LGGF        774

SEQ ID NO: 5            moltype = AA  length = 774
FEATURE                 Location/Qualifiers
REGION                  1..774
                        note = Description of Unknown:Candidatus altiarchaeales
                        archaeon sequence
source                  1..774
                        mol_type = protein
                        organism = unidentified
SEQUENCE: 5
MMKKTLLDAD YITREEKAVV RLFYKTEEGR EIQEVADFRP YMYVLPEEHD LKKLQREIKE   60
LKNITNVEIK RMIEGDREVE VLKVMVNQPR DVPNLRGLIK ELEGCKEVRE AHIPFAERYL  120
IDSGLIPMQD CENFDLRIAA FAMAVYNPRG EPKAERDPII IISYADNRGL RRVWTYKTVE  180
NLNLDYMEVL KDEREIIRRF IDTIREREID IIVTYNGDNF DFPYLKERAE KHRIPVSLGV  240
DGSPLRLERR GMNLGARVTG RPHIDMYPVC RQIFNLSRYT LEDVYLEITG REKKDIRVGE  300
MAGIWDNPEK EKFKELIEYA MSDAESTLEI AITLLPLHYE ISRITRELIY QSSRAGSGQR  360
VESLLIKKAF EKSILVPNRP SDRVVNERQR KTYIGAYVVE PKRGIHDNIL LFDFRSYAGS  420
IIIISHNIDPS TIDCECCPED SYRSPTGHYF CKKKRGLIPE TLNELVQRRI EVKKGLKNEK  480
NPERRRFLDV KQQSLKLLAN SMYGYFGFPR ARWYCLECAE SITALGRKYH LHTIDIVPKF  540
GFDVIYGDTD SVYLIKPNIT DRERVMKDAE HFLDKINSEL PEAMELEFEG FYPRGIFITK  600
KRYALIDERG KLIVKGLETK RRDWANIAKD TQEKVLDALL KDKNPEKAAS IVKDVIRNIK  660
TGKIPLKDLA INTQITRGMA EYKTEGPHIV AAKKAMKRGL EFKQGNIVTY VVTKKGKSIS  720
DKARVIDFVE EGDYDPDYYI NNQVLPSVLR ILEALGYSED ELKGLGKQMK LGGF        774

SEQ ID NO: 6            moltype = AA  length = 775
FEATURE                 Location/Qualifiers
REGION                  1..775
                        note = Description of Artificial Sequence:
                        Syntheticpolypeptide
source                  1..775
                        mol_type = protein
                        organism = synthetic construct
SEQUENCE: 6
MILDTDYITE NGKPVIRVFK KENGEFKIEY DRTFEPYFYA LLKDDSAIED VKKVTAKRHG   60
TVVKVKRAEK VQKKFLGRPI EVWKLYFNHP QDVPAIRDRI RAHPAVVDIY EYDIPFAKRY  120
LIDKGLIPAE GDEELTMLAF DIETLYHEGE EFGTGPILMI SYADGSEARV ITWKKIDLPY  180
VDVVSTEKEM IKRFLRVVRE KDPDVLITYN GDNFDFAYLK KRCEELGIKF TLGRDGSEPK  240
IQRMGDRFAV EVKGRIHFDL YPVIRRTINL PTYTLEAVYE AVFGKPKEKV YAEEIAQAWE  300
SGEGLERVAR YSMEDAKVTY ELGREFFPME AQLSRLIGQS LWDVSRSSTG NLVEWFLLRK  360
AYKRNELAPN KPDERELARR RGGYAGGYVK EPERGLWDNI VYLDFRSLYP SIIITHNVSP  420
DTLNREGCKE YDVAPEVGHK FCKDFPGFIP SLLGDLLEER QKIKRKMKAT VDPLEKKLLD  480
YRQRAIKILA NSFYGYYGYA KARWYCKECA ESVTAWGREY IEMVIRELEE KFGFKVLYAD  540
TDGLHATIPG ADAETVKKKA KEFLKYINPK LPGLLELEYE GFYVRGFFVT KKKYAVIDEE  600
GKITTRGLEI VRRDWSEIAK ETQARVLEAI LKHGDVEEAV RIVKEVTEKL SKYEVPPEKL  660
VIHEQITRDL RDYKATGPHV AVAKRLAARG VKIRPGTVIS YIVLKGSGRI GDRAIPADEF  720
DPTKHRYDAE YYIENQVLPA VERILKAFGY RKEDLRYQKT KQVGLGAWLK VKGKK       775

SEQ ID NO: 7            moltype = AA  length = 775
FEATURE                 Location/Qualifiers
REGION                  1..775
                        note = Description of Artificial Sequence:
                        Syntheticpolypeptide
source                  1..775
                        mol_type = protein
```

```
                          organism = synthetic construct
SEQUENCE: 7
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPME GDEELTMLAF DIETLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLYP SIIITHNVSP   420
DTLNREGCKE YDVAPEVGHK FCKDFPGFIP SLLGDLLEER QKIKRKMKAT VDPLEKKLLD   480
YRQRAIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 8              moltype = AA   length = 775
FEATURE                   Location/Qualifiers
REGION                    1..775
                          note = Description of Artificial Sequence:
                           Syntheticpolypeptide
source                    1..775
                          mol_type = protein
                          organism = synthetic construct
SEQUENCE: 8
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPAE GDEELTMLAF AIATLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLYP SIIITHNVSP   420
DTLNREGCKE YDVAPEVGHK FCKDFPGFIP SLLGDLLEER QKIKRKMKAT VDPLEKKLLD   480
YRQRLIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 9              moltype = AA   length = 1702
FEATURE                   Location/Qualifiers
source                    1..1702
                          mol_type = protein
                          organism = Thermococcus litoralis
SEQUENCE: 9
MILDTDYITK DGKPIIRIFK KENGEFKIEL DPHFQPYIYA LLKDDSAIEE IKAIKGERHG    60
KTVRVLDAVK VRKKFLGREV EVWKLIFEHP QDVPAMRGKI REHPAVVDIY EYDIPFAKRY   120
LIDKGLIPME GDEELKLLAF DIETFYHEGD EFGKGEIIMI SYADEEEARV ITWKNIDLPY   180
VDVVSNEREM IKRFVQVVKE KDPDVIITYN GDNFDLPYLI KRAEKLGVRL VLGRDKEHPE   240
PKIQRMGDSF AVEIKGRIHF DLFPVVRRTI NLPTYTLEAV YEAVLGKTKS KLGAEEIAAI   300
WETEESMKKL AQYSMEDARA TYELGKEFFP MEAELAKLIG QSVWDVSRSS TGNLVEWYLL   360
RVAYARNELA PNKPDEEEYK RRLRTTYLGG YVKEPEKGLW ENIIYLDFRS LYPSIIVTHN   420
VSPDTLEKEG CKNYDVAPIV GYRFCKDFPG FIPSILGDLI AMRQDIKKKM KSTIDPIEKK   480
MLDYRQRAIK LLANSILPNE WLPIIENGEI KFVKIGEFIN SYMEKQKENV KTVENTEVLE   540
VNNLFAFSFN KKIKESEVKK VKALIRHKYK GKAYEIQLSS GRKINITAGH SLFTVRNGEI   600
KEVSGDGIKE GDLIVAPKKI KLNEKGVSIN IPELISDLSE EETADIVMTI SAKGRKNFFK   660
GMLRTLRWMF GEENRRIRTF NRYLFHLEKL GLIKLLPRGY EVTDWERLKK YKQLYEKLAG   720
SVKYNGNKRE YLVMFNEIKD FISYFPQKEL EEWKIGTLNG FRTNCILKVD EDFGKLLGYY   780
VSEGYAGAQK NKTGGISYSV KLYNEDPNVL ESMKNVAEGF FGKVRVDRNC VSISKKMAYL   840
VMKCLCGALA ENKRIPSVIL TSPEPVRWSF LEAYFTGDGD IHPSKRFRLS TKSELLANQL   900
VFLLNSLGIS SVKIGFDSGV YRVYINEDLQ FPQTSREKNT YYSNLIPKEI LRDVFGKEFQ   960
KNMTFKKFKE LVDSGKLNRE KAKLLEFFIN GDIVLDRVKS VKEKDYEGYV YDLSVEDNEN  1020
FLVGFGLLYA HNSYYGYMGY PKARWYSKEC AESVTAWGRH YIEMTIREIE EKFGFKVLYA  1080
DSVSGESEII IRQNGKIRFV KIKDLFSKVD YSIGEKEYCI LEGVEALTLD DDGKLVWKPV  1140
PYVMRHRANK RMFRIWLTNS WYIDVTEDHS LIGYLNTSKT KTAKKIGERL KEVKPFELGK  1200
AVKSLICPNA PLKDENTKTS EIAVKFWELV GLIVGDGNWG GDSRWAEYYL GLSTGKDAEE  1260
IKQKLLEPLK TYGVISNYYP KNEKGDFNIL AKSLVKFMKR HFKDEKGRRK IPEFMYELPV  1320
TYIEAFLRGL FSADGTVTIR KGVPEIRLTN IDADFLREIR KLLWIVGISN SIFAETTPNR  1380
YNGVSTGTYS KHLRIKNKWR FAERIGFLIE RKQKRLLEHL KSARVKRNTI DFGFDLVHVK  1440
KVEEIPYEGY VYDIEVEETH RFFANNILVH NTDGFYATIP GEKPELIKKK AKEFLNYINS  1500
KLPGLLELEY EGFYLRGFFV TKKRYAVIDE EGRITTRGLE VVRRDWSEIA KETQAKVLEA  1560
ILKEGSVEKA VEVVRDVVEK IAKYRVPLEK LVIHEQITRD LKDYKAIGPH VAIAKRLAAR  1620
GIKVKPGTII SYIVLKGSGK ISDRVILLTE YDPRKHKYDP DYYIENQVLP AVLRILEAFG  1680
YRKEDLRYQS SKQTGLDAWL KR                                          1702

SEQ ID NO: 10             moltype = AA   length = 1312
FEATURE                   Location/Qualifiers
source                    1..1312
                          mol_type = protein
```

```
                        organism = Pyrococcus sp.
SEQUENCE: 10
MILDADYITE DGKPIIRIFK KENGEFKVEY DRNFRPYIYA LLKDDSQIDE VRKITAERHG    60
KIVRIIDAEK VRKKFLGRPI EVWRLYFEHP QDVPAIRDKI REHSAVIDIF EYDIPFAKRY   120
LIDKGLIPME GDEELKLLAF DIETLYHEGE EFAKGPIIMI SYADEEEAKV ITWKKIDLPY   180
VEVVSSEREM IKRFLKVIRE KDPDVIITYN GDSFDLPYLV KRAEKLGIKL PLGRDSEPK    240
MQRLGDMTAV EIKGRIHFDL YHVIRRTINL PTYTLEAVYE AIFGKPKEKV YAHEIAEAWE   300
TGKGLERVAK YSMEDAKVTY ELGREFFPME AQLSRLVGQP LWDVSRSSTG NLVEWYLLRK   360
AYERNELAPN KPDEREYERR LRESYAGGYV KEPEKGLWEG LVSLDFRSLY PSIIITHNVS   420
PDTLNREGCR EYDVAPEVGH KFCKDFPGFI PSLLKRLLDE RQEIKRKMKA SKDPIEKKML   480
DYRQRAIKIL ANSILPEEWV PLIKNGKVKI FRIGDFVDGL MKANQGKVKK TGDTEVLEVA   540
GIHAFSFDRK SKKARVMAVK AVIRHRYSGN VYRIVLNSGR KITITEGHSL FVYRNGDLVE   600
ATGEDVKIGD LLAVPRSVNL PEKRERLNIV ELLLNLSPEE TEDIILTIPV KGRKNFFKGM   660
LRTLRWIFGE EKRVRTASRY LRHLENLGYI RLRKIGYDII DKEGLEKYRT LYEKLVDVVR   720
YNGNKREYLV EFNAVRDVIS LMPEEELKEW RIGTRNGFRM GTFVDIDEDF AKLLGYYVSE   780
GSARKWKNQT GGWSYTVRLY NENDEVLDDM EHLAKKFFGK VKRGKNYVEI PKKMAYIIFE   840
SLCGTLAENK RVPEVIFTSS KGVRWAFLEG YFIGDGVDHP SKRVRLSTKS ELLVNGLVLL   900
LNSLGVSAIK LGYDSGVYRV YVNEELKFTE YRKKKNVYHS HIVPKDILKE TFGKVFQKNI   960
SYKKFRELVE NGKLDREKAK RIEWLLNGDI VLDRVVEIKR EYYDGYVYDL SVDEDENFLA  1020
GFGFLYAHNS YYGYYGYAKA RWYCKECAES VTAWGREYIE FVRKELEEKF GFKVLYIDTD  1080
GLYATIPGAK PEEIKKKALE FVDYINAKLP GLLELEYEGF YVRGFFVTKK KYALIDEEGK  1140
IITRGLEIVR RDWSEIAKET QAKVLEAILK HGNVEEAVKI VKEVTEKLSK YEIPPEKLVI  1200
YEQITRPLHE YKAIGPHVAV AKRLAARGVK VRPGMVIGYI VLRGDGPISK RAILAEEFDL  1260
RKHKYDAEYY IENQVLPAVL RILEAFGYRK EDLRWQKTKQ TGLTAWLNIK KK          1312

SEQ ID NO: 11           moltype = AA   length = 775
FEATURE                 Location/Qualifiers
source                  1..775
                        mol_type = protein
                        organism = Pyrococcus furiosus
SEQUENCE: 11
MILDVDYITE EGKPVIRLFK KENGKFKIEH DRTFRPYIYA LLRDDSKIEE VKKITGERHG    60
KIVRIVDVEK VEKKFLGKPI TVWKLYLEHP QDVPTIREKV REHPAVVDIF EYDIPFAKRY   120
LIDKGLIPME GEEELKILAF DIETLYHEGE EFGKGPIIMI SYADENEAKV ITWKNIDLPY   180
VEVVSSEREM IKRFLRIIRE KDPDIIVTYN GDSFDFPYLA KRAEKLGIKL TIGRDGSEPK   240
MQRIGDMTAV EVKGRIHFDL YHVITRTINL PTYTLEAVYE AIFGKPKEKV YADEIAKAWE   300
SGENLERVAK YSMEDAKATY ELGKEFLPME IQLSRLVGQP LWDVSRSSTG NLVEWFLLRK   360
AYERNELAPN KPSEEEYQRR LRESYTGGFV KEPEKGLWEN IVYLDFRALY PSIIITHNVS   420
PDTLNLEGCK NYDIAPQVGH KFCKDIPGFI PSLLGHLLEE RQKIKTKMKE TQDPIEKILL   480
DYRQKAIKLL ANSFYGYYGY AKARWYCKEC AESVTAWGRK YIELVWKELE EKFGFKVLYI   540
DTDGLYATIP GGESEEIKKK ALEFVKYINS KLPGLLELEY EGFYKRGFFV TKKRYAVIDE   600
EGKVITRGLE IVRRDWSEIA KETQARVLET ILKHGDVEEA VRIVKEVIQK LANYEIPPEK   660
LAIYEQITRP LHEYKAIGPH VAVAKKLAAK GVKIKPGMVI GYIVLRGDGP ISNRAILAEE   720
YDPKKHKYDA EYYIENQVLP AVLRILEGFG YRKEDLRYQK TRQVGLTSWL NIKKS         775

SEQ ID NO: 12           moltype = AA   length = 771
FEATURE                 Location/Qualifiers
source                  1..771
                        mol_type = protein
                        organism = Pyrococcus abyssi
SEQUENCE: 12
MIIDADYITE DGKPIIRIFK KEKGEFKVEY DRTFRPYIYA LLKDDSAIDE VKKITAERHG    60
KIVRITEVEK VQKKFLGRPI EVWKLYLEHP QDVPAIREKI REHPAVVDIF EYDIPFAKRY   120
LIDKGLTPME GNEELTFLAV DIETLYHEGE EFGKGPIIMI SYADEEGAKV ITWKSIDLPY   180
VEVVSSEREM IKRLVKVIRE KDPDVIITYN GDNFDFPYLL KRAEKLGIKL PLGRDNSEPK   240
MQRMGDSLAV EIKGRIHFDL FPVIRRTINL PTYTLEAVYE AIFGKSKEKV YAHEIAEAWE   300
TGKGLERVAK YSMEDAKVTF ELGKEFFPME AQLARLVGQP VWDVSRSSTG NLVEWFLLRK   360
AYERNELAPN KPDEREYERR LRESYEGGYV KEPEKGLWEG IVSLDFRSLY PSIIITHNVS   420
PDTLNRENCK EYDVAPQVGH RFCKDFPGFI PSLLGNLLEE RQKIKKRMKE SKDPVEKKLL   480
DYRQRAIKIL ANSYYGYYGY AKARWYCKEC AESVTAWGRQ YIDLVRRELE SRGFKVLYID   540
TDGLYATIPG AKHEEIKEKA LKFVEYINSK LPGLLELEYE GFYARGFFVT KKKYALIDEE   600
GKIVTRGLEI VRRDWSEIAK ETQAKVLEAI LKHGNVDEAV KIVKEVTEKL SKYEIPPEKL   660
VIYEQITRPL SEYKAIGPHV AVAKRLAAKG VKVKPGMVIG YIVLRGDGPI SKRAIAIEEF   720
DPKKHKYDAE YYIENQVLPA VERILRAFGY RKEDLKYQKT KQVGLGAWLK F            771

SEQ ID NO: 13           moltype = AA   length = 903
FEATURE                 Location/Qualifiers
REGION                  1..903
                        note = Description of Unknown:Escherichia phage RB69
source                  1..903
                        mol_type = protein
                        organism = unidentified
SEQUENCE: 13
MKEFYLTVEQ IGDSIFERYI DSNGRERTRE VEYKPSLFAH CPESQATKYF DIYGKPCTRK    60
LFANMRDASQ WIKRMEDIGL EALGMDDFKL AYLSDTYNYE IKYDHTKIRV ANFDIEVTSP   120
DGFPEPSQAK HPIDAITHYD SIDDRFYVFD LLNSPYGNVE EWSIEIAAKL QEEQGGDEVPS  180
EIIDKIIYMP FDNEKELLME YLNFWQQKTP VILTGWNVES FDIPYVYNRI KNIFGESTAK   240
RLSPHRKTRV KVIENMYGSR EIITLFGISV LDYIDLYKKF SFTNQPSYSL DYISEFELNV   300
GKLKYDGPIS KLRESNHQRY ISYNIIDVYR VLQIDAKRQF INLSLDMGYY AKIQIQSVFS   360
```

```
PIKTWDAIIF NSLKEQNKVI PQGRSHPVQP YPGAFVKEPI PNRYKYVMSF DLTSLYPSII   420
RQVNISPETI AGTFKVAPLH DYINAVAERP SDVYSCSPNG MMYYKDRDGV VPTEITKVFN   480
QRKEHKGYML AAQRNGEIIK EALHNPNLSV DEPLDVDYRF DFSDEIKEKI KKLSAKSLNE   540
MLFRAQRTEV AGMTAQINRK LLINSLYGAL GNVWFRYYDL RNATAITTFG QMALQWIERK   600
VNEYLNEVCG TEGEAFVLYG DTDSIYVSAD KIIDKVGESK FRDTNHWVDF LDKFARERME   660
PAIDRGFREM CEYMNNKQHL MFMDREAIAG PPLGSKGIGG FWTGKKRYAL NVWDMEGTRY   720
AEPKLKIMGL ETQKSSTPKA VQKALKECIR RMLQEGEESL QEYFKEFEKE FRQLNYISIA   780
SVSSANNIAK YDVGGFPGPK CPFHIRGILT YNRAIKGNID APQVVEGEKV YVLPLREGNP   840
FGDKCIAWPS GTEITDLIKD DVLHWMDYTV LLEKTFIKPL EGFTSAAKLD YEKKASLFDM   900
FDF                                                               903

SEQ ID NO: 14           moltype =    length =
SEQUENCE: 14
000

SEQ ID NO: 15           moltype =    length =
SEQUENCE: 15
000

SEQ ID NO: 16           moltype =    length =
SEQUENCE: 16
000

SEQ ID NO: 17           moltype =    length =
SEQUENCE: 17
000

SEQ ID NO: 18           moltype =    length =
SEQUENCE: 18
000

SEQ ID NO: 19           moltype =    length =
SEQUENCE: 19
000

SEQ ID NO: 20           moltype =    length =
SEQUENCE: 20
000

SEQ ID NO: 21           moltype =    length =
SEQUENCE: 21
000

SEQ ID NO: 22           moltype =    length =
SEQUENCE: 22
000

SEQ ID NO: 23           moltype =    length =
SEQUENCE: 23
000

SEQ ID NO: 24           moltype =    length =
SEQUENCE: 24
000

SEQ ID NO: 25           moltype =    length =
SEQUENCE: 25
000

SEQ ID NO: 26           moltype =    length =
SEQUENCE: 26
000

SEQ ID NO: 27           moltype =    length =
SEQUENCE: 27
000

SEQ ID NO: 28           moltype =    length =
SEQUENCE: 28
000

SEQ ID NO: 29           moltype =    length =
SEQUENCE: 29
000

SEQ ID NO: 30           moltype =    length =
SEQUENCE: 30
000
```

| | | |
|---|---|---|
| SEQ ID NO: 31<br>SEQUENCE: 31<br>000 | moltype = | length = |
| SEQ ID NO: 32<br>SEQUENCE: 32<br>000 | moltype = | length = |
| SEQ ID NO: 33<br>SEQUENCE: 33<br>000 | moltype = | length = |
| SEQ ID NO: 34<br>SEQUENCE: 34<br>000 | moltype = | length = |
| SEQ ID NO: 35<br>SEQUENCE: 35<br>000 | moltype = | length = |
| SEQ ID NO: 36<br>SEQUENCE: 36<br>000 | moltype = | length = |
| SEQ ID NO: 37<br>SEQUENCE: 37<br>000 | moltype = | length = |
| SEQ ID NO: 38<br>SEQUENCE: 38<br>000 | moltype = | length = |
| SEQ ID NO: 39<br>SEQUENCE: 39<br>000 | moltype = | length = |
| SEQ ID NO: 40<br>SEQUENCE: 40<br>000 | moltype = | length = |
| SEQ ID NO: 41<br>SEQUENCE: 41<br>000 | moltype = | length = |
| SEQ ID NO: 42<br>SEQUENCE: 42<br>000 | moltype = | length = |
| SEQ ID NO: 43<br>SEQUENCE: 43<br>000 | moltype = | length = |
| SEQ ID NO: 44<br>SEQUENCE: 44<br>000 | moltype = | length = |
| SEQ ID NO: 45<br>SEQUENCE: 45<br>000 | moltype = | length = |
| SEQ ID NO: 46<br>SEQUENCE: 46<br>000 | moltype = | length = |
| SEQ ID NO: 47<br>SEQUENCE: 47<br>000 | moltype = | length = |
| SEQ ID NO: 48<br>SEQUENCE: 48<br>000 | moltype = | length = |
| SEQ ID NO: 49<br>SEQUENCE: 49<br>000 | moltype = | length = |
| SEQ ID NO: 50<br>SEQUENCE: 50<br>000 | moltype = | length = |

| | | |
|---|---|---|
| SEQ ID NO: 51 SEQUENCE: 51 000 | moltype = | length = |
| SEQ ID NO: 52 SEQUENCE: 52 000 | moltype = | length = |
| SEQ ID NO: 53 SEQUENCE: 53 000 | moltype = | length = |
| SEQ ID NO: 54 SEQUENCE: 54 000 | moltype = | length = |
| SEQ ID NO: 55 SEQUENCE: 55 000 | moltype = | length = |
| SEQ ID NO: 56 SEQUENCE: 56 000 | moltype = | length = |
| SEQ ID NO: 57 SEQUENCE: 57 000 | moltype = | length = |
| SEQ ID NO: 58 SEQUENCE: 58 000 | moltype = | length = |
| SEQ ID NO: 59 SEQUENCE: 59 000 | moltype = | length = |
| SEQ ID NO: 60 SEQUENCE: 60 000 | moltype = | length = |
| SEQ ID NO: 61 SEQUENCE: 61 000 | moltype = | length = |
| SEQ ID NO: 62 SEQUENCE: 62 000 | moltype = | length = |
| SEQ ID NO: 63 SEQUENCE: 63 000 | moltype = | length = |
| SEQ ID NO: 64 SEQUENCE: 64 000 | moltype = | length = |
| SEQ ID NO: 65 SEQUENCE: 65 000 | moltype = | length = |
| SEQ ID NO: 66 SEQUENCE: 66 000 | moltype = | length = |
| SEQ ID NO: 67 SEQUENCE: 67 000 | moltype = | length = |
| SEQ ID NO: 68 SEQUENCE: 68 000 | moltype = | length = |
| SEQ ID NO: 69 SEQUENCE: 69 000 | moltype = | length = |
| SEQ ID NO: 70 SEQUENCE: 70 | moltype = | length = |

000

SEQ ID NO: 71         moltype =    length =
SEQUENCE: 71
000

SEQ ID NO: 72         moltype =    length =
SEQUENCE: 72
000

SEQ ID NO: 73         moltype =    length =
SEQUENCE: 73
000

SEQ ID NO: 74         moltype =    length =
SEQUENCE: 74
000

SEQ ID NO: 75         moltype =    length =
SEQUENCE: 75
000

SEQ ID NO: 76         moltype =    length =
SEQUENCE: 76
000

SEQ ID NO: 77         moltype =    length =
SEQUENCE: 77
000

SEQ ID NO: 78         moltype =    length =
SEQUENCE: 78
000

SEQ ID NO: 79         moltype =    length =
SEQUENCE: 79
000

SEQ ID NO: 80         moltype =    length =
SEQUENCE: 80
000

SEQ ID NO: 81         moltype =    length =
SEQUENCE: 81
000

SEQ ID NO: 82         moltype =    length =
SEQUENCE: 82
000

SEQ ID NO: 83         moltype =    length =
SEQUENCE: 83
000

SEQ ID NO: 84         moltype =    length =
SEQUENCE: 84
000

SEQ ID NO: 85         moltype =    length =
SEQUENCE: 85
000

SEQ ID NO: 86         moltype =    length =
SEQUENCE: 86
000

SEQ ID NO: 87         moltype =    length =
SEQUENCE: 87
000

SEQ ID NO: 88         moltype =    length =
SEQUENCE: 88
000

SEQ ID NO: 89         moltype =    length =
SEQUENCE: 89
000

SEQ ID NO: 90         moltype =    length =

| | | |
|---|---|---|
| SEQUENCE: 90 000 | | |
| SEQ ID NO: 91 SEQUENCE: 91 000 | moltype = | length = |
| SEQ ID NO: 92 SEQUENCE: 92 000 | moltype = | length = |
| SEQ ID NO: 93 SEQUENCE: 93 000 | moltype = | length = |
| SEQ ID NO: 94 SEQUENCE: 94 000 | moltype = | length = |
| SEQ ID NO: 95 SEQUENCE: 95 000 | moltype = | length = |
| SEQ ID NO: 96 SEQUENCE: 96 000 | moltype = | length = |
| SEQ ID NO: 97 SEQUENCE: 97 000 | moltype = | length = |
| SEQ ID NO: 98 SEQUENCE: 98 000 | moltype = | length = |
| SEQ ID NO: 99 SEQUENCE: 99 000 | moltype = | length = |
| SEQ ID NO: 100 SEQUENCE: 100 000 | moltype = | length = |
| SEQ ID NO: 101 SEQUENCE: 101 000 | moltype = | length = |
| SEQ ID NO: 102 SEQUENCE: 102 000 | moltype = | length = |
| SEQ ID NO: 103 SEQUENCE: 103 000 | moltype = | length = |
| SEQ ID NO: 104 SEQUENCE: 104 000 | moltype = | length = |
| SEQ ID NO: 105 SEQUENCE: 105 000 | moltype = | length = |
| SEQ ID NO: 106 SEQUENCE: 106 000 | moltype = | length = |
| SEQ ID NO: 107 SEQUENCE: 107 000 | moltype = | length = |
| SEQ ID NO: 108 SEQUENCE: 108 000 | moltype = | length = |
| SEQ ID NO: 109 SEQUENCE: 109 000 | moltype = | length = |

| | | |
|---|---|---|
| SEQ ID NO: 110<br>SEQUENCE: 110<br>000 | moltype = | length = |
| SEQ ID NO: 111<br>SEQUENCE: 111<br>000 | moltype = | length = |
| SEQ ID NO: 112<br>SEQUENCE: 112<br>000 | moltype = | length = |
| SEQ ID NO: 113<br>SEQUENCE: 113<br>000 | moltype = | length = |
| SEQ ID NO: 114<br>SEQUENCE: 114<br>000 | moltype = | length = |
| SEQ ID NO: 115<br>SEQUENCE: 115<br>000 | moltype = | length = |
| SEQ ID NO: 116<br>SEQUENCE: 116<br>000 | moltype = | length = |
| SEQ ID NO: 117<br>SEQUENCE: 117<br>000 | moltype = | length = |
| SEQ ID NO: 118<br>SEQUENCE: 118<br>000 | moltype = | length = |
| SEQ ID NO: 119<br>SEQUENCE: 119<br>000 | moltype = | length = |
| SEQ ID NO: 120<br>SEQUENCE: 120<br>000 | moltype = | length = |
| SEQ ID NO: 121<br>SEQUENCE: 121<br>000 | moltype = | length = |
| SEQ ID NO: 122<br>SEQUENCE: 122<br>000 | moltype = | length = |
| SEQ ID NO: 123<br>SEQUENCE: 123<br>000 | moltype = | length = |
| SEQ ID NO: 124<br>SEQUENCE: 124<br>000 | moltype = | length = |
| SEQ ID NO: 125<br>SEQUENCE: 125<br>000 | moltype = | length = |
| SEQ ID NO: 126<br>SEQUENCE: 126<br>000 | moltype = | length = |
| SEQ ID NO: 127<br>SEQUENCE: 127<br>000 | moltype = | length = |
| SEQ ID NO: 128<br>SEQUENCE: 128<br>000 | moltype = | length = |
| SEQ ID NO: 129<br>SEQUENCE: 129<br>000 | moltype = | length = |

| | | |
|---|---|---|
| SEQ ID NO: 130 SEQUENCE: 130 000 | moltype = | length = |
| SEQ ID NO: 131 SEQUENCE: 131 000 | moltype = | length = |
| SEQ ID NO: 132 SEQUENCE: 132 000 | moltype = | length = |
| SEQ ID NO: 133 SEQUENCE: 133 000 | moltype = | length = |
| SEQ ID NO: 134 SEQUENCE: 134 000 | moltype = | length = |
| SEQ ID NO: 135 SEQUENCE: 135 000 | moltype = | length = |
| SEQ ID NO: 136 SEQUENCE: 136 000 | moltype = | length = |
| SEQ ID NO: 137 SEQUENCE: 137 000 | moltype = | length = |
| SEQ ID NO: 138 SEQUENCE: 138 000 | moltype = | length = |
| SEQ ID NO: 139 SEQUENCE: 139 000 | moltype = | length = |
| SEQ ID NO: 140 SEQUENCE: 140 000 | moltype = | length = |
| SEQ ID NO: 141 SEQUENCE: 141 000 | moltype = | length = |
| SEQ ID NO: 142 SEQUENCE: 142 000 | moltype = | length = |
| SEQ ID NO: 143 SEQUENCE: 143 000 | moltype = | length = |
| SEQ ID NO: 144 SEQUENCE: 144 000 | moltype = | length = |
| SEQ ID NO: 145 SEQUENCE: 145 000 | moltype = | length = |
| SEQ ID NO: 146 SEQUENCE: 146 000 | moltype = | length = |
| SEQ ID NO: 147 SEQUENCE: 147 000 | moltype = | length = |
| SEQ ID NO: 148 SEQUENCE: 148 000 | moltype = | length = |
| SEQ ID NO: 149 SEQUENCE: 149 | moltype = | length = |

000

SEQ ID NO: 150        moltype =     length =
SEQUENCE: 150
000

SEQ ID NO: 151        moltype =     length =
SEQUENCE: 151
000

SEQ ID NO: 152        moltype =     length =
SEQUENCE: 152
000

SEQ ID NO: 153        moltype =     length =
SEQUENCE: 153
000

SEQ ID NO: 154        moltype =     length =
SEQUENCE: 154
000

SEQ ID NO: 155        moltype =     length =
SEQUENCE: 155
000

SEQ ID NO: 156        moltype =     length =
SEQUENCE: 156
000

SEQ ID NO: 157        moltype =     length =
SEQUENCE: 157
000

SEQ ID NO: 158        moltype =     length =
SEQUENCE: 158
000

SEQ ID NO: 159        moltype =     length =
SEQUENCE: 159
000

SEQ ID NO: 160        moltype =     length =
SEQUENCE: 160
000

SEQ ID NO: 161        moltype =     length =
SEQUENCE: 161
000

SEQ ID NO: 162        moltype =     length =
SEQUENCE: 162
000

SEQ ID NO: 163        moltype =     length =
SEQUENCE: 163
000

SEQ ID NO: 164        moltype =     length =
SEQUENCE: 164
000

SEQ ID NO: 165        moltype =     length =
SEQUENCE: 165
000

SEQ ID NO: 166        moltype =     length =
SEQUENCE: 166
000

SEQ ID NO: 167        moltype =     length =
SEQUENCE: 167
000

SEQ ID NO: 168        moltype =     length =
SEQUENCE: 168
000

SEQ ID NO: 169        moltype =     length =

| | | |
|---|---|---|
| SEQUENCE: 169 000 | | |
| SEQ ID NO: 170 SEQUENCE: 170 000 | moltype = | length = |
| SEQ ID NO: 171 SEQUENCE: 171 000 | moltype = | length = |
| SEQ ID NO: 172 SEQUENCE: 172 000 | moltype = | length = |
| SEQ ID NO: 173 SEQUENCE: 173 000 | moltype = | length = |
| SEQ ID NO: 174 SEQUENCE: 174 000 | moltype = | length = |
| SEQ ID NO: 175 SEQUENCE: 175 000 | moltype = | length = |
| SEQ ID NO: 176 SEQUENCE: 176 000 | moltype = | length = |
| SEQ ID NO: 177 SEQUENCE: 177 000 | moltype = | length = |
| SEQ ID NO: 178 SEQUENCE: 178 000 | moltype = | length = |
| SEQ ID NO: 179 SEQUENCE: 179 000 | moltype = | length = |
| SEQ ID NO: 180 SEQUENCE: 180 000 | moltype = | length = |
| SEQ ID NO: 181 SEQUENCE: 181 000 | moltype = | length = |
| SEQ ID NO: 182 SEQUENCE: 182 000 | moltype = | length = |
| SEQ ID NO: 183 SEQUENCE: 183 000 | moltype = | length = |
| SEQ ID NO: 184 SEQUENCE: 184 000 | moltype = | length = |
| SEQ ID NO: 185 SEQUENCE: 185 000 | moltype = | length = |
| SEQ ID NO: 186 SEQUENCE: 186 000 | moltype = | length = |
| SEQ ID NO: 187 SEQUENCE: 187 000 | moltype = | length = |
| SEQ ID NO: 188 SEQUENCE: 188 000 | moltype = | length = |

| | | |
|---|---|---|
| SEQ ID NO: 189
SEQUENCE: 189
000 | moltype = | length = |
| SEQ ID NO: 190
SEQUENCE: 190
000 | moltype = | length = |
| SEQ ID NO: 191
SEQUENCE: 191
000 | moltype = | length = |
| SEQ ID NO: 192
SEQUENCE: 192
000 | moltype = | length = |
| SEQ ID NO: 193
SEQUENCE: 193
000 | moltype = | length = |
| SEQ ID NO: 194
SEQUENCE: 194
000 | moltype = | length = |
| SEQ ID NO: 195
SEQUENCE: 195
000 | moltype = | length = |
| SEQ ID NO: 196
SEQUENCE: 196
000 | moltype = | length = |
| SEQ ID NO: 197
SEQUENCE: 197
000 | moltype = | length = |
| SEQ ID NO: 198
SEQUENCE: 198
000 | moltype = | length = |
| SEQ ID NO: 199
SEQUENCE: 199
000 | moltype = | length = |
| SEQ ID NO: 200
SEQUENCE: 200
000 | moltype = | length = |
| SEQ ID NO: 201
SEQUENCE: 201
000 | moltype = | length = |
| SEQ ID NO: 202
SEQUENCE: 202
000 | moltype = | length = |
| SEQ ID NO: 203
SEQUENCE: 203
000 | moltype = | length = |
| SEQ ID NO: 204
SEQUENCE: 204
000 | moltype = | length = |
| SEQ ID NO: 205
SEQUENCE: 205
000 | moltype = | length = |
| SEQ ID NO: 206
SEQUENCE: 206
000 | moltype = | length = |
| SEQ ID NO: 207
SEQUENCE: 207
000 | moltype = | length = |
| SEQ ID NO: 208
SEQUENCE: 208
000 | moltype = | length = |

-continued

```
SEQ ID NO: 209           moltype =    length =
SEQUENCE: 209
000

SEQ ID NO: 210           moltype =    length =
SEQUENCE: 210
000

SEQ ID NO: 211           moltype =    length =
SEQUENCE: 211
000

SEQ ID NO: 212           moltype =    length =
SEQUENCE: 212
000

SEQ ID NO: 213           moltype =    length =
SEQUENCE: 213
000

SEQ ID NO: 214           moltype =    length =
SEQUENCE: 214
000

SEQ ID NO: 215           moltype = DNA   length = 56
FEATURE                  Location/Qualifiers
misc_feature             1..56
                         note = Description of Artificial Sequence: Syntheticprimer
misc_feature             1..56
                         note = Description of Combined DNA/RNA Molecule:
                            Syntheticprimer
source                   1..56
                         mol_type = other DNA
                         organism = synthetic construct
misc_feature             1..53
                         note = DNA
misc_feature             54..56
                         note = RNA
SEQUENCE: 215
catgtaatgc acgtactttc agggtaaaca tgtaatgcac gtactttcag ggtttt      56

SEQ ID NO: 216           moltype = DNA   length = 52
FEATURE                  Location/Qualifiers
misc_feature             1..52
                         note = Description of Artificial Sequence: Syntheticprimer
misc_feature             1..52
                         note = Description of Combined DNA/RNA Molecule:
                            Syntheticprimer
source                   1..52
                         mol_type = other DNA
                         organism = synthetic construct
misc_feature             1..49
                         note = DNA
misc_feature             50..52
                         note = RNA
SEQUENCE: 216
gatcaggtga ggctgcgacg actaaagatc aggtgaggct gcgacgactt tt          52

SEQ ID NO: 217           moltype =    length =
SEQUENCE: 217
000

SEQ ID NO: 218           moltype =    length =
SEQUENCE: 218
000

SEQ ID NO: 219           moltype =    length =
SEQUENCE: 219
000

SEQ ID NO: 220           moltype =    length =
SEQUENCE: 220
000

SEQ ID NO: 221           moltype = AA   length = 773
FEATURE                  Location/Qualifiers
REGION                   1..773
                         note = Description of Unknown:Candidatus altiarchaeales
```

```
                        archaeon sequence
source                  1..773
                        mol_type = protein
                        organism = unidentified
SEQUENCE: 221
MKKTLLDADY ITREEKAVVR LFYKTEEGRE IQEVADFRPY MYVLPEEHDL KKLQREIKEL    60
KNITNVEIKR MIEGDREVEV LKVMVNQPRD VPNLRGLIKE LEGCKEVREA HIPFAERYLI   120
DSGLIPMQDC ENFDLRIAAF DMEVYNPRGE PKAERDPIII ISYADNRGLR RVWTYKTVEN   180
LNLDYMEVLK DEREIIRRFI DTIREREIDI IVTYNGDNPD FPYLKERAEK HRIPVSLGVD   240
GSPLRLERRG MNLGARVTGR PHIDMYPVCR QIFNLSRYTL EDVYLEITGR EKKDIRVGEM   300
AGIWDNPEKE KFKELIEYAM SDAESTLEIA ITLLPLHYEI SRITRELIYQ SSRAGSGQRV   360
ESLLIKKAFE KSILVPNRPS DRVVNERQRK TYIGAYVVEP KRGIHDNILL FDFRSLYPSI   420
IISHNIDPST IDCECCPEDS YRSPTGHYFC KKKRGLIPET LNELVQRRIE VKKGLKNEKN   480
PERRRFLDVK QQALKLLANS MYGYFGFPRA RWYCRECAES ITALGRKYIL HTIDIVPKFG   540
FDVIYGDTDS VYLIKPNITD RERVMKNAEH FLDKINSELP EAMELEFEGF YPRGIFITKK   600
RYALIDERGK LIVKGLETKR RDWANIAKDT QEKVLDALLK DKNPEKAASI VKDVIRNIKT   660
GKIPLKDLAI NTQITRGMAE YKTEGPHIVA AKKMKRGLE FKQGNIVTYV VTKKGKSISD    720
KARVIDFVEE GDYDPDYYIN NQVLPSVLRI LEALGYSEDE LKGLGKQMKL GGF          773

SEQ ID NO: 222          moltype = AA  length = 773
FEATURE                 Location/Qualifiers
REGION                  1..773
                        note = Description of Unknown:Candidatus altiarchaeales
                        archaeon sequence
source                  1..773
                        mol_type = protein
                        organism = unidentified
SEQUENCE: 222
MKKTLLDADY ITREEKAVVR LFYKTEEGRE IQEVADFRPY MYVLPEEHDL KKLQREIKEL    60
KNITNVEIKR MIEGDREVEV LKVMVNQPRD VPNLRGLIKE LEGCKEVREA HIPFAERYLI   120
DSGLIPMQDC ENFDLRIAAF AMAVYNPRGE PKAERDPIII ISYADNRGLR RVWTYKTVEN   180
LNLDYMEVLK DEREIIRRFI DTIREREIDI IVTYNGDNPD FPYLKERAEK HRIPVSLGVD   240
GSPLRLERRG MNLGARVTGR PHIDMYPVCR QIFNLSRYTL EDVYLEITGR EKKDIRVGEM   300
AGIWDNPEKE KFKELIEYAM SDAESTLEIA ITLLPLHYEI SRITRELIYQ SSRAGSGQRV   360
ESLLIKKAFE KSILVPNRPS DRVVNERQRK TYIGAYVVEP KRGIHDNILL FDFRSSAGSI   420
IISHNIDPST IDCECCPEDS YRSPTGHYFC KKKRGLIPET LNELVQRRIE VKKGLKNEKN   480
PERRRFLDVK QQSLKLLANS MYGYFGFPRA RWYCLECAES ITALGRKYHL HTIDIVPKFG   540
FDVIYGDTDS VYLIKPNITD RERVMKNAEH FLDKINSELP EAMELEFEGF YPRGIFITKK   600
RYALIDERGK LIVKGLETKR RDWANIAKDT QEKVLDALLK DKNPEKAASI VKDVIRNIKT   660
GKIPLKDLAI NTQITRGMAE YKTEGPHIVA AKKMKRGLE FKQGNIVTYV VTKKGKSISD    720
KARVIDFVEE GDYDPDYYIN NQVLPSVLRI LEALGYSEDE LKGLGKQMKL GGF          773

SEQ ID NO: 223          moltype = AA  length = 773
FEATURE                 Location/Qualifiers
REGION                  1..773
                        note = Description of Unknown:Candidatus altiarchaeales
                        archaeon sequence
source                  1..773
                        mol_type = protein
                        organism = unidentified
SEQUENCE: 223
MKKTLLDADY ITREEKAVVR LFYKTEEGRE IQEVADFRPY MYVLPEEHDL KKLQREIKEL    60
KNITNVEIKR MIEGDREVEV LKVMVNQPRD VPNLRGLIKE LEGCKEVREA HIPFAERYLI   120
DSGLIPMQDC ENFDLRIAAF AMAVYNPRGE PKAERDPIII ISYADNRGLR RVWTYKTVEN   180
LNLDYMEVLK DEREIIRRFI DTIREREIDI IVTYNGDNPD FPYLKERAEK HRIPVSLGVD   240
GSPLRLERRG MNLGARVTGR PHIDMYPVCR QIFNLSRYTL EDVYLEITGR EKKDIRVGEM   300
AGIWDNPEKE KFKELIEYAM SDAESTLEIA ITLLPLHYEI SRITRELIYQ SSRAGSGQRV   360
ESLLIKKAFE KSILVPNRPS DRVVNERQRK TYIGAYVVEP KRGIHDNILL FDFRSSAGSI   420
IISHNIDPST IDCECCPEDS YRSPTGHYFC KKKRGLIPET LNELVQRRIE VKKGLKNEKN   480
PERRRFLDVK QQSLKLLANS MYGYFGFPRA RWYCLECAES ITALGRKYHL HTIDIVPKFG   540
FDVIYGDTDS VYLIKPNITD RERVMKDAEH FLDKINSELP EAMELEFEGF YPRGIFITKK   600
RYALIDERGK LIVKGLETKR RDWANIAKDT QEKVLDALLK DKNPEKAASI VKDVIRNIKT   660
GKIPLKDLAI NTQITRGMAE YKTEGPHIVA AKKMKRGLE FKQGNIVTYV VTKKGKSISD    720
KARVIDFVEE GDYDPDYYIN NQVLPSVLRI LEALGYSEDE LKGLGKQMKL GGF          773

SEQ ID NO: 224          moltype = AA  length = 773
FEATURE                 Location/Qualifiers
REGION                  1..773
                        note = Description of Unknown:Candidatus altiarchaeales
                        archaeon sequence
source                  1..773
                        mol_type = protein
                        organism = unidentified
SEQUENCE: 224
MKKTLLDADY ITREEKAVVR LFYKTEEGRE IQEVADFRPY MYVLPEEHDL KKLQREIKEL    60
KNITNVEIKR MIEGDREVEV LKVMVNQPRD VPNLRGLIKE LEGCKEVREA HIPFAERYLI   120
DSGLIPMQDC ENFDLRIAAF AMAVYNPRGE PKAERDPIII ISYADNRGLR RVWTYKTVEN   180
LNLDYMEVLK DEREIIRRFI DTIREREIDI IVTYNGDNPD FPYLKERAEK HRIPVSLGVD   240
GSPLRLERRG MNLGARVTGR PHIDMYPVCR QIFNLSRYTL EDVYLEITGR EKKDIRVGEM   300
```

```
AGIWDNPEKE KFKELIEYAM SDAESTLEIA ITLLPLHYEI SRITRELIYQ SSRAGSGQRV    360
ESLLIKKAFE KSILVPNRPS DRVVNERQRK TYIGAYVVEP KRGIHDNILL FDFRSFAGSI    420
IISHNIDPST IDCECCPEDS YRSPTGHYFC KKKRGLIPET LNELVQRRIE VKKGLKNEKN    480
PERRRFLDVK QQSLKLLANS MYGYFGFPRA RWYCLECAES ITALGRKYHL HTIDIVPKFG    540
FDVIYGDTDS VYLIKPNITD RERVMKDAEH FLDKINSELP EAMELEFEGF YPRGIFITKK    600
RYALIDERGK LIVKGLETKR RDWANIAKDT QEKVLDALLK DKNPEKAASI VKDVIRNIKT    660
GKIPLKDLAI NTQITRGMAE YKTEGPHIVA AKKAMKRGLE FKQGNIVTYV VTKKGKSISD    720
KARVIDFVEE GDYDPDYYIN NQVLPSVLRI LEALGYSEDE LKGLGKQMKL GGF           773

SEQ ID NO: 225         moltype = AA  length = 773
FEATURE                Location/Qualifiers
REGION                 1..773
                       note = Description of Unknown:Candidatus altiarchaeales
                        archaeon sequence
source                 1..773
                       mol_type = protein
                       organism = unidentified
SEQUENCE: 225
MKKTLLDADY ITREEKAVVR LFYKTEEGRE IQEVADFRPY MYVLPEEHDL KKLQREIKEL     60
KNITNVEIKR MIEGDREVEV LKVMVNQPRD VPNLRGLIKE LEGCKEVREA HIPFAERYLI    120
DSGLIPMQDC ENFDLRIAAF AMAVYNPRGE PKAERDPIII ISYADNRGLR RVWTYKTVEN    180
LNLDYMEVLK DEREIIRRFI DTIREREIDI IVTYNGDNFI FPYLKERAEK HRIPVSLGVD    240
GSPLRLERRG MNLGARVTGR PHIDMYPVCR QIFNLSRYTL EDVYLEITGR EKKDIRVGEM    300
AGIWDNPEKE KFKELIEYAM SDAESTLEIA ITLLPLHYEI SRITRELIYQ SSRAGSGQRV    360
ESLLIKKAFE KSILVPNRPS DRVVNERQRK TYIGAYVVEP KRGIHDNILL FDFRSYAGSI    420
IISHNIDPST IDCECCPEDS YRSPTGHYFC KKKRGLIPET LNELVQRRIE VKKGLKNEKN    480
PERRRFLDVK QQSLKLLANS MYGYFGFPRA RWYCLECAES ITALGRKYHL HTIDIVPKFG    540
FDVIYGDTDS VYLIKPNITD RERVMKDAEH FLDKINSELP EAMELEFEGF YPRGIFITKK    600
RYALIDERGK LIVKGLETKR RDWANIAKDT QEKVLDALLK DKNPEKAASI VKDVIRNIKT    660
GKIPLKDLAI NTQITRGMAE YKTEGPHIVA AKKAMKRGLE FKQGNIVTYV VTKKGKSISD    720
KARVIDFVEE GDYDPDYYIN NQVLPSVLRI LEALGYSEDE LKGLGKQMKL GGF           773

SEQ ID NO: 226         moltype = AA  length = 775
FEATURE                Location/Qualifiers
REGION                 1..775
                       note = Description of Artificial Sequence:
                        Syntheticpolypeptide
source                 1..775
                       mol_type = protein
                       organism = synthetic construct
SEQUENCE: 226
MILDTDYITE NGKPVIRVFK KENGEFKIEY DRTFEPYFYA LLKDDSAIED VKKVTAKRHG     60
TVVKVKRAEK VQKKFLGRPI EVWKLYFNHP QDVPAIRDRI RAHPAVVDIY EYDIPFAKRY    120
LIDKGLIPAE GDEELTMLAF DIETLYHEGE EFGTGPILMI SYADGSEARV ITWKKIDLPY    180
VDVVSTEKEM IKRFLRVVRE KDPDVLITYN GDNFDFAYLK KRCEELGIKF TLGRDGSEPK    240
IQRMGDRFAV EVKGRIHFDL YPVIRRTINL PTYTLEAVYE AVFGKPKEKV YAEEIAQAWE    300
SGEGLERVAR YSMEDAKVTY ELGREFFPME AQLSRLIGQS LWDVSRSSTG NLVEWFLLRK    360
AYKRNELAPN KPDERELARR RGGYAGGYVK EPERGLWDNI VYLDFRSLYP SIIITHNVSP    420
DTLNREGCKE YDVAPEVGHK FCKDFPGFIP SLLGDLLEER QKIKRKMKAT VDPLEKKLLD    480
YRQRAIKILA NSFYGYYGYA KARWYCKECA ESVTAWGREY IEMVIRELEE KFGFKVLYAD    540
TDGLHATIPG ADAETVKKKA KEFLKYINPK LPGLLELEYE GFYVRGFFVT KKKYAVIDEE    600
GKITTRGLEI VRRDWSEIAK ETQARVLEAI LKHGDVEEAV RIVKEVTEKL SKYEVPPEKL    660
VIHEQITRDL RDYKATGPHV AVAKRLAARG VKIRPGTVIS YIVLKGSGRI GDRAIPADEF    720
DPTKHRYDAE YYIENQVLPA VERILKAFGY RKEDLRYQKT KQVGLGAWLK VKGKK         775

SEQ ID NO: 227         moltype = AA  length = 775
FEATURE                Location/Qualifiers
REGION                 1..775
                       note = Description of Artificial Sequence:
                        Syntheticpolypeptide
source                 1..775
                       mol_type = protein
                       organism = synthetic construct
SEQUENCE: 227
MILDTDYITE NGKPVIRVFK KENGEFKIEY DRTFEPYFYA LLKDDSAIED VKKVTAKRHG     60
TVVKVKRAEK VQKKFLGRPI EVWKLYFNHP QDVPAIRDRI RAHPAVVDIY EYDIPFAKRY    120
LIDKGLIPME GDEELTMLAF DIETLYHEGE EFGTGPILMI SYADGSEARV ITWKKIDLPY    180
VDVVSTEKEM IKRFLRVVRE KDPDVLITYN GDNFDFAYLK KRCEELGIKF TLGRDGSEPK    240
IQRMGDRFAV EVKGRIHFDL YPVIRRTINL PTYTLEAVYE AVFGKPKEKV YAEEIAQAWE    300
SGEGLERVAR YSMEDAKVTY ELGREFFPME AQLSRLIGQS LWDVSRSSTG NLVEWFLLRK    360
AYKRNELAPN KPDERELARR RGGYAGGYVK EPERGLWDNI VYLDFRSLYP SIIITHNVSP    420
DTLNREGCKE YDVAPEVGHK FCKDFPGFIP SLLGDLLEER QKIKRKMKAT VDPLEKKLLD    480
YRQRAIKILA NSFYGYYGYA KARWYCKECA ESVTAWGREY IEMVIRELEE KFGFKVLYAD    540
TDGLHATIPG ADAETVKKKA KEFLKYINPK LPGLLELEYE GFYVRGFFVT KKKYAVIDEE    600
GKITTRGLEI VRRDWSEIAK ETQARVLEAI LKHGDVEEAV RIVKEVTEKL SKYEVPPEKL    660
VIHEQITRDL RDYKATGPHV AVAKRLAARG VKIRPGTVIS YIVLKGSGRI GDRAIPADEF    720
DPTKHRYDAE YYIENQVLPA VERILKAFGY RKEDLRYQKT KQVGLGAWLK VKGKK         775

SEQ ID NO: 228         moltype = AA  length = 775
```

```
FEATURE                 Location/Qualifiers
REGION                  1..775
                        note = Description of Artificial Sequence:
                        Syntheticpolypeptide
source                  1..775
                        mol_type = protein
                        organism = synthetic construct
SEQUENCE: 228
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPAE GDEELTMLAF AIATLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLYP SIIITHNVSP   420
DTLNREGCKE YDVAPEVGHK FCKDFPGFIP SLLGDLLEER QKIKRKMKAT VDPLEKKLLD   480
YRQRLIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 229          moltype = AA  length = 1702
FEATURE                 Location/Qualifiers
source                  1..1702
                        mol_type = protein
                        organism = Thermococcus litoralis
SEQUENCE: 229
MILDTDYITK DGKPIIRIFK KENGEFKIEL DPHFQPYIYA LLKDDSAIEE IKAIKGERHG    60
KTVRVLDAVK VRKKFLGREV EVWKLIFEHP QDVPAMRGKI REHPAVVDIY EYDIPFAKRY   120
LIDKGLIPME GDEELKLLAF DIETFYHEGD EFGKGEIIMI SYADEEEARV ITWKNIDLPY   180
VDVVSNEREM IKRFVQVVKE KDPDVIITYN GDNFDLPYLI KRAEKLGVRL VLGRDKEHPE   240
PKIQRMGDSF AVEIKGRIHF DLFPVVRRTI NLPTYTLEAV YEAVLGKTKS KLGAEEIAAI   300
WETEESMKKL AQYSMEDARA TYELGKEFFP MEAELAKLIG QSVWDVSRSS TGNLVEWYLL   360
RVAYARNELA PNKPDEEEYK RRLRTTYLGG YVKEPEKGLW ENIIYLDFRS LYPSIIVTHN   420
VSPDTLEKEG CKNYDVAPIV GYRFCKDFPG FIPSILGDLI AMRQDIKKKM KSTIDPIEKK   480
MLDYRQRAIK LLANSILPNE WLPIIENGEI KFVKIGEFIN SYMEKQKENV KTVENTEVLE   540
VNNLFAFSFN KKIKESEVKK VKALIRHKYK GKAYEIQLSS GRKINITAGH SLFTVRNGEI   600
KEVSGDGIKE GDLIVAPKKI KLNEKGVSIN IPELISDLSE EETADIVMTI SAKGRKNFFK   660
GMLRTLRWMF GEENRRIRTF NRYLFHLEKL GLIKLLPRGY EVTDWERLKK YKQLYEKLAG   720
SVKYNGNKRE YLVMFNEIKD FISYFPQKEL EEWKIGTLNG FRTNCILKVD EDFGKLLGYY   780
VSEGYAGAQK NKTGGISYSV KLYNEDPNVL ESMKNVAEKF FGKVRVDRNC VSISKKMAYL   840
VMKCLCGALA ENKRIPSVIL TSPEPVRWSF LEAYFTGDGD IHPSKRFRLS TKSELLANQL   900
VFLLNSLGIS SVKIGFDSGV YRVYINEDLQ FPQTSREKNT YYSNLIPKEI LRDVFGKEFQ   960
KNMTFKKFKE LVDSGKLNRE KAKLLEFFIN GDIVLDRVKS VKEKDYEGYV YDLSVEDNEN  1020
FLVGFGLLYA HNSYYGYMGY PKARWYSKEC AESVTAWGRH YIEMTIREIE EKFGFKVLYA  1080
DSVSGESEII IRQNGKIRFV KIKDLFSKVD YSIGEKEYCI KGVEALTLD DDGKLVWKPV   1140
PYVMRHRANK RMFRIWLTNS WYIDVTEDHS LIGYLNTSKT KTAKKIGERL KEVKPFELGK  1200
AVKSLICPNA PLKDENTKTS EIAVKFWELV GLIVGDGNWG GDSRWAEYYL GLSTGKDAEE  1260
IKQKLLEPLK TYGVISNYYP KNEKGDFNIL AKSLVKFMKR HFKDEKGRRK IPEFMYELPV  1320
TYIEAFLRGL FSADGTVTIR KGVPEIRLTN IDADFLREVH LKLWIVGISN SIFAETTPNR  1380
YNGVSTGTYS KHLRIKNKWR FAERIGFLIE RKQKRLLEHL KSARVKRNTI DFGFDLVHVK  1440
KVEEIPYEGY VYDIEVEETH RFFANNILVH NTDGFYATIP GEKPELIKKK AKEFLNYINS  1500
KLPGLLELEY EGFYLRGFFV TKKRYAVIDE EGRITTRGLE VVRRDWSEIA KETQAKVLEA  1560
ILKEGSVEKA VEVVRDVVEK IAKYRVPLEK LVIHEQITRD LKDYKAIGPH VAIAKRLAAR  1620
GIKVKPGTII SYIVLKGSGK ISDRVILLTE YDPRKHKYPD DYYIENQVLP AVLRILEAFG  1680
YRKEDLRYQS SKQTGLDAWL KR                                          1702

SEQ ID NO: 230          moltype = AA  length = 1312
FEATURE                 Location/Qualifiers
source                  1..1312
                        mol_type = protein
                        organism = Pyrococcus sp.
SEQUENCE: 230
MILDADYITE DGKPIIRIFK KENGEFKVEY DRNFRPYIYA LLKDDSQIDE VRKITAERHG    60
KIVRIIDAEK VRKKFLGRPI EVWRLYFEHP QDVPAIRDKI REHSAVIDIF EYDIPFAKRY   120
LIDKGLIPME GDEELKLLAF DIETLYHEGE EFAKGPIIMI SYADEEEAKV ITWKKIDLPY   180
VEVVSSEREM IKRFLKVIRE KDPDVIITYN GDSPDLPYLV KRAEKLGIKL PLGRDGSEPK   240
MQRLGDMTAV EIKGRIHFDL YHVIRRTINL PTYTLEAVYE AIFGKPKEKV YAHEIAEAWE   300
TGKGLERVAK YSMEDAKVTY ELGREFFPME AQLSRLVGQP LWDVSRSSTG NLVEWYLLRK   360
AYERNELAPN KPDEREYERR LRESYAGGYV KEPEKGLWEG LVSLDFRSLY PSIIITHNVS   420
PDTLNREGCR EYDVAPEVGH KFCKDFPGFI PSLLKRLLDE RQEIKRKMKA SKDPIEKKML   480
DYRQRAIKIL ANSILPEEWV PLIKNGKVKI FRIGDFVGGL MKANQGKVKK TGDTEVLEVA   540
GIHAFSFDRK SKKARVMAVK AVIRHRYSGN VYRIVLNSGR KITITEGHSL FVYRNGDLVE   600
ATGEDVKIGD LLAVPRSVNL PEKRERLNIV ELLLNLSPEE TEDIILTIPV KGRKNFFKGM   660
LRTLRWIFGE EKRVRTASRY LRHLENLGYI RLRKIGYDII DKEGLEKYRT LYEKLVDVVR   720
YNGNKREYLV EFNAVRDVIS LMPEEELKEW RIGTRNGFRM GTFVDIDEDF AKLLGYYVSE   780
GSARKWKNQT GGWSYTVRLY NENDEVLDDM EHLAKKFFGK VKRGKNYVEI PKKMAYIIFE   840
SLCGTLAENK RVPEVIFTSS KGVRWAFLEG YFIGDGDVHP SKRVRLSTKS ELLVNGLVLL   900
```

```
LNSLGVSAIK LGYDSGVYRV YVNEELKFTE YRKKKNVYHS HIVPKDILKE TFGKVFQKNI   960
SYKKFRELVE NGKLDREKAK RIEWLLNGDI VLDRVVEIKR EYYDGYVYDL SVDEDENFLA  1020
GFGFLYAHNS YYGYYGYAKA RWYCKECAES VTAWGREYIE FVRKELEEKF GFKVLYIDTD  1080
GLYATIPGAK PEEIKKKALE FVDYINAKLP GLLELEYEGF YVRGFFVTKK KYALIDEEGK  1140
IITRGLEIVR RDWSEIAKET QAKVLEAILK HGNVEEAVKI VKEVTEKLSK YEIPPEKLVI  1200
YEQITRPLHE YKAIGPHVAV AKRLAARGVK VRPGMVIGYI VLRGDGPISK RAILAEEFDL  1260
RKHKYDAEYY IENQVLPAVL RILEAFGYRK EDLRWQKTKQ TGLTAWLNIK KK         1312

SEQ ID NO: 231          moltype = AA   length = 775
FEATURE                 Location/Qualifiers
source                  1..775
                        mol_type = protein
                        organism = Pyrococcus furiosus
SEQUENCE: 231
MILDVDYITE EGKPVIRLFK KENGKFKIEH DRTFRPYIYA LLRDDSKIEE VKKITGERHG    60
KIVRIVDVEK VEKKFLGKPI TVWKLYLEHP QDVPTIREKV REHPAVVDIF EYDIPFAKRY   120
LIDKGLIPME GEEELKILAF DIETLYHEGE EFGKGPIIMI SYADENEAKV ITWKNIDLPY   180
VEVVSSEREM IKRFLRIIRE KDPDIIVTYN GDSFDFPYLA KRAEKLGIKL TIGRDGSEPK   240
MQRIGDMTAV EVKGRIHFDL YHVITRTINL PTYTLEAVYE AIFGKPKEKV YADEIAKAWE   300
SGENLERVAK YSMEDAKATY ELGKEFLPME IQLSRLVGQP LWDVSRSSTG NLVEWFLLRK   360
AYERNEVAPN KPSEEEYQRR LRESYTGGFV KEPEKGLWEN IVYLDFRALY PSIIITHNVS   420
PDTLNLEGCK NYDIAPQVGH KFCKDIPGFI PSLLGHLLEE RQKIKTKMKE TQDPIEKILL   480
DYRQKAIKLL ANSFGYYGY AKARWYCKEC AESVTAWGRK YIELVWKELE EKFGFKVLYI   540
DTDGLYATIP GGESEEIKKK ALEFVKYINS KLPGLLELEY EGFYKRGFFV TKKRYAVIDE   600
EGKVITRGLE IVRRDWSEIA KETQARVLET ILKHGDVEEA VRIVKEVIQK LANYEIPPEK   660
LAIYEQITRP LHEYKAIGPH VAVAKKLAAK GVKIKPGMVI GYIVLRGDGP ISNRAILAEE   720
YDPKKHKYDA EYYIENQVLP AVLRILEGFG YRKEDLRYQK TRQVGLTSWL NIKKS        775

SEQ ID NO: 232          moltype = AA   length = 771
FEATURE                 Location/Qualifiers
source                  1..771
                        mol_type = protein
                        organism = Pyrococcus abyssi
SEQUENCE: 232
MIIDADYITE DGKPIIRIFK KEKGEFKVEY DRTFRPYIYA LLKDDSAIDE VKKITAERHG    60
KIVRITEVEK VQKKFLGRPI EVWKLYLEHP QDVPAIREKI REHPAVVDIF EYDIPFAKRY   120
LIDKGLTPME GNEELTFLAV DIETLYHEGE EFGKGPIIMI SYADEEGAKV ITWKSIDLPY   180
VEVVSSEREM IKRLVKVIRE KDPDVIITYN GDNFDFPYLL KRAEKLGIKL PLGRDNSEPK   240
MQRMGDSLAV EIKGRIHFDL FPVIRRTINL PTYTLEAVYE AIFGKSKEKV YAHEIAEAWE   300
TGKGLERVAK YSMEDAKVTF ELGKEFFPME AQLARLVGQP VWDVSRSSTG NLVEWFLLRK   360
AYERNELAPN KPDEREYERR LRESYEGGYV KEPEKGLWEG IVSLDFRSLY PSIIITHNVS   420
PDTLNRENCK EYDVAPQVGH RFCKDFPGFI PSLLGNLLEE RQKIKKRMKE SKDPVEKKLL   480
DYRQRAIKIL ANSYYGYYGY AKARWYCKEC AESVTAWGRQ YIDLVRRELE SRGFKVLYID   540
TDGLYATIPG AKHEEIKEKA LKFVEYINSK LPGLLELEYE GFYARGFFVT KKKYALIDEE   600
GKIVTRGLEI VRRDWSEIAK ETQAKVLEAI LKHGNVDEAV KIVKEVTEKL SKYEIPPEKL   660
VIYEQITRPL SEYKAIGPHV AVAKRLAAKG VKVKPGMVIG YIVLRGDGPI SKRAIAIEEF   720
DPKKHKYDAE YYIENQVLPA VERILRAFGY RKEDLKYQKT KQVGLGAWLK F            771

SEQ ID NO: 233          moltype = AA   length = 903
FEATURE                 Location/Qualifiers
REGION                  1..903
                        note = Description of Unknown:Escherichia phage RB69
source                  1..903
                        mol_type = protein
                        organism = unidentified
SEQUENCE: 233
MKEFYLTVEQ IGDSIFERYI DSNGRERTRE VEYKPSLFAH CPESQATKYF DIYGKPCTRK    60
LFANMRDASQ WIKRMEDIGL EALGMDDFKL AYLSDTYNYE IKYDHTKIRV ANFDIEVTSP   120
DGFPEPSQAK HPIDAITHYD SIDDRFYVFD LLNSPYGNVE EWSIEIAAKL QEQGGDEVPS   180
EIIDKIIYMP FDNEKELLME YLNFWQQKTP VILTGWNVES FDIPYVYNRI KNIFGESTAK   240
RLSPHRKTRV KVIENMYGSR EIITLFGISV LDYIDLYKKF SFTNQPSYSL DYISEFELNV   300
GKLKYDGPIS KLRESNHQRY ISYNIIDVYR VLQIDAKRQF INLSLDMGYY AKIQIQSVFS   360
PIKTWDAIIF NSLKEQNKVI PQGRSHPVQP YPGAFVKEPI PNRYKYVMSF DLTSLYPSII   420
RQVNISPETI AGTFKVAPLH DYINAVAERP SDVYSCSPNG MMYYKDRDGV VPTEITKVFN   480
QRKEHKGYML AAQRNGEIIK EALHNPNLSV DEPLDVDYRF DFSDEIKEKI KKLSAKSLNE   540
MLFRAQRTEV AGMTAQINRK LLINSLYGAL GNVWFRYYDL RNATAITTFG QMALQWIERK   600
VNEYLNEVCG TEGEAFVLYG DTDSIYVSAD KIIDKVGESK FRDTNHWVDF LDKFARERME   660
PAIDRGFREM CEYMNNKQHL MFMDREAIAG PPLGSKGIGG FWTGKKRYAL NVWDMEGTRY   720
AEPKLKIMGL ETQKSSTPKA VQKALKECIR RMLQEGEESL QEYFKEFEKE FRQLNYISIA   780
SVSSANNIAK YDVGGFPGPK CPFHIRGILT YNRAIKGNID APQVVEGEKV YVLPLREGNP   840
FGDKCIAWPS GTEITDLIKD DVLHWMDYTV LLEKTFIKPL EGFTSAAKLD YEKKASLFDM   900
FDF                                                                903
```

What is claimed:

1. A method of analyzing a nucleic acid sequence, the method comprising:

(a) providing a fluorescently-labeled nucleotide conjugate comprising (i) a core, (ii) a plurality of nucleotide moieties coupled to the core, and (iii) one or more fluorophores coupled to the core;

(b) bringing the nucleic acid sequence in contact with the fluorescently-labeled nucleotide conjugate and a polymerizing enzyme under conditions sufficient to form a binding complex comprising (i) the polymerizing enzyme and (ii) a nucleotide of the nucleic acid sequence bound to a nucleotide moiety of the plurality of nucleotide moieties of the fluorescently-labeled nucleotide conjugate, wherein the binding complex persists for a persistence time of 1 second or more before it is removed;

(c) contacting the binding complex with an imaging reagent, wherein the imaging reagent comprises a photobleaching reducing agent; and (d) obtaining a fluorescent image of the binding complex in a presence of the imaging reagent.

2. The method of claim 1, wherein the photobleaching reducing agent comprises (i) ascorbate, (ii) Trolox, or (iii) a combination of the ascorbate and the Trolox.

3. The method of claim 2, wherein in (d), the fluorescent image exhibits no residual fluorescent signal from the fluorescently-labeled nucleotide conjugate of the binding complex when (i) the photobleaching reducing agent comprises 50 millimolar (mM) of the ascorbate and 2 mM of the Trolox, wherein the Trolox is non-aged Trolox and (ii) the obtaining comprises performing a 90 second exposure by a laser having a power of between 75-200 milliwatt (mW).

4. The method of claim 2, wherein the photobleaching reducing agent comprises ascorbate.

5. The method of claim 4, wherein a concentration of the ascorbate is at least 20 millimolar (mM).

6. The method of claim 4, wherein a concentration of the ascorbate is between about 10 millimolar (mM) and about 100 mM.

7. The method of claim 4, wherein a concentration of the ascorbate is about millimolar (50 mM).

8. The method of claim 1, further comprising bringing the nucleic acid sequence into contact with a second fluorescently-labeled nucleotide conjugate under conditions sufficient to form a second binding complex comprising a second nucleotide of the nucleic acid sequence bound to a second nucleotide moiety of the fluorescently-labeled nucleotide conjugate, wherein the nucleotide is adjacent to the second nucleotide in the nucleic acid sequence.

9. The method of claim 1, wherein the nucleic acid sequence is comprised in a concatemer nucleic acid molecule comprising tandem repeats of the nucleic acid sequence.

10. The method of claim 1, wherein the nucleic acid sequence further comprises at least one universal adapter sequence.

11. The method of claim 1, wherein the fluorescently-labeled nucleotide conjugate further comprises a core attachment moiety linking the plurality of the nucleotide moieties to the core.

12. The method of claim 1, wherein the nucleotide moiety is selected from the group consisting of dATP, dGTP, dCTP, dTTP and dUTP.

13. The method of claim 1, further comprising bringing the nucleic acid sequence into contact with a plurality of fluorescently-labeled nucleotide conjugates comprising the fluorescently-labeled nucleotide conjugate and an additional fluorescently-labeled nucleotide conjugate, wherein the nucleotide moiety of the fluorescently-labeled nucleotide conjugate is different than an additional nucleotide moiety of the additional fluorescently-labeled nucleotide conjugate.

14. The method of claim 13, wherein the additional nucleotide moiety is selected from the group consisting of dATP, dGTP, dCTP, dTTP and dUTP.

15. The method of claim 1, wherein the nucleotide moiety comprises between about 3 and about 10 phosphate groups.

16. The method of claim 1, wherein the nucleotide of the nucleic acid sequence comprises a removable chain terminating moiety.

17. The method of claim 16, wherein the removable chain terminating moiety has a blocking moiety at the 3' sugar position of the nucleotide configured to prevent incorporation of the nucleotide moiety into the nucleic acid sequence.

18. The method of claim 1, wherein the polymerizing enzyme is a DNA polymerase.

19. The method of claim 1, wherein the polymerizing enzyme lacks a detectable label.

20. The method of claim 1, wherein the binding complex is immobilized to a surface of a support, and wherein the surface comprises a hydrophilic coating layer coupled thereto.

21. The method of claim 20, wherein the image of the surface exhibits a contrast to noise ratio (CNR) that is greater than or equal to about 20 when the fluorescently-labeled nucleotide conjugate of the binding complex comprises a detectable label comprising Cyanine dye-3 (Cy3) and when the image of the surface is acquired using an inverted fluorescence microscope and a camera under non-signal saturating conditions while the surface is immersed in a buffer.

22. The method of claim 20, wherein the hydrophilic coating layer comprises a water contact angle of less than 50 degrees.

23. The method of claim 20, wherein a plurality of the nucleic acid sequence is immobilized to the surface, and wherein a surface density of the plurality of the nucleic acid sequence comprises about $10^3$ molecules/millimeter $(mm)^2$ to about $5 \times 10^5$ molecules/$mm^2$.

24. The method of claim 1, wherein the imaging reagent comprises a non-catalytic divalent cation that inhibits incorporation of the nucleotide moiety of the fluorescently-labeled nucleotide conjugate.

25. The method of claim 24, wherein the non-catalytic divalent cation comprises strontium, barium, scandium, titanium, calcium, vanadium, chromium, iron, cobalt, nickel, copper, zinc, gallium, germanium, arsenic, selenium, rhodium, europium, tin or terbium ions.

26. The method of claim 1, wherein the nucleic acid sequence comprises a template nucleic acid sequence for a sequencing reaction and at least one universal adaptor sequence.

27. The method of claim 1, wherein the imaging reagent further comprises methyl viologen, Tris-HCl EDTA, NaCl, a non-ionic detergent, sucrose, strontium acetate or glycerol, or any combination thereof.

28. The method of claim 1, wherein said persistence time is more than 1 second.

29. The method of claim 1, further comprising identifying the nucleotide by analyzing the image obtained in (d).

* * * * *